United States Patent
Kuduk et al.

(10) Patent No.: US 9,663,513 B2
(45) Date of Patent: *May 30, 2017

(54) PYRIMIDINE PDE10 INHIBITORS

(71) Applicant: Merck Sharp & Dohme Corp., Rahway, NJ (US)

(72) Inventors: Scott D. Kuduk, Harleysville, PA (US); Casey C. McComas, Phoenixville, PA (US); Thomas S. Reger, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/443,619

(22) PCT Filed: Nov. 15, 2013

(86) PCT No.: PCT/US2013/070214
§ 371 (c)(1),
(2) Date: May 18, 2015

(87) PCT Pub. No.: WO2014/081619
PCT Pub. Date: May 30, 2014

(65) Prior Publication Data
US 2015/0307489 A1    Oct. 29, 2015

Related U.S. Application Data

(60) Provisional application No. 61/728,464, filed on Nov. 20, 2012.

(51) Int. Cl.
| | | |
|---|---|---|
| *C07D 471/04* | (2006.01) | |
| *C07D 405/14* | (2006.01) | |
| *C07D 401/12* | (2006.01) | |
| *C07D 401/14* | (2006.01) | |
| *C07D 413/14* | (2006.01) | |
| *C07D 417/14* | (2006.01) | |

(52) U.S. Cl.
CPC ......... *C07D 471/04* (2013.01); *C07D 401/12* (2013.01); *C07D 401/14* (2013.01); *C07D 405/14* (2013.01); *C07D 413/14* (2013.01); *C07D 417/14* (2013.01)

(58) Field of Classification Search
CPC .. C07D 471/04; C07D 405/14; C07D 401/14; C07D 401/12; C07D 413/14
See application file for complete search history.

(56) References Cited

U.S. PATENT DOCUMENTS

| | | | |
|---|---|---|---|
| 6,407,098 B1 | 6/2002 | Kruger et al. | |
| 8,975,261 B2 * | 3/2015 | Breslin | C07D 401/14 514/255.05 |
| 9,273,033 B2 * | 3/2016 | Kuduk | C07D 401/14 |
| 2010/0249093 A1 | 9/2010 | Hennebohle et al. | |
| 2011/0028501 A1 | 2/2011 | Wood et al. | |
| 2012/0095031 A1 | 4/2012 | Terauchi et al. | |

FOREIGN PATENT DOCUMENTS

| | | |
|---|---|---|
| WO | WO2012044561 | 4/2012 |
| WO | WO2012162213 | 11/2012 |
| WO | WO2013028590 | 2/2013 |
| WO | WO2013052395 | 4/2013 |

OTHER PUBLICATIONS

Kehler et al.,Curr Pharm Des. 2011, 17(20:137-50.*
CAS Abstract of U.S. Pat. No. 8,975,261 (2015).*
Becker et al, Phosphodiesterase Inhibitors-Are They Potential Neuroleptic Drugs?, Behavioural Brain research, 2008, pp. 155-160, 186.
Fujishige et al., Cloning and Characterization of a Novel Human Phosphodiesterase that Hydrolyzes Both cAMP and cGMP (PDE10A), J. Bilogical Chemical, 1999, pp. 18438-18445, 274.
Huang et al., A Fluroescence Polarization Assay for Cyclic Nucleotide Phosphodiesterases, J. of Biomolecular Screening, 2002, pp. 215-222, 7.
Kehler, The Potential Therapeutic Use of Phosphodiesterase 10 Inhibitors, Expert Opinion, 2007, pp. 147-158, 17.
Lieberman et al, Effectiveness of Antipsychotic Drugs in Patients with Chronic Schizophrenia, New England J. of Medicine, Sep. 22, 2005, pp. 1209-1223, 353, US.
Loughney et al., Isolation and Characterization of PDE10A, a Novel Human 3', 5'-Cyclic Nucleotide Phosphodiesterase, Gene, 1999, pp. 109-117, 234.
Schmidt et al., Pre-clincal Characterization of Selective PHosphodiesterease 10A Inhibitors: A New Therapeutic Approach to the Treatment of Schizophrenia, J. of Pharmacology and Experimental Thereapeutics, 2008, pp. 690-690, 325.
Siuciak et al., Inhibiton of the Striatum-Enriched Phosphodiesterease PDE10A: A novel Approach to the Treament of Psychosis, Neuropharmacology, 2006, pp. 386-396, 51.
Soderling et al., Isolation and Characterization of a Dual-Substrate Phosphodiesterase Gene Family: PDE10A, Proc. Natl. Acad. Sci. USA, Jun. 1999, pp. 7071-7076, 96.
Threlfell et al., Inhibition of Phosphodiesterase 10A Increases the Responsiveness of Striatal Projection Neurons to the Cortical Stimulation, J. of Pharmacology and Experimental Therapeutics, J. of Pharmacology and Experimental Therapeutics, 2009, pp. 785-795, 328.

* cited by examiner

*Primary Examiner* — Alexander R Pagano
*Assistant Examiner* — Ebenezer O Sackey
(74) *Attorney, Agent, or Firm* — Sylvia A. Ayler; John C. Todaro

(57) ABSTRACT

The present invention is directed to pyrimidine compounds which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

10 Claims, No Drawings

PYRIMIDINE PDE10 INHIBITORS

CROSS REFERENCE TO RELATED APPLICATIONS

This application is the National Stage of International Application No. PCT/US2013/070214 filed on Nov. 15, 2013, which claims the benefit under 35 U.S.C. 119(e) of U.S. Provisional Application No. 61/728,464, filed Nov. 20, 2012.

FIELD OF THE INVENTION

The invention relates generally to compounds which act as inhibitors of the phosphodiesterase (PDE) 10 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., *N. Engl. J. Med.* (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3', 5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of PDE10 was reported by three groups independently and was distinguished from other PDEs on the basis of its amino acid sequence, functional properties, and tissue distribution (Fujishige et al., *J. Biol. Chem.* (1999) 274:18438-18445; Loughney et al., *Gene* (1999) 234: 109-117; Soderling et al., *PNAS, USA* (1999) 96: 7071-7076). The PDE10 subtype at present consists of a sole member, PDE10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PKA phosphorylation site that upon activation, i.e. PKA phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., *Expert Opin. Ther. Patents* (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions. See PCT applications PCT/US12/051522 filed Aug. 20, 2012 (Provisional U.S. Ser. No. 61/527,392) and PCT/US12/038759 filed May 21, 2012 (Provisional U.S. Ser. No. 61/489,457) for background discussion.

Inhibition of PDE10 is believed to be useful in the treatment of schizophrenia and a wide variety of conditions or disorders that would benefit from increasing levels of cAMP and/or cGMP within neurons, including a variety neurological, psychotic, anxiety and/or movement disorders. Accordingly, agents that inhibit PDE10 and especially PDE10A would be desirable as therapeutics for neurological and psychiatric disorders.

SUMMARY OF THE INVENTION

The present invention is directed to pyrimidine compounds which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

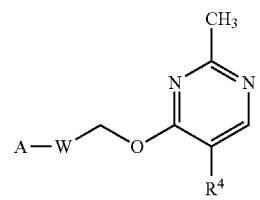

wherein:
A is selected from the group consisting of:
 (1) pyridyl,
 (2) quinolinyl,
 (3) cyclopentapyridinyl, and
 (4) tetrahydroquinolinyl;

said pyridyl, quinolinyl, cyclopentapyridinyl, and tetrahydroquinolinyl optionally substituted with 1 to 3 groups of $R^a$
W is cycylopropyl or —CH(CH$_3$)—CH$_2$—
$R^4$ is selected from the group consisting of:
(1) oxazolyl,
(2) oxadiazolyl,
(3) triazolyl,
(4) isoxazolone,
(5) pyrazolone,
(6) pyrazolopyridinyl,
(7) dioxaspirodecanyl,
(8) pyrazinyl,
(9) pyrrolyl,
(10) imidazopyridinyl,
(11) pyridyl,
(12) pyrimidinyl,
(13) indolyl,
(14) pyranone,
(15) pyranyl,
(16) pyridazinyl,
(17) furanone,
(18) isothiazolyl,
(19) dihydropyrazolone,
(20) pyrazolyl,
(21) thiazolyl,
(22) phenyl,
(23) cyclohexanone,
(24) cyclohexyl,
(25) cyclohexenone,
(26) cyclopentenone
(27) cyclopentanone,
(28) cyclopentanyl,
(29) pyridinone
(30) $C_{2-6}$ alkenyl,
said group (1) through (29) optionally substituted with 1 to 3 groups of $R^{a'}$,
$R^{a'}$ selected from the group consisting of:
(1) $(O)_m C_{1-4}$, haloalkyl, said alkyl optionally substituted with 1 to 3 groups of $R^b$,
(2) halogen,
(3) OR,
(4) $C_{1-6}$ alkyl, where the alkyl is unsubstituted or substituted with one or more substituents selected from $R^b$,
(5) $C_{3-6}$ cycloalkyl, where the cycloalkyl is unsubstituted or substituted with one or more substituents selected from $R^b$,
(6) —O(CH$_2$)$_n$cycloalkyl, where the cycloalkyl is unsubstituted or substituted with one or more substituents selected from $R^b$,
(7) $C_{5-10}$heterocyclyl, where the heterocyclyl is unsubstituted or substituted with one or more substituents selected from $R^b$,
(8) —(C=O)$_m$—N(R)$_2$,
(9) —CO$_2$R,
(10) —CN,
(11) —O—,
(12) —O(CHR)CH$_2$OR, and
(13) S(O)pR;
$R^b$ is selected from the group consisting of:
(1) (CH$_2$)nOR,
(2) CF$_3$,
(3) CF$_2$
(4) $C_{1-6}$ alkyl,
(5) cyano,
(6) N(R)$_2$,
(7) halogen;

R is selected from the group consisting of:
(1) hydrogen,
(2) $C_{1-6}$ alkyl, said alkyl optionally substituted with 1 to 3 groups of $R^b$, and
(3) $(O)_m C_{1-4}$, haloalkyl,
m is 0 or 1,
n is 0, 1, 2, 3, or 4,
p is 1 or 2,
or a pharmaceutically acceptable salt thereof, with the proviso that
1) when A is methoxypyridyl and $R^4$ is pyrazole then the pyrazole cannot be substituted with ethanol, methanol, propanol, methoxyethyl, methylbutyl, methylpropranol, pyridyl, CH$_2$pyridyl, methylmethanol, or with only methyl groups;
2) when A is methylpyridyl or pyridyl and $R^4$ is pyrazole then the pyrazole can't only be substituted with methyl;
3) when A is methoxypyridyl or methyl pyridyl and $R^4$ is pyridyl, then the pyridyl must be substituted and when substituted with a methyl, methoxy, or propanol must contain at least one other substituent;
4) when $R^4$ is pyridinone then A cannot be pridyl;
5) A is not methoxypyridyl when $R^4$ is imidazopyridine;
6) when A is methoxypyridyl then $R^4$ is not methyltriazole;
7) when A is cyclopentapyridine and $R^4$ is pyrazole then the pyrazole cannot be substituted with three methyl groups;
8) when A is methylpyridyl or methoxypyridyl and $R^4$ is a substituted cyclohexyl or cyclohexenol then the substituent can't only be a hydroxyl group.

An embodiment of the present invention includes compounds wherein A is optionally substituted pyridyl. A subembodiment of this invention is realized when the pyridyl is substituted with 1 to 3 groups selected from $C_{1-6}$ alkyl and —OC$_{1-6}$ alkyl. Still another embodiment of this invention is realized when the substituent is methyl, ethyl, or methoxy.

An embodiment of the present invention includes compounds wherein A is optionally substituted quinolinyl. A subembodiment of this invention is realized when the quinolinyl is unsubstituted. Still another embodiment of this invention is realized when the quinolinyl optionally substituted with 1 to 3 groups selected from $C_{1-6}$ alkyl and —OC$_{1-6}$ alkyl.

An embodiment of the present invention includes compounds wherein A is optionally substituted cyclopentapyridinyl. A subembodiment of this invention is realized when the cyclopentapyridinyl is unsubstituted. Still another embodiment of this invention is realized when cyclopentapyridinyl is optionally substituted with 1 to 3 groups selected from $C_{1-6}$alkyl and —OC$_{1-6}$alkyl.

An embodiment of the present invention includes compounds wherein A is optionally substituted tetrahydroquinolinyl. A subembodiment of this invention is realized when the tetrahydroquinolinyl is substituted with 1 to 3 groups selected from $C_{1-6}$alkyl and —OC$_{1-6}$alkyl. Still another embodiment of this invention is realized when the substituent is methyl, ethyl, or methoxy.

Another embodiment of the present invention includes compounds wherein W is cyclopropyl.

Another embodiment of the present invention includes compounds wherein W is —CH(CH$_3$)—CH$_2$—.

Another embodiment of the present invention includes compounds wherein $R^4$ is an optionally substituted oxadiazolyl, dioxaspirodecanyl, imidazopyridinyl, pyridyl, phenyl, cyclohexanone, cyclohexyl, cyclohexenone, dihydropyrazolone, and pyrazolyl. A further subembodiment of this invention is realized when $R^4$ is an optionally dioxaspirodecanyl. Still another subembodiment of this invention is realized when R⁴ is optionally substituted pyridyl. Another subembodiment of this invention is realized when R⁴ is optionally substituted phenyl. Another subembodiment of this invention is realized when R⁴ is optionally substituted pyrazolyl. Another subembodiment of this invention is realized when R⁴ is optionally substituted cyclohexyl. Another subembodiment of this invention is realized when R⁴ is optionally substituted imidazopyridinyl. Another subembodiment of this invention is realized when R⁴ is optionally substituted dihydropyrazolone. Another subembodiment of this invention is realized when R⁴ is optionally substituted cyclohexanone. Another subembodiment of this invention is realized when R⁴ is optionally substituted cyclohexenone.

Still another embodiment of the present invention includes compounds wherein R⁴ is optionally substituted $C_{2-6}$ alkenyl.

Another embodiment of the present invention includes compounds wherein $R^a$ is selected from the group consisting of OH, CH₂OH, OCH(CH₃)₂, OCF₃, halogen, CF₃, OCH₃, COOR, CN, NH₂, methoxyethoxy, CHCH₃OH, OCH₂CH₃, C(CH₃)OH, S(O)CH₃, CH(CF₂)OH, OCH(CH₂)₂OH, OCH₂cyclopropyl, CH(CF₃)OH, CONHCH₃, CONHCH₂CF₃, CONH₂, and optionally substituted $C_{1-6}$ alkyl, cyclopropyl, oxetanyl, tetrazolyl, and oxadiazolyl.

Another embodiment of the present invention includes compounds wherein $R^b$ is selected from the group consisting of CH₂OH, OCH₃, $C_{1-6}$ alkyl, and CF₂.

An embodiment of this aspect of the invention is represented by formula Iaa and Iaaa:

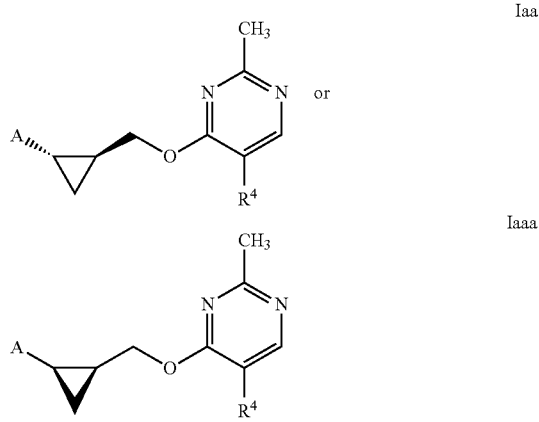

wherein A, and R⁴, are as originally defined herein; or a pharmaceutically acceptable salt thereof An embodiment of the present invention includes compounds of the formula Ia:

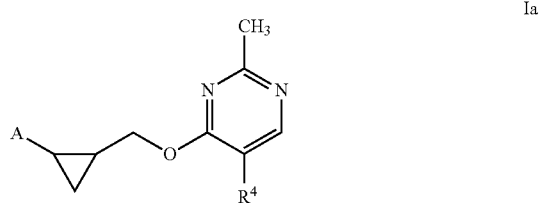

wherein A, and R⁴, are as originally defined herein; or a pharmaceutically acceptable salt, thereof A subembodiment of formula Ia is realized when A is optionally substituted pyridyl and R⁴ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ia is realized when A is optionally substituted pyridyl and R⁴ is an optionally substituted phenyl. Another subembodiment of the invention of formula Ia is realized when A is optionally substituted pyridyl and R⁴ is an optionally substituted imidazopyridinyl. Another subembodiment of the invention of formula Ia is realized when A is optionally substituted pyridyl and R⁴ is an optionally substituted pyridyl. Another subembodiment of the invention of formula Ia is realized when A is optionally substituted pyridyl and R⁴ is an optionally substituted pyrazolyl. Another subembodiment of the invention of formula Ia is realized when A is optionally substituted pyridyl and R⁴ is an optionally substituted dioxaspirodecanyl. Another subembodiment of the invention of formula Ia is realized when A is optionally substituted pyridyl and R⁴ is an optionally substituted cyclohexyl. Another subembodiment of the invention of formula Ia is realized when A is optionally substituted pyridyl and R⁴ is an optionally substituted cyclohexanone. Another subembodiment of the invention of formula Ia is realized when A is optionally substituted pyridyl and R⁴ is an optionally substituted cyclohexenone.

Another subembodiment of the formula Ia is realized when A is optionally substituted pyridyl as represented by structural formula Ia':

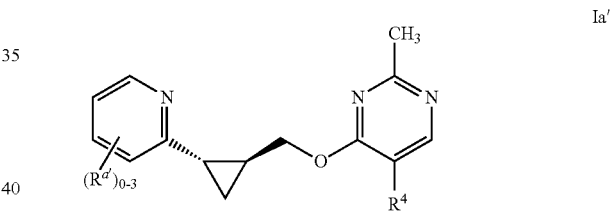

or a pharmaceutically acceptable salt thereof wherein $R^{a'}$ is $R^a$ and $R^a$ and R⁴ are as originally described. A subembodiment of formula Ia' is realized when $R^{a'}$ is $C_{1-6}$ alkyl, or OR. A further subembodiment of formula Ia' is realized when $R^{a'}$ is methyl or methoxy. A subembodiment of formula Ia' is realized when $R^{a'}$ is methyl or methoxy R⁴ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ia' is realized when R⁴ is an optionally substituted phenyl. Another subembodiment of the invention of formula Ia' is realized when R⁴ is an optionally substituted imidazopyridinyl. Another subembodiment of the invention of formula Ia' is realized when R⁴ is an optionally substituted pyridyl. Another subembodiment of the invention of formula Ia' is realized when R⁴ is an optionally substituted pyrazolyl. Another subembodiment of the invention of formula Ia' is realized when R⁴ is an optionally substituted dioxaspirodecanyl. Another subembodiment of the invention of formula Ia' is realized when R⁴ is an optionally substituted cyclohexyl. Another subembodiment of the invention of formula Ia' is realized when R⁴ is an optionally substituted cyclohexanone or cyclohexenone. Another subembodiment of the invention of formula Ia' is realized when the oxadiazolyl, dioxaspirodecanyl, imidazopyridinyl, pyridyl, phenyl, cyclohexanone, cyclohexyl, cyclohexenone, dihydropyrazolone, or pyrazolyl of $R^4$ is optionally substituted with 1 to 3 groups selected from the group consisting of OH, $CH_2OH$, $OCH(CH_3)_2$, $OCF_3$, halogen, $CF_3$, $OCH_3$, COOR, CN, $NH_2$, methoxyethoxy, $CHCH_3OH$, $OCH_2CH_3$, $C(CH_3)OH$, $S(O)CH_3$, $CH(CF_2)OH$, $OCH(CH_2)_2OH$, $OCH_2$cyclopropyl, $CH(CF_3)OH$, $CONHCH_3$, $CONHCH_2CF_3$, $CONH_2$, and optionally substituted $C_{1-6}$ alkyl, cyclopropyl, oxetanyl, tetrazolyl, and oxadiazolyl.

Yet another subembodiment of formula Ia is realized when A is optionally substituted quinolinyl and $R^4$ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ia is realized when A is optionally substituted quinolinyl and $R^4$ is an optionally substituted phenyl. Another subembodiment of the invention of formula Ia is realized when A is optionally substituted quinolinyl and $R^4$ is an optionally substituted imidazopyridinyl. Another subembodiment of the invention of formula Ia is realized when A is optionally substituted quinolinyl and $R^4$ is an optionally substituted pyridyl. Another subembodiment of the invention of formula Ia is realized when A is optionally substituted quinolinyl and $R^4$ is an optionally substituted pyrazolyl. Another subembodiment of the invention of formula Ia is realized when A is optionally substituted quinolinyl and $R^4$ is an optionally substituted dioxaspirodecanyl. Another subembodiment of the invention of formula Ia is realized when A is optionally substituted quinolinyl and $R^4$ is an optionally substituted cyclohexyl. Another subembodiment of the invention of formula Ia is realized when A is optionally substituted quinolinyl and $R^4$ is an optionally substituted cyclohexanone. Another subembodiment of the invention of formula Ia is realized when A is optionally substituted quinolinyl and $R^4$ is an optionally substituted cyclohexenone.

A subembodiment of formula Ia where A is optionally substituted quinolinyl as represented by structural formula Ib':

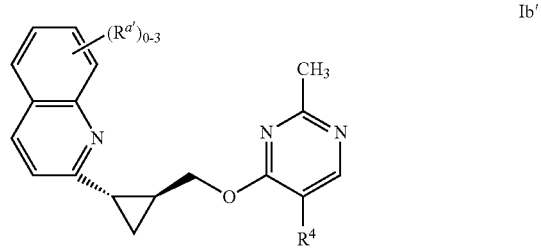

or a pharmaceutically acceptable salt thereof wherein $R^{a'}$ is $R^a$ and $R^a$ and $R^4$ are as originally described. A subembodiment of formula Ib' is realized when $R^{a'}$ is not present. A further subembodiment of formula Ib' is realized when $R^{a'}$ is methyl or methoxy. Another subembodiment of the invention of formula Ib' is realized when $R^{a'}$ is absent and $R^4$ is selected from the group consisting of optionally substituted oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ib' is realized when $R^4$ is an optionally substituted phenyl. Another subembodiment of the invention of formula Ib' is realized when $R^4$ is an optionally substituted imidazopyridinyl. Another subembodiment of the invention of formula Ib' is realized when $R^4$ is an optionally substituted pyridyl. Another subembodiment of the invention of formula Ib' is realized when $R^4$ is an optionally substituted pyrazolyl. Another subembodiment of the invention of formula Ib' is realized when $R^4$ is an optionally substituted dioxaspirodecanyl. Another subembodiment of the invention of formula Ib' is realized when $R^4$ is an optionally substituted cyclohexyl. Another subembodiment of the invention of formula Ib' is realized when $R^4$ is an optionally substituted cyclohexanone or cyclohexenone. Another subembodiment of the invention of formula Ib' is realized when the oxadiazolyl, dioxaspirodecanyl, imidazopyridinyl, pyridyl, phenyl, cyclohexanone, cyclohexyl, cyclohexenone, dihydropyrazolone, or pyrazolyl of $R^4$ is optionally substituted with 1 to 3 groups selected from the group consisting of OH, $CH_2OH$, $OCH(CH_3)_2$, $OCF_3$, halogen, $CF_3$, $OCH_3$, COOR, CN, $NH_2$, methoxyethoxy, $CHCH_3OH$, $OCH_2CH_3$, $C(CH_3)OH$, $S(O)CH_3$, $CH(CF_2)OH$, $OCH(CH_2)_2OH$, $OCH_2$cyclopropyl, $CH(CF_3)OH$, $CONHCH_3$, $CONHCH_2CF_3$, $CONH_2$, and optionally substituted $C_{1-6}$ alkyl, cyclopropyl, oxetanyl, tetrazolyl, and oxadiazolyl.

Still another subembodiment of formula Ia is realized when A is optionally substituted cyclopentapyridinyl and $R^4$ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ia is realized when A is optionally substituted cyclopentapyridinyl and $R^4$ is an optionally substituted phenyl. Another subembodiment of the invention of formula Ia is realized when A is optionally substituted cyclopentapyridinyl and $R^4$ is an optionally substituted imidazopyridinyl. Another subembodiment of the invention of formula Ia is realized when A is optionally substituted cyclopentapyridinyl and $R^4$ is an optionally substituted pyridyl. Another subembodiment of the invention of formula Ia is realized when A is optionally substituted cyclopentapyridinyl and $R^4$ is an optionally substituted pyrazolyl. Another subembodiment of the invention of formula Ia is realized when A is optionally substituted cyclopentapyridinyl and $R^4$ is an optionally substituted dioxaspirodecanyl. Another subembodiment of the invention of formula Ia is realized when A is optionally substituted cyclopentapyridinyl and $R^4$ is an optionally substituted cyclohexyl. Another subembodiment of the invention of formula Ia is realized when A is optionally substituted cyclopentapyridinyl and $R^4$ is an optionally substituted cyclohexanone. Another subembodiment of the invention of formula Ia is realized when A is optionally substituted cyclopentapyridinyl and $R^4$ is an optionally substituted cyclohexenone.

Still another subembodiment of formula Ia is realized when A is optionally substituted tetrahydroquinolinyl and $R^4$ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ia is realized when A is optionally substituted tetrahydroquinolinyl and $R^4$ is an optionally substituted phenyl. Another subembodiment of the invention of formula Ia is realized when A is optionally substituted tetrahydroquinolinyl and $R^4$ is an optionally substituted imidazopyridinyl. Another subembodiment of the invention of formula Ia is realized when A is optionally substituted tetrahydroquinolinyl and $R^4$ is an optionally substituted pyridyl. Another subembodiment of the invention of formula Ia is realized when A is optionally substituted tetrahydroquinolinyl and R⁴ is an optionally substituted pyrazolyl. Another subembodiment of the invention of formula Ia is realized when A is optionally substituted tetrahydroquinolinyl and R⁴ is an optionally substituted dioxaspirodecanyl. Another subembodiment of the invention of formula Ia is realized when A is optionally substituted tetrahydroquinolinyl and R⁴ is an optionally substituted cyclohexyl. Another subembodiment of the invention of formula Ia is realized when A is optionally substituted tetrahydroquinolinyl and R⁴ is an optionally substituted cyclohexanone. Another subembodiment of the invention of formula Ia is realized when A is optionally substituted tetrahydroquinolinyl and R⁴ is an optionally substituted cyclohexenone.

Another embodiment of the invention of formula I is represented by structural formula Ib:

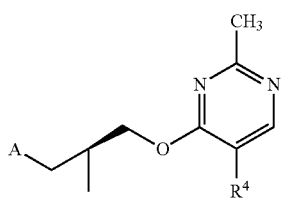

Ib or a pharmaceutically acceptable salt thereof wherein A and R⁴ are as originally described. A subembodiment of formula Ib is realized when A is optionally substituted pyridyl and R⁴ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ib is realized when A is optionally substituted quinolinyl and R⁴ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ib is realized when A is optionally substituted cyclopentapyridinyl and R⁴ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl. Another subembodiment of the invention of formula Ib is realized when A is optionally substituted tetrahydroquinolinyl and R⁴ is an optionally substituted group selected from of oxadiazolyl, dioxaspirodecanyl, imidazopyridinyl, pyridyl, phenyl, cyclohexanone, cyclohexyl, cyclohexenone, dihydropyrazolone, and pyrazolyl.

Specific embodiments of the present invention include a compound which is selected from the group consisting of the subject compounds of the Examples herein and pharmaceutically acceptable salts thereof and individual enantiomers and diastereomers thereof.

Specific embodiments of the present invention include a compound which is selected from the group consisting of the subject compounds of the Examples herein and pharmaceutically acceptable salts thereof and individual enantiomers and diastereomers thereof.

When any variable (e.g. aryl, heterocycle, R¹, R⁵ etc.) occurs more than one time in any constituent, its definition on each occurrence is independent at every other occurrence. Also, combinations of substituents/or variables are permissible only if such combinations result in stable compounds.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyls are $C_2$-$C_6$ alkynyl.

"Alkenyl," "alkynyl" and other like terms include carbon chains containing at least one unsaturated C≡C bond.

As used herein, "haloalkyl" refers to an alkyl substituent as described herein containing at least one halogen substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" or "O-alkyl" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "heteroatom" means O, S or N, selected on an independent basis.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2,4 fluor-3-propylphenyl. As another non-limiting example, substituted n-octyls include 2, 4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one moieties listed in (a), above.

"Halogen" or "halo" refer to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

Compounds described herein may contain one or more double bonds and may thus give rise to cis/trans isomers as well as other conformational isomers. The present invention includes all such possible isomers as well as mixtures of such isomers unless specifically stated otherwise.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of generic Formula I, Ia, Iaa, Iaaa, Ia', Ib', and Ib, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE10 dysfunction in a patient such as a mammal in need of such inhibition comprising the administration of an effective amount of the compound. In addition to primates, especially humans, a variety of other mammals may be treated according to the method of the present invention. The subject compounds may be useful in a method of inhibiting PDE10 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals may be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE10 and, in particular inhibitors of PDE10A, may provide therapeutic benefit to those individuals suffering from psychiatric and cognitive disorders. The unique and exclusive distribution of PDE10A in the medium spiny projection neurons of the striatum, which form the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum may result in increased cAMP/cGMP signaling and striatal output, which has the potential to restore behavioral inhibition that is impaired in cognitive disease such as schizophrenia. Regulation and integration of glutamatergic and dopaminergic inputs may enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

As used herein, the term "selective PDE10 inhibitor" refers to an organic molecule that effectively inhibits an enzyme from the PDE10 family to a greater extent than enzymes from the PDE 1-9 or PDE11 families. In one embodiment, a selective PDE10 inhibitor is an organic molecule having a Ki for inhibition of PDE10 that is less than or about one-tenth that for a substance that is an inhibitor for another PDE enzyme. In other words, the organic molecule inhibits PDE10 activity to the same degree at a concentration of about one-tenth or less than the concentration required for any other PDE enzyme. Preferably, a selective PDE10 inhibitor is an organic molecule, having a Ki for inhibition of PDE10 that is less than or about one-hundredth that for a substance that is an inhibitor for another PDE enzyme. In other words, the organic molecule inhibits PDE10 activity to the same degree at a concentration of about one-hundredth or less than the concentration required for any other PDE enzyme. A "selective PDE10 inhibitor" can be identified, for example, by comparing the ability of an organic molecule to inhibit PDE10 activity to its ability to inhibit PDE enzymes from the other PDE families. For example, an organic molecule may be assayed for its ability to inhibit PDE10 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, and/or PDE11A.

Phosphodiesterase enzymes including PDE10 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention may provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention may provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention may provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention may provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention may provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention may provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention may provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention may provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy. Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE10 inhibitors may be readily determined without undue experimentation using a fluorescence polarization (FP) methodology that is well known in the art (Huang, W., et al., *J. Biomol Screen*, 2002, 7: 215). In particular, the compounds of the following examples had activity in reference assays by exhibiting the ability to inhibit the hydrolysis of the phosphosphate ester bond of a cyclic nucleotide. Any compound exhibiting a Ki (inhibitory constant) below 1 µM would be considered a PDE10 inhibitor as defined herein.

In a typical experiment the PDE10 inhibitory activity of the compounds of the present invention was determined in accordance with the following experimental method. PDE10A2 was amplified from human fetal brain cDNA (Clontech, Mountain View, Calif.) using a forward primer corresponding to nucleotides 56-77 of human PDE10A2 (Accession No. AF127480, Genbank Identifier 4894716), containing a Kozak consensus sequence, and a reverse primer corresponding to nucleotides 2406-2413 of human PDE10A2 (Accession No. AF127480, Genbank Identifier 4894716). Amplification with Easy-A polymerase (Stratagene, La Jolla, Calif.) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, Calif.) according to standard protocol. AD293 cells with 70-80% confluency were transiently transfected with human PDE10A2/pcDNA3.2-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE10A2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to phosphodiesterase assays (Huang, W., et al., *J. Biomol Screen*, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. *Neuropharmacology* (2006) 51:386-396; Becker, et al. *Behav Brain Res* (2008) 186(2): 155-60; Threlfell, et al., *J Pharmacol Exp Ther* (2009) 328(3):785-795), 2-{4-[pyridin-4-yl-1-(2,2,2-trifluoroethyl)-1H-pyrazol-3-yl]phenoxymethyl}quinoline succinic acid or 2-[4-(1-methyl-4-pyridin-4-yl-1H-pyrazol-3-yl)-phenoxymethyl]quinoline succinic acid (see Schmidt, et al. *J Pharmacol Exp Ther* (2008) 325:681-690; Threlfell, et al., *J Pharmacol Exp Ther* (2009) 328(3): 785-795). 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. A solution of enzyme (1/1600 dilution from aliquots; sufficient to produce 20% substrate conversion) and a separate solution of FAM-labeled cAMP PDE from Molecular Devices (product # R7506), at a final concentration of 50 nM are made in the assay buffer (10 mM Tris HCl, pH 7.2, 10 mM MgCl$_2$, 0.05% NaN$_3$ 0.01% Tween-20, and 1 mM DTT). The enzyme and the substrate are then added to the assay plates in two consecutive additions of 10 µL, and then shaken to mix. The reaction is allowed to proceed at room temperature for 30 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 10 seconds. The plate was incubated at room temperature for at least one hour prior to determining the fluorescence polarization (FP). The parallel and perpendicular fluorescence of each well of the plate was measured using a Perkin Elmer EnVision™ plate reader (Waltham, Mass.).

Fluorescence polarization (mP) was calculated from the parallel (S) and perpendicular (P) fluorescence of each sample well and the analogous values for the median control well, containing only substrate (So and Po), using the following equation:

Polarization($mP$)=1000*($S/So-P/Po$)/($S/So+P/Po$).

Dose-inhibition profiles for each compound were characterized by fitting the mP data to a four-parameter equation given below. The apparent inhibition constant ($K_I$) the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., *JALA*, 2003, 8: 54-63, using the following equation:

$$mP = \frac{(0\% \, mP - 100\% \, mP)(Imax - Imin)}{1 + \left[\frac{[Drug]}{\left(10^{-pK_I}\left(1 + \frac{[Substrate]}{K_M}\right)\right)}\right]^{nH}} +$$

$$100\% \, mP + (0\% \, mP - 100\% \, mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE10, as compared to other PDE families, was assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM MgCl$_2$, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 μL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 μL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

All of the final compounds of the following examples had activity in inhibiting the human PDE10 enzyme in the aforementioned assays, generally with an Ki of less than about 1 μM. In particular, all of the final compounds of the following examples had activity in inhibiting the human PDE10 enzyme in the aforementioned assays, generally with an Ki of less than about 0.1 μM. Additional data is provided in the following Examples. Such a result is indicative of the intrinsic activity of the compounds in use as inhibitors of the PDE10 enzyme. In general, one of ordinary skill in the art would appreciate that a substance is considered to effectively inhibit PDE10 activity if it has a Ki of less than or about 1 μM, preferably less than or about 0.1 μM. The present invention also includes compounds within the generic scope of the invention which possess activity as inhibitors of other phosphodiesterase enzymes. With respect to 2-alkoxy pyrimidine compounds, the present compounds exhibit unexpected properties, such as regarding increased potency, oral bioavailability, metabolic stability, and/or decreased off target activity.

The subject compounds are further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $5\text{-HT}_{1A}$ agonists or antagonists, especially $5\text{-HT}_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

SCHEME 1

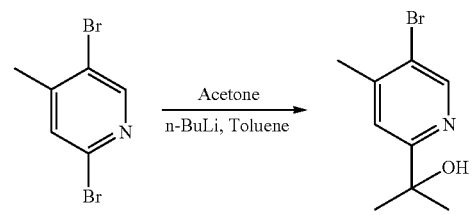

Intermediate 1

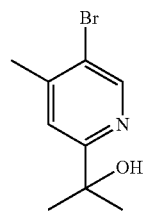

Step A: 2-(5-bromo-4-methylpyridin-2-yl)propan-2-ol

A Solution of 2,5-dibromo-4-methylpyridine (500 mg, 2 mmol) in toluene (5 mL) was cooled to −78° C. and slowly added with n-BuLi (2.5 M, 0.8 mL, 2 mmol) and keep stirring for 1 h, then added acetone (0.15 ml). The solution was warmed to rt and stirred for 1 h. To the solution was added aq.NH$_4$Cl and the solvent was removed by evaporation under vacuum and the residue was purified by chromatography on a silica gel column (2% to 5% EA in PE) to afford the title compound.

The following intermediate 2 in Table 1 was prepared using the procedure of Intermediate 1, substituting the appropriate starting material.

TABLE 1

| Compound number | Structure |
| --- | --- |
| 1 | 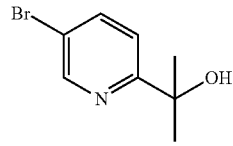 |
| 2 | 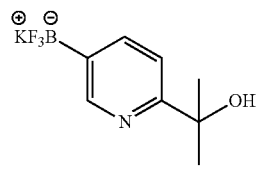 |

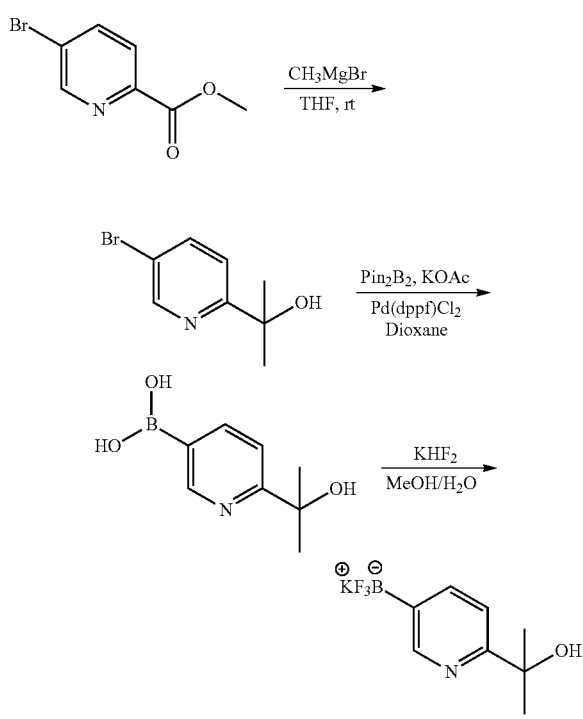

Intermediate 3

Step A: 2-(5-bromopyridin-2-yl)propan-2-ol

To a solution of methyl 5-bromopicolinate (2.16 g, 10 mmol) in THF (50 mL) at 0° C. was added a solution of 10 mL of 3.0 M methyl magnesium bromide in diethyl ether (30 mmol) dropwise over 0.5 h. The reaction mixture was stirred at rt for 1 h, quenched with saturated NH$_4$Cl (1 mL) and partitioned between saturated NaHCO$_3$ (10 mL) and EtOAc (2*15 mL). The combined organic layers were dried over Na$_2$SO$_4$ and concentrated. The residue was purified by gradient elution on silica gel (0 to 20% EtOAc in petroleum) to afford the title compound as a yellow oil (1.75 g, 81%). LRMS m/z (M+H) 218.1 found, 218.1 required.

Intermediate 4

Step A: 6-(2-hydroxypropan-2-yl)pyridin-3-ylboronic acid

A solution of 2-(5-bromopyridin-2-yl)propan-2-ol (0.432 g, 2 mmol), bispinacolatodiboron (0.61 g, 2.4 mmol) and KOAc (0.392 g, 4 mmol) in 1,4-dioxane (15 mL) was degassed by flushing with nitrogen for 15 min. Pd(dppf)Cl$_2$.CH$_2$Cl$_2$ (0.163 g, 0.2 mmol) was then added to the reaction mixture, which was again degassed by nitrogen for 15 min. The resulting reaction mixture was heated to 85° C. for 6 h. The reaction mixture was filtered through celite and the filtrate was concentrated to get the crude residue as yellow oil (0.235 g, 65%). LRMS m/z (M+H) 182.1 found, 182.1 required.

Step B: potassium trifluoro(6-(2-hydroxypropan-2-yl)pyridin-3-yl)borate

To a solution of 6-(2-hydroxypropan-2-yl)pyridin-3-ylboronic acid (0.14 g, 0.77 mmol) in MeOH (0.5 mL) under N$_2$ was added KHF$_2$ (0.181 g, 2.32 mmol) in one portion at 0° C. To the suspension was added H$_2$O dropwise (0.8 mL) at 0° C. The ice-water bath was removed, and the reaction was stirred at rt for 20 min. The crude mixture was concentrated and dried overnight in vacuo. The crude solid was dissolved in acetone (10 mL) and filtrated. The filtration was concentrated and then redissolved in a minimal amount of acetone (1 mL). The addition of ether (4 mL) led to the precipitation of the product. The product was filtered, concentrated, and dried in vacuo to afford the pure compound (0.165 g, 88%) as a light orange solid. LRMS m/z (M-KF+H) 186.1 found, 186.1 required.

The following intermediates 5-6 in Table 2 were prepared using the procedure of Intermediate 3, substituting the appropriate starting materials.

TABLE 2

| Compound number | Structure |
|---|---|
| 3 | 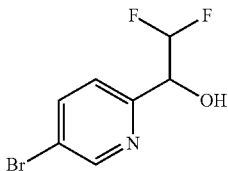 |
| 4 | 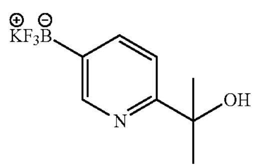 |
| 5 | 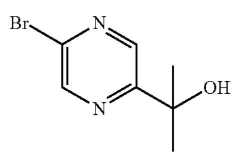 |
| 6 | 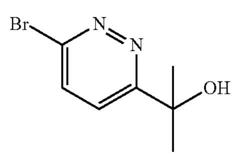 |

SCHEME 3

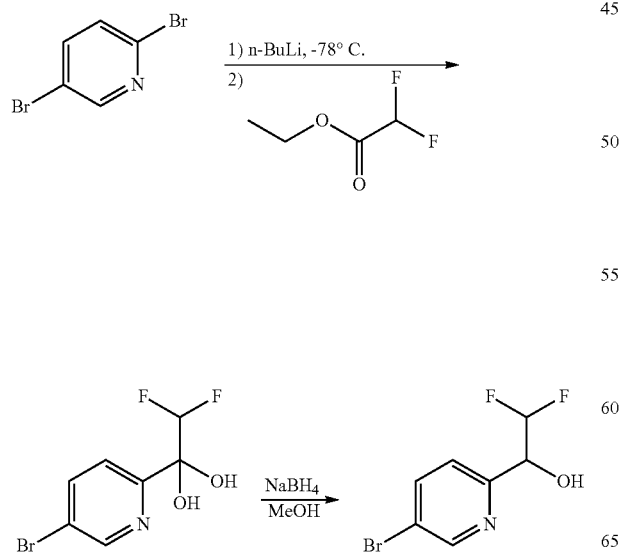

Intermediate 7

Step A: 1-(5-bromopyridin-2-yl)-2,2-difluoroethanol

To a solution of 2,5-dibromopyridine (1 g, 4.22 mmol) in anhydrous toluene (2 ml) at −78° C. under $N_2$ was added dropwise n-BuLi (2.5 M) (1.69 ml, 4.22 mmol), the mixture was stirred for 2 hours at −78° C., then ethyl 2,2-difluoroacetate (0.73 g, 5.28 mmol) in 3 ml of toluene was added dropwise and it was allowed to warm to rt slowly. Then the mixture was partitioned between EA and brine, the EA phase was dried over $MgSO_4$, filtered and concentrated in vacuo to get the crude product (0.8 g, 80%) as a brown solid. LRMS m/z (M+H) 253.9 found, 253.95 required.

Step B: 1-(5-bromopyridin-2-yl)-2,2-difluoroethanol

To a solution of 1-(5-bromopyridin-2-yl)-2,2-difluoroethane-1,1-diol (300 mg, 1.28 mmol) in MeOH (15 ml) was added $NaBH_4$ (194 mg, 5 mmol) in an ice bath. The mixture was stirred for 1 h then 5 ml of water was added, the mixture was concentrated in vacuo and extracted with EA (20 ml*3), the organic phase was washed with brine, dried over $MgSO_4$, filtered and concentrated in vacuo. The resulting residue was purified by Pre-TLC (Hex/EA=3:1) to afford the title compound (135 mg, 44%) as a white solid. LRMS m/z (M+H) 237.9 found, 237.96 required.

The following intermediate 8 in Table 3 was prepared using the procedure of Intermediate 7, substituting the appropriate starting material.

TABLE 3

| Compound number | Structure |
|---|---|
| 7 | 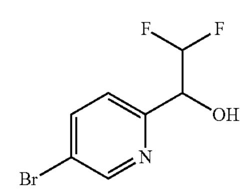 [SMILES: OC(c1ccc(Br)cn1)C(F)F] |
| 8 | 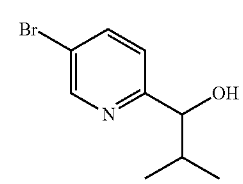 |

SCHEME 4

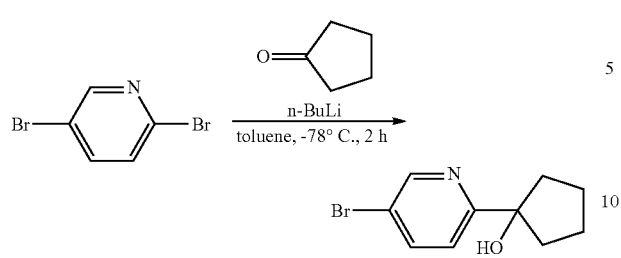

Intermediate 9

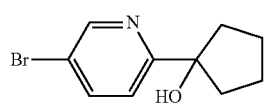

Step A: 1-(5-bromopyridin-2-yl)cyclopentanol

Under nitrogen, to the solution of 2,5-dibromopyridine (500 mg, 2.11 mmol) in THF (10 mL), 2.5 M n-BuLi (1.01 mL, 2.53 mmol) was added slowly at −78° C. The mixture was stirred for 1 h then cyclopentanone (177 mg, 2.11 mmol) was added. It was stirred for 2 h before ammonium chloride aqueous solution was added. The residue was extracted with EtOAc (20 mL*4), dried over $MgSO_4$, filtered and concentrated under reduce pressure. The residue was purified with silica gel column (Petroleum ether: ethyl acetate=10:1-5:1) to obtained product (235 mg, 46%). LRMS (ESI) calculated M+H for $C_{10}H_{12}BrNO$: 242.01. Found: 242.0.

The following intermediates 10-11 in Table 4 were prepared using the procedure of Intermediate 9, substituting the appropriate starting material.

TABLE 4

| Compound number | Structure |
| --- | --- |
| 9 | 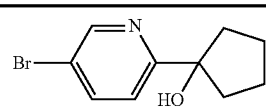 |
| 10 | 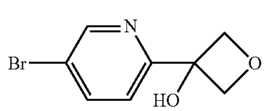 [SMILES: OC1(c2ccc(Br)cn2)COC1] |
| 11 | 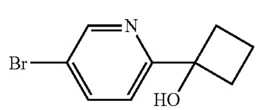 [SMILES: OC1(c2ccc(Br)cn2)CCC1] |

SCHEME 5

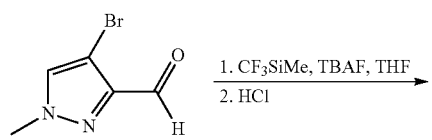

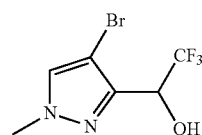

Intermediate 12

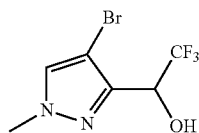

Step A: 1-(4-bromo-1-methyl-1H-pyrazol-3-yl)-2,2,2-trifluoroethanol (Trifluoromethyl)trimethylsilane (642 mg, 4.52 mmol) and TBAF (14 mg, 0.05 mmol) were added to a solution of 4-bromo-1-methyl-1H-pyrazole-3-carbaldehyde (500 mg, 2.66 mmol) in THF (7 mL) at room temperature under nitrogen atmosphere, and the resulting mixture was stirred for 2 h, then a 6N solution of HCl (2.3 mL) was added and the reaction mixture was stirred for 1 h, water (2.3 mL) was added and the aqueous layer was extracted with DCM (30 mL×3), organic layer was washed with brine (10 mL), dried over $Na_2SO_4$, and concentrated to give a yellow oil, which was purified by reverse phase chromatograph (0-95% methanol in water) to afford the title compound (474 mg, 69%) as a white solid; LRMS ESI m/z (M+H) 259.2 found; 259.0 required.

The following intermediate 13 in Table 5 was prepared using the procedure of Intermediate 12, substituting the appropriate starting material.

TABLE 5

| Compound number | Structure |
| --- | --- |
| 12 | 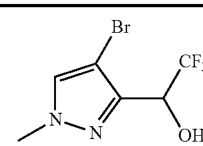 |
| 13 | 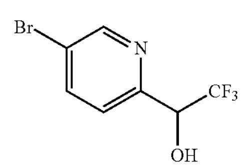 [SMILES: OC(c1ccc(Br)cn1)C(F)(F)F] |

SCHEME 6

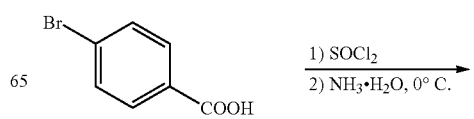

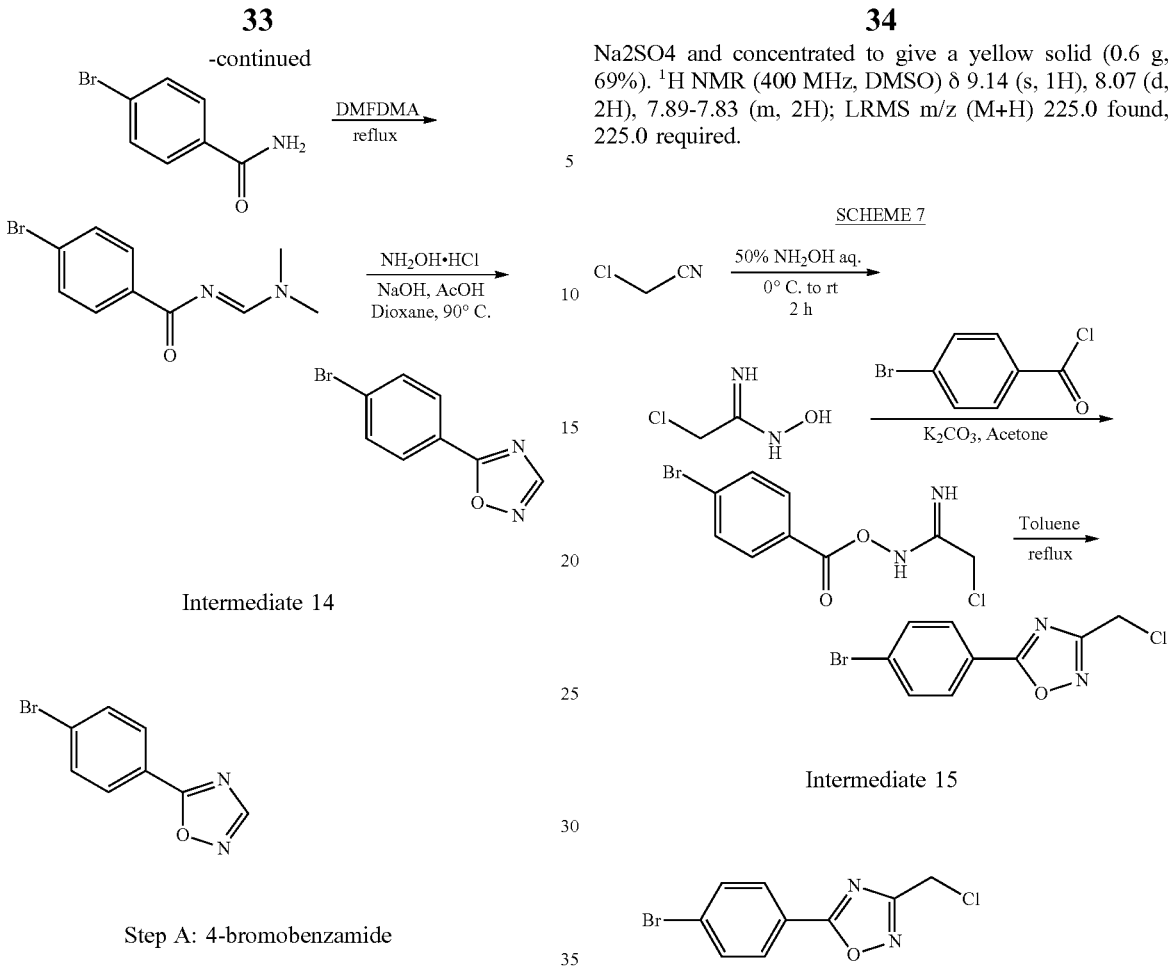

Na2SO4 and concentrated to give a yellow solid (0.6 g, 69%). $^1$H NMR (400 MHz, DMSO) δ 9.14 (s, 1H), 8.07 (d, 2H), 7.89-7.83 (m, 2H); LRMS m/z (M+H) 225.0 found, 225.0 required.

SCHEME 7

Intermediate 14

Intermediate 15

Step A: 4-bromobenzamide 4-bromobenzoic acid (0.5 g, 2.5 mmol) in SOCl$_2$ (5 ml) was refluxed for 2 hours, the excess of SOCl$_2$ was removed under reduced pressure, the residue was dissolved in CH$_2$Cl$_2$ (1 ml) and added to ammonia aqueous solution (10 ml) at 0° C. After stirred for 1 h at room temperature, the solution was extracted with CH$_2$Cl$_2$ (10 ml*3), the organic layer was washed with brine, dried over Na$_2$SO$_4$ and concentrated to give a white solid (0.5 g, 98%). $^1$H NMR (400 MHz, d6-DMSO) δ 8.03 (s, 1H), 7.80 (d, 2H), 7.65 (d, 2H), 7.44 (s, 1H).

Step B: 4-bromo-N-((dimethylamino)methylene)benzamide 4-bromobenzamide (1 g, 5 mmol) in DMFDMA (5 ml) was heated at 80° C. for 2 hours. The DMFDMA was removed under reduced pressure, and the residue was used for next step without purification. LRMS m/z (M+H) 256.9 found, 256.1 required.

Step C: 5-(4-bromophenyl)-1,2,4-oxadiazole

To a solution of hydroxylamine hydrochloride (370 mg, 5.4 mmol) in a mixture of aqueous 5 N sodium hydroxide solution (5 ml), AcOH (50 ml) and dioxane (40 ml) was added 4-bromo-N-((dimethylamino)methylene)benzamide (1 g, 3.9 mmol). The reaction solution was stirred at room temperature for 30 min, and white solid was formed, then the solution was heated at 80° C. for 30 min. Water (50 ml) was added. The solution was extracted with EtOAc (20 ml*3), the combined organic layer was washed with saturated Na$_2$CO$_3$ solution (50 ml), brine, dried over anhydrous Na2SO4 and concentrated to give a yellow solid (0.6 g, 69%). $^1$H NMR (400 MHz, DMSO) δ 9.14 (s, 1H), 8.07 (d, 2H), 7.89-7.83 (m, 2H); LRMS m/z (M+H) 225.0 found, 225.0 required.

Step A: 2-chloro-N-hydroxyacetimidamide

Chloroacetonitrile (1 g, 13 mmol) was added to a solution of hydroxylamine aqueous (0.89 ml, 50%, 0.013 mmol) and EtOH (1 ml) at 0° C., then the solution was stirred at room temperature for 1 hour. Water (10 ml) was added, the solution was extracted with Et$_2$O (10 ml*3), the organic layers were washed with brine, dried over anhydrous Na$_2$SO$_4$ and concentrated to give a yellow solid (280 mg, 20%). LRMS m/z (M+H) 109.9 found; 109.5 required.

Step B: 5-(4-bromophenyl)-3-(chloromethyl)-1,2,4-oxadiazole 4-bromobenzoic acid (300 mg, 1.5 mmol) was refluxed in SOCl$_2$ (5 ml) for 2 h. The excess of SOCl$_2$ was removed under reduced pressure to give the crude acid chloride. It was dissolved in dry acetone (1 ml) and added to a solution of 2-chloro-N-hydroxyacetimidamide (137 mg, 1.28 mmol) and K$_2$CO$_3$ (353 mg, 2.56 mmol) in dry acetone (10 ml) at 0° C., then solution was stirred at room temperature for 2 h. Water (20 ml) was added, and the solution was extracted with EtOAc (10 ml*3). Organic layer was washed with brine, dried over Na$_2$SO$_4$ and concentrated to give a yellow solid. The solid was dissolved in dry toluene (20 ml) and refluxed overnight. The solvent was removed and the residue was purified on silica gel chromatography (EtOAc/PE=1/10) to yield a white solid (70 mg, 20%). $^1$H NMR (500 MHz, CDCl$_3$) δ 8.08-7.96 (m, 2H), 7.74-7.64 (m, 2H), 4.67 (s, 2H); LRMS m/z (M+H) 272.9 found; 272.9 required.

SCHEME 8

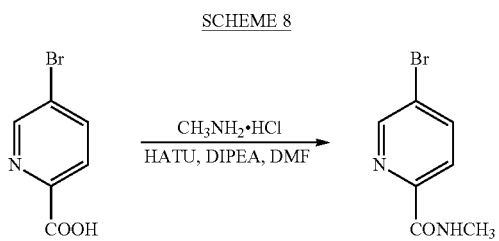

Intermediate 16

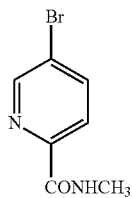

Step A: 5-bromo-N-methylpicolinamide 5-bromopicolinic acid (100 mg, 0.5 mmol) and HATU (208 mg, 0.54 mmol) were dissolved in DMF (2 mL), the mixture was stirred at room temperature for 30 min, DIPEA (129 mg, 1 mmol) and methylamine hydrochloride (20 mg, 0.64 mmol) were added to the mixture, the mixture was stirred at room temperature over night. The reaction sample was diluted with water (5 mL), extracted with EtOAc (15×3 mL), dried over $Na_2SO_4$, concentrated under reduced pressure. the residue was purified by gradient elution on silica gel (0 to 20% EtOAc in petroleum) to afford the title compound (60 mg, 56.1%). LRMS (ES) calculated M+H for LRMS (ES) calculated M+H for $C_{21}H_{20}N_8O_2$: 215.0. found: 215.1.

The following intermediate 17 in Table 6 was prepared using the procedure of Intermediate 16, substituting the appropriate starting material.

TABLE 6

| Compound number | Structure |
|---|---|
| 16 | Br—pyridine—CONHCH3 |
| 17 | Br—pyridine—CONHCH2CF3 |

SCHEME 9

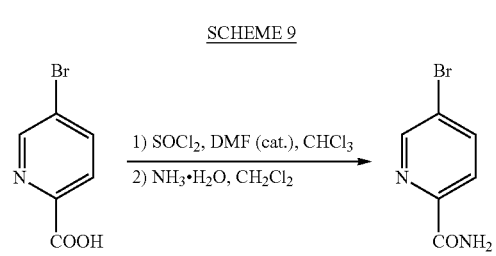 [SMILES: O=C(O)c1ccc(Br)cn1 ; NC(=O)c1ccc(Br)cn1]

Intermediate 18

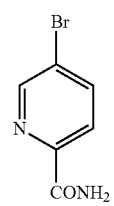

Step A: 5-bromopicolinamide

To a mixture of 5-bromopicolinic acid (200 mg, 1 mmol) in $CH_2Cl_2$ (5 mL) was added dropwise thionyl chloride (1 mL) and a drop of DMF. The mixture was heated to 80° C. for 1 h. After cooled to room temperature, the mixture was concentrated and dissolved in $CH_2Cl_2$ (2 mL). The resulting solution was added dropwise to $NH_3.H_2O$ (3 mL) at room temperature; the mixture was stirred at room temperature for 1.5 h, and then concentrated to afford the title compound (85 mg, 92.4%) as a white solid. LRMS (ESI) m/z (M+H) 201.2 found; 201.0 required. The following intermediate 19 in Table 7 was prepared using the procedure of Intermediate 18, substituting the appropriate starting material.

TABLE 7

| Compound number | Structure |
|---|---|
| 18 | Br—pyridine—CONH2 |
| 19 | Br—pyridine—CONHCH2CH2OH |

SCHEME 10

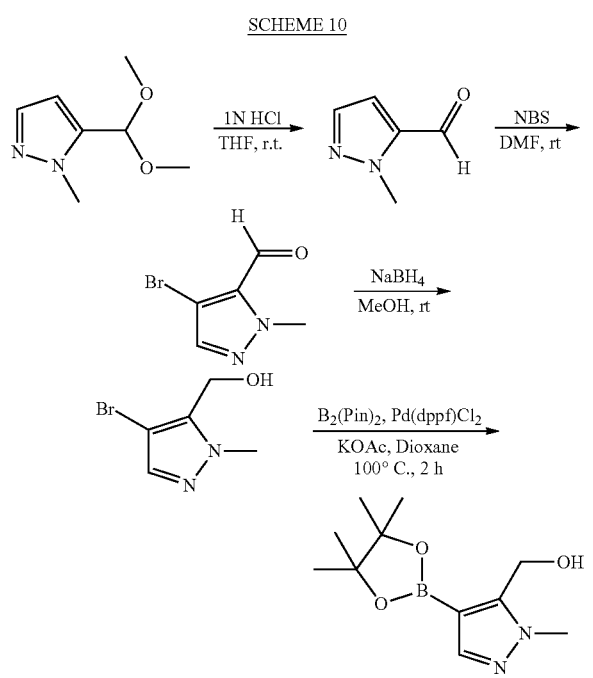

Intermediate 20

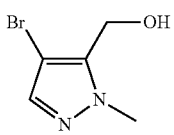

Step A: 1-methyl-1H-pyrazole-5-carbaldehyde

To a solution of 5-(dimethoxymethyl)-1-methyl-1H-pyrazole (5.0 g, 32.45 mmol) in THF (20 mL) was slowly added 1 N HCl at 0° C. The mixture was stirred for 2 days at room temperature. Stop the reaction, The mixture was then diluted with EtOAc (100 mL), washed with sodium bicarbonate (100 mL) until pH=8 and brine (100 mL), dried over MgSO₄, filtered and concentrated in vacuo to afford a brown oil (3.49 g). LRMS m/z (M+H) 110.0 found, 110.0 required.

Step B: 4-bromo-1-methyl-1H-pyrazole-5-carbaldehyde

To a solution of 1-methyl-1H-pyrazole-5-carbaldehyde (1.0 g, 9.09 mmol) in DMF (8 mL) was slowly added NBS (1.62 g, 9.09 mmol) in DMF (5 mL). The mixture was stirred for overnight at room temperature. 1 N NaOH (9.1 mL) was added and the solution was stirred for 10 min, diluted with water (100 mL), extracted with EtOAc (30 mL*3), dried over MgSO₄, filtered and concentrated to afford an orange solid (1.57 g, 92%). LRMS m/z (M+H) 187.9 found, 188.0 required.

Step C: (4-bromo-1-methyl-1H-pyrazol-5-yl)methanol

To a solution of compound 4-bromo-1-methyl-1H-pyrazole-5-carbaldehyde (200 mg, 1.06 mmol) in methanol (20 mL) was added NaBH₄ (80 mg, 2.13 mmol) at 0° C. The mixture was stirred for 1 h and allowed to warm to room temperature. After concentrated under reduce pressure, the residue was purified on silica gel (Petroleum ether:ethyl acetate=8:1) to give a white solid (160 mg, 79%). LRMS m/z (M+H) 190.0 found, 190.0 required.

Intermediate 21

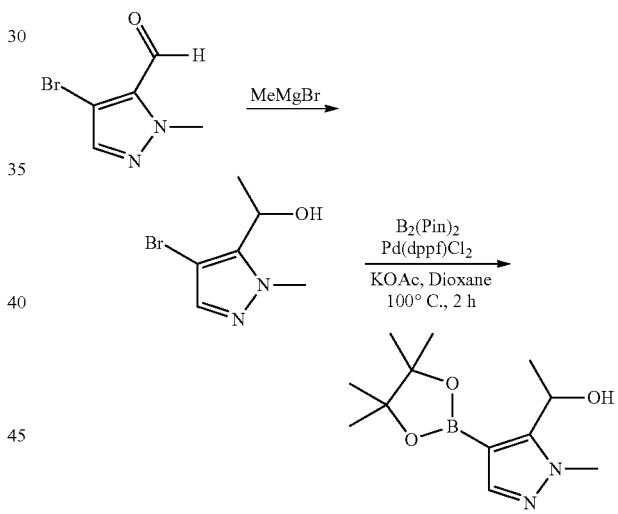

Step A: (1-methyl-4-(4,4,5,5-tetramethyl-1,3,2-dioxaborolan-2-yl)-1H-pyrazol-5-yl) methanol Intermediate 21 was synthesized according to the procedure in step A of Intermediate 4.

SCHEME 11

Intermediate 22

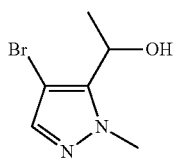

Step A: 1-(4-bromo-1-methyl-1H-pyrazol-5-yl)ethanol

To a solution of 4-bromo-1-methyl-1H-pyrazole-5-carbaldehyde (300 mg, 1.60 mmol) in ether (15 mL) was slowly added CH₃MgBr (1.07 mL, 3.2 mmol) at 0° C. The mixture was stirred for 2 h and warmed to room temperature. aq. NH₄Cl was added, the resulting mixture was extracted with EtOAc (20 mL*4), dried over MgSO₄, filtered, concentrated and purified with silica gel column (Petroleum ether:ethyl acetate=5:1) to give a white solid (160 mg, 49%).

Intermediate 23

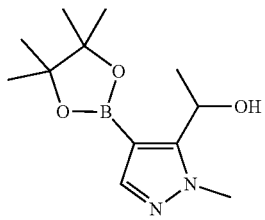 [SMILES: CC(O)c1c(B2OC(C)(C)C(C)(C)O2)cnn1C]

Step B: 1-(1-methyl-4-(4,4,5,5-tetramethyl-1,3,2-dioxaborolan-2-yl)-1H-pyrazol-5-yl) ethanol Intermediate 23 was synthesized according to the procedure in step A of Intermediate 4.

SCHEME 12

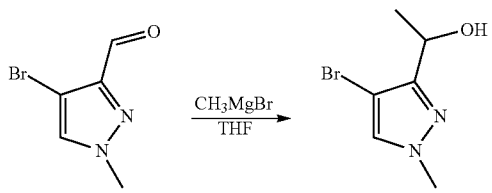

Intermediate 24

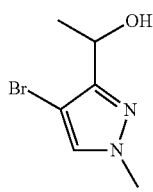

Step A: 1-(4-bromo-1-methyl-1H-pyrazol-3-yl)ethanol

To a solution of 4-bromo-1-methyl-1H-pyrazole-3-carbaldehyde (300 mg, 1.60 mmol) in diethyl ether (15 mL) was slowly added methylmagnesium bromide (1.07 mL, 3.2 mmol) at 0° C. under nitrogen. The mixture was stirred for 2 h and allowed to warmed to room temperature overnight. The mixture was quenched with ammonium chloride (sat), extracted with ethyl acetate (20 mL×4), dried over MgSO₄, filtered and concentrated under reduced pressure. The residue was purified with silica gel column (Petroleum ether: ethyl acetate=5:1) to obtained the title compound (160 mg, 49%). ¹H NMR δ (400 MHz, CDCl₃): δ 7.35 (s, 1H), 4.95 (s, 1H), 3.86 (s, 3H). 1.57 (s, 3H); LRMS (ES) calculated M+H for C₆H₉BrN₂O: 204.99. Found: 205.0. Enantiomers were resolved by chiral preparative SFC (3.0 cm i.d.×25 cm ChiralTech IC, 20% IPA (0.1 DEA)/CO₂, 70 mL/min) and analyzed by chiral analytical SFC (4.6 mm i.d.×25 cm ChiralTech IC, 20% IPA (0.1 DEA) EtOH/CO₂, 2.4 mL/min). ent1=2.89 min; ent2=3.89 min

SCHEME 13

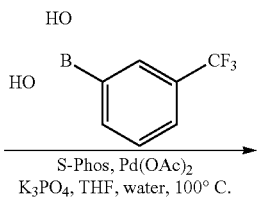

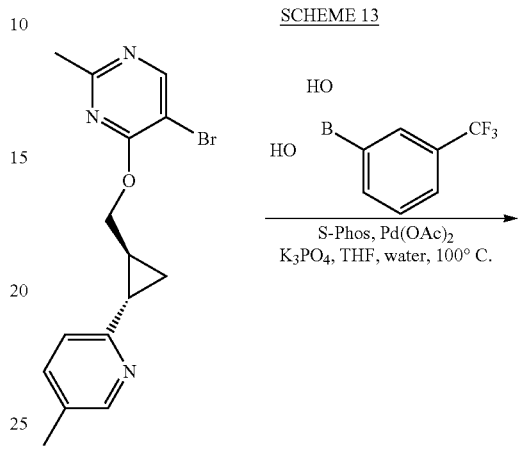

Example 1

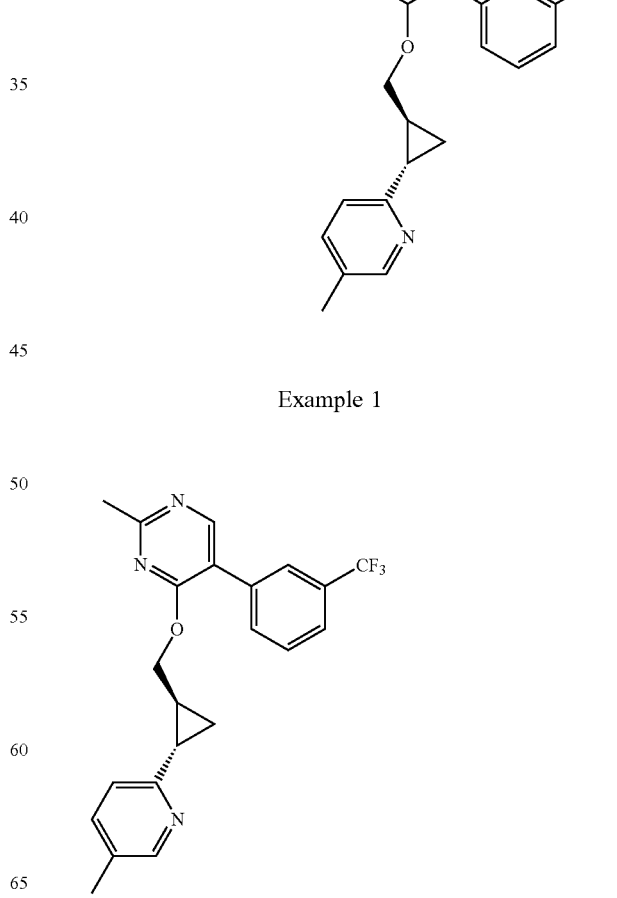

Step A: 2-Methyl-4-(((1S,2S)-2-(5-methylpyridin-2-yl)cyclopropyl)methoxy)-5-(3-(trifluoromethyl)phenyl)pyrimidine (Example 1)

A mixture of 5-bromo-2-methyl-4-(((1S,2S)-2-(5-methylpyridin-2-yl)cyclopropyl)methoxy)pyrimidine (100 mg, 0.30 mmol), 3-(trifluoromethyl)phenylboronic acid (114 mg, 0.60 mmol), tripotassium phosphate (200 mg, 0.75 mmol), S-Phos (14 mg, 0.03 mmol), and Pd(OAc)$_2$ (4 mg, 0.02 mmol) in THF (4 mL) and water (1 mL) was heated at 100° C. for 14 hours. The reaction mixture was allowed to cool to room temperature. The mixture was then diluted with EtOAc (10 mL), washed with sodium bicarbonate (2 mL) and brine (2 mL), dried over MgSO$_4$, filtered and concentrated in vacuo. The resulting residue was purified by Prep-TLC TLC using PE/EtOAc=1/1 to afford the title compound (55 mg, 46%) as a white solid, 1H NMR (500 MHz, CD3OD) δ 8.46 (s, 1H), 8.19 (d, 1H), 7.93 (s, 1H), 7.84 (d, 1H), 7.68 (d, 1H), 7.62 (t, 1H), 7.51 (dd, 1H), 7.12 (d, 1H), 4.60 (dd, 1H), 4.47 (dd, 1H), 2.64 (s, 3H), 2.30 (s, 3H), 2.21-2.11 (m, 1H), 1.97-1.77 (m, 1H), 1.26 (dt, 1H), 1.17-1.06 (m, 1H); MS m/z=399 (M+H).

The following EXAMPLE 2-44 in Table 8 was prepared using the procedure of EXAMPLE 1, substituting the appropriate starting materials.

TABLE 8

| Example | Structure | Name | MS m/z (M + H) |
|---|---|---|---|
| 1 | 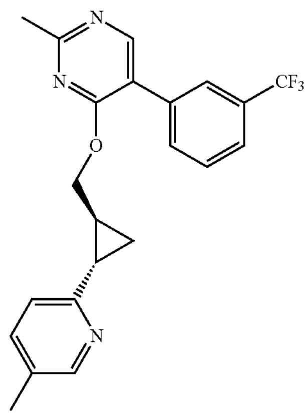 [SMILES: Cc1ccc([C@H]2C[C@@H]2COc2nc(C)ncc2-c2cccc(C(F)(F)F)c2)nc1] | 2-Methyl-4-(((1S,2S)-2-(5-methylpyridin-2-yl)cyclopropyl)methoxy)-5-(3-(trifluoromethyl)phenyl)pyrimidine | 399.2 |
| 2 | 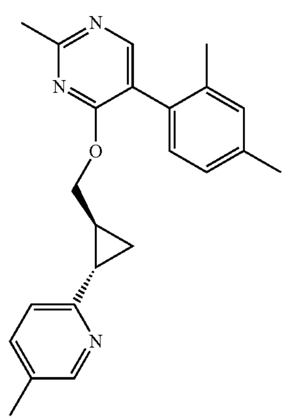 [SMILES: Cc1ccc([C@H]2C[C@@H]2COc2nc(C)ncc2-c2ccc(C)cc2C)nc1] | 5-(2,4-dimethylphenyl)-2-methyl-4-(((1S,2S)-2-(5-methylpyridin-2-yl)cyclopropyl)methoxy)pyrimidine | 360.3 |
| 3 | 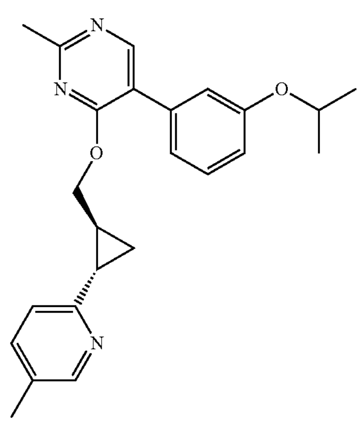 [SMILES: Cc1ccc([C@H]2C[C@@H]2COc2nc(C)ncc2-c2cccc(OC(C)C)c2)nc1] | 5-(3-isopropoxyphenyl)-2-methyl-4-(((1S,2S)-2-(5-methylpyridin-2-yl)cyclopropyl)methoxy)pyrimidine | 390.2 |

TABLE 8-continued

| Example | Structure | Name | MS m/z (M + H) |
|---|---|---|---|
| 4 | 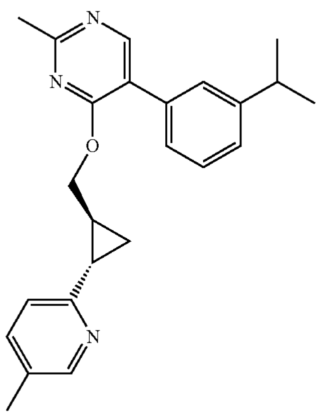 [SMILES: Cc1ccc([C@H]2C[C@@H]2COc2nc(C)ncc2-c2cccc(C(C)C)c2)nc1] | 5-(3-isopropylphenyl)-2-methyl-4-(((1S,2S)-2-(5-methylpyridin-2-yl)cyclopropyl)methoxy)pyrimidine | 374.2 |
| 5 | 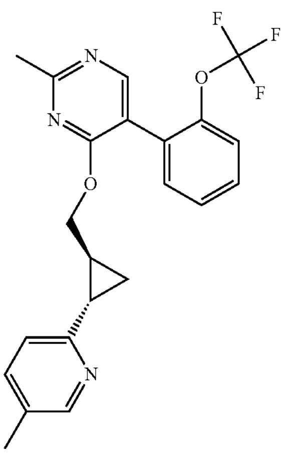 [SMILES: Cc1ccc([C@H]2C[C@@H]2COc2nc(C)ncc2-c2ccccc2OC(F)(F)F)nc1] | 2-methyl-4-(((1S,2S)-2-(5-methylpyridin-2-yl(cyclopropyl)methoxy)-5-(2-(trifluoromethoxy)phenyl)pyrimidine | 416.2 |
| 6 | 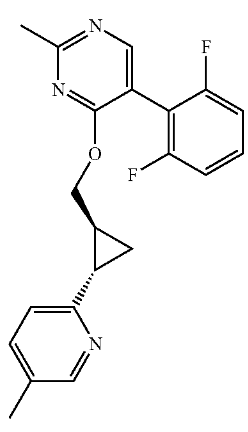 [SMILES: Cc1ccc([C@H]2C[C@@H]2COc2nc(C)ncc2-c2c(F)cccc2F)nc1] | 5-(2,6-difluorophenyl)-2-methyl-4-(((1S,2S)-2-(5-methylpyridin-2-yl)cyclopropyl)methoxy)pyrimidine | 368.1 |

TABLE 8-continued

| Example | Structure | Name | MS m/z (M + H) |
|---|---|---|---|
| 7 | 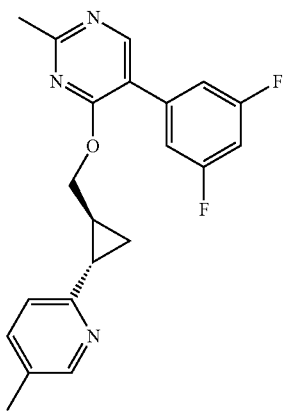 [SMILES: Cc1ccc([C@H]2C[C@@H]2COc2nc(C)ncc2-c2cc(F)cc(F)c2)nc1] | 5-(3,5-difluorophenyl)-2-methyl-4-(((1S,2S)-2-(5-methylpyridin-2-yl)cyclopropyl)methoxy)pyrimidine | 368.1 |
| 8 | 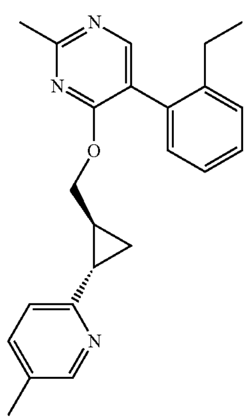 [SMILES: CCc1ccccc1-c1cnc(C)nc1OC[C@H]1C[C@@H]1c1ccc(C)cn1] | 5-(2-ethylphenyl)-2-methyl-4-(((1S,2S)-2-(5-methylpyridin-2-yl)cyclopropyl(methoxy)pyrimidine | 360.2 |
| 9 | 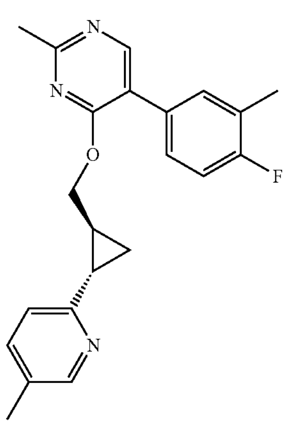 [SMILES: Cc1ccc([C@H]2C[C@@H]2COc2nc(C)ncc2-c2ccc(F)c(C)c2)nc1] | 5-(4-fluoro-3-methylphenyl)-2-methyl-4-(((1S,2S)-2-(5-methylpyridin-2-yl)cyclopropyl)methoxy)pyrimidine | 364.2 |

TABLE 8-continued

| Example | Structure | Name | MS m/z (M + H) |
|---------|-----------|------|----------------|
| 10 | 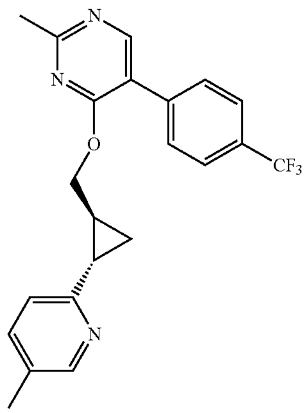 [SMILES: Cc1ccc([C@H]2C[C@@H]2COc2nc(C)ncc2-c2ccc(C(F)(F)F)cc2)nc1] | 2-methyl-4-(((1S,2S)-2-(5-methylpyridin-2-yl)cyclopropyl)methoxy)-5-(4-(trifluoromethyl)phenyl)pyrimidine | 400.2 |
| 11 | 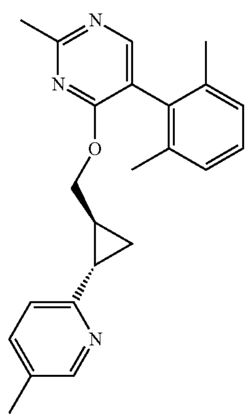 [SMILES: Cc1ccc([C@H]2C[C@@H]2COc2nc(C)ncc2-c2c(C)cccc2C)nc1] | 5-(2,6-dimethylphenyl)-2-methyl-4-(((1S,2S)-2-(5-methylpyridin-2-yl)cyclopropyl)methoxy)pyrimidine | 360.2 |
| 12 | 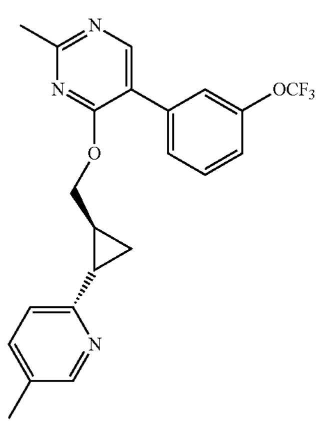 | 2-methyl-4-(((1S,2S)-2-(5-methylpyridin-2-yl)cyclopropyl)methoxy)-5-(3-(trifluoromethoxy)phenyl)pyrimidine | 416.2 |

TABLE 8-continued

| Example | Structure | Name | MS m/z (M + H) |
|---|---|---|---|
| 13 | 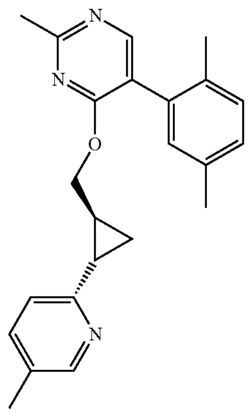 | 5-(2,5-dimethylphenyl)-2-methyl-4-(((1S,2S)-2-(5-methylpyridin-2-yl)cyclopropyl)methoxy)pyrimidine | 360.2 |
| 14 | 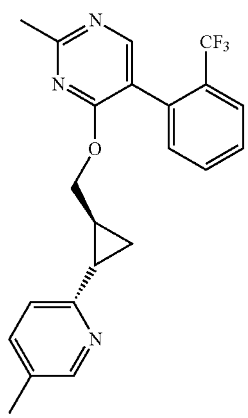 | 2-methyl-4-(((1S,2S)-2-(5-methylpyridin-2-yl)cyclopropyl)methoxy)-5-(2-(trifluoromethyl)phenyl)pyrimidine | 400.2 |
| 15 | 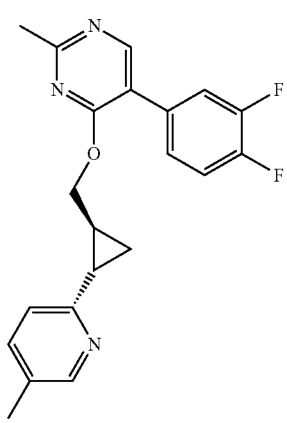 | 5-(3,4-difluorophenyl)-2-methyl-4-(((1S,2S)-2-(5-methylpyridin-2-yl)cyclopropyl)methoxy)pyrimidine | 368.1 |

TABLE 8-continued

| Example | Structure | Name | MS m/z (M + H) |
|---|---|---|---|
| 16 | 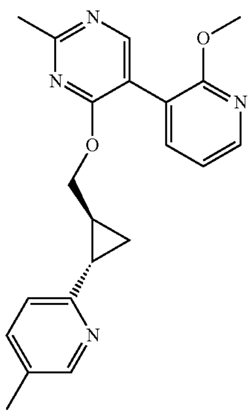 [SMILES: COc1ncccc1-c1cnc(C)nc1OC[C@H]1C[C@@H]1c1ccc(C)cn1] | 5-(2-methoxypyridin-3-yl)-2-methyl-4-(((1S,2S)-2-(5-methylpyridin-2-yl)cyclopropyl)methoxy)pyrimidine | 363.2 |
| 17 | 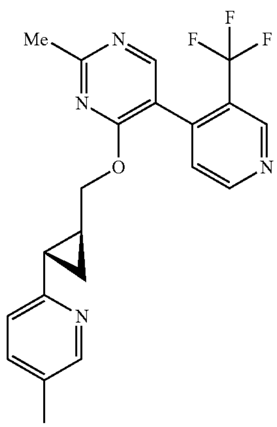 [SMILES: Cc1ccc([C@H]2C[C@@H]2COc2nc(C)ncc2-c2ccncc2C(F)(F)F)nc1] | 2-methyl-4-(((1S,2S)-2-(5-methylpyridin-2-yl)cyclopropyl)methoxy)-5-(3-(trifluoromethyl)pyridin-4-yl)pyrimidine | 401.2 |
| 18 | 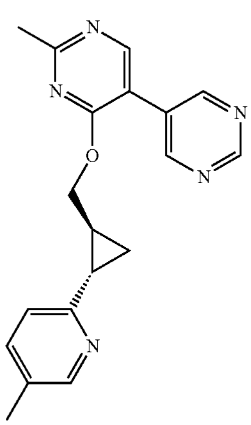 [SMILES: Cc1ccc([C@H]2C[C@@H]2COc2nc(C)ncc2-c2cncnc2)nc1] | 2-methyl-4-(((1S,2S)-2-(5-methylpyridin-2-yl)cyclopropyl)methoxy)-5,5'-bipyrimidine | 458.2 |

TABLE 8-continued

| Example | Structure | Name | MS m/z (M + H) |
|---|---|---|---|
| 19 | 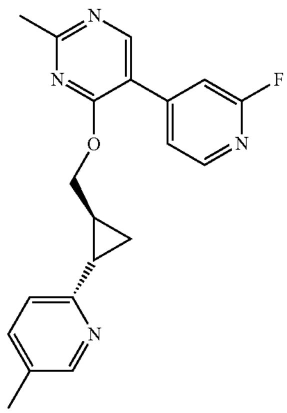 | 5-(2-fluoropyridin-4-yl)-2-methyl-4-(((1S,2S)-2-(5-methylpyridin-2-yl)cyclopropyl)methoxy)pyrimidine | 351.2 |
| 20 | 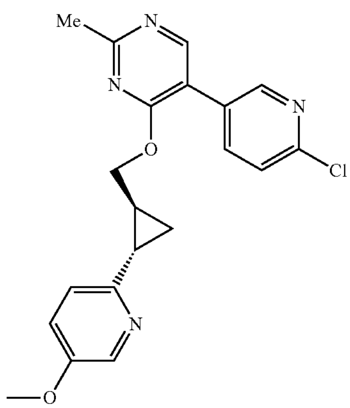 [SMILES: COc1ccc([C@H]2C[C@@H]2COc2nc(C)ncc2-c2ccc(Cl)nc2)nc1] | 5-(6-chloropyridin-3-yl)-4-(((1S,2S)-2-(5-methoxypyridin-2-yl)cyclopropyl)methoxy)-2-methylpyrimidine | 392.1 |
| 21 | 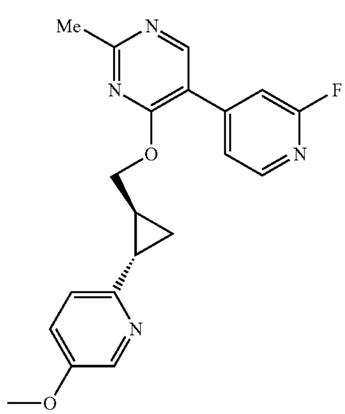 [SMILES: COc1ccc([C@H]2C[C@@H]2COc2nc(C)ncc2-c2ccnc(F)c2)nc1] | 5-(2-fluoropyridin-4-yl)-4-(((1S,2S)-2-(5-methoxypyridin-2-yl)cyclopropyl)methoxy)-2-methylpyrimidine | 367.1 |

TABLE 8-continued

| Example | Structure | Name | MS m/z (M + H) |
|---|---|---|---|
| 22 | 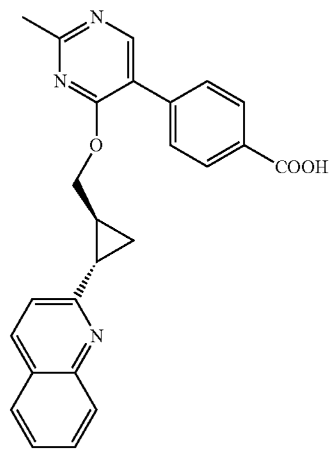 [SMILES: Cc1ncc(-c2ccc(C(=O)O)cc2)c(OC[C@H]2C[C@@H]2c2ccc3ccccc3n2)n1] | 4-(2-methyl-4-(((1S,2S)-2-(quinolin-2-yl)cyclopropyl)methoxy)pyrimidin-5-yl)benzoic acid (enantiomer A) | 412.2 |
| 23 | 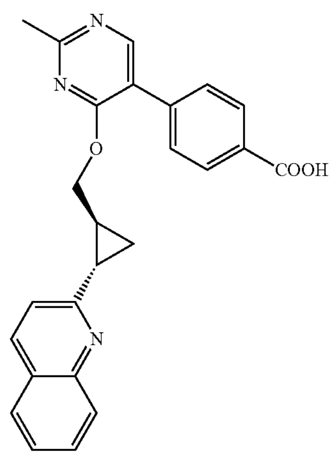 [SMILES: Cc1ncc(-c2ccc(C(=O)O)cc2)c(OC[C@H]2C[C@@H]2c2ccc3ccccc3n2)n1] | 4-(2-methyl-4-(((1S,2S)-2-(quinolin-2-yl)cyclopropyl)methoxy)pyrimidin-5-yl)benzoic acid (enantiomer B) | 412.2 |
| 24 | 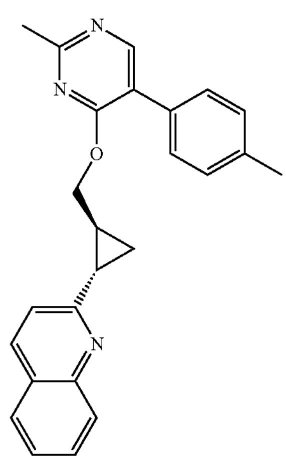 [SMILES: Cc1ccc(-c2cnc(C)nc2OC[C@H]2C[C@@H]2c2ccc3ccccc3n2)cc1] | 2-((1S,2S)-2-((2-methyl-5-p-tolylpyrimidin-4-yloxy)methyl)cyclopropyl)quinoline (enantiomer A) | 382.2 |

TABLE 8-continued

| Example | Structure | Name | MS m/z (M + H) |
|---|---|---|---|
| 25 | 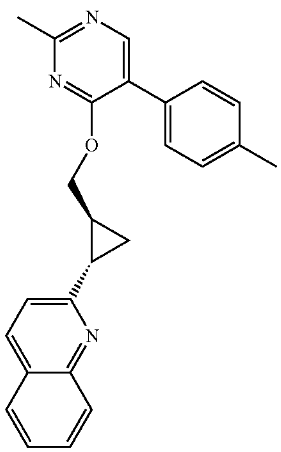 [SMILES: Cc1ccc(-c2cnc(C)nc2OC[C@H]2C[C@@H]2c2ccc3ccccc3n2)cc1] | 2-((1S,2S)-2-((2-methyl-5-p-tolylpyrimidin-4-yloxy)methyl)cyclopropyl)quinoline (enantiomer B) | 382.2 |
| 26 | 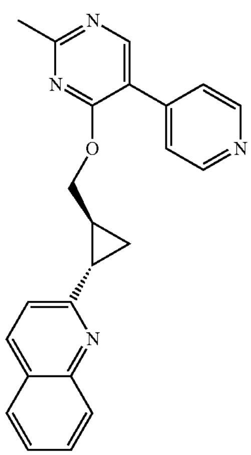 [SMILES: Cc1ncc(-c2ccncc2)c(OC[C@H]2C[C@@H]2c2ccc3ccccc3n2)n1] | 2-((1S,2S)-2-((2-methyl-5-(pyridin-4-yl)pyrimidin-4-yloxy)methyl)cyclopropyl)quinoline (enantiomer A) | 369.2 |
| 27 | 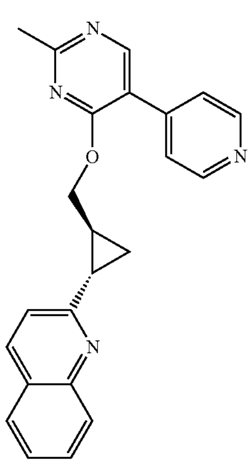 [SMILES: Cc1ncc(-c2ccncc2)c(OC[C@H]2C[C@@H]2c2ccc3ccccc3n2)n1] | 2-((1S,2S)-2-((2-methyl-5-(pyridin-4-yl)pyrimidin-4-yloxy)methyl)cyclopropyl)quinoline (enantiomer B) | 369.2 |

TABLE 8-continued

| Example | Structure | Name | MS m/z (M + H) |
|---|---|---|---|
| 28 | 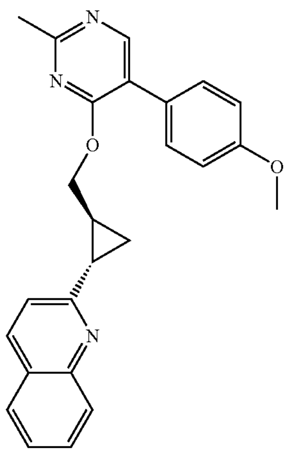 [SMILES: COc1ccc(-c2cnc(C)nc2OC[C@H]2C[C@@H]2c2ccc3ccccc3n2)cc1] | 2-((1S,2S)-2-((5-(4-methoxyphenyl)-2-methylpyrimidin-4-yloxy)methyl)cyclopropyl)quinoline (enantiomer A) | 398.2 |
| 29 | 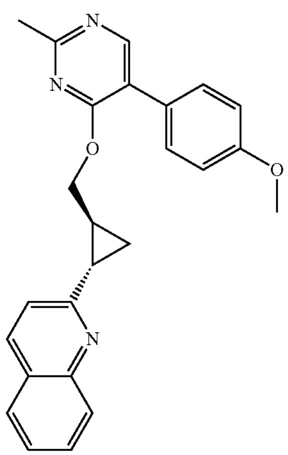 [SMILES: COc1ccc(-c2cnc(C)nc2OC[C@H]2C[C@@H]2c2ccc3ccccc3n2)cc1] | 2-((1S,2S)-2-((5-(4-methoxyphenyl)-2-methylpyrimidin-4-yloxy)methyl)cyclopropyl)quinoline (enantiomer B) | 398.2 |
| 30 | 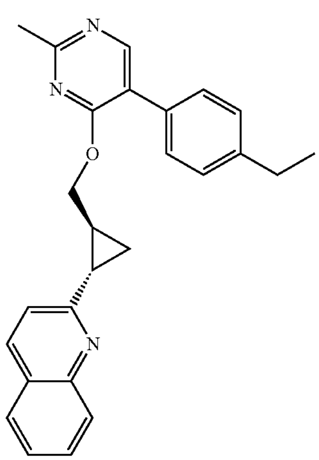 [SMILES: CCc1ccc(-c2cnc(C)nc2OC[C@H]2C[C@@H]2c2ccc3ccccc3n2)cc1] | 2-((1S,2S)-2-((5-(4-ethylphenyl)-2-methylpyrimidin-4-yloxy)methyl)cyclopropyl)quinoline (enantiomer A) | 396.3 |

TABLE 8-continued

| Example | Structure | Name | MS m/z (M + H) |
|---|---|---|---|
| 31 | 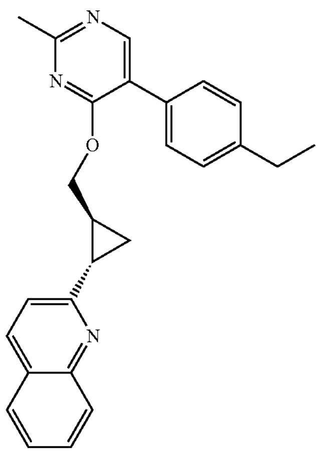 [SMILES: CCc1ccc(-c2cnc(C)nc2OC[C@H]2C[C@@H]2c2ccc3ccccc3n2)cc1] | 2-((1S,2S)-2-((5-(4-ethylphenyl)-2-methylpyrimidin-4-yloxy)methyl)cyclopropyl)quinoline (enantiomer B) | 396.3 |
| 32 | 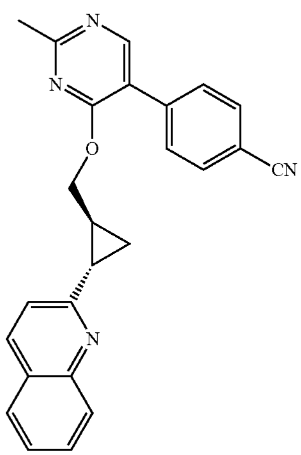 [SMILES: Cc1ncc(-c2ccc(C#N)cc2)c(OC[C@H]2C[C@@H]2c2ccc3ccccc3n2)n1] | 4-(2-methyl-4-(((1S,2S)-2-(quinolin-2-yl)cyclopropyl)methoxy)pyrimidin-5-yl)benzonitrile (enantiomer A) | 393.3 |
| 33 | 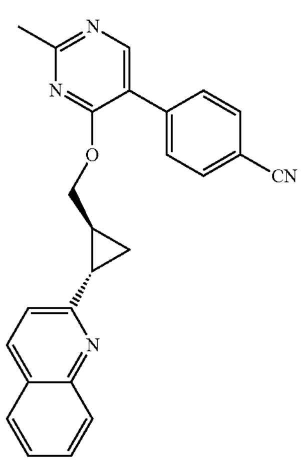 [SMILES: Cc1ncc(-c2ccc(C#N)cc2)c(OC[C@H]2C[C@@H]2c2ccc3ccccc3n2)n1] | 4-(2-methyl-4-(((1S,2S)-2-(quinolin-2-yl)cyclopropyl)methoxy)pyrimidin-5-yl)benzonitrile (enantiomer B) | 393.3 |

TABLE 8-continued

| Example | Structure | Name | MS m/z (M + H) |
|---|---|---|---|
| 34 | 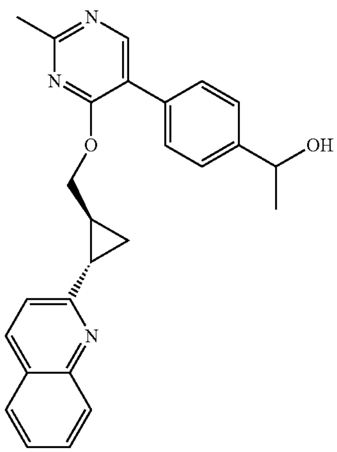 [SMILES: Cc1ncc(-c2ccc(C(C)O)cc2)c(OC[C@H]2C[C@@H]2c2ccc3ccccc3n2)n1] | 1-(4-(2-methyl-4-(((1S,2S)-2-(quinolin-2-yl)cyclopropyl)methoxy)pyrimidin-5-yl)phenyl)ethanol (enantiomer A) | 412.3 |
| 35 | 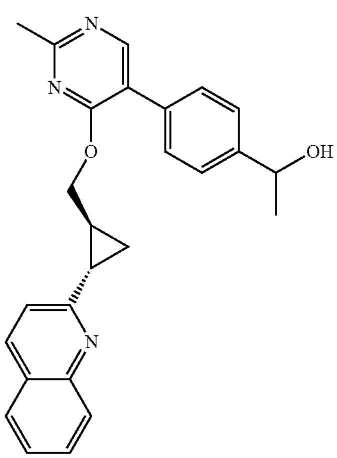 [SMILES: Cc1ncc(-c2ccc(C(C)O)cc2)c(OC[C@H]2C[C@@H]2c2ccc3ccccc3n2)n1] | 1-(4-(2-methyl-4-(((1S,2S)-2-(quinolin-2-yl)cyclopropyl)methoxy)pyrimidin-5-yl)phenyl)ethanol (enantiomer B) | 412.3 |
| 36 | 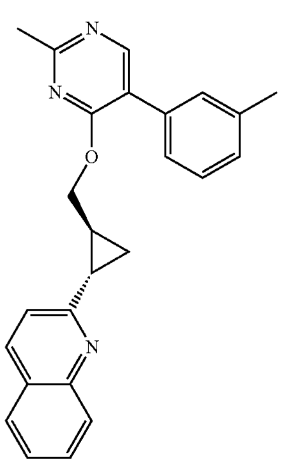 [SMILES: Cc1cccc(-c2cnc(C)nc2OC[C@H]2C[C@@H]2c2ccc3ccccc3n2)c1] | 2-((1S,2S)-2-((2-methyl-5-m-tolylpyrimidin-4-yloxy)methyl)cyclopropyl)quinoline (enantiomer A) | 382.2 |

TABLE 8-continued

| Example | Structure | Name | MS m/z (M + H) |
|---|---|---|---|
| 37 | 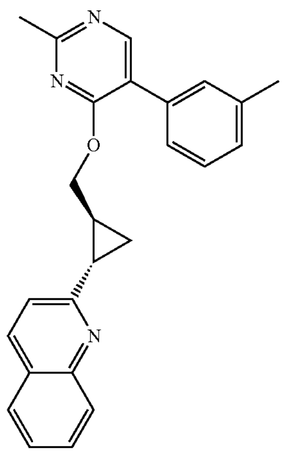 [SMILES: Cc1cccc(-c2cnc(C)nc2OC[C@H]2C[C@@H]2c2ccc3ccccc3n2)c1] | 2-((1S,2S)-2-((2-methyl-5-m-tolylpyrimidin-4-yloxy)methyl)cyclopropyl)quinoline (enantiomer B) | 382.2 |
| 38 | 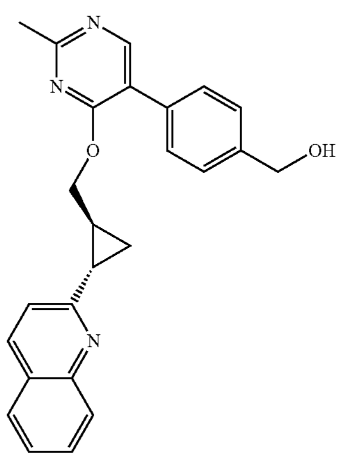 [SMILES: Cc1ncc(-c2ccc(CO)cc2)c(OC[C@H]2C[C@@H]2c2ccc3ccccc3n2)n1] | (4-(2-methyl-4-(((1S,2S)-2-(quinolin-2-yl)cyclopropyl)methoxy)pyrimidin-5-yl)phenyl)methanol (enantiomer A) | 398.2 |
| 39 | 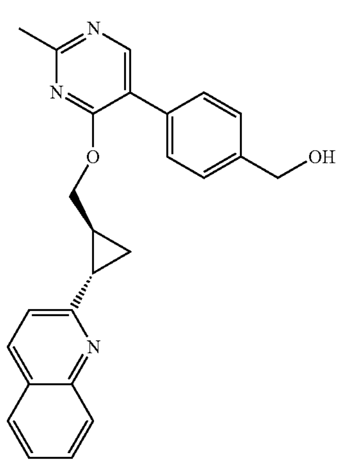 [SMILES: Cc1ncc(-c2ccc(CO)cc2)c(OC[C@H]2C[C@@H]2c2ccc3ccccc3n2)n1] | (4-(2-methyl-4-(((1S,2S)-2-(quinolin-2-yl)cyclopropyl)methoxy)pyrimidin-5-yl)phenyl)methanol (enantiomer B) | 398.2 |

TABLE 8-continued
| Example | Structure | Name | MS m/z (M + H) |
|---|---|---|---|
| 40 | 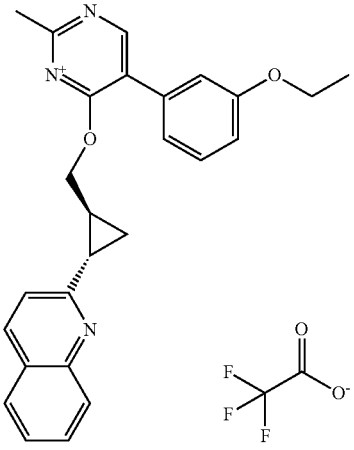 [SMILES: CCOc1cccc(-c2cnc(C)[nH+]c2OC[C@H]2C[C@@H]2c2ccc3ccccc3n2)c1 ; O=C([O-])C(F)(F)F] | 5-(3-ethoxyphenyl)-2-methyl-6-(((1S,2S)-2-(quinolin-2-yl)cyclopropyl)methoxy)pyrimidin-1-ium 2,2,2-trifluoroacetate (enantiomer A) | 413.2 |
| 41 | 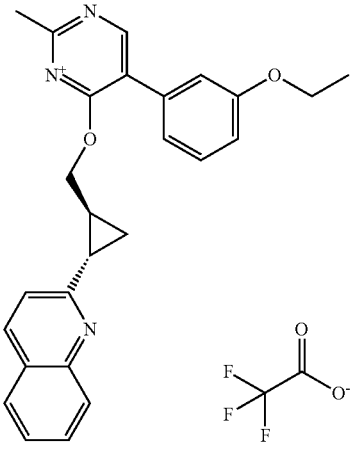 [SMILES: CCOc1cccc(-c2cnc(C)[nH+]c2OC[C@H]2C[C@@H]2c2ccc3ccccc3n2)c1 ; O=C([O-])C(F)(F)F] | 5-(3-ethoxyphenyl)-2-methyl-6-(((1S,2S)-2-(quinolin-2-yl)cyclopropyl)methoxy)pyrimidin-1-ium 2,2,2-trifluoroacetate (enantiomer B) | 413.2 |
| 42 | 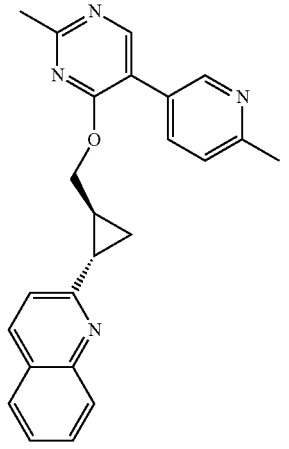 [SMILES: Cc1ccc(-c2cnc(C)nc2OC[C@H]2C[C@@H]2c2ccc3ccccc3n2)cn1] | 2-((1S,2S)-2-((2-methyl-5-(6-methylpyridin-3-yl)pyrimidin-4-yloxy)methyl)cyclopropyl)quinoline | 383.3 |

TABLE 8-continued
| Example | Structure | Name | MS m/z (M + H) |
|---|---|---|---|
| 43 | 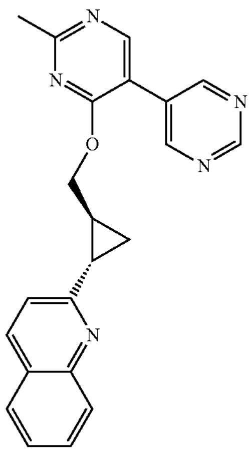 [SMILES: Cc1ncc(-c2cncnc2)c(OC[C@H]2C[C@@H]2c2ccc3ccccc3n2)n1] | 2-((1S,2S)-2-((2-methyl-5,5'-bipyrimidin-4-yloxy)methyl)cyclopropyl)quinoline (enantiomer A) | 370.2 |
| 44 | 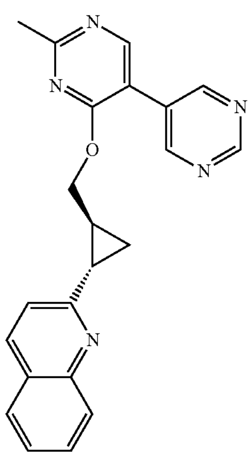 [SMILES: Cc1ncc(-c2cncnc2)c(OC[C@H]2C[C@@H]2c2ccc3ccccc3n2)n1] | 2-((1S,2S)-2-((2-methyl-5,5'-bipyrimidin-4-yloxy)methyl)cyclopropyl)quinoline (enantiomer B) | 370.2 |
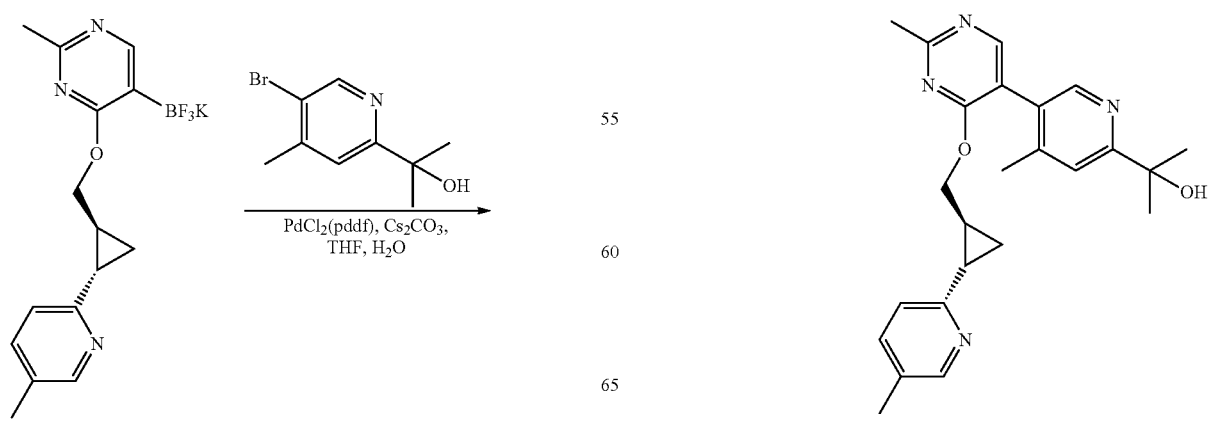
SCHEME 14

Example 45

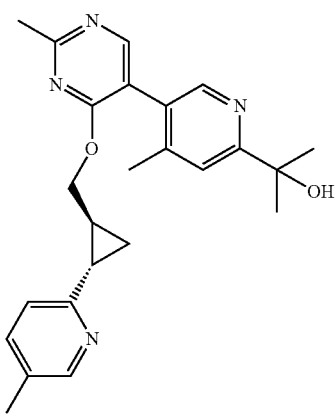 [SMILES: Cc1ccc([C@H]2C[C@@H]2COc2nc(C)ncc2-c2cnc(C(C)(C)O)cc2C)nc1]

Step A: 2-(4-Methyl-5-(2-methyl-4-(((1S,2S)-2-(5-methylpyridin-2-yl)cyclopropyl) methoxy)pyrimidin-5-yl)pyridin-2-yl)propan-2-ol (Example 45)

A mixture of Potassium 5-trifluorobarate-4-{[(1S,2S)-2-(5-methylpyridin-2-yl)cyclopropyl]methoxy}-2-methylpyrimidine (100 mg, 0.27 mmol), 2-(5-bromo-4-methylpyridin-2-yl)propan-2-ol (73 mg, 0.32 mmol), $PdCl_2(dppf)$ (17 mg, 0.024 mmol), $Cs_2CO_3$ (260 mg, 0.80 mmol) in THF (3 mL) and water (0.5 mL) was heated at 100° C. for 14 hours. The reaction mixture was allowed to cool to room temperature. The mixture was then diluted with EtOAc (10 mL), washed with sodium bicarbonate (2 mL) and brine (2 mL), dried over $MgSO_4$, filtered and concentrated in vacuo. The resulting residue was purified by Pre-TLC (Hex/EA=2:1) to afford the title compound (45 mg, 40%) as a white solid 1H NMR (400 MHz, CD3OD) δ 8.31-8.08 (m, 3H), 7.61 (s, 1H), 7.51 (d, 1H), 7.09 (d, 1H), 4.57 (dd, 1H), 4.40 (dd, 1H), 2.67 (s, 3H), 2.29 (s, 3H), 2.20 (s, 3H), 2.14-2.03 (m, 1H), 1.81 (m, 1H), 1.57 (s, 6H), 1.30-1.16 (m, 1H), 1.18-0.98 (m, 1H). MS m/z=405 (M+H).

The following EXAMPLE 46-137 in Table 9 was prepared using the procedure of EXAMPLE 45, substituting the appropriate starting materials.

TABLE 9

| Example | Structure | Name | MS m/z (M + H) |
|---|---|---|---|
| 45 | 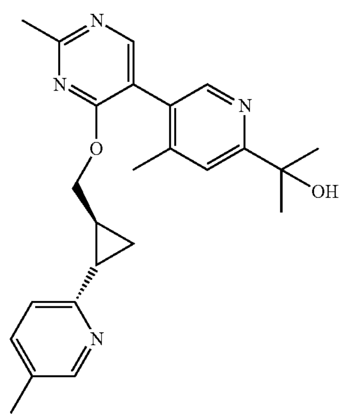 | 2-(4-Methyl-5-(2-methyl-4-(((1S,2S)-2-(5-methylpyridin-2-yl)cyclopropyl)methoxy)pyrimidin-5-yl)pyridin-2-yl)propan-2-ol | 405.2 |
| 46 | 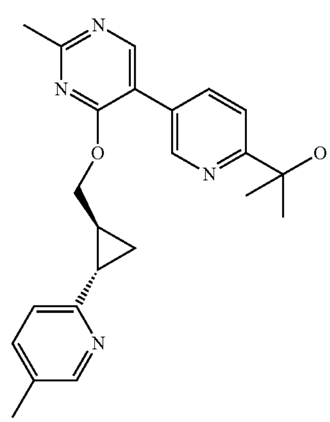 [SMILES: Cc1ccc([C@H]2C[C@@H]2COc2nc(C)ncc2-c2ccc(C(C)(C)O)nc2)nc1] | 2-(5-(2-methyl-4-(((1S,2S)-2-(5-methylpyridin-2-yl)cyclopropyl)methoxy)pyrimidin-5-yl)pyridin-2-yl)propan-2-ol (enantiomer A) | 391.2 |

TABLE 9-continued

| Example | Structure | Name | MS m/z (M + H) |
|---|---|---|---|
| 47 | 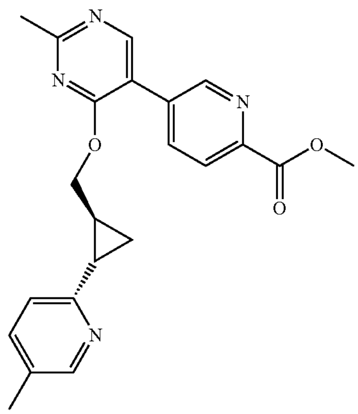 | methyl 5-(2-methyl-4-(((1S,2S)-2-(5-methylpyridin-2-yl)cyclopropyl)methoxy)pyrimidin-5-yl)picolinate | 391.2 |
| 48 | 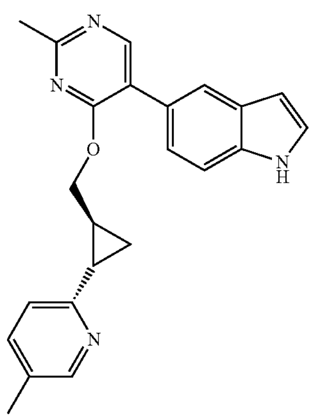 | 5-(2-methyl-4-(((1S,2S)-2-(5-methylpyridin-2-yl)cyclopropyl)methoxy)pyrimidin-5-yl)-1H-indole | 371.2 |
| 49 | 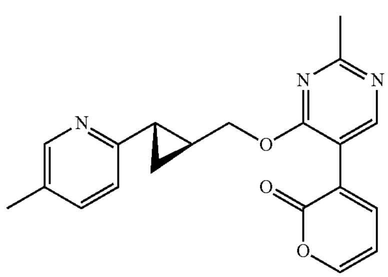 [SMILES: Cc1ccc([C@H]2C[C@@H]2COc2nc(C)ncc2-c2cccoc2=O)nc1] | 3-(2-methyl-4-(((1S,2S)-2-(5-methylpyridin-2-yl)cyclopropyl)methoxy)pyrimidin-5-yl)-2H-pyran-2-one | 350.2 |
| 50 | 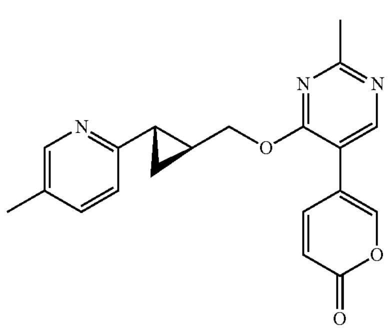 [SMILES: Cc1ccc([C@H]2C[C@@H]2COc2nc(C)ncc2-c2ccc(=O)oc2)nc1] | 5-(2-methyl-4-(((1S,2S)-2-(5-methylpyridin-2-yl)cyclopropyl)methoxy)pyrimidin-5-yl)-2H-pyran-2-one | 350.3 |

TABLE 9-continued

| Example | Structure | Name | MS m/z (M + H) |
|---|---|---|---|
| 51 | 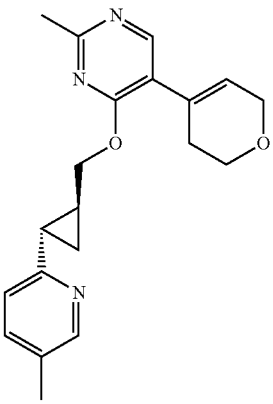 [SMILES: Cc1ccc([C@H]2C[C@@H]2COc2nc(C)ncc2C2=CCOCC2)nc1] | 5-(3,6-dihydro-2H-pyran-4-yl)-2-methyl-4-(((1S,2S)-2-(5-methylpyridin-2-yl)cyclopropyl)methoxy)pyrimidine | 338.2 |
| 52 | 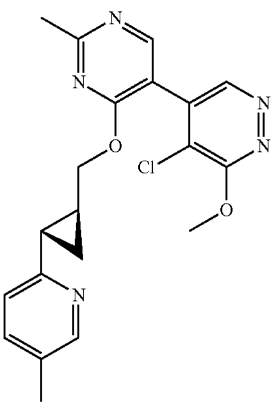 [SMILES: COc1nncc(-c2cnc(C)nc2OC[C@H]2C[C@@H]2c2ccc(C)cn2)c1Cl] | 4-chloro-3-methoxy-5-(2-methyl-4-(((1S,2S)-2-(5-methylpyridin-2-yl)cyclopropyl)methoxy)pyrimidin-5-yl)pyridazine | 398.2 |
| 53 | 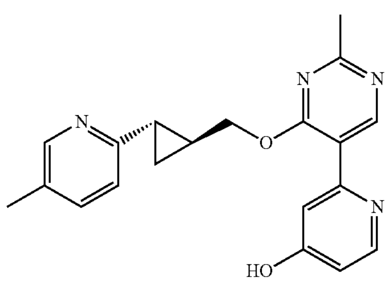 [SMILES: Cc1ccc([C@H]2C[C@@H]2COc2nc(C)ncc2-c2cc(O)ccn2)nc1] | 2-(2-methyl-4-(((1S,2S)-2-(5-methylpyridin-2-yl)cyclopropyl)methoxy)pyrimidin-5-yl)pyridin-4-ol | 349.3 |
| 54 | 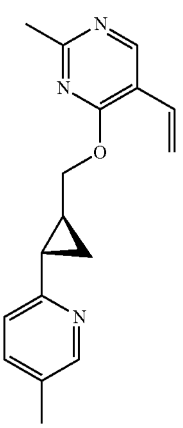 [SMILES: C=Cc1cnc(C)nc1OC[C@H]1C[C@@H]1c1ccc(C)cn1] | 2-methyl-4-(((1S,2S)-2-(5-methylpyridin-2-yl)cyclopropyl)methoxy)-5-vinylpyrimidine | 282.3 |

TABLE 9-continued

| Example | Structure | Name | MS m/z (M + H) |
|---|---|---|---|
| 55 | 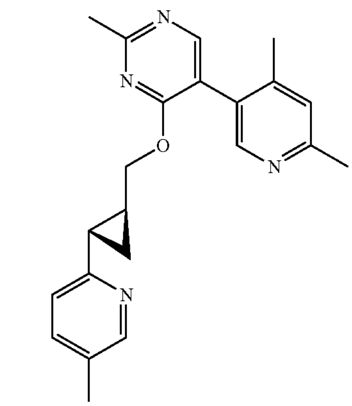 [SMILES: Cc1ccc([C@H]2C[C@@H]2COc2nc(C)ncc2-c2cnc(C)cc2C)nc1] | 5-(4,6-dimethylpyridin-3-yl)-2-methyl-4-(((1S,2S)-2-(5-methylpyridin-2-yl)cyclopropyl)methoxy)pyrimidine | 361.2 |
| 56 | 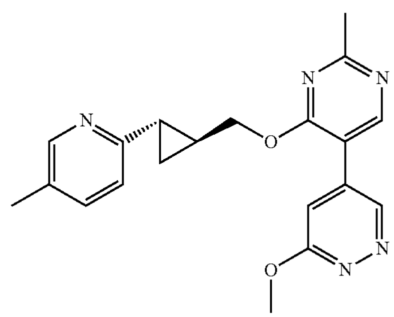 [SMILES: COc1cc(-c2cnc(C)nc2OC[C@H]2C[C@@H]2c2ccc(C)cn2)cnn1] | 3-methoxy-5-(2-methyl-4-(((1S,2S)-2-(5-methylpyridin-2-yl)cyclopropyl)methoxy)pyrimidin-5-yl)pyridazine | 364.3 |
| 57 | 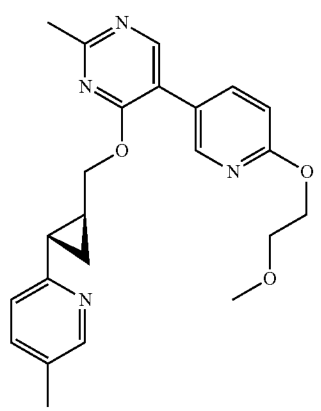 [SMILES: COCCOc1ccc(-c2cnc(C)nc2OC[C@H]2C[C@@H]2c2ccc(C)cn2)cn1] | 5-(6-(2-methoxyethoxy)pyridin-3-yl)-2-methyl-4-(((1S,2S)-2-(5-methylpyridin-2-yl)cyclopropyl)methoxy)pyrimidine | 407.3 |
| 58 | 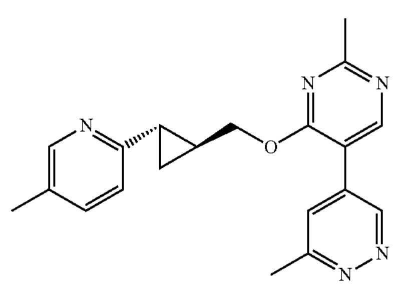 [SMILES: Cc1ccc([C@H]2C[C@@H]2COc2nc(C)ncc2-c2cnnc(C)c2)nc1] | 3-methyl-5-(2-methyl-4-(((1S,2S)-2-(5-methylpyridin-2-yl)cyclopropyl)methoxy)pyrimidin-5-yl)pyridazine | 348.3 |

TABLE 9-continued

| Example | Structure | Name | MS m/z (M + H) |
|---|---|---|---|
| 59 | 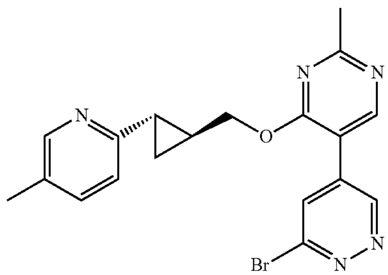 [SMILES: Cc1ccc([C@H]2C[C@@H]2COc2nc(C)ncc2-c2cnnc(Br)c2)nc1] | 3-bromo-5-(2-methyl-4-(((1S,2S)-2-(5-methylpyridin-2-yl)cyclopropyl)methoxy)pyrimidin-5-yl)pyridazine | 412.3 |
| 60 | 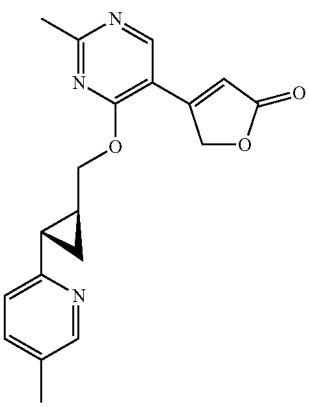 [SMILES: Cc1ccc([C@H]2C[C@@H]2COc2nc(C)ncc2C2=CC(=O)OC2)nc1] | 4-(2-methyl-4-(((1S,2S)-2-(5-methylpyridin-2-yl)cyclopropyl)methoxy)pyrimidin-5-yl)furan-2(5H)-one | 338.3 |
| 61 | 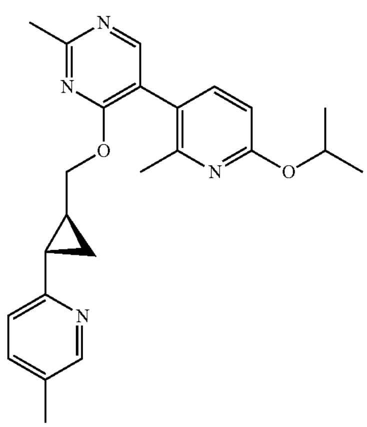 [SMILES: Cc1ccc([C@H]2C[C@@H]2COc2nc(C)ncc2-c2ccc(OC(C)C)nc2C)nc1] | 5-(6-isopropoxy-2-methylpyridin-3-yl)-2-methyl-4-(((1S,2S)-2-(5-methylpyridin-2-yl)cyclopropyl)methoxy)pyrimidine | 405.1 |
| 62 | 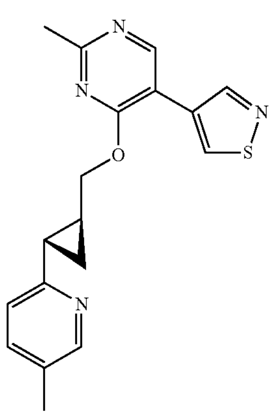 [SMILES: Cc1ccc([C@H]2C[C@@H]2COc2nc(C)ncc2-c2cnsc2)nc1] | 4-(2-methyl-4-(((1S,2S)-2-(5-methylpyridin-2-yl)cyclopropyl)methoxy)pyrimidin-5-yl)isothiazole | 339.2 |

TABLE 9-continued

| Example | Structure | Name | MS m/z (M + H) |
|---|---|---|---|
| 63 | 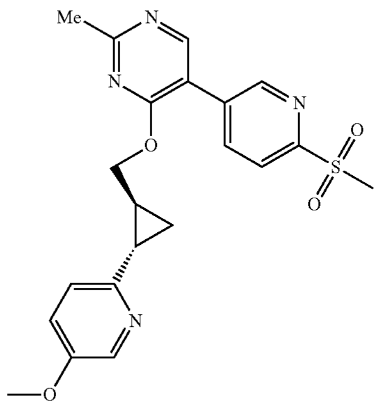 | 4-(((1S,2S)-2-(5-methoxypyridin-2-yl)cyclopropyl)methoxy)-2-methyl-5-(6-(methylsulfonyl)pyridin-3-yl)pyrimidine | 427.1 |
| 64 | 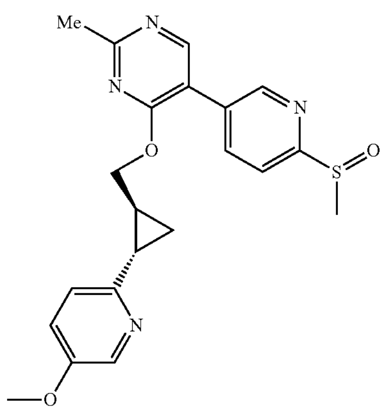 [SMILES: COc1ccc([C@H]2C[C@@H]2COc2nc(C)ncc2-c2ccc(S(C)=O)nc2)nc1] | 4-(((1S,2S)-2-(5-methoxypyridin-2-yl)cyclopropyl)methoxy)-2-methyl-5-(6-(methylsulfinyl)pyridin-3-yl)pyrimidine (R or S) | 411.1 |
| 65 | 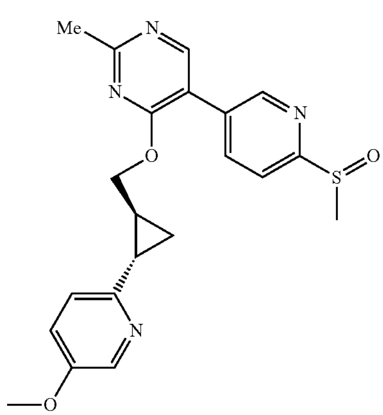 [SMILES: COc1ccc([C@H]2C[C@@H]2COc2nc(C)ncc2-c2ccc(S(C)=O)nc2)nc1] | 4-(((1S,2S)-2-(5-methoxypyridin-2-yl)cyclopropyl)methoxy)-2-methyl-5-(6-(methylsulfinyl)pyridin-3-yl)pyrimidine (S or R) | 411.1 |

TABLE 9-continued

| Example | Structure | Name | MS m/z (M + H) |
|---|---|---|---|
| 66 | 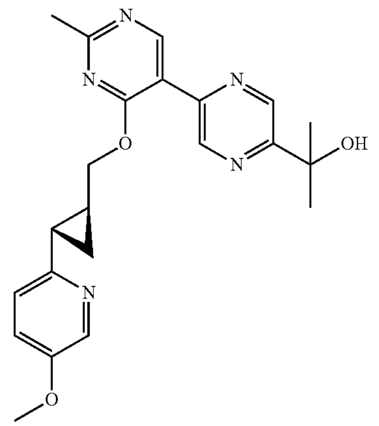 [SMILES: COc1ccc([C@H]2C[C@@H]2COc2nc(C)ncc2-c2cnc(C(C)(C)O)cn2)nc1] | 2-(5-(4-(((1S,2S)-2-(5-methoxypyridin-2-yl)cyclopropyl)methoxy)-2-methylpyrimidin-5-yl)pyrazin-2-yl)propan-2-ol | 408.1 |
| 67 | 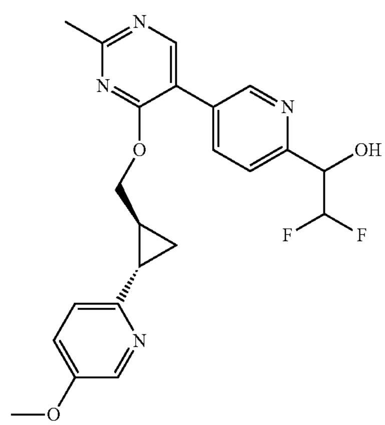 [SMILES: COc1ccc([C@H]2C[C@@H]2COc2nc(C)ncc2-c2ccc(C(O)C(F)F)nc2)nc1] | 2,2-difluoro-1-(5-(4-(((1S,2S)-2-(5-methoxypyridin-2-yl)cyclopropyl)methoxy)-2-methylpyrimidin-5-yl)pyridin-2-yl)ethanol (R or S) | 429.1 |
| 68 | 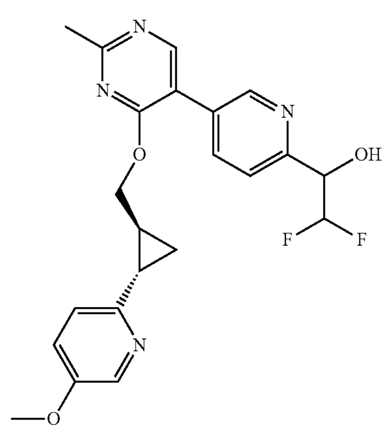 [SMILES: COc1ccc([C@H]2C[C@@H]2COc2nc(C)ncc2-c2ccc(C(O)C(F)F)nc2)nc1] | 2,2-difluoro-1-(5-(4-(((1S,2S)-2-(5-methoxypyridin-2-yl)cyclopropyl)methoxy)-2-methylpyrimidin-5-yl)pyridin-2-yl)ethanol (S or R) | 429.1 |

TABLE 9-continued

| Example | Structure | Name | MS m/z (M + H) |
|---|---|---|---|
| 69 | 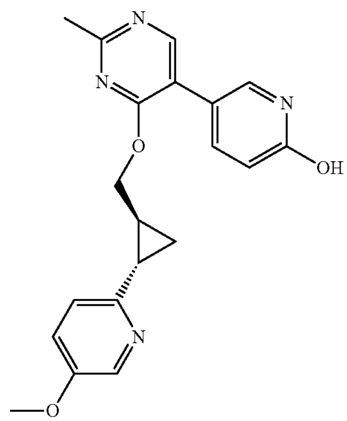 [SMILES: COc1ccc([C@H]2C[C@@H]2COc2nc(C)ncc2-c2ccc(O)nc2)nc1] | 5-(4-(((1S,2S)-2-(5-methoxypyridin-2-yl)cyclopropyl)methoxy)-2-methylpyrimidin-5-yl)pyridin-2-ol | 365.2 |
| 70 | 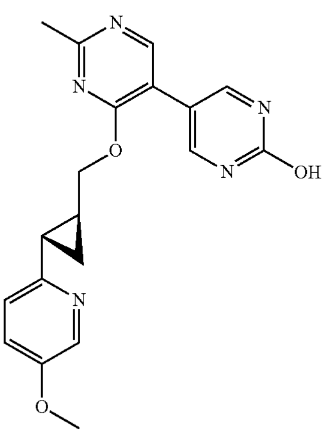 [SMILES: COc1ccc([C@H]2C[C@@H]2COc2nc(C)ncc2-c2cnc(O)nc2)nc1] | 4'-(((1S,2S)-2-(5-methoxypyridin-2-yl)cyclopropyl)methoxy)-2'-methyl-5,5'-bipyrimidin-2-ol | 366.2 |
| 71 | 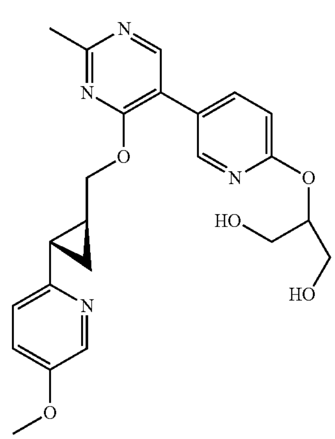 [SMILES: COc1ccc([C@H]2C[C@@H]2COc2nc(C)ncc2-c2ccc(OC(CO)CO)nc2)nc1] | 2-(5-(4-(((1S,2S)-2-(5-methoxypyridin-2-yl)cyclopropyl)methoxy)-2-methylpyrimidin-5-yl)pyridin-2-yloxy)propane-1,3-diol | 439.2 |

TABLE 9-continued

| Example | Structure | Name | MS m/z (M + H) |
|---|---|---|---|
| 72 | 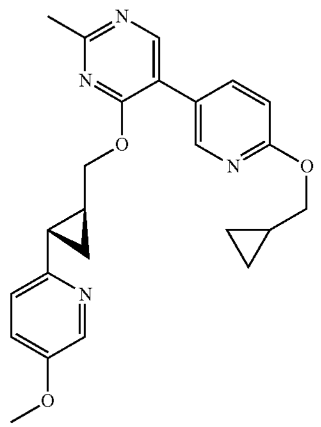 [SMILES: COc1ccc([C@H]2C[C@@H]2COc2nc(C)ncc2-c2ccc(OCC3CC3)nc2)nc1] | 5-(6-(cyclopropylmethoxy)pyridin-3-yl)-4-(((1S,2S)-2-(5-methoxypyridin-2-yl)cyclopropyl)methoxy)-2-methylpyrimidine | 419.3 |
| 73 | 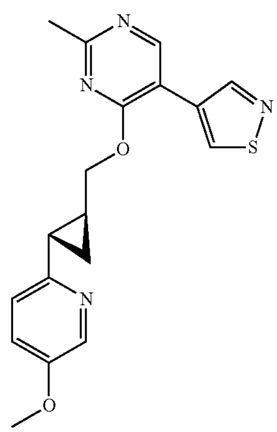 [SMILES: COc1ccc([C@H]2C[C@@H]2COc2nc(C)ncc2-c2cnsc2)nc1] | 4-(4-(((1S,2S)-2-(5-methoxypyridin-2-yl)cyclopropyl)methoxy)-2-methylpyrimidin-5-yl)isothiazole | 355.1 |
| 74 | 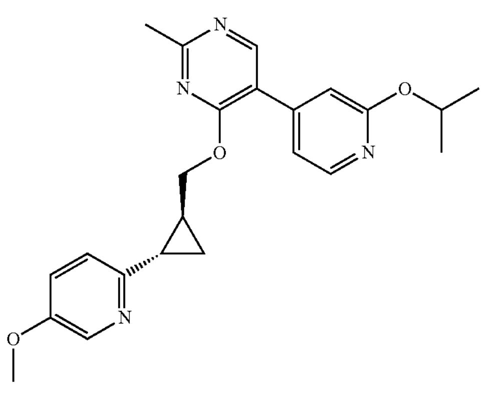 [SMILES: COc1ccc([C@H]2C[C@@H]2COc2nc(C)ncc2-c2ccnc(OC(C)C)c2)nc1] | 5-(2-isopropoxypyridin-4-yl)-4-(((1S,2S)-2-(5-methoxypyridin-2-yl)cyclopropyl)methoxy)-2-methylpyrimidine | 407.3 |

TABLE 9-continued

| Example | Structure | Name | MS m/z (M + H) |
|---|---|---|---|
| 75 | 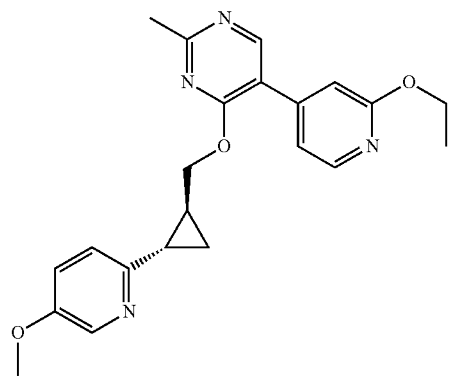 [SMILES: CCOc1cc(-c2cnc(C)nc2OC[C@H]2C[C@@H]2c2ccc(OC)cn2)ccn1] | 5-(2-ethoxypyridin-4-yl)-4-(((1S,2S)-2-(5-methoxypyridin-2-yl)cyclopropyl)methoxy)-2-methylpyrimidine | 393.2 |
| 76 | 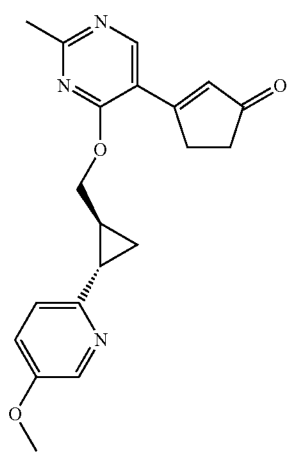 [SMILES: COc1ccc([C@H]2C[C@@H]2COc2nc(C)ncc2C2=CC(=O)CC2)nc1] | 3-(4-(((1S,2S)-2-(5-methoxypyridin-2-yl)cyclopropyl)methoxy)-2-methylpyrimidin-5-yl)cyclopent-2-enone | 352.2 |
| 77 | 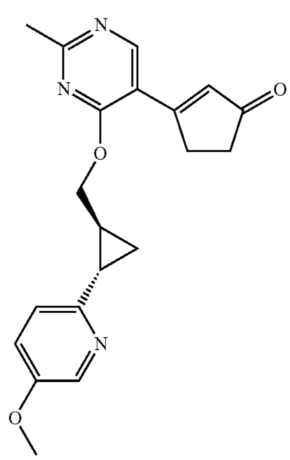 [SMILES: COc1ccc([C@H]2C[C@@H]2COc2nc(C)ncc2C2=CC(=O)CC2)nc1] | 3-(4-(((1S,2S)-2-(5-methoxypyridin-2-yl)cyclopropyl)methoxy)-2-methylpyrimidin-5-yl)cyclopent-2-enone (R,R) | 352.2 |

TABLE 9-continued

| Example | Structure | Name | MS m/z (M + H) |
|---|---|---|---|
| 78 | 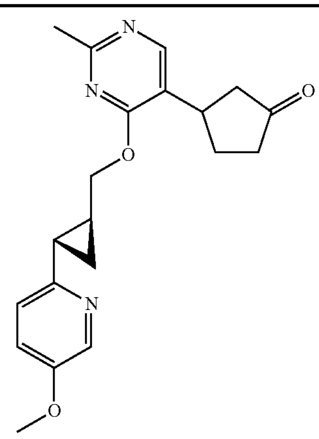 | 3-(4-((((1S,2S)-2-(5-methoxypyridin-2-yl)cyclopropyl(methoxy)-2-methylpyrimidin-5-yl)cyclopentanone | 354.1 |
| 79 | 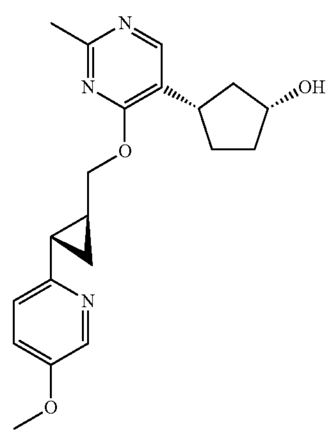 [SMILES: COc1ccc([C@H]2C[C@@H]2COc2nc(C)ncc2[C@H]2CC[C@@H](O)C2)nc1] | (1R,3S)-3-(4-(((1S,2S)-2-(5-methoxypyridin-2-yl)cyclopropyl)methoxy)-2-methylpyrimidin-5-yl)cyclopentanol | 356.2 |
| 80 | 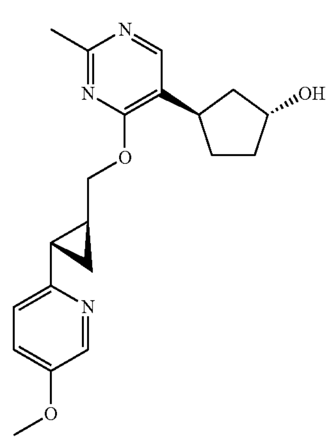 [SMILES: COc1ccc([C@H]2C[C@@H]2COc2nc(C)ncc2[C@@H]2CC[C@@H](O)C2)nc1] | (1R,3R)-3-(4-(((1S,2S)-2-(5-methoxypyridin-2-yl)cyclopropyl)methoxy)-2-methylpyrimidin-5-yl)cyclopentanol | 356.2 |

TABLE 9-continued

| Example | Structure | Name | MS m/z (M + H) |
|---|---|---|---|
| 81 | 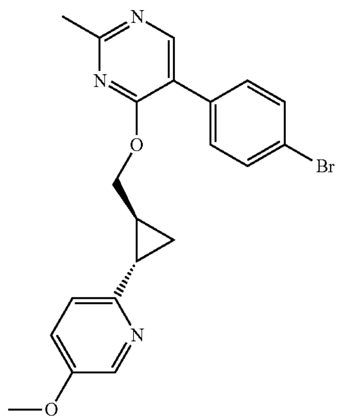 [SMILES: COc1ccc([C@H]2C[C@@H]2COc2nc(C)ncc2-c2ccc(Br)cc2)nc1] | 5-(4-bromophenyl)-4-(((1S,2S)-2-(5-methoxypyridin-2-yl)cyclopropyl)methoxy)-2-methylpyrimidine | 426.1 |
| 82 | 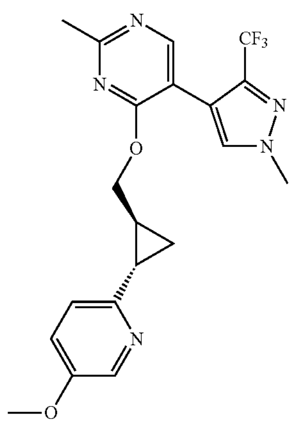 | 4-(((1S,2S)-2-(5-methoxypyridin-2-yl)cyclopropyl)methoxy)-2-methyl-5-(1-methyl-3-(trifluoromethyl)-1H-pyrazol-4-yl)pyrimidine | 420.2 |
| 83 | 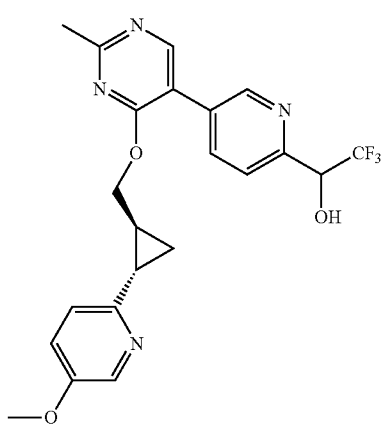 [SMILES: COc1ccc([C@H]2C[C@@H]2COc2nc(C)ncc2-c2ccc(C(O)C(F)(F)F)nc2)nc1] | 2,2,2-trifluoro-1-(5-(4-(((1S,2S)-2-(5-methoxypyridin-2-yl)cyclopropyl)methoxy)-2-methylpyrimidin-5-yl)pyridin-2-yl)ethanol (R or S) | 447.2 |

TABLE 9-continued

| Example | Name | MS m/z (M + H) |
|---|---|---|
| 84 | 2,2,2-trifluoro-1-(5-(4-(((1S,2S)-2-(5-methoxypyridin-2-yl)cyclopropyl)methoxy)-2-methylpyrimidin-5-yl)pyridin-2-yl)ethanol (S or R) | 447.2 |
| 85 | 5-(6-ethylpyridin-3-yl)-4-(((1S,2S)-2-(5-methoxypyridin-2-yl)cyclopropyl)methoxy)-2-methylpyrimidine | 377.1 |
| 86 | 5-(5-bromopyridin-2-yl)-4-(((1S,2S)-2-(5-methoxypyridin-2-yl)cyclopropyl)methoxy)-2-methylpyrimidine | 427.3 |
| 87 | 5-(2-chloro-5-(trifluoromethyl)pyridin-3-yl)-4-(((1S,2S)-2-(5-methoxypyridin-2-yl)cyclopropyl)methoxy)-2-methylpyrimidine | 451.1 |

| Example | Structure | Name | MS m/z (M + H) |
|---|---|---|---|
| 88 | 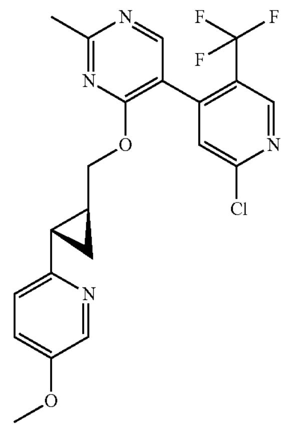 [SMILES: COc1ccc([C@H]2C[C@@H]2COc2nc(C)ncc2-c2cc(Cl)ncc2C(F)(F)F)nc1] | 5-(2-chloro-5-(trifluoromethyl)pyridin-4-yl)-4-((((1S,2S)-2-(5-methoxypyridin-2-yl)cyclopropyl)methoxy)-2-methylpyrimidine | 451.1 |
| 89 | 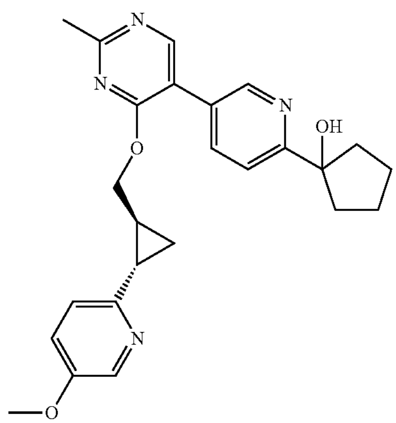 [SMILES: COc1ccc([C@H]2C[C@@H]2COc2nc(C)ncc2-c2ccc(C3(O)CCCC3)nc2)nc1] | 1-(5-(4-((((1S,2S)-2-(5-methoxypyridin-2-yl)cyclopropyl)methoxy)-2-methylpyrimidin-5-yl)pyridin-2-yl)cyclopentanol | 433.2 |
| 90 | 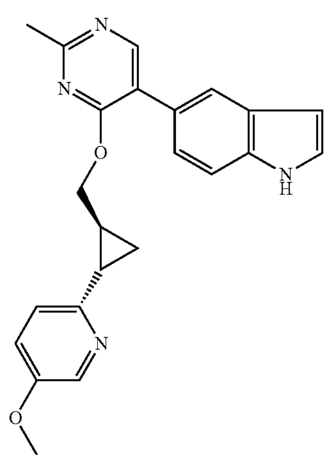 | 5-(4-((((1S,2S)-2-(5-methoxypyridin-2-yl)cyclopropyl)methoxy)-2-methylpyrimidin-5-yl)-1H-indole | 387.2 |

TABLE 9-continued

| Example | Structure | Name | MS m/z (M + H) |
|---|---|---|---|
| 91 | 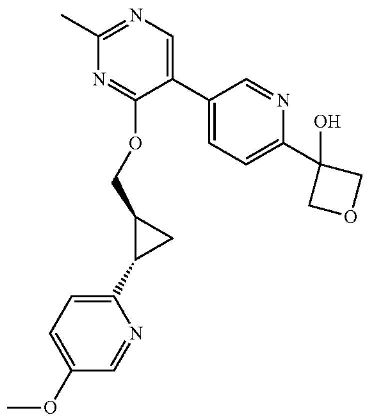 [SMILES: COc1ccc([C@H]2C[C@@H]2COc2nc(C)ncc2-c2ccc(C3(O)COC3)nc2)nc1] | 3-(5-(4-(((1S,2S)-2-(5-methoxypyridin-2-yl)cyclopropyl(methoxy)-2-methylpyrimidin-5-yl)pyridin-2-yl)oxetan-3-ol | 421.2 |
| 92 | 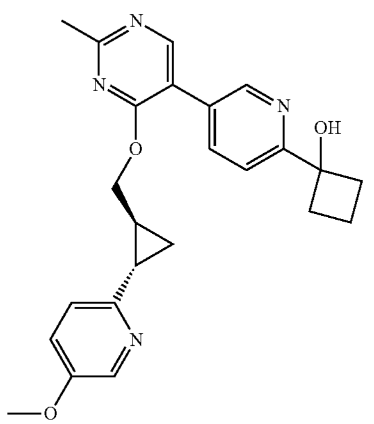 [SMILES: COc1ccc([C@H]2C[C@@H]2COc2nc(C)ncc2-c2ccc(C3(O)CCC3)nc2)nc1] | 1-(5-(4-(((1S,2S)-2-(5-methoxypyridin-2-yl)cyclopropyl)methoxy)-2-methylpyrimidin-5-yl)pyridin-2-yl)cyclobutanol | 419.2 |
| 93 | 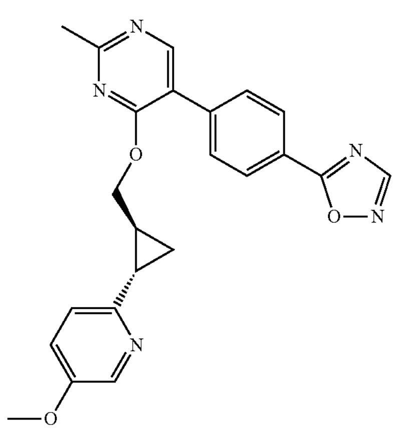 [SMILES: COc1ccc([C@H]2C[C@@H]2COc2nc(C)ncc2-c2ccc(-c3ncno3)cc2)nc1] | 5-(4-(4-(((1S,2S)-2-(5-methoxypyridin-2-yl)cyclopropyl)methoxy)-2-methylpyrimidin-5-yl)phenyl)-1,2,4-oxadiazole | 416.2 |

TABLE 9-continued

| Example | Structure | Name | MS m/z (M + H) |
|---|---|---|---|
| 94 | 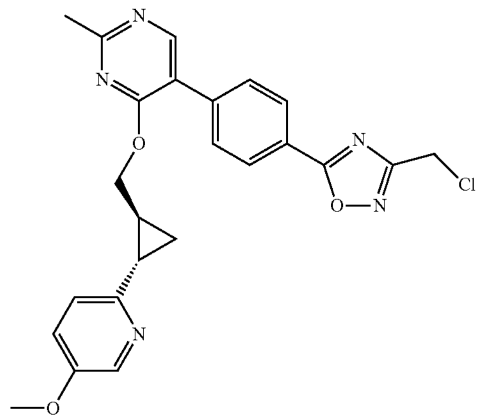 [SMILES: COc1ccc([C@H]2C[C@@H]2COc2nc(C)ncc2-c2ccc(-c3nc(CCl)no3)cc2)nc1] | 3-(chloromethyl)-5-(4-(4-(((1S,2S)-2-(5-methoxypyridin-2-yl)cyclopropyl)methoxy)-2-methylpyrimidin-5-yl)phenyl)-1,2,4-oxadiazole | 464.1 |
| 95 | 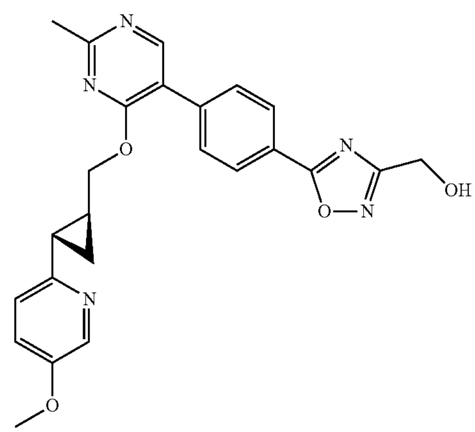 [SMILES: COc1ccc([C@H]2C[C@@H]2COc2nc(C)ncc2-c2ccc(-c3nc(CO)no3)cc2)nc1] | (5-(4-(4-(((1S,2S)-2-(5-methoxypyridin-2-yl)cyclopropyl)methoxy)-2-methylpyrimidin-5-yl)phenyl)-1,2,4-oxadiazol-3-yl)methanol | 446.2 |
| 96 | 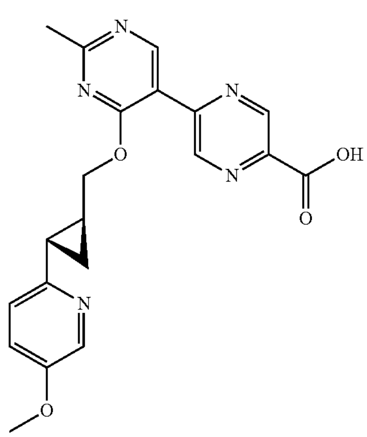 [SMILES: COc1ccc([C@H]2C[C@@H]2COc2nc(C)ncc2-c2cnc(C(=O)O)cn2)nc1] | 5-(4-(((1S,2S)-2-(5-methoxypyridin-2-yl)cyclopropyl)methoxy)-2-methylpyrimidin-5-yl)pyrazine-2-carboxylic acid | 394.1 |

TABLE 9-continued

| Example | Structure | Name | MS m/z (M + H) |
|---------|-----------|------|----------------|
| 97 | 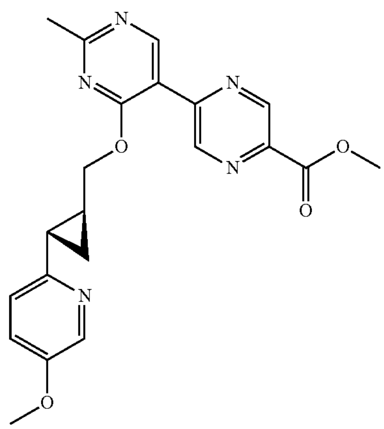 [SMILES: COC(=O)c1cnc(-c2cnc(C)nc2OC[C@H]2C[C@@H]2c2ccc(OC)cn2)cn1] | methyl 5-(4-(((1S,2S)-2-(5-methoxypyridin-2-yl)cyclopropyl)methoxy)-2-methylpyrimidin-5-yl)pyrazine-2-carboxylate | 408.2 |
| 98 | 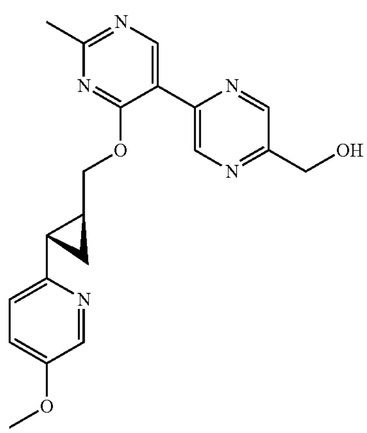 [SMILES: COc1ccc([C@H]2C[C@@H]2COc2nc(C)ncc2-c2cnc(CO)cn2)nc1] | (5-(4-(((1S,2S)-2-(5-methoxypyridin-2-yl)cyclopropyl)methoxy)-2-methylpyrimidin-5-yl)pyrazin-2-yl)methanol | 380.2 |
| 99 | 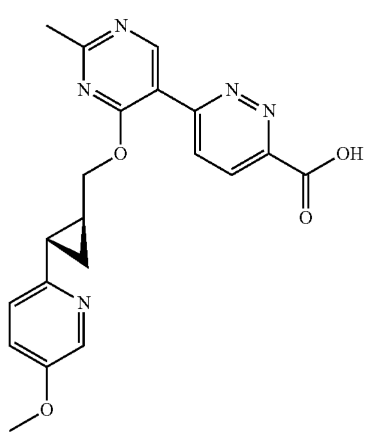 [SMILES: COc1ccc([C@H]2C[C@@H]2COc2nc(C)ncc2-c2ccc(C(=O)O)nn2)nc1] | 6-(4-(((1S,2S)-2-(5-methoxypyridin-2-yl)cyclopropyl)methoxy)-2-methylpyrimidin-5-yl)pyridazine-3-carboxylic acid | 394.1 |

TABLE 9-continued

| Example | Structure | Name | MS m/z (M + H) |
|---|---|---|---|
| 100 | 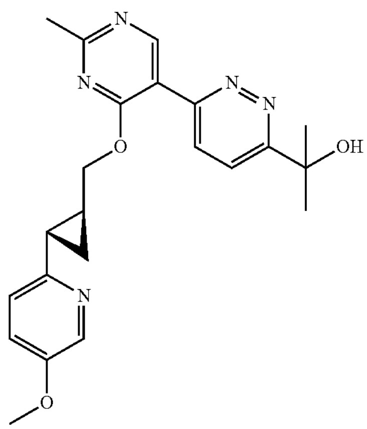 [SMILES: COc1ccc([C@H]2C[C@@H]2COc2nc(C)ncc2-c2ccc(C(C)(C)O)nn2)nc1] | 2-(6-(4-(((1S,2S)-2-(5-methoxypyridin-2-yl)cyclopropyl)methoxy)-2-methylpyrimidin-5-yl)pyridazin-3-yl)propan-2-ol | 408.2 |
| 101 | 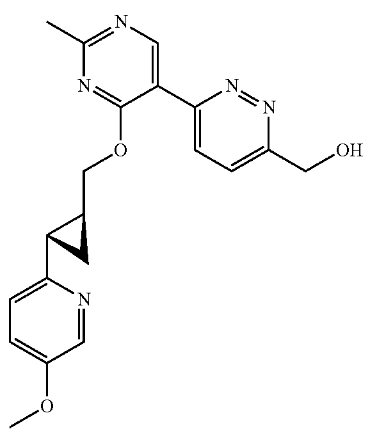 [SMILES: COc1ccc([C@H]2C[C@@H]2COc2nc(C)ncc2-c2ccc(CO)nn2)nc1] | (6-(4-(((1S,2S)-2-(5-methoxypyridin-2-yl)cyclopropyl)methoxy)-2-methylpyrimidin-5-yl)pyridazin-3-yl)methanol | 380.2 |
| 102 | 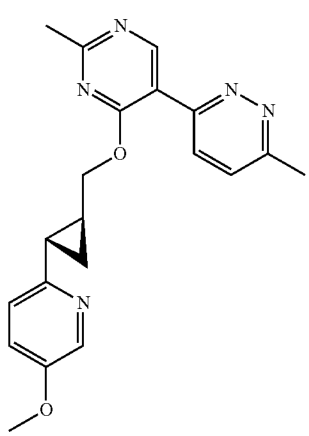 [SMILES: COc1ccc([C@H]2C[C@@H]2COc2nc(C)ncc2-c2ccc(C)nn2)nc1] | 3-(4-(((1S,2S)-2-(5-methoxypyridin-2-yl)cyclopropyl)methoxy)-2-methylpyrimidin-5-yl)-6-methylpyridazine | 364.2 |

TABLE 9-continued

| Example | Structure | Name | MS m/z (M + H) |
|---|---|---|---|
| 103 | 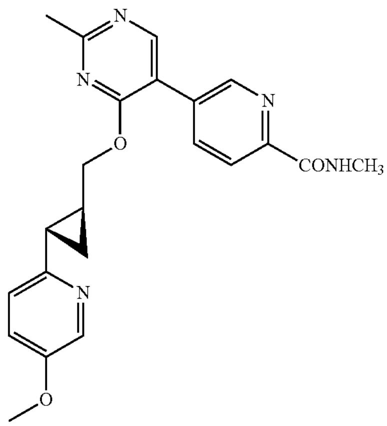 | 5-(4-(((1S,2S)-2-(5-methoxypyridin-2-yl)cyclopropyl)methoxy)-2-methylpyrimidin-5-yl)-N-methylpicolinamide | 406.2 |
| 104 | 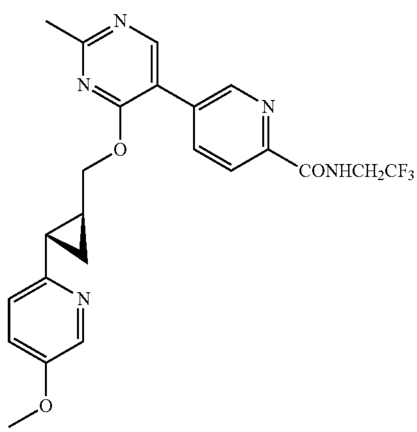 | 5-(4-(((1S,2S)-2-(5-methoxypyridin-2-yl)cyclopropyl)methoxy)-2-methylpyrimidin-5-yl)-N-(2,2,2-trifluoroethyl)picolinamide | 474.2 |
| 105 | 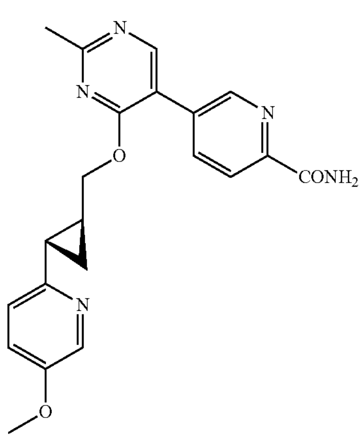 [SMILES: COc1ccc([C@H]2C[C@@H]2COc2nc(C)ncc2-c2ccc(C(N)=O)nc2)nc1] | 5-(4-(((1S,2S)-2-(5-methoxypyridin-2-yl)cyclopropyl)methoxy)-2-methylpyrimidin-5-yl)picolinamide | 392.2 |

TABLE 9-continued
| Example | Structure | Name | MS m/z (M + H) |
|---|---|---|---|
| 106 | 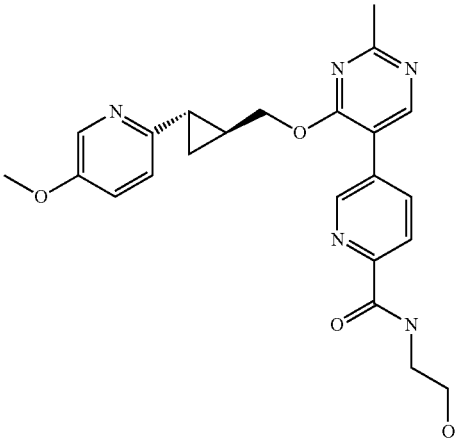 [SMILES: COc1ccc([C@H]2C[C@@H]2COc2nc(C)ncc2-c2ccc(C(=O)NCCO)nc2)nc1] | N-(2-hydroxyethyl)-5-(4-(((1S,2S)-2-(5-methoxypyridin-2-yl)cyclopropyl)methoxy)-2-methylpyrimidin-5-yl)picolinamide | 436.2 |
| 107 | 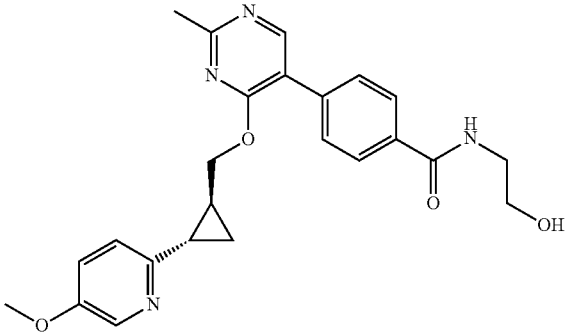 [SMILES: COc1ccc([C@H]2C[C@@H]2COc2nc(C)ncc2-c2ccc(C(=O)NCCO)cc2)nc1] | N-(2-hydroxyethyl)-4-(4-(((1S,2S)-2-(5-methoxypyridin-2-yl)cyclopropyl)methoxy)-2-methylpyrimidin-5-yl)benzamide | 435.3 |
| 108 | 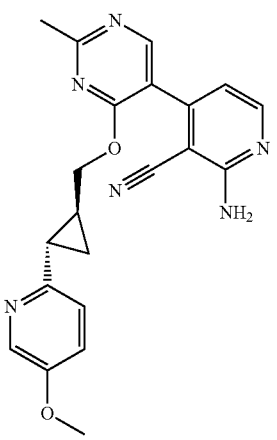 [SMILES: COc1ccc([C@H]2C[C@@H]2COc2nc(C)ncc2-c2ccnc(N)c2C#N)nc1] | 2-amino-4-(4-(((1S,2S)-2-(5-methoxypyridin-2-yl)cyclopropyl)methoxy)-2-methylpyrimidin-5-yl)nicotinonitrile | 389.3 |

TABLE 9-continued

| Example | Structure | Name | MS m/z (M + H) |
|---|---|---|---|
| 109 | 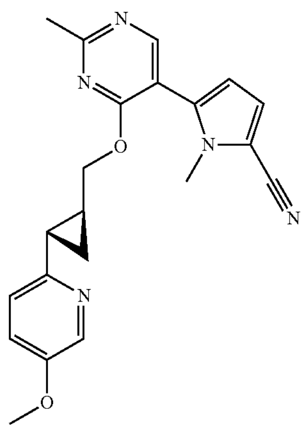 [SMILES: COc1ccc([C@H]2C[C@@H]2COc2nc(C)ncc2-c2ccc(C#N)n2C)nc1] | 5-(4-(((1S,2S)-2-(5-methoxypyridin-2-yl)cyclopropyl)methoxy)-2-methylpyrimidin-5-yl)-1-methyl-1H-pyrrole-2-carbonitrile | 376.2 |
| 110 | 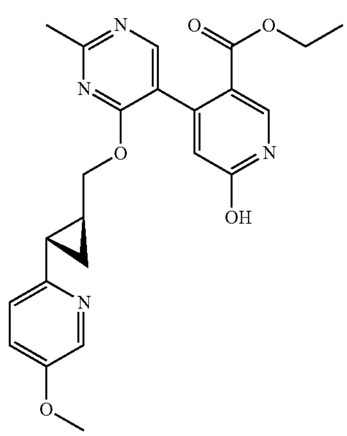 [SMILES: CCOC(=O)c1cnc(O)cc1-c1cnc(C)nc1OC[C@H]1C[C@@H]1c1ccc(OC)cn1] | ethyl 6-hydroxy-4-(4-(((1S,2S)-2-(5-methoxypyridin-2-yl)cyclopropyl)methoxy)-2-methylpyrimidin-5-yl)nicotinate | 437.3 |
| 111 | 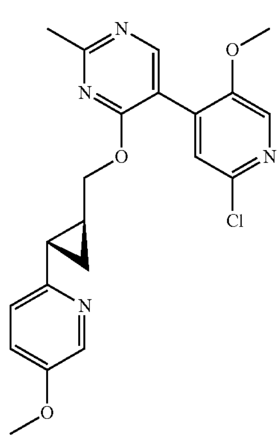 [SMILES: COc1ccc([C@H]2C[C@@H]2COc2nc(C)ncc2-c2cc(Cl)ncc2OC)nc1] | 5-(2-chloro-5-methoxypyridin-4-yl)-4-(((1S,2S)-2-(5-methoxypyridin-2-yl)cyclopropyl)methoxy)-2-methylpyrimidine | 413.1 |

TABLE 9-continued

| Example | Structure | Name | MS m/z (M + H) |
|---|---|---|---|
| 112 | 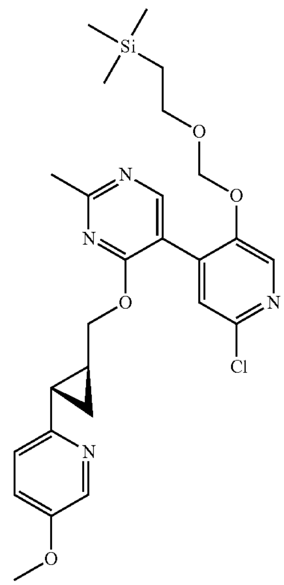 [SMILES: COc1ccc([C@H]2C[C@@H]2COc2nc(C)ncc2-c2cc(Cl)ncc2OCOCC[Si](C)(C)C)nc1] | 5-(2-chloro-5-((2-(trimethylsilyl)ethoxy)methoxy)pyridin-4-yl)-4-(((1S,2S)-2-(5-methoxypyridin-2-yl)cyclopropyl)methoxy)-2-methylpyrimidine | 529.1 |
| 113 | 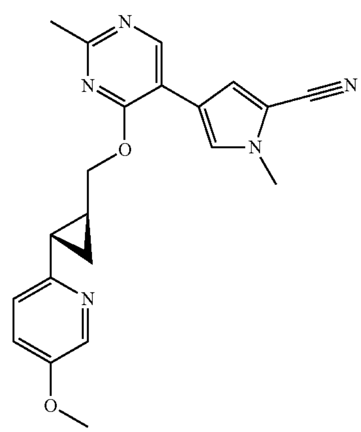 [SMILES: COc1ccc([C@H]2C[C@@H]2COc2nc(C)ncc2-c2cc(C#N)n(C)c2)nc1] | 4-(4-(((1S,2S)-2-(5-methoxypyridin-2-yl)cyclopropyl)methoxy)-2-methylpyrimidin-5-yl)-1-methyl-1H-pyrrole-2-carbonitrile | 376.2 |
| 114 | 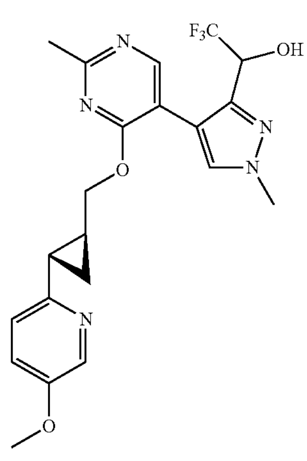 [SMILES: COc1ccc([C@H]2C[C@@H]2COc2nc(C)ncc2-c2cn(C)nc2C(O)C(F)(F)F)nc1] | 2,2,2-trifluoro-1-(4-(4-(((1S,2S)-2-(5-methoxypyridin-2-yl)cyclopropyl)methoxy)-2-methylpyrimidin-5-yl)-1-methyl-1H-pyrazol-3-yl)ethanol | 450.2 |

TABLE 9-continued

| Example | Structure | Name | MS m/z (M + H) |
|---|---|---|---|
| 115 | 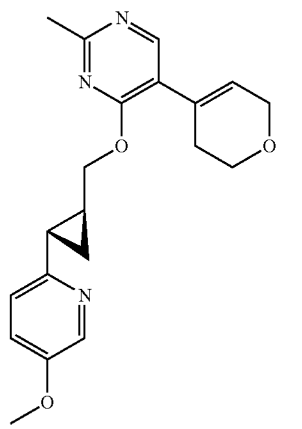 [SMILES: COc1ccc([C@H]2C[C@@H]2COc2nc(C)ncc2C2=CCOCC2)nc1] | 5-(3,6-dihydro-2H-pyran-4-yl)-4-(((1S,2S)-2-(5-methoxypyridin-2-yl)cyclopropyl)methoxy)-2-methylpyrimidine | 354.2 |
| 116 | 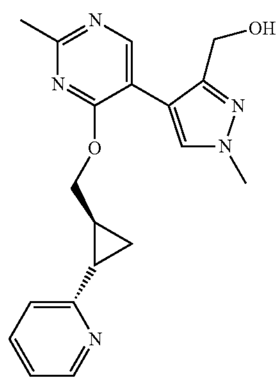 | (1-methyl-4-(2-methyl-4-(((1S,2S)-2-(pyridin-2-yl)cyclopropyl)methoxy)pyrimidin-5-yl)-1H-pyrazol-3-yl)methanol(1S,2S) | 352.2 |
| 117 | 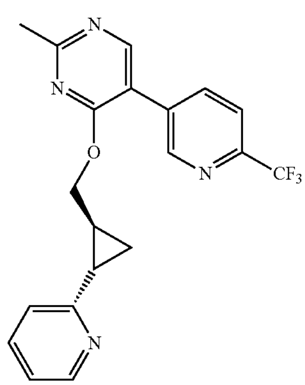 | 2-methyl-4-(((1S,2S)-2-(pyridin-2-yl)cyclopropyl)methoxy)-5-(6-(trifluoromethyl)pyridin-3-yl)pyrimidine | 387.1 |
| 118 | 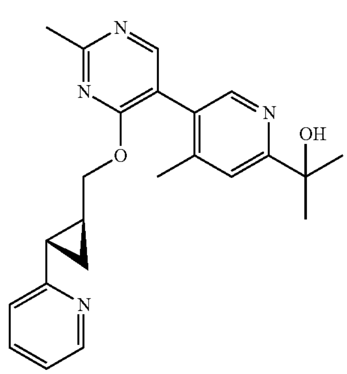 [SMILES: Cc1ncc(-c2cnc(C(C)(C)O)cc2C)c(OC[C@H]2C[C@@H]2c2ccccn2)n1] | 2-(4-methyl-5-(2-methyl-4-(((1S,2S)-2-(pyridin-2-yl)cyclopropyl)methoxy)pyrimidin-5-yl)pyridin-2-yl)propan-2-ol | 391.2 |

TABLE 9-continued

| Example | Structure | Name | MS m/z (M + H) |
|---|---|---|---|
| 119 | 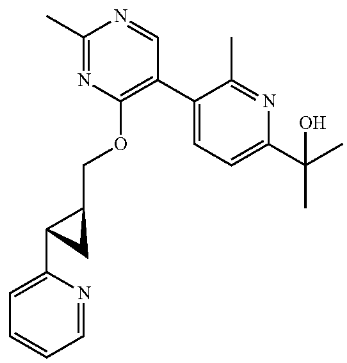 [SMILES: Cc1ncc(-c2ccc(C(C)(C)O)nc2C)c(OC[C@H]2C[C@@H]2c2ccccn2)n1] | 2-(6-methyl-5-(2-methyl-4-(((1S,2S)-2-(pyridin-2-yl)cyclopropyl)methoxy)pyrimidin-5-yl)pyridin-2-yl)propan-2-ol | 391.2 |
| 120 | 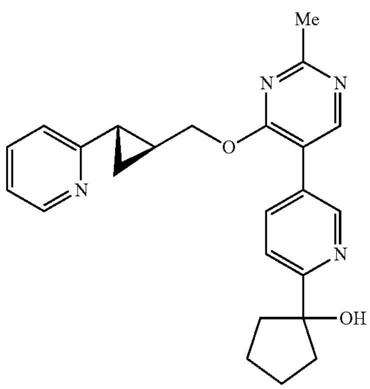 [SMILES: Cc1ncc(-c2ccc(C3(O)CCCC3)nc2)c(OC[C@H]2C[C@@H]2c2ccccn2)n1] | 1-(5-(2-methyl-4-(((1S,2S)-2-(pyridin-2-yl)cyclopropyl)methoxy)pyrimidin-5-yl)pyridin-2-yl)cyclopentanol | 403.3 |
| 121 | 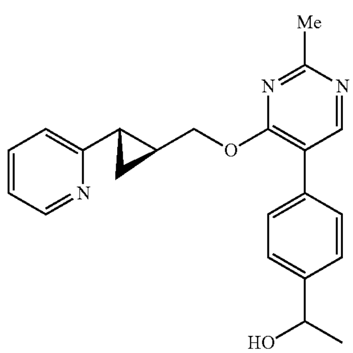 [SMILES: Cc1ncc(-c2ccc(C(C)O)cc2)c(OC[C@H]2C[C@@H]2c2ccccn2)n1] | 1-(4-(2-methyl-4-(((1S,2S)-2-(pyridin-2-yl)cyclopropyl)methoxy)pyrimidin-5-yl)phenyl)ethanol | 362.2 |
| 122 | 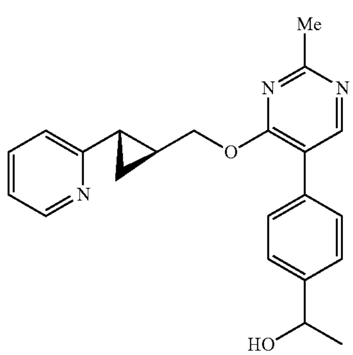 [SMILES: Cc1ncc(-c2ccc(C(C)O)cc2)c(OC[C@H]2C[C@@H]2c2ccccn2)n1] | 1-(4-(2-methyl-4-(((1S,2S)-2-(pyridin-2-yl)cyclopropyl)methoxy)pyrimidin-5-yl)phenyl)ethanol | 362.2 |

TABLE 9-continued

| Example | Structure | Name | MS m/z (M + H) |
|---|---|---|---|
| 123 | 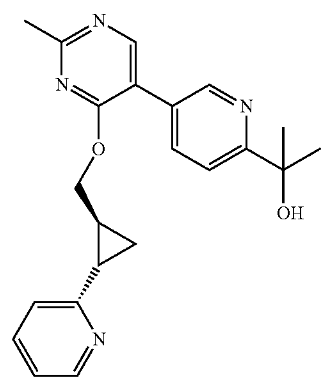 | 2-(5-(2-methyl-4-(((1S,2S)-2-(pyridin-2-yl)cyclopropyl)methoxy)pyrimidin-5-yl)pyridin-2-yl)propan-2-ol | 377.2 |
| 124 | 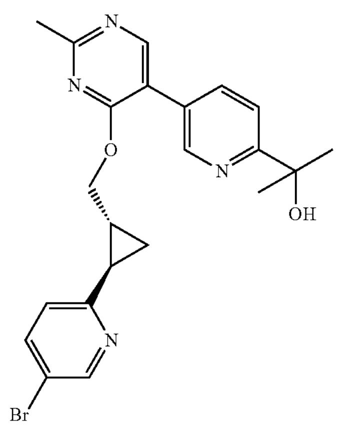 [SMILES: Cc1ncc(-c2ccc(C(C)(C)O)nc2)c(OC[C@@H]2C[C@H]2c2ccc(Br)cn2)n1] | 2-(5-(4-(((1R,2R)-2-(5-bromopyridin-2-yl)cyclopropyl)methoxy)-2-methylpyrimidin-5-yl)pyridin-2-yl)propan-2-ol | 455.1 |
| 125 | 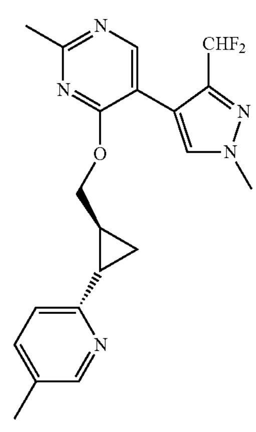 | 5-(3-(difluoromethyl)-1-methyl-1H-pyrazol-4-yl)-2-methyl-4-(((1S,2S)-2-(5-methylpyridin-2-yl)cyclopropyl)methoxy)pyrimidine | 386.2 |

TABLE 9-continued

| Example | Structure | Name | MS m/z (M + H) |
|---|---|---|---|
| 126 | 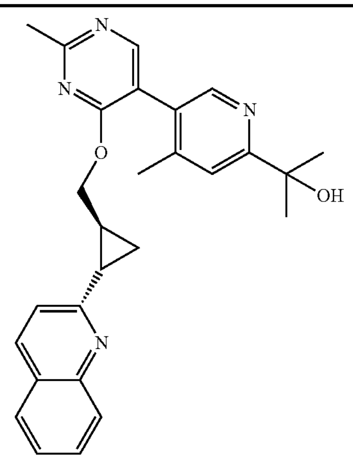 | 2-(4-methyl-5-(2-methyl-4-(((1S,2S)-2-(quinolin-2-yl)cyclopropyl)methoxy)pyrimidin-5-yl)pyridin-2-yl)propan-2-ol | 441.2 |
| 127 | 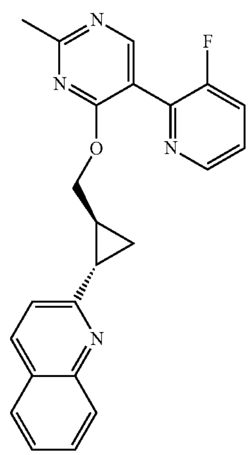 [SMILES: Cc1ncc(-c2ncccc2F)c(OC[C@H]2C[C@@H]2c2ccc3ccccc3n2)n1] | 2-((1S,2S)-2-((5-(3-fluoropyridin-2-yl)-2-methylpyrimidin-4-yloxy)methyl)cyclopropyl)quinoline | 387.2 |
| 128 | 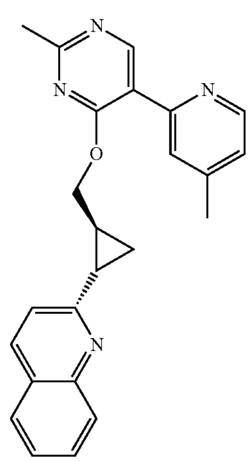 | 2-((1S,2S)-2-((2-methyl-5-(4-methylpyridin-2-yl)pyrimidin-4-yloxy)methyl)cyclopropyl)quinoline | 383.2 |

TABLE 9-continued

| Example | Structure | Name | MS m/z (M + H) |
|---|---|---|---|
| 129 | 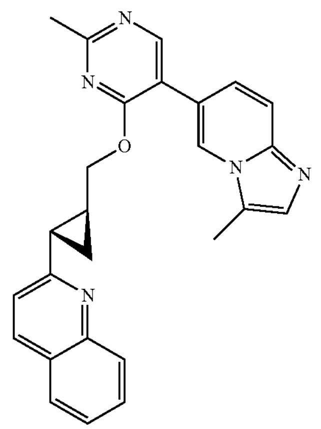 [SMILES: Cc1ncc(-c2ccc3ncc(C)n3c2)c(OC[C@H]2C[C@@H]2c2ccc3ccccc3n2)n1] | 2-((1S,2S)-2-((2-methyl-5-(3-methylimidazo[1,2-a]pyridin-6-yl)pyrimidin-4-yloxy)methyl)cyclopropyl)quinoline | 422.3 |
| 130 | 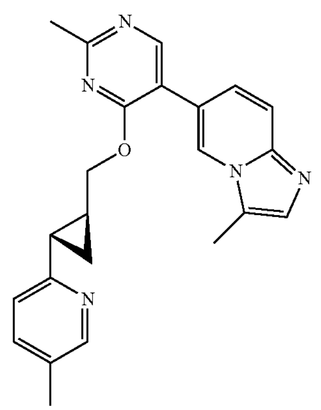 [SMILES: Cc1ccc([C@H]2C[C@@H]2COc2nc(C)ncc2-c2ccc3ncc(C)n3c2)nc1] | 3-methyl-6-(2-methyl-4-(((1S,2S)-2-(5-methylpyridin-2-yl)cyclopropyl)methoxy)pyrimidin-5-yl)imidazo[1,2-a]pyridine | 386.3 |
| 131 | 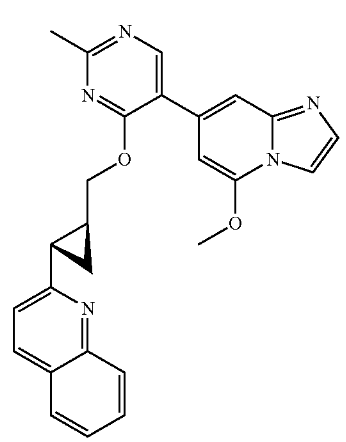 [SMILES: COc1cc(-c2cnc(C)nc2OC[C@H]2C[C@@H]2c2ccc3ccccc3n2)cc2nccn12] | 2-((1S,2S)-2-((5-(5-methoxyimidazo[1,2-a]pyridin-7-yl)-2-methylpyrimidin-4-yloxy)methyl)cyclopropyl)quinoline | 438.3 |

TABLE 9-continued

| Example | Structure | Name | MS m/z (M + H) |
|---|---|---|---|
| 132 | 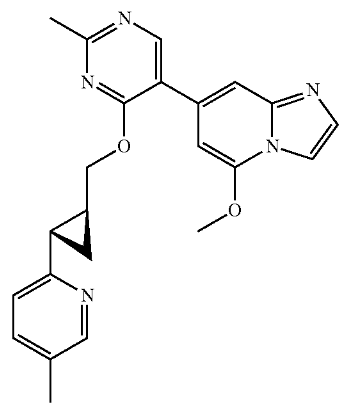 [SMILES: COc1cc(-c2cnc(C)nc2OC[C@H]2C[C@@H]2c2ccc(C)cn2)cc2nccn12] | 5-methoxy-7-(2-methyl-4-(((1S,2S)-2-(5-methylpyridin-2-yl)cyclopropyl)methoxy)pyrimidin-5-yl)imidazo[1,2-a]pyridine | 402.3 |
| 133 | 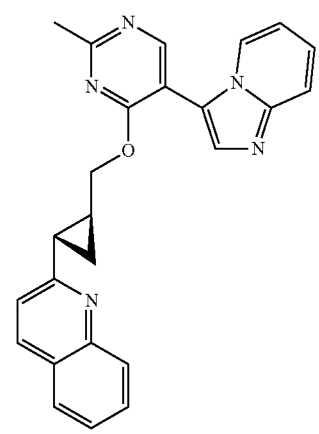 [SMILES: Cc1ncc(-c2cnc3ccccn23)c(OC[C@H]2C[C@@H]2c2ccc3ccccc3n2)n1] | 2-((1S,2S)-2-((5-(imidazo[1,2-a]pyridin-3-yl)-2-methylpyrimidin-4-yloxy)methyl)cyclopropyl)quinoline | 408.3 |
| 134 | 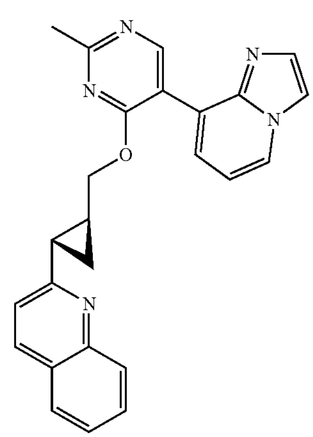 [SMILES: Cc1ncc(-c2cccn3ccnc23)c(OC[C@H]2C[C@@H]2c2ccc3ccccc3n2)n1] | 2-((1S,2S)-2-((5-(imidazo[1,2-a]pyridin-8-yl)-2-methylpyrimidin-4-yloxy)methyl)cyclopropyl)quinoline | 408.3 |

TABLE 9-continued

| Example | Structure | Name | MS m/z (M + H) |
|---|---|---|---|
| 135 | 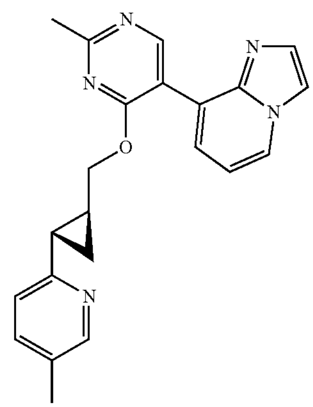 [SMILES: Cc1ccc([C@H]2C[C@@H]2COc2nc(C)ncc2-c2cccn3ccnc23)nc1] | 8-(2-methyl-4-(((1S,2S)-2-(5-methylpyridin-2-yl)cyclopropyl)methoxy)pyrimidin-5-yl)imidazo[1,2-a]pyridine | 372.3 |
| 136 | 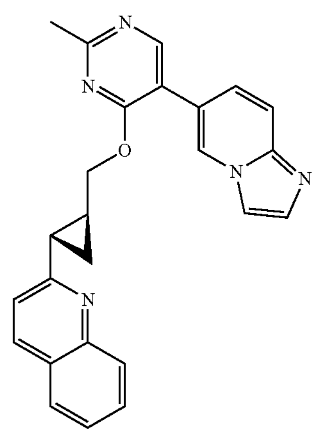 [SMILES: Cc1ncc(-c2ccc3nccn3c2)c(OC[C@H]2C[C@@H]2c2ccc3ccccc3n2)n1] | 2-((1S,2S)-2-((5-(imidazo[1,2-a]pyridin-6-yl)-2-methylpyrimidin-4-yloxy)methyl)cyclopropyl)quinoline | 408.3 |
| 137 | 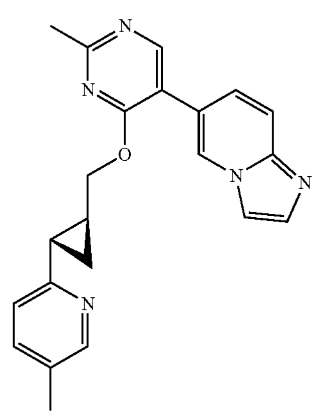 [SMILES: Cc1ccc([C@H]2C[C@@H]2COc2nc(C)ncc2-c2ccc3nccn3c2)nc1] | 6-(2-methyl-4-(((1S,2S)-2-(5-methylpyridin-2-yl)cyclopropyl)methoxy)pyrimidin-5-yl)imidazo[1,2-a]pyridine | 372.3 |

SCHEME 15

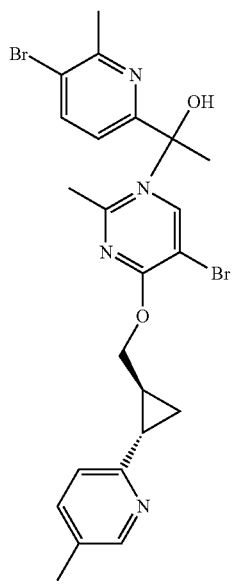

1) Pin₂B₂, PdCl₂(dppf), KOAc
Dioxane, 100° C.
2) Cs₂CO₃, H₂O, 100° C.

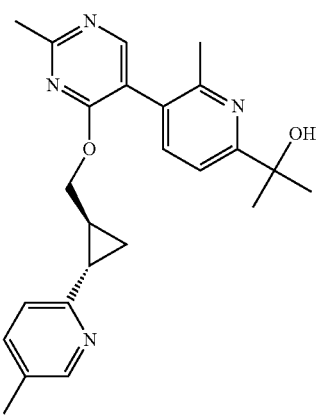 [SMILES: Cc1ccc([C@H]2C[C@@H]2COc2nc(C)ncc2-c2ccc(C(C)(C)O)nc2C)nc1]

Example 138

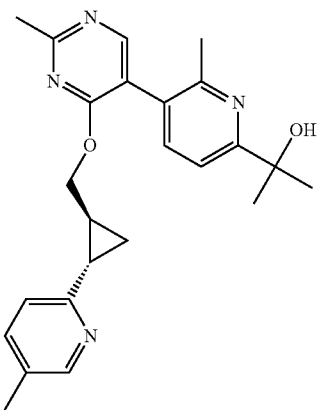 [SMILES: Cc1ccc([C@H]2C[C@@H]2COc2nc(C)ncc2-c2ccc(C(C)(C)O)nc2C)nc1]

Step A: 2-(6-Methyl-5-(2-methyl-4-(((1S,2S)-2-(5-methylpyridin-2-yl)cyclopropyl)methoxy)pyrimidin-5-yl)pyridin-2-yl)propan-2-ol (Example 138)

A mixture of 2-(5-bromo-6-methylpyridin-2-yl) propan-2-ol (360 mg, 1.60 mmol), bis(pinacolato)diboron (478 mg, 1.88 mmol), potassium acetate (627 mg, 6.4 mmol) and PdCl₂(dppf) (117 mg, 0.16 mmol) in dioxane (5 mL) under N₂ was heated at 100° C. for 2 hours. A solution of 5-bromo-2-methyl-4-(((1S,2S)-2-(5-methylpyridin-2-yl)cyclopropyl)methoxy)pyrimidine (266 mg, 0.8 mmol) in dioxane (1 mL) was added followed by aqueous cesium carbonate (1 M, 3.2 mL, 3.2 mmol). The resulting mixture was heated at 110° C. for 14 hours. The mixture was cooled to ambient temperature, diluted with EtOAc (5 mL), washed with sodium bicarbonate (1 mL) and brine (1 mL), dried over MgSO₄, filtered and concentrated. The resulting residue was purified by reverse phase chromatography (Waters Sunfire Prep C18 OBD, 5-95% acetonitrile in water with 0.1% NH₃.H₂O modifier) to afford the title compound (80 mg, 24.7%) as a white solid. ¹H NMR (400 MHz, CD3OD) δ 8.22 (s, 1H), 8.17 (s, 1H), 7.57 (d, 1H), 7.51-7.49 (m, 2H), 7.09 (d, 1H), 4.58 (dd, 1H), 4.39 (dd, 1H), 2.66 (s, 3H), 2.33 (s, 3H), 2.29 (s, 3H), 2.09 (dt, 1H), 1.84-1.81 (m, 1H), 1.56 (s, 6H), 1.31-1.18 (m, 1H), 1.08 (dt, 1H); MS m/z=405.5 (M+H).

The following EXAMPLE 138-170 in Table 10 was prepared using the procedure of EXAMPLE 138, substituting the appropriate starting materials.

TABLE 10

| Example | Structure | Name | MS m/z (M + H) |
|---|---|---|---|
| 138 | 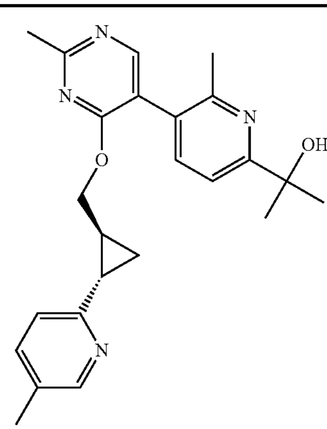 | 2-(6-Methyl-5-(2-methyl-4-(((1S,2S)-2-(5-methylpyridin-2-yl)cyclopropyl)methoxy)pyrimidin-5-yl)pyridin-2-yl)propan-2-ol | 405.5 |

TABLE 10-continued

| Example | Structure | Name | MS m/z (M + H) |
|---|---|---|---|
| 139 | 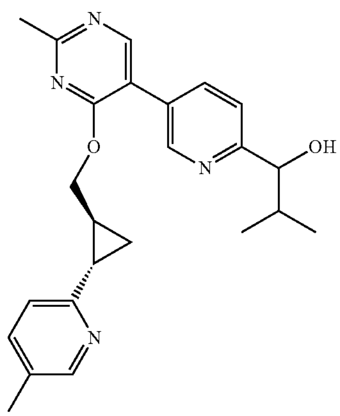 [SMILES: Cc1ccc([C@H]2C[C@@H]2COc2nc(C)ncc2-c2ccc(C(O)C(C)C)nc2)nc1] | 2-methyl-1-(5-(2-methyl-4-(((1S,2S)-2-(5-methylpyridin-2-yl)cyclopropyl)methoxy)pyrimidin-5-yl)pyridin-2-yl)propan-1-ol | 405.2 |
| 140 | 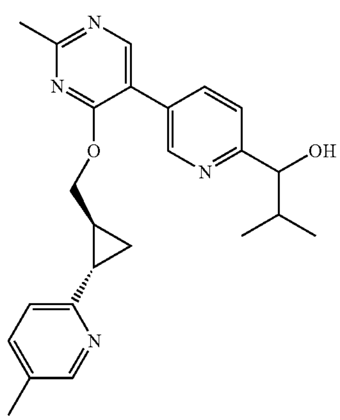 [SMILES: Cc1ccc([C@H]2C[C@@H]2COc2nc(C)ncc2-c2ccc(C(O)C(C)C)nc2)nc1] | 2-methyl-1-(5-(2-methyl-4-(((1S,2S)-2-(5-methylpyridin-2-yl)cyclopropyl)methoxy)pyrimidin-5-yl)pyridin-2-yl)propan-1-ol | 405.2 |
| 141 | 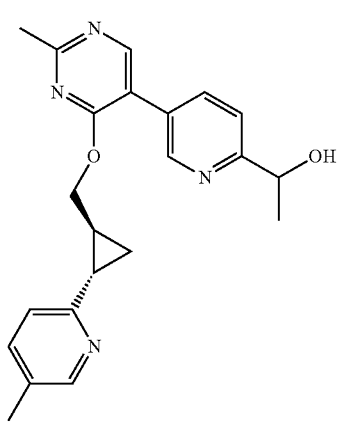 [SMILES: Cc1ccc([C@H]2C[C@@H]2COc2nc(C)ncc2-c2ccc(C(C)O)nc2)nc1] | 1-(5-(2-methyl-4-(((1S,2S)-2-(5-methylpyridin-2-yl)cyclopropyl)methoxy)pyrimidin-5-yl)pyridin-2-yl)ethanol | 377.3 |

TABLE 10-continued

| Example | Structure | Name | MS m/z (M + H) |
|---|---|---|---|
| 142 | 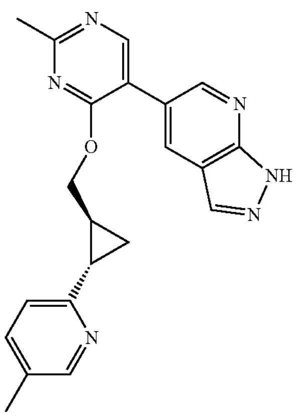 [SMILES: Cc1ccc([C@H]2C[C@@H]2COc2nc(C)ncc2-c2cnc3[nH]ncc3c2)nc1] | 5-(2-methyl-4-(((1S,2S)-2-(5-methylpyridin-2-yl)cyclopropyl)methoxy)pyrimidin-5-yl)-1H-pyrazolo[3,4-b]pyridine | 373.1 |
| 143 | 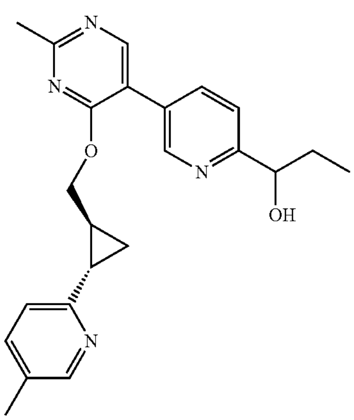 [SMILES: CCC(O)c1ccc(-c2cnc(C)nc2OC[C@H]2C[C@@H]2c2ccc(C)cn2)cn1] | 1-(5-(2-methyl-4-(((1S,2S)-2-(5-methylpyridin-2-yl)cyclopropyl)methoxy)pyrimidin-5-yl)pyridin-2-yl)propan-1-ol | 391.2 |
| 144 | 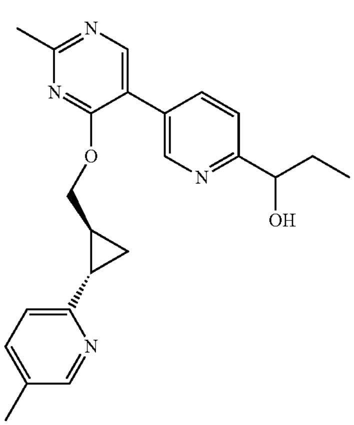 [SMILES: CCC(O)c1ccc(-c2cnc(C)nc2OC[C@H]2C[C@@H]2c2ccc(C)cn2)cn1] | 1-(5-(2-methyl-4-(((1S,2S)-2-(5-methylpyridin-2-yl)cyclopropyl)methoxy)pyrimidin-5-yl)pyridin-2-yl)propan-1-ol | 391.2 |

TABLE 10-continued

| Example | Structure | Name | MS m/z (M + H) |
|---|---|---|---|
| 145 | 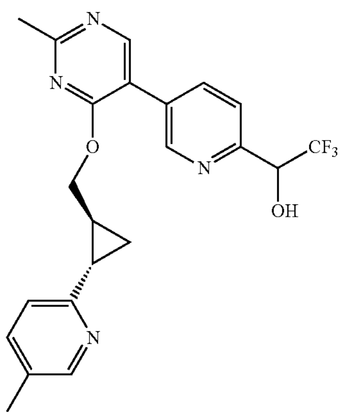 [SMILES: Cc1ccc([C@H]2C[C@@H]2COc2nc(C)ncc2-c2ccc(C(O)C(F)(F)F)nc2)nc1] | 2,2,2-trifluoro-1-(5-(2-methyl-4-(((1S,2S)-2-(5-methylpyridin-2-yl)cyclopropyl)methoxy)pyrimidin-5-yl)pyridin-2-yl)ethanol | 431.1 |
| 147 | 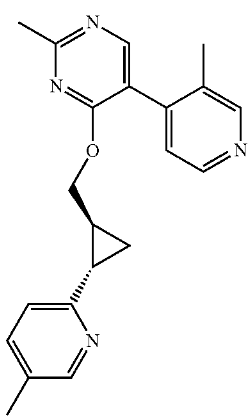 [SMILES: Cc1ccc([C@H]2C[C@@H]2COc2nc(C)ncc2-c2ccncc2C)nc1] | 2-methyl-4-(((1S,2S)-2-(5-methylpyridin-2-yl)cyclopropyl)methoxy)-5-(3-methylpyridin-4-yl)pyrimidine | 347.2 |
| 148 | 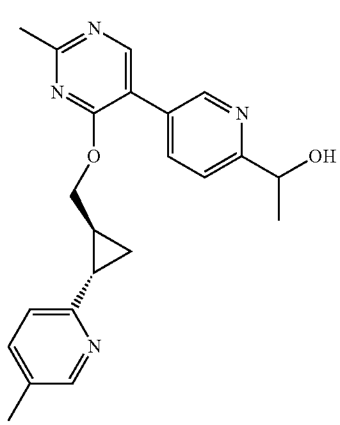 [SMILES: Cc1ccc([C@H]2C[C@@H]2COc2nc(C)ncc2-c2ccc(C(C)O)nc2)nc1] | 1-(5-(2-methyl-4-(((1S,2S)-2-(5-methylpyridin-2-yl)cyclopropyl)methoxy)pyrimidin-5-yl)pyridin-2-yl)ethanol | 377.2 |

TABLE 10-continued

| Example | Structure | Name | MS m/z (M + H) |
|---|---|---|---|
| 149 | 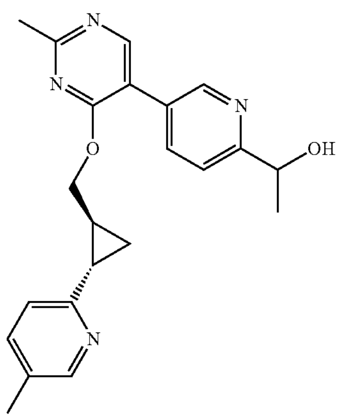 [SMILES: Cc1ccc([C@H]2C[C@@H]2COc2nc(C)ncc2-c2ccc(C(C)O)nc2)nc1] | 1-(5-(2-methyl-4-(((1S,2S)-2-(5-methylpyridin-2-yl)cyclopropyl)methoxy)pyrimidin-5-yl)pyridin-2-yl)ethanol | 377.2 |
| 150 | 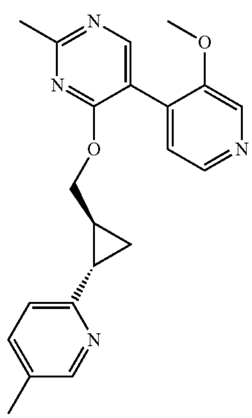 [SMILES: COc1cnccc1-c1cnc(C)nc1OC[C@H]1C[C@@H]1c1ccc(C)cn1] | 5-(3-methoxypyridin-4-yl)-2-methyl-4-(((1S,2S)-2-(5-methylpyridin-2-yl)cyclopropyl)methoxy)pyrimidine | 363.3 |
| 151 | 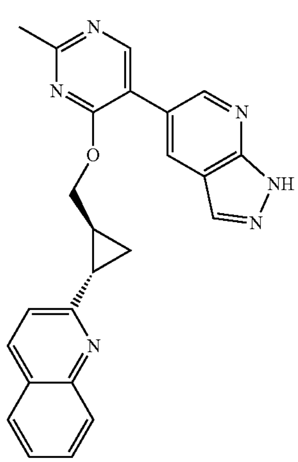 [SMILES: Cc1ncc(-c2cnc3[nH]ncc3c2)c(OC[C@H]2C[C@@H]2c2ccc3ccccc3n2)n1] | 2-((1S,2S)-2-((2-methyl-5-(1H-pyrazolo[3,4-b]pyridin-5-yl)pyrimidin-4-yloxy)methyl)cyclopropyl)quinoline (enantiomer A) | 409.1 |

TABLE 10-continued

| Example | Structure | Name | MS m/z (M + H) |
|---|---|---|---|
| 152 | 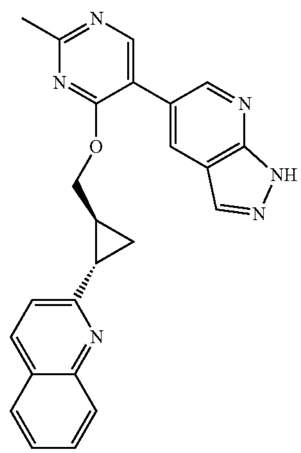 [SMILES: Cc1ncc(-c2cnc3[nH]ncc3c2)c(OC[C@H]2C[C@@H]2c2ccc3ccccc3n2)n1] | 2-((1S,2S)-2-((2-methyl-5-(1H-pyrazolo[3,4-b]pyridin-5-yl)pyrimidin-4-yloxy)methyl)cyclopropyl)quinoline (enantiomer B) | 409.1 |
| 153 | 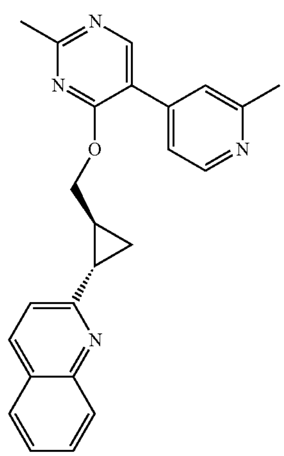 [SMILES: Cc1cc(-c2cnc(C)nc2OC[C@H]2C[C@@H]2c2ccc3ccccc3n2)ccn1] | 2-((1S,2S)-2-((2-methyl-5-(2-methylpyridin-4-yl)pyrimidin-4-yloxy)methyl)cyclopropyl)quinoline | 383.2 |
| 154 | 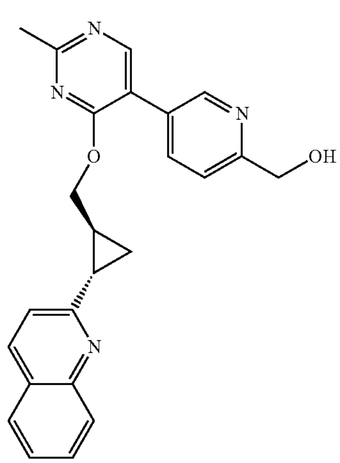 [SMILES: Cc1ncc(-c2ccc(CO)nc2)c(OC[C@H]2C[C@@H]2c2ccc3ccccc3n2)n1] | (5-(2-methyl-4-(((1S,2S)-2-(quinolin-2-yl)cyclopropyl)methoxy)pyrimidin-5-yl)pyridin-2-yl)methanol | 399.2 |

TABLE 10-continued

| Example | Structure | Name | MS m/z (M + H) |
|---|---|---|---|
| 155 | 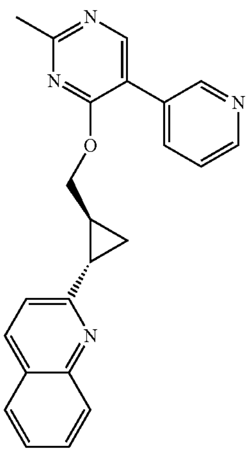 | 2-((1S,2S)-2-((2-methyl-5-(pyridin-3-yl)pyrimidin-4-yloxy)methyl)cyclopropyl)quinoline | 369.1 |
| 156 | 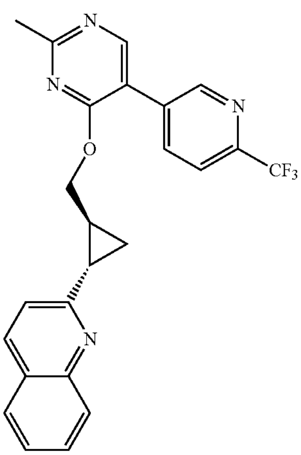 [SMILES: Cc1ncc(-c2ccc(C(F)(F)F)nc2)c(OC[C@H]2C[C@@H]2c2ccc3ccccc3n2)n1] | 2-((1S,2S)-2-((2-methyl-5-(6-(trifluoromethyl)pyridin-3-yl)pyrimidin-4-yloxy)methyl)cyclopropyl)quinoline | 437.0 |
| 157 | 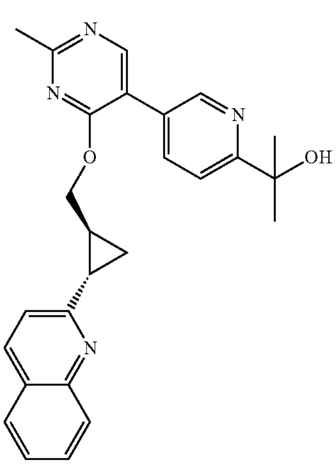 [SMILES: Cc1ncc(-c2ccc(C(C)(C)O)nc2)c(OC[C@H]2C[C@@H]2c2ccc3ccccc3n2)n1] | 2-(5-(2-methyl-4-(((1S,2S)-2-(quinolin-2-yl)cyclopropyl)methoxy)pyrimidin-5-yl)pyridin-2-yl)propan-2-ol | 427.2 |

TABLE 10-continued

| Example | Structure | Name | MS m/z (M + H) |
|---|---|---|---|
| 158 | 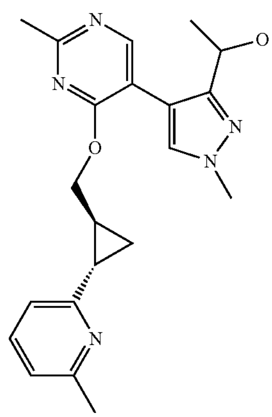 [SMILES: Cc1cccc([C@H]2C[C@@H]2COc2nc(C)ncc2-c2cn(C)nc2C(C)O)n1] | 1-(1-methyl-4-(2-methyl-4-(((1S,2S)-2-(6-methylpyridin-2-yl)cyclopropyl)methoxy)pyrimidin-5-yl)-1H-pyrazol-3-yl)ethanol | 380.2 |
| 159 | 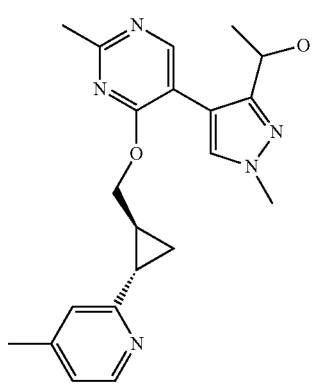 [SMILES: Cc1ccnc([C@H]2C[C@@H]2COc2nc(C)ncc2-c2cn(C)nc2C(C)O)c1] | 1-(1-methyl-4-(2-methyl-4-(((1S,2S)-2-(4-methylpyridin-2-yl)cyclopropyl)methoxy)pyrimidin-5-yl)-1H-pyrazol-3-yl)ethanol | 380.2 |
| 160 | 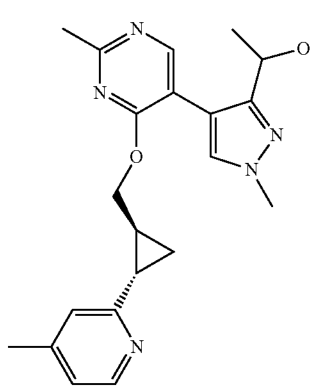 [SMILES: Cc1ccnc([C@H]2C[C@@H]2COc2nc(C)ncc2-c2cn(C)nc2C(C)O)c1] | 1-(1-methyl-4-(2-methyl-4-(((1S,2S)-2-(4-methylpyridin-2-yl)cyclopropyl)methoxy)pyrimidin-5-yl)-1H-pyrazol-3-yl)ethanol | 380.2 |

TABLE 10-continued

| Example | Name | MS m/z (M + H) |
|---|---|---|
| 161 | 1-(1-methyl-4-(2-methyl-4-(((1S,2S)-2-(6-methylpyridin-2-yl)cyclopropyl)methoxy)pyrimidin-5-yl)-1H-pyrazol-3-yl)ethanol | 380.2 |
| 162 | 1-(4-(4-(((1S,2S)-2-(5-ethylpyridin-2-yl)cyclopropyl)methoxy)-2-methylpyrimidin-5-yl)-1-methyl-1H-pyrazol-3-yl)ethanol | 394.3 |
| 163 | 1-(4-(4-(((1S,2S)-2-(5-ethylpyridin-2-yl)cyclopropyl)methoxy)-2-methylpyrimidin-5-yl)-1-methyl-1H-pyrazol-3-yl)ethanol | 394.3 |
| 164 | 1-(4-(4-(((1R,2R)-2-(6,7-dihydro-5H-cyclopenta[b]pyridin-2-yl)cyclopropyl)methoxy)-2-methylpyrimidin-5-yl)-1-methyl-1H-pyrazol-3-yl)ethanol(enantiomer A, R or S) | 406.2 |

TABLE 10-continued

| Example | Structure | Name | MS m/z (M + H) |
|---|---|---|---|
| 165 | 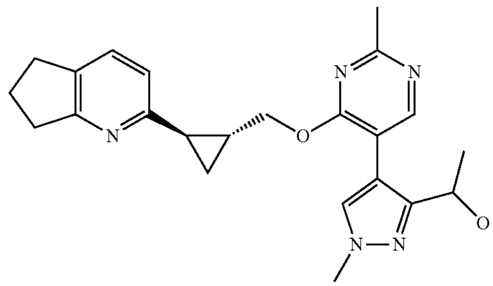 [SMILES: Cc1ncc(-c2cn(C)nc2C(C)O)c(OC[C@@H]2C[C@H]2c2ccc3c(n2)CCC3)n1] | 1-(4-(4-(((1R,2R)-2-(6,7-dihydro-5H-cyclopenta[b]pyridin-2-yl)cyclopropyl)methoxy)-2-methylpyrimidin-5-yl)-1-methyl-1H-pyrazol-3-yl)ethanol(enantiomer A, S or R) | 406.2 |
| 166 | 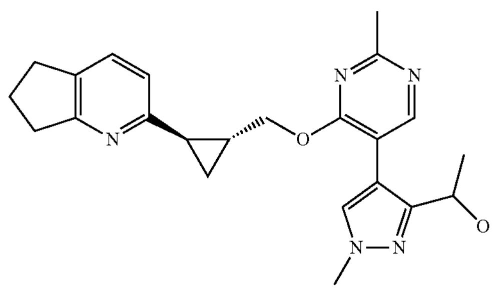 [SMILES: Cc1ncc(-c2cn(C)nc2C(C)O)c(OC[C@@H]2C[C@H]2c2ccc3c(n2)CCC3)n1] | 1-(4-(4-(((1R,2R)-2-(6,7-dihydro-5H-cyclopenta[b]pyridin-2-yl)cyclopropyl)methoxy)-2-methylpyrimidin-5-yl)-1-methyl-1H-pyrazol-3-yl)ethanol(enantiomer B, R or S) | 406.2 |
| 167 | 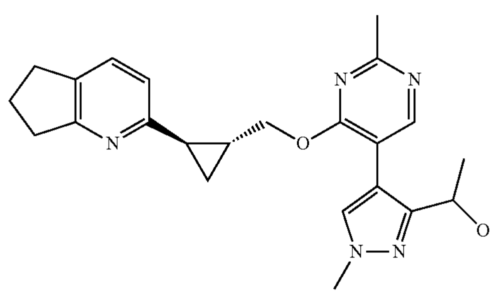 [SMILES: Cc1ncc(-c2cn(C)nc2C(C)O)c(OC[C@@H]2C[C@H]2c2ccc3c(n2)CCC3)n1] | 1-(4-(4-(((1R,2R)-2-(6,7-dihydro-5H-cyclopenta[b]pyridin-2-yl)cyclopropyl)methoxy)-2-methylpyrimidin-5-yl)-1-methyl-1H-pyrazol-3-yl)ethanol(enantiomer B, S or R) | 406.2 |
| 168 | 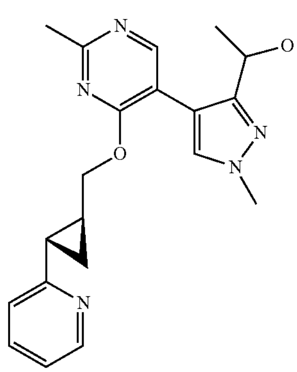 [SMILES: Cc1ncc(-c2cn(C)nc2C(C)O)c(OC[C@H]2C[C@@H]2c2ccccn2)n1] | 1-(1-methyl-4-(2-methyl-4-(((1S,2S)-2-(pyridin-2-yl)cyclopropyl)methoxy)pyrimidin-5-yl)-1H-pyrazol-3-yl)ethanol(R or S) | 366.2 |

TABLE 10-continued
| Example | Structure | Name | MS m/z (M + H) |
|---|---|---|---|
| 169 | 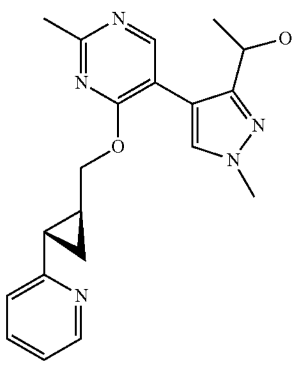 [SMILES: Cc1ncc(-c2cn(C)nc2C(C)O)c(OC[C@H]2C[C@@H]2c2ccccn2)n1] | 1-(1-methyl-4-(2-methyl-4-(((1S,2S)-2-(pyridin-2-yl)cyclopropyl)methoxy)pyrimidin-5-yl)-1H-pyrazol-3-yl)ethanol(S or R) | 366.2 |
| 170 | 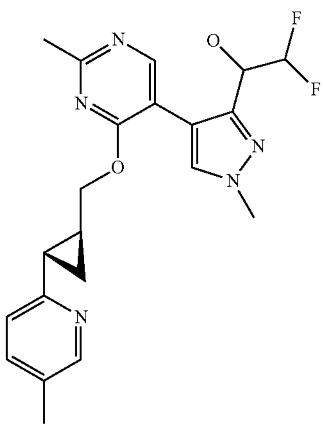 [SMILES: Cc1ccc([C@H]2C[C@@H]2COc2nc(C)ncc2-c2cn(C)nc2C(O)C(F)F)nc1] | 2,2-difluoro-1-(1-methyl-4-(2-methyl-4-(((1S,2S)-2-(5-methylpyridin-2-yl)cyclopropyl)methoxy)pyrimidin-5-yl)-1H-pyrazol-3-yl)ethanol | 416.2 |
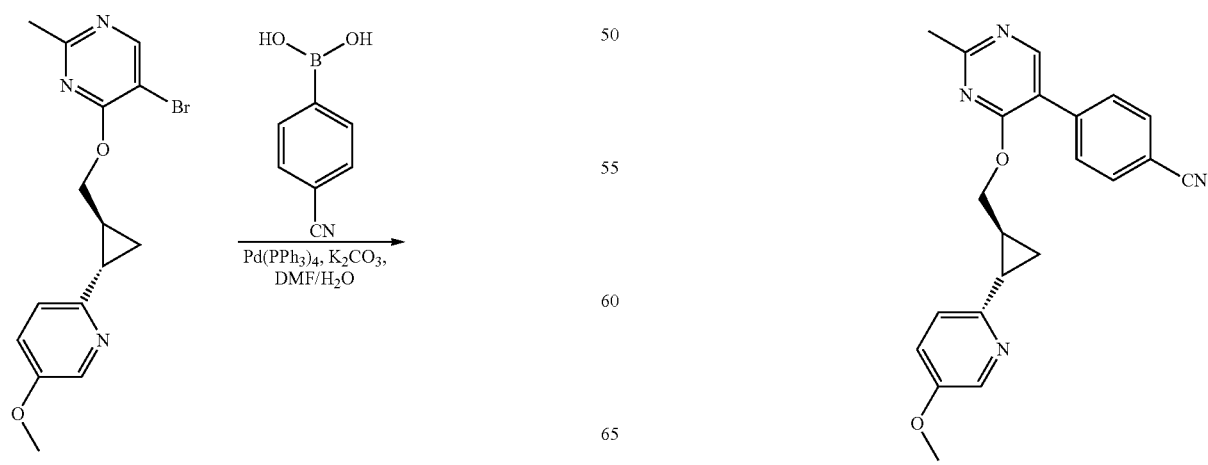
SCHEME 16
-continued

151

Example 171

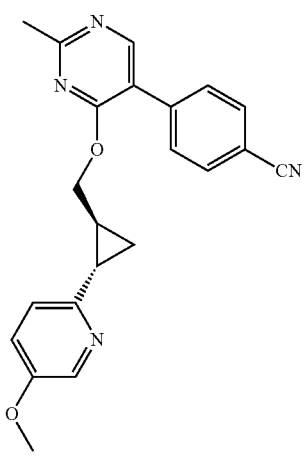 [SMILES: COc1ccc([C@H]2C[C@@H]2COc2nc(C)ncc2-c2ccc(C#N)cc2)nc1]

152

Step A: 4-(4-((((1S,2S)-2-(5-methoxypyridin-2-yl)cyclopropyl)methoxy)-2-methylpyrimidin-5-yl)benzonitrile (Example 171)

A mixture of 5-bromo-4-(((1S,2S)-2-(5-methoxypyridin-2-yl)cyclopropyl)methoxy)-2-methylpyrimidine (1 g, 2.9 mmol), 4-cyanophenylboronic acid (546 mg, 3.7 mmol), Pd(PPh$_3$)$_4$ (297 mg, 0.26 mmol), and K$_2$CO$_3$ (1.18 g, 8.7 mmol) was heated at 100° C. for overnight. The reaction mixture was diluted with EtOAc (200 mL), washed with sat. aq. NaHCO$_3$ (250 mL) and brine (250 mL), dried over MgSO$_4$, filtered, and concentrated in vacuo. The resulting residue was purified by gradient elution on silica gel (20 to 50% EtOAc in hexanes) to afford the title compound as a white solid (1.1 g, 90%). $^1$H NMR (500 MHz, CD3OD) δ 8.35 (s, 1H), 7.95 (d, 1H), 7.67 (td, 4H), 7.19 (dd, 1H), 7.05 (d, 1H), 4.49 (dd, 1H), 4.32 (dd1H), 3.74 (s, 3H), 2.53 (s, 3H), 2.07-1.99 (m, 1H), 1.69 (d, 1H), 1.16-1.09 (m, 1H), 1.04-0.95 (m, 1H); MS m/z=373 (M+H).

The following EXAMPLE 171-183 in Table 11 was prepared using the procedure of EXAMPLE 171, substituting the appropriate starting materials.

TABLE 11

| Example | Structure | Name | MS m/z (M + H) |
|---|---|---|---|
| 171 | 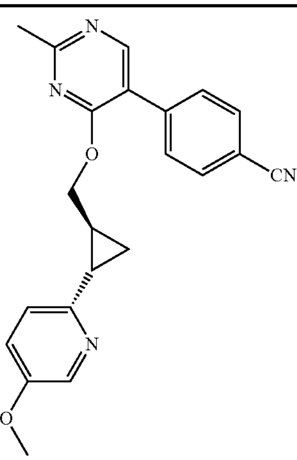 | 4-(4-(((1S,2S)-2-(5-methoxypyridin-2-yl)cyclopropyl)methoxy)-2-methylpyrimidin-5-yl)benzonitrile | 373.3 |
| 172 | 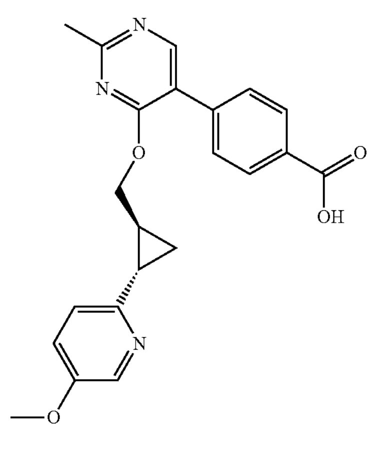 [SMILES: COc1ccc([C@H]2C[C@@H]2COc2nc(C)ncc2-c2ccc(C(=O)O)cc2)nc1] | 4-(4-(((1S,2S)-2-(5-methoxypyridin-2-yl)cyclopropyl)methoxy)-2-methylpyrimidin-5-yl)benzoic acid | 392.2 |

TABLE 11-continued

| Example | Structure | Name | MS m/z (M + H) |
|---|---|---|---|
| 173 | 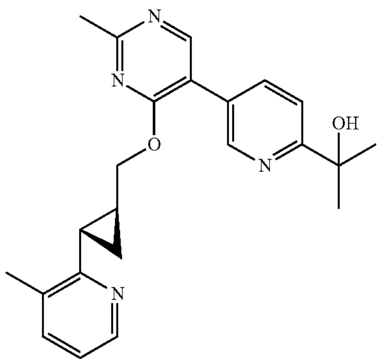 [SMILES: Cc1ncc(-c2ccc(C(C)(C)O)nc2)c(OC[C@H]2C[C@@H]2c2ncccc2C)n1] | 2-(5-(2-methyl-4-(((1S,2S)-2-(3-methylpyridin-2-yl)cyclopropyl)methoxy)pyrimidin-5-yl)pyridin-2-yl)propan-2-ol (enantiomer B) | 390.7 |
| 174 | 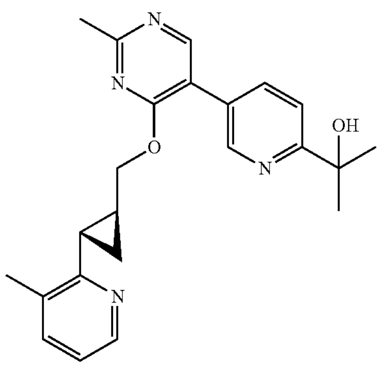 [SMILES: Cc1ncc(-c2ccc(C(C)(C)O)nc2)c(OC[C@H]2C[C@@H]2c2ncccc2C)n1] | 2-(5-(2-methyl-4-(((1S,2S)-2-(3-methylpyridin-2-yl)cyclopropyl)methoxy)pyrimidin-5-yl)pyridin-2-yl)propan-2-ol (enantiomer A) | 390.7 |
| 175 | 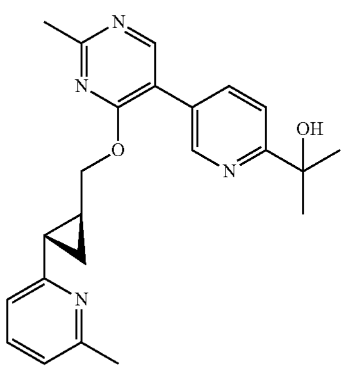 [SMILES: Cc1cccc([C@H]2C[C@@H]2COc2nc(C)ncc2-c2ccc(C(C)(C)O)nc2)n1] | 2-(5-(2-methyl-4-(((1S,2S)-2-(6-methylpyridin-2-yl)cyclopropyl)methoxy)pyrimidin-5-yl)pyridin-2-yl)propan-2-ol (enantiomer A) | 391.0 |
| 176 | 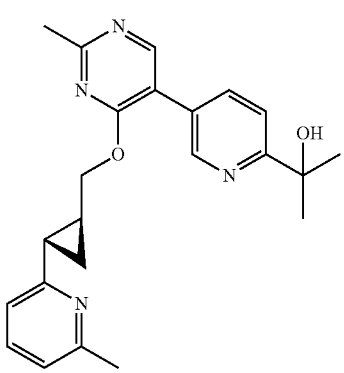 [SMILES: Cc1cccc([C@H]2C[C@@H]2COc2nc(C)ncc2-c2ccc(C(C)(C)O)nc2)n1] | 2-(5-(2-methyl-4-(((1S,2S)-2-(6-methylpyridin-2-yl)cyclopropyl)methoxy)pyrimidin-5-yl)pyridin-2-yl)propan-2-ol (1R,2R,mixture) | 391.0 |

TABLE 11-continued

| Example | Structure | Name | MS m/z (M + H) |
|---|---|---|---|
| 177 | 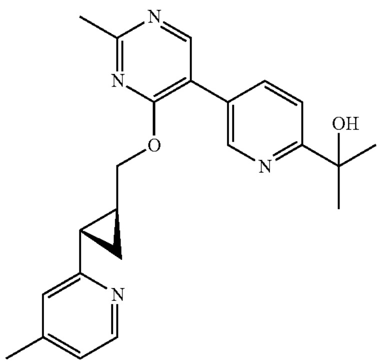 [SMILES: Cc1ccnc([C@H]2C[C@@H]2COc2nc(C)ncc2-c2ccc(C(C)(C)O)nc2)c1] | 2-(5-(2-methyl-4-(((1S,2S)-2-(4-methylpyridin-2-yl)cyclopropyl)methoxy)pyrimidin-5-yl)pyridin-2-yl)propan-2-ol (enantiomer A) | 391.1 |
| 178 | 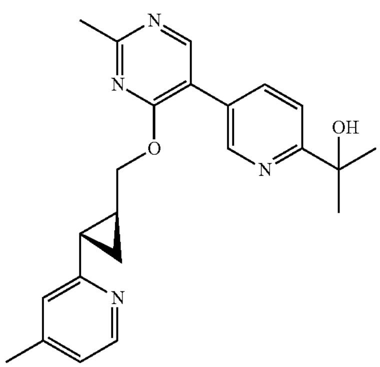 [SMILES: Cc1ccnc([C@H]2C[C@@H]2COc2nc(C)ncc2-c2ccc(C(C)(C)O)nc2)c1] | 2-(5-(2-methyl-4-(((1S,2S)-2-(4-methylpyridin-2-yl)cyclopropyl)methoxy)pyrimidin-5-yl)pyridin-2-yl)propan-2-ol (enantiomer B) | 391.1 |
| 179 | 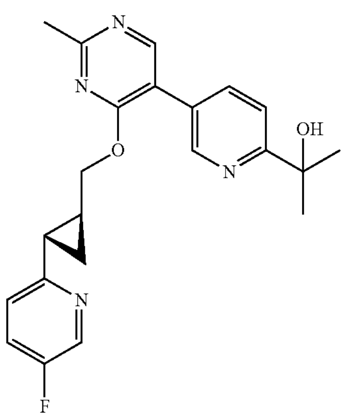 [SMILES: Cc1ncc(-c2ccc(C(C)(C)O)nc2)c(OC[C@H]2C[C@@H]2c2ccc(F)cn2)n1] | 2-(5-(4-(((1S,2S)-2-(5-fluoropyridin-2-yl)cyclopropyl)methoxy)-2-methylpyrimidin-5-yl)pyridin-2-yl)propan-2-ol | 394.5 |
| 180 | 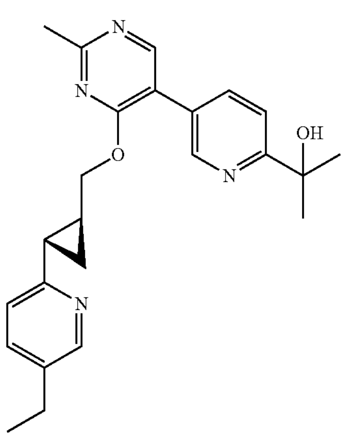 [SMILES: CCc1ccc([C@H]2C[C@@H]2COc2nc(C)ncc2-c2ccc(C(C)(C)O)nc2)nc1] | 2-(5-(4-(((1S,2S)-2-(5-ethylpyridin-2-yl)cyclopropyl)methoxy)-2-methylpyrimidin-5-yl)pyridin-2-yl)propan-2-ol (enantiomer A) | 405.2 |

TABLE 11-continued

| Example | Structure | Name | MS m/z (M + H) |
|---|---|---|---|
| 181 | 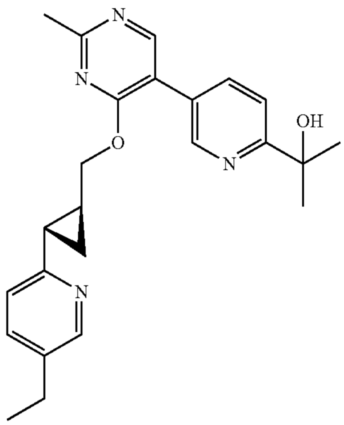 [SMILES: CCc1ccc([C@H]2C[C@@H]2COc2nc(C)ncc2-c2ccc(C(C)(C)O)nc2)nc1] | 2-(5-(4-(((1S,2S)-2-(5-ethylpyridin-2-yl)cyclopropyl)methoxy)-2-methylpyrimidin-5-yl)pyridin-2-yl)propan-2-ol (enantiomer B) | 405.2 |
| 182 | 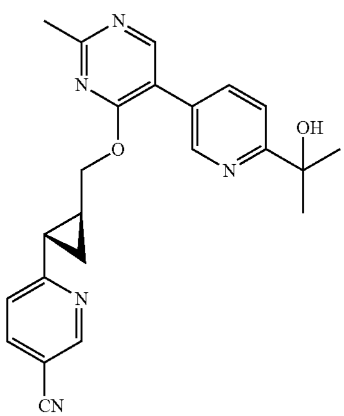 [SMILES: Cc1ncc(-c2ccc(C(C)(C)O)nc2)c(OC[C@H]2C[C@@H]2c2ccc(C#N)cn2)n1] | 6-(((1S,2S)-2-((5-(6-(2-hydroxypropan-2-yl)pyridin-3-yl)-2-methylpyrimidin-4-yloxy)methyl)cyclopropyl)nicotinonitrile | 402.2 |
| 183 | 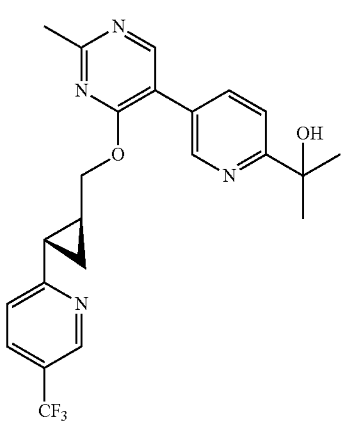 [SMILES: Cc1ncc(-c2ccc(C(C)(C)O)nc2)c(OC[C@H]2C[C@@H]2c2ccc(C(F)(F)F)cn2)n1] | 2-(5-(2-methyl-4-(((1S,2S)-2-(5-(trifluoromethyl)pyridin-2-yl)cyclopropyl)methoxy)pyrimidin-5-yl)pyridin-2-yl)propan-2-ol | 445.1 |

SCHEME 17
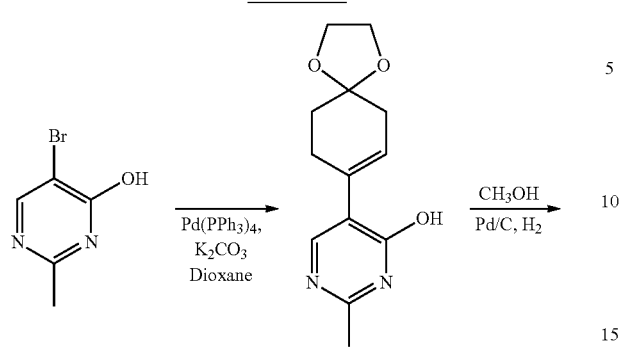
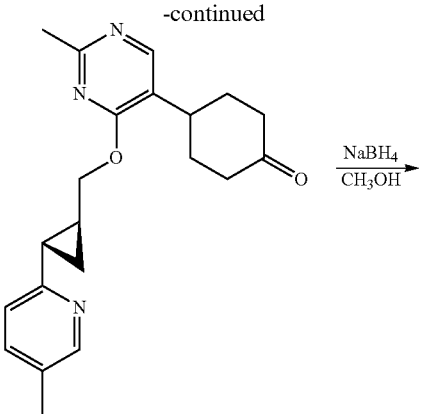
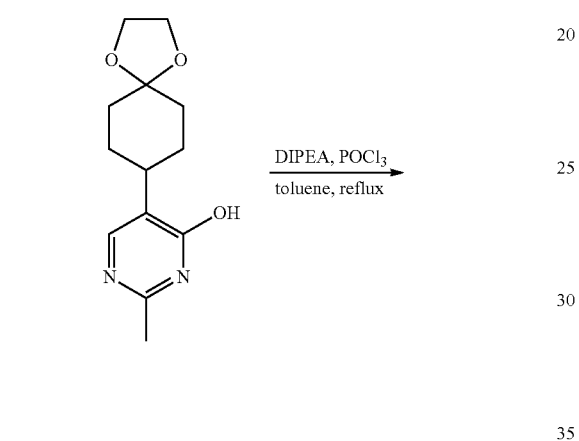
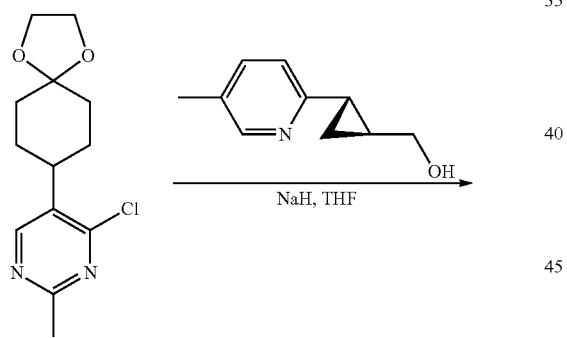
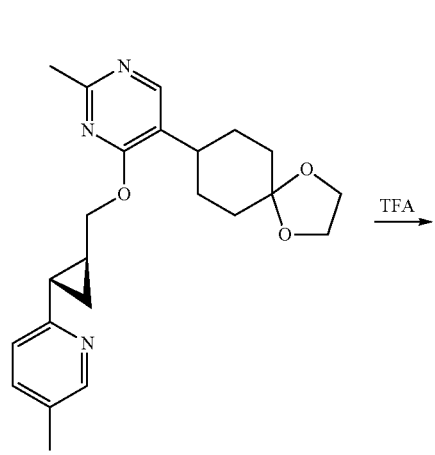
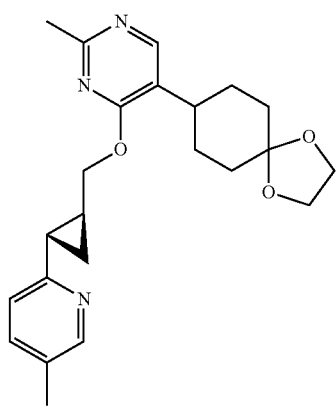 [SMILES: Cc1ccc([C@H]2C[C@@H]2COc2nc(C)ncc2C2CCC3(CC2)OCCO3)nc1]
Example 184
2-methyl-4-(((1S,2S)-2-(5-methylpyridin-2-yl)cyclopropyl)methoxy)-5-(1,4-dioxaspiro[4.5]decan-8-yl)pyrimidine Step A: 2-methyl-5-(1,4-dioxaspiro[4.5]dec-7-en-8-yl)pyrimidin-4-ol

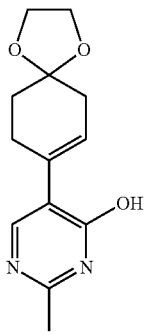

A mixture of 5-bromo-2-methylpyrimidin-4-ol (100 mg, 0.53 mmol), 4,4,5,5-tetramethyl-2-(1,4-dioxaspiro[4.5]dec-7-en-8-yl)-1,3,2-dioxaborolane (155 mg, 0.59 mmol), $K_2CO_3$ (146 mg, 1.06 mmol), $Pd(PPh_3)_4$ (31 mg, 0.026 mmol) in Dioxane (4 mL) and water (1 mL) was stirred at 100° C. for 16 hours. Then the reaction mixture was allowed to cool to ambient temperature and diluted with EA (10 mL) which was washed with water (10 mL), dried and concentrated. The resulting residue was purified by column (PE: EA=8:1) to afford the product (35 mg, 27%) as a white solid: LC/MS m/z=249.1 $(M+H)^+$.

Step B: 2-Methyl-5-(1,4-dioxaspiro[4.5]decan-8-yl)pyrimidin-4-ol

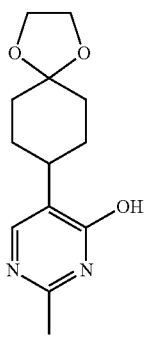 [SMILES: Cc1ncc(C2CCC3(CC2)OCCO3)c(O)n1]

A solution of 2-methyl-5-(1,4-dioxaspiro[4.5]dec-7-en-8-yl)pyrimidin-4-ol (500 mg, 2.0 mmol) in $CH_3OH$ (10 mL) was treated with Pd/C (50 mg) under $H_2$ and stirred overnight at room temperature. The reaction mixture was filtered and concentrated to afford title product (430 mg, 86%) as a white solid: LC/MS m/z=251.1 $(M+H)^+$.

Step C: 4-Chloro-2-methyl-5-(1,4-dioxaspiro[14.5]decan-8-yl)pyrimidine

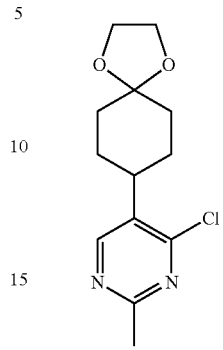

To a solution 2-methyl-5-(1,4-dioxaspiro[4.5]decan-8-yl)pyrimidin-4-ol (1) (200 mg, 0.8 mmol) in toluene (5 mL) was slowly added $POCl_3$ (0.15 mL, 1.6 mmol) and DIPEA (0.4 mL, 2.4 mmol). The resulting mixture was allowed to stir at 110° C. for 3 hours. The reaction mixture was concentrated and neutralized with aqueous $NaHCO_3$, extracted with EtOAc (2×20 mL), dried over $Na_2SO_4$, filtered and concentrated. The crude residue was purified by column chromatography to afford the title compound (160 mg, 75%) as a yellow solid: LC/MS m/z=269.1 $(M+H)^+$.

Step D: 2-Methyl-4-(((1S,2S)-2-(5-methylpyridin-2-yl)cyclopropyl)methoxy)-5-(1,4-dioxaspiro[4.5]-decan-8-yl)pyrimidine

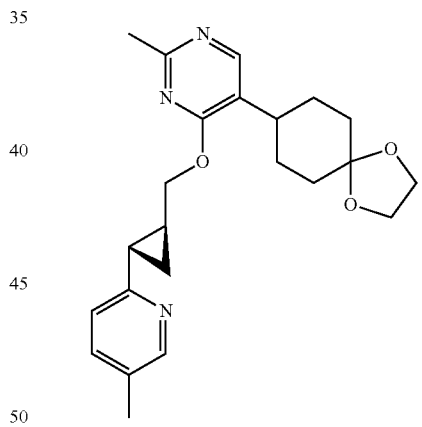

To a solution ((1S,2S)-2-(pyridin-2-yl)cyclopropyl)methanol (88 mg, 0.59 mmol) and NaH (28 mg, 0.7 mmol) in THF (3 mL) at 0° C. was slowly added 4-chloro-2-methyl-5-(1,4-dioxaspiro[4.5]decan-8-yl)pyrimidine (157 mg, 0.59 mmol). The resulting mixture was allowed to warm to room temperature and stirred at the same temperature for 1 hour. The reaction mixture was concentrated and neutralized with aqueous $Na_2CO_3$, extracted with EtOAc (2×25 mL), dried over $Na_2SO_4$, filtered and concentrated. The crude residue was purified by column chromatography (PE: EA=1:1) to afford the title compound (101 mg, 77%) as a colorless oil: $^1H$ NMR (400 MHz, $CDCl_3$) δ 8.17 (s, 1H), 7.42 (t, 1H), 6.90 (t, 2H), 4.41 (d, 2H), 3.97 (s, 4H), 2.75 (m, 1H), 2.55 (s, 3H), 2.48 (s, 3H), 2.17 (s, 1H), 2.09 (s, 1H), 1.87 (t, 4H), 1.70 (m, 4H), 1.36 (m, 1H), 1.08 (m, 1H); LC/MS m/z=396.2 $[M+H]^+$

Example 185

4-(2-Methyl-4-(((1S,2S)-2-(5-methylpyridin-2-yl)cyclopropyl)methoxy)pyrimidin-5-yl)cyclohexanone

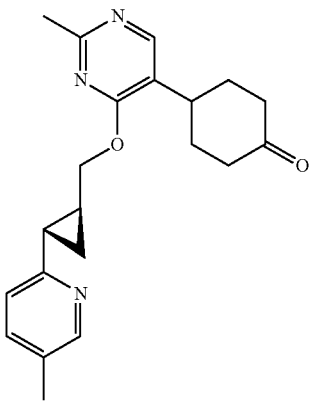 [SMILES: Cc1ccc([C@H]2C[C@@H]2COc2nc(C)ncc2C2CCC(=O)CC2)nc1]

Step A: 4-(2-Methyl-4-(((1S,2S)-2-(5-methylpyridin-2-yl)cyclopropyl)methoxy)pyrimidin-5-yl)cyclohexanone A mixture of 2-methyl-4-(((1S,2S)-2-(pyridin-2-yl)cyclopropyl)methoxy)-5-(1,4-dioxaspiro[4.5]decan-8-yl)pyrimidine (186 mg, 0.48 mmol), trifluoroacetic acid (2 mL) was stirred at room temperature for 30 minutes. The reaction mixture was concentrated and the resulting residue was purified by flash chromatography (25% to 100% EtOAc in petroleum) to afford the title compound as white foam (106 mg, 64.2%). LC/MS m/z=352.1 [M+H]$^+$. The following EXAMPLE 184-203 in Table 12 was prepared using the procedure of EXAMPLE 184, substituting the appropriate starting materials.

TABLE 12

| Example | Structure | IUPAC Name | LCMS m/z [M + H]$^+$ |
| --- | --- | --- | --- |
| 184 | 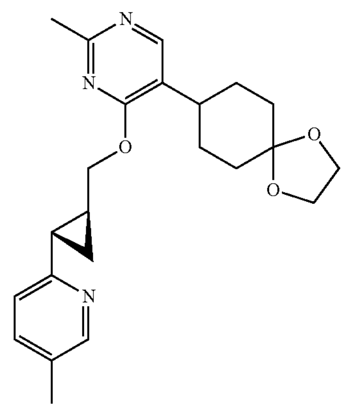 [SMILES: Cc1ccc([C@H]2C[C@@H]2COc2nc(C)ncc2C2CCC3(CC2)OCCO3)nc1] | 2-methyl-4-(((1S,2S)-2-(5-methylpyridin-2-yl)cyclopropyl)methoxy)-5-(1,4-dioxaspiro[4.5]decan-8-yl)pyrimidine | 396.1 |
| 185 | 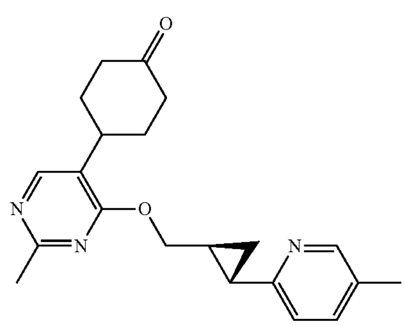 [SMILES: Cc1ccc([C@H]2C[C@@H]2COc2nc(C)ncc2C2CCC(=O)CC2)nc1] | 4-(2-methyl-4-(((1S,2S)-2-(5-methylpyridin-2-yl)cyclopropyl)methoxy)pyrimidin-5-yl)cyclohexanone | 352.1 |

TABLE 12-continued

| Example | Structure | IUPAC Name | LCMS m/z [M + H]+ |
|---|---|---|---|
| 186 | 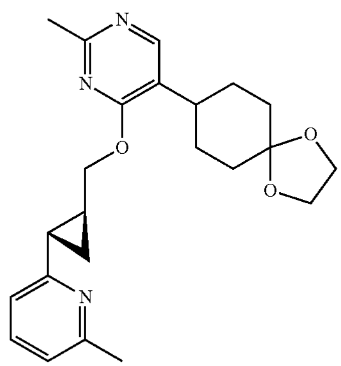 [SMILES: Cc1cccc([C@H]2C[C@@H]2COc2nc(C)ncc2C2CCC3(CC2)OCCO3)n1] | 2-methyl-4-(((1S,2S)-2-(6-methylpyridin-2-yl)cyclopropyl)methoxy)-5-(1,4-dioxaspiro[4.5]decan-8-yl)pyrimidine | 396.1 |
| 187 | 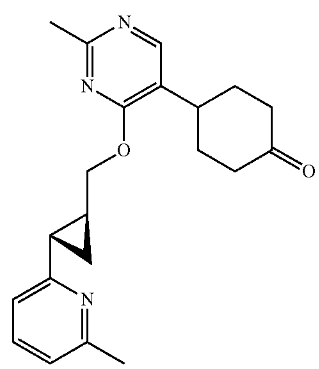 [SMILES: Cc1cccc([C@H]2C[C@@H]2COc2nc(C)ncc2C2CCC(=O)CC2)n1] | 4-(2-methyl-4-(((1S,2S)-2-(6-methylpyridin-2-yl)cyclopropyl)methoxy)pyrimidin-5-yl)cyclohexanone | 352.1 |
| 188 | 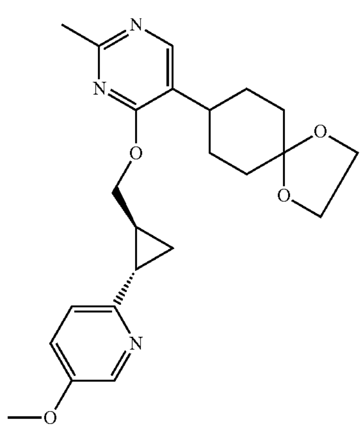 [SMILES: COc1ccc([C@H]2C[C@@H]2COc2nc(C)ncc2C2CCC3(CC2)OCCO3)nc1] | 4-(((1S,2S)-2-(5-methoxypyridin-2-yl)cyclopropyl)methoxy)-2-methyl-5-(1,4-dioxaspiro[4.5]decan-8-yl)pyrimidine | 412.1 |
| 189 | 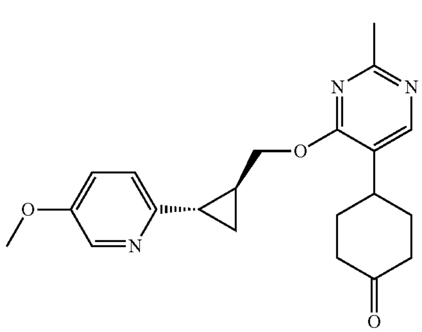 [SMILES: COc1ccc([C@H]2C[C@@H]2COc2nc(C)ncc2C2CCC(=O)CC2)nc1] | 4-(4-(((1S,2S)-2-(5-methoxypyridin-2-yl)cyclopropyl)methoxy)-2-methylpyrimidin-5-yl)cyclohexanone | 368.1 |

TABLE 12-continued

| Example | Structure | IUPAC Name | LCMS m/z [M + H]+ |
|---|---|---|---|
| 190 | 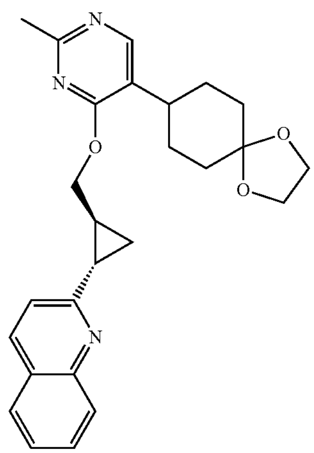 [SMILES: Cc1ncc(C2CCC3(CC2)OCCO3)c(OC[C@H]2C[C@@H]2c2ccc3ccccc3n2)n1] | 2-((1S,2S)-2-((2-methyl-5-(1,4-dioxaspiro[4.5]decan-8-yl)pyrimidin-4-yloxy)methyl)cyclopropyl)quinoline | 432.1 |
| 191 | 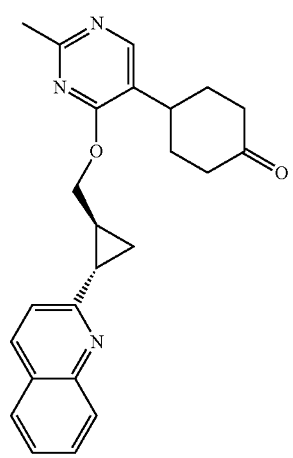 [SMILES: Cc1ncc(C2CCC(=O)CC2)c(OC[C@H]2C[C@@H]2c2ccc3ccccc3n2)n1] | 4-(2-methyl-4-(((1S,2S)-2-(quinolin-2-yl)cyclopropyl)methoxy)pyrimidin-5-yl)cyclohexanone | 388.1 |
| 192 | 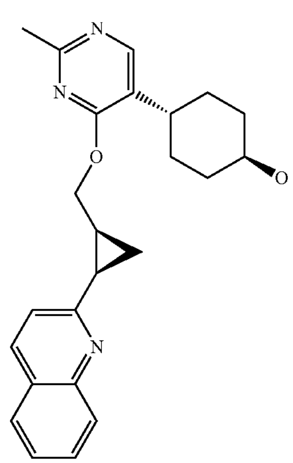 [SMILES: Cc1ncc([C@H]2CC[C@H](O)CC2)c(OC[C@H]2C[C@H]2c2ccc3ccccc3n2)n1] | Trans-4-(2-methyl-4-(((1S,2R)-2-(quinolin-2-yl)cyclopropyl)methoxy)pyrimidin-5-yl)cyclohexanol | 390.1 |

TABLE 12-continued

| Example | Structure | IUPAC Name | LCMS m/z [M + H]+ |
|---|---|---|---|
| 193 | 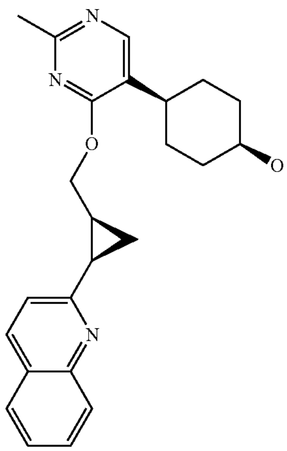 [SMILES: Cc1ncc([C@H]2CC[C@@H](O)CC2)c(OC[C@H]2C[C@H]2c2ccc3ccccc3n2)n1] | (1R,4s)-4-(2-methyl-4-(((1S,2R)-2-(quinolin-2-yl)cyclopropyl)methoxy)pyrimidin-5-yl)cyclohexanol | 390.1 |
| 194 | 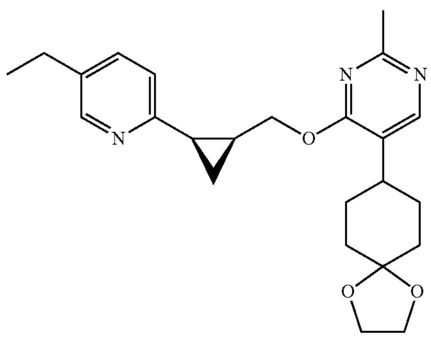 [SMILES: CCc1ccc([C@@H]2C[C@@H]2COc2nc(C)ncc2C2CCC3(CC2)OCCO3)nc1] | 4-(((1S,2R)-2-(5-ethylpyridin-2-yl)cyclopropyl)methoxy)-2-methyl-5-(1,4-dioxaspiro[4.5]decan-8-yl)pyrimidine | 410.1 |
| 195 | 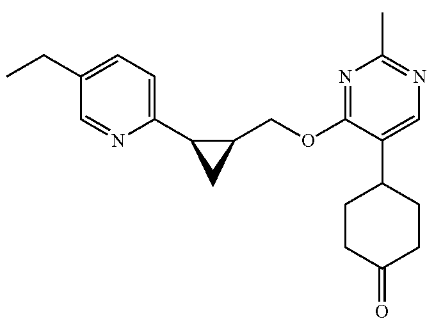 [SMILES: CCc1ccc([C@@H]2C[C@@H]2COc2nc(C)ncc2C2CCC(=O)CC2)nc1] | 4-(4-(((1S,2R)-2-(5-ethylpyridin-2-yl)cyclopropyl)methoxy)-2-methylpyrimidin-5-yl)cyclohexanone | 366.1 |
| 196 | 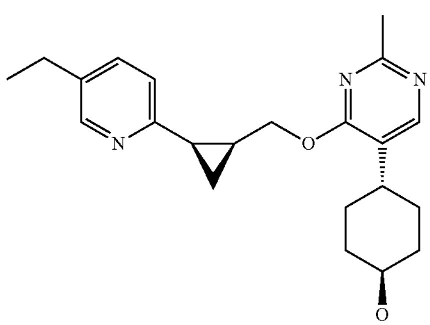 [SMILES: CCc1ccc([C@@H]2C[C@@H]2COc2nc(C)ncc2[C@H]2CC[C@H](O)CC2)nc1] | Trans-4-(4-(((1S,2R)-2-(5-ethylpyridin-2-yl)cyclopropyl)methoxy)-2-methylpyrimidin-5-yl)cyclohexanol | 368.1 |

TABLE 12-continued

| Example | Structure | IUPAC Name | LCMS m/z [M + H]+ |
|---|---|---|---|
| 197 | 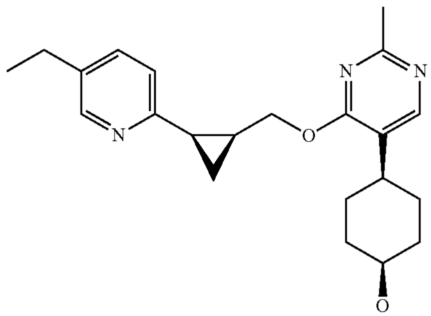 [SMILES: CCc1ccc([C@@H]2C[C@@H]2COc2nc(C)ncc2[C@H]2CC[C@@H](O)CC2)nc1] | (1R,4s)-4-(4-(((1S,2R)-2-(5-ethylpyridin-2-yl)cyclopropyl)methoxy)-2-methylpyrimidin-5-yl)cyclohexanol | 368.1 |
| 198 | 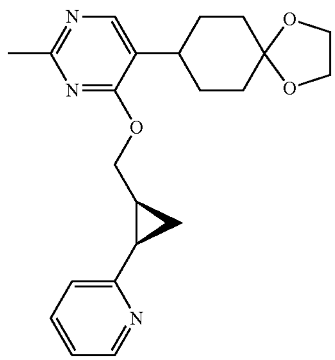 [SMILES: Cc1ncc(C2CCC3(CC2)OCCO3)c(OC[C@H]2C[C@H]2c2ccccn2)n1] | 2-methyl-4-(((1S,2R)-2-(pyridin-2-yl)cyclopropyl)methoxy)-5-(1,4-dioxaspiro[4.5]decan-8-yl)pyrimidine | 382.1 |
| 199 | 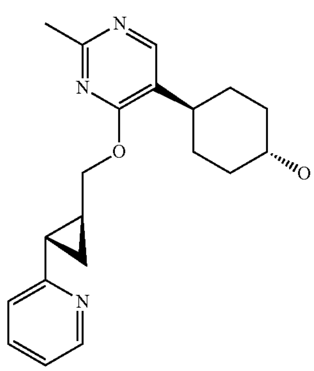 [SMILES: Cc1ncc([C@H]2CC[C@H](O)CC2)c(OC[C@H]2C[C@@H]2c2ccccn2)n1] | Trans-4-(2-methyl-4-(((1S,2S)-2-(pyridin-2-yl)cyclopropyl)methoxy)pyrimidin-5-yl)cyclohexanol | 340.1 |
| 200 | 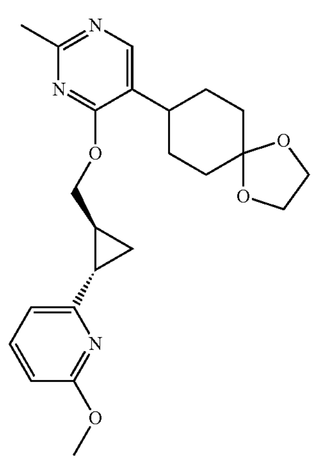 [SMILES: COc1cccc([C@H]2C[C@@H]2COc2nc(C)ncc2C2CCC3(CC2)OCCO3)n1] | 4-(((1S,2S)-2-(6-methoxypyridin-2-yl)cyclopropyl)methoxy)-2-methyl-5-(1,4-dioxaspiro[4.5]decan-8-yl)pyrimidine | 412.1 |

TABLE 12-continued

| Example | Structure | IUPAC Name | LCMS m/z [M + H]+ |
|---|---|---|---|
| 201 | 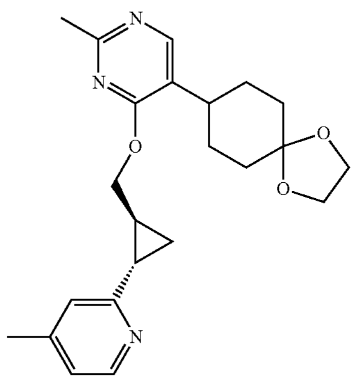 [SMILES: Cc1ccnc([C@H]2C[C@@H]2COc2nc(C)ncc2C2CCC3(CC2)OCCO3)c1] | 2-methyl-4-(((1S,2S)-2-(4-methylpyridin-2-yl)cyclopropyl)methoxy)-5-(1,4-dioxaspiro[4.5]decan-8-yl)pyrimidine | 396.1 |
| 202 | 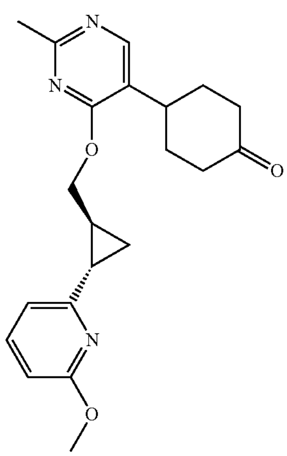 [SMILES: COc1cccc([C@H]2C[C@@H]2COc2nc(C)ncc2C2CCC(=O)CC2)n1] | 4-(4-(((1S,2S)-2-(6-methoxypyridin-2-yl)cyclopropyl)methoxy)-2-methylpyrimidin-5-yl)cyclohexanone | 368.1 |
| 203 | 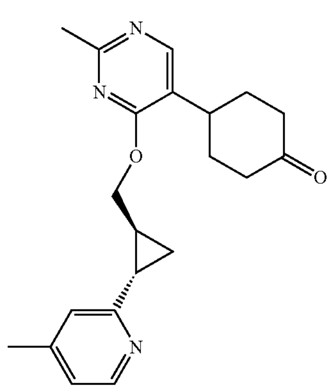 [SMILES: Cc1ccnc([C@H]2C[C@@H]2COc2nc(C)ncc2C2CCC(=O)CC2)c1] | 4-(2-methyl-4-(((1S,2S)-2-(4-methylpyridin-2-yl)cyclopropyl)methoxy)pyrimidin-5-yl)cyclohexanone | 352.1 |

SCHEME 18

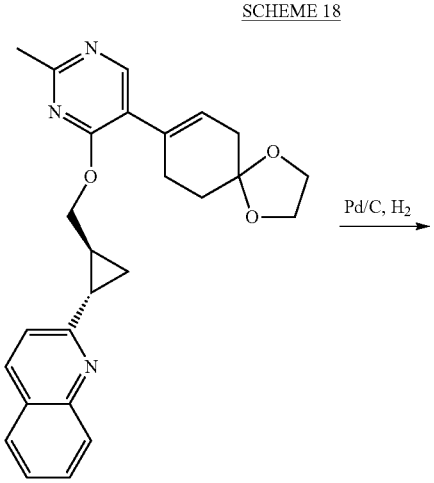

1

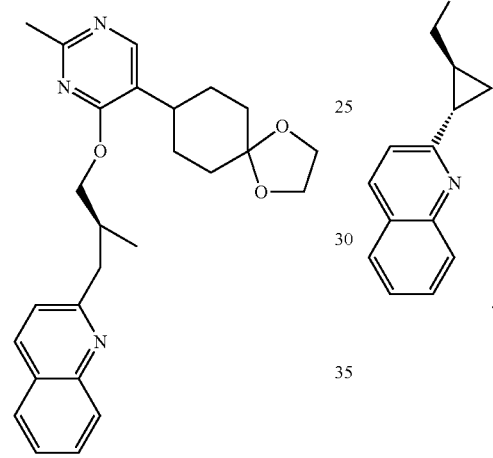

2

Example 204

Step A: 2-((2S)-2-methyl-3-(2-methyl-5-(1,4-dioxaspiro[4.5]decan-8-yl)pyrimidin-4 yloxy)propyl)quinoline

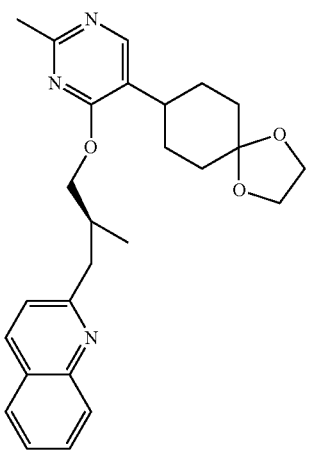 [SMILES: Cc1ncc(C2CCC3(CC2)OCCO3)c(OC[C@@H](C)Cc2ccc3ccccc3n2)n1]

To 2-((1S,2S)-2-((2-methyl-5-(1,4-dioxaspiro[4.5]dec-7-en-8-yl)pyrimidin-4-yloxy)methyl)cyclopropyl)quinoline (400 mg, 0.93 mmol) in ethanol (18 mL) was carefully added 10% palladium on carbon (90 mg, 0.09 mmol) under nitrogen. The reaction mixture was evacuated and backfilled three times with hydrogen via balloon and then stirred at 40° C. for 20 h. Upon completion, the mixture was filtered through celite washing with methanol and concentrated in vacuum. The mixture was purified by reverse phase chromatography (Waters Sunfire Prep C18OBD, 5-60% acetonitrile in water with 0.1% TFA modifier) to afford the product as a white solid (15 mg, 4% yield): $^1$H NMR (400 MHz, MeOD) δ 8.18 (d, 1H), 7.99 (s, 1H), 7.88 (d, 1H), 7.82 (d, 1H), 7.65 (dd, 1H), 7.48 (t, 1H), 7.39 (d, 1H), 4.35 (m, 2H), 3.85 (s, 4H), 3.11 (dd, 1H), 2.92 (dd, 1H), 2.60 (td, 1H), 2.41 (d, 4H), 1.71 (d, 4H), 1.64 (dd, 2H), 1.48 (m, 2H), 1.05 (d, 3H); LC/MS m/z=434.2 [M+H]$^+$

SCHEME 19

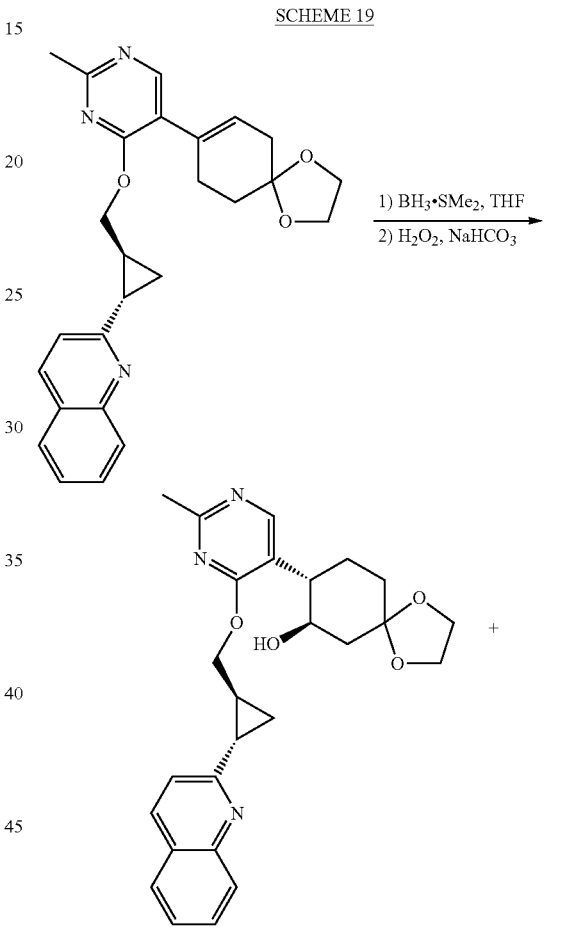

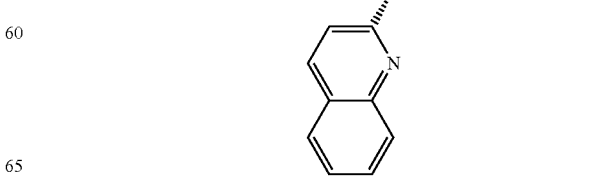

Example 205 and 206

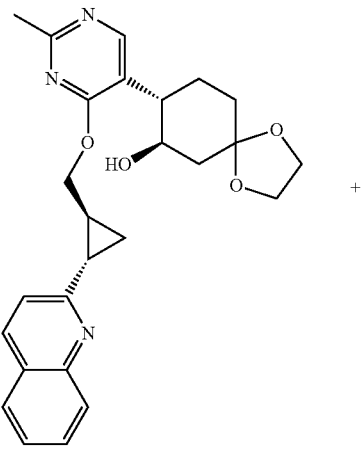

+

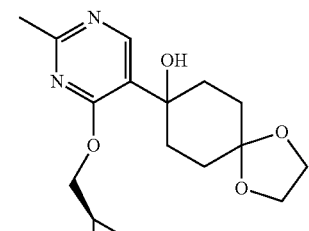

Step A: (7R,8S)-8-(2-Methyl-4-(((1S,2S)-2-(quinolin-2-yl)cyclopropyl)methoxy)pyrimidin-5-yl)-1,4-dioxaspiro[4.5]decan-7-ol (Example 205) and 8-(2-Methyl-4-(((1S,2S)-2-(quinolin-2-yl)cyclopropyl)methoxy)pyrimidin-5-yl)-1,4-dioxaspiro[4.5]decan-8-ol (Example 206)

Borane dimethylsulfide complex (72 mg, 0.95 mmol) was added dropwise via stirring at rt to a solution of compound 1-10 (80 mg, 0.19 mmol) in anhydrous THF (5 ml). The reaction was stirred at rt for 3 hours. Aqueous solution of $H_2O_2$ (0.83 ml, 28%) was added slowly at rt for 2 min. A saturated solution of sodium bicarbonate (4 mL) was added. The mixture was stirred at rt for another 15 min. The mixture was extracted with EtOAc (3×10 mL). The combined organics were dried over $MgSO_4$, filtered and concentrated in vacuum. The mixture was purified by reverse phase chromatography (Waters Sunfire Prep C18OBD, 5-60% acetonitrile in water with 0.1% TFA modifier) to afford example 205 as a white solid (10 mg, 11.8% yield) and example 206 as a white solid (10 mg, 11.8% yield).

Example 205

$^1$H NMR (400 MHz, MeOD) δ 8.20 (m, 2H), 7.95 (d, 1H), 7.86 (d, 1H), 7.70 (m, 1H), 7.51 (t, 1H), 7.35 (dd, 1H), 4.65 (m, 1H), 4.40 (m, 1H), 4.14 (m, 1H), 3.90-3.55 (m, 4H), 2.64 (m, 1H), 2.55 (s, 3H), 2.41 (brs, 1H), 2.04 (m, 2H), 1.90 (m, 1H), 1.74 (m, 5H), 1.32 (m, 1H); LC/MS m/z=448.2 [M+H]$^+$.

Example 206

$^1$H NMR (400 MHz, MeOD) δ 8.53 (s, 1H), 8.19 (d, 1H), 7.95 (d, 1H), 7.86 (d, 1H), 7.70 (t, 1H), 7.51 (t, 1H), 7.35 (d, 1H), 4.69 (dd, 1H), 4.43 (dd, 1H), 3.78 (m, 1H), 3.65 (m, 2H), 3.40 (m, 1H), 2.68 (m, 2H), 2.57 (s, 3H), 2.40 (m, 1H), 2.10 (m, 1H), 1.95 (m, 2H), 1.55 (m, 4H), 1.36 (m, 2H); LC/MS m/z=448.2 [M+H]$^+$.

TABLE 14

| Example | Structure | IUPAC Name | LCMS m/z [M + H] |
|---|---|---|---|
| 205 | 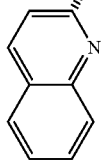 | (7R,8S)-8-(2-methyl-4-(((1S,2S)-2-(quinolin-2-yl)cyclopropyl)methoxy)pyrimidin-5-yl)-1,4-dioxaspiro[4.5]decan-7-ol | 448.2 |

TABLE 14-continued
| Example | Structure | IUPAC Name | LCMS m/z [M + H] |
|---|---|---|---|
| 206 | 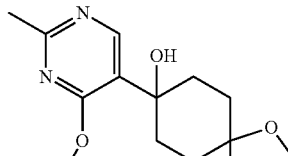 | 8-(2-methyl-4-(((1S,2S)-2-(quinolin-2-yl)cyclopropyl)methoxy)pyrimidin-5-yl)-1,4-dioxaspiro[4.5]decan-8-ol | 448.2 |
SCHEME 20
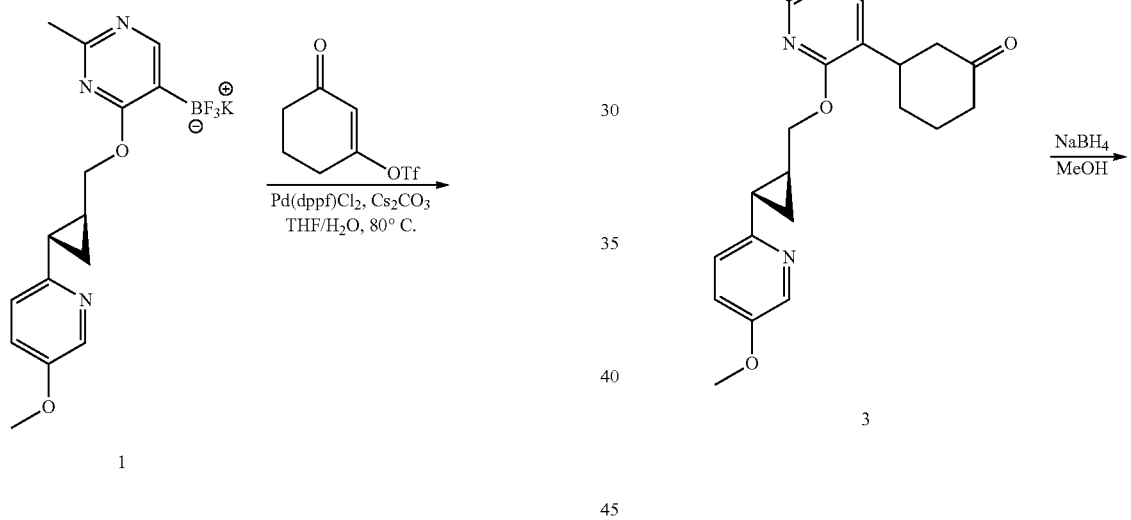
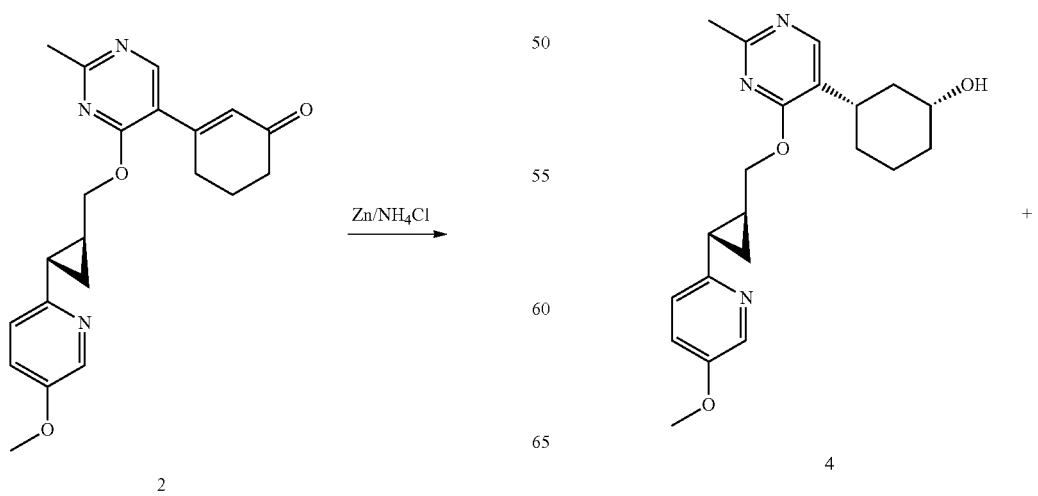

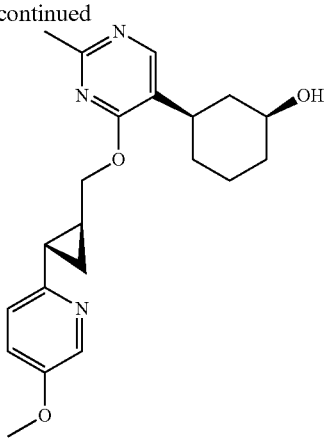

Example 207

3-(4-(((1S,2S)-2-(5-Methoxypyridin-2-yl)cyclopropyl)methoxy)-2-methylpyrimidin-5-yl)cyclohexanone

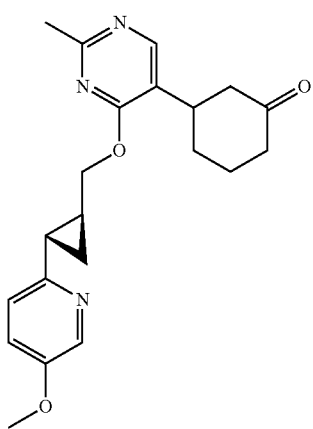 [SMILES: COc1ccc([C@H]2C[C@@H]2COc2nc(C)ncc2C2CCCC(=O)C2)nc1]

Step A: 3-(4-(((1S,2S)-2-(5-Methoxypyridin-2-yl)cyclopropyl)methoxy)-2-methylpyrimidin-5-yl)cyclohex-2-enone

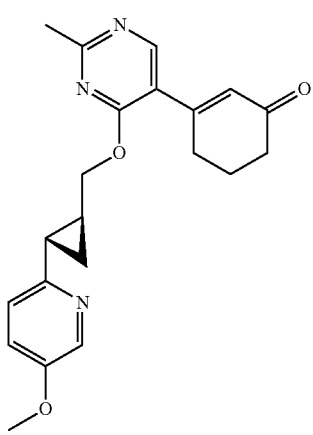 [SMILES: COc1ccc([C@H]2C[C@@H]2COc2nc(C)ncc2C2=CC(=O)CCC2)nc1]

A 10 mL reaction vial was charged with potassium trifluoro(4-(((1S,2S)-2-(5-methoxypyridin-2-yl)cyclopropyl)methoxy)-2-methylpyrimidin-5-yl)borate (200 mg, 0.52 mmol), 3-oxocyclohex-1-enyl trifluoromethanesulfonate (130 mg, 0.52 mmol), Pd(dppf)Cl$_2$ (42 mg, 0.052 mmol) and Cs$_2$CO$_3$ (506 mg, 1.56 mmol) in THF (2.0 mL) and water (0.5 mL). The vial was purged with nitrogen for several minutes and sealed. The reaction mixture was stirred at 80° C. for 16 h. The reaction mixture was diluted with EtOAc (20 mL), washed with sat. aq. NaHCO$_3$ (15 mL) and brine (15 mL), dried over Na$_2$SO$_4$, filtered, and concentrated in vacuo. The resulting residue was purified by Pre-TLC (Petroleum ether/EtOAc=1/2) to afford compound as a yellow oil (160 mg, 84%): $^1$H NMR (400 MHz, CDCl$_3$) δ 8.23 (s, 1H), 8.07 (s, 1H), 7.01 (m, 2H), 6.22 (s, 1H), 4.37 (m, 2H), 3.74 (s, 3H), 2.63 (t, 2H), 2.52 (s, 3H), 2.39 (t, 2H), 2.06-1.94 (m, 3H), 1.75 (m, 1H), 1.26 (m, 1H), 0.95 (m, 1H); LC/MS m/z=366.1 [M+H]$^+$.

Step B: 3-(4-(((1S,2S)-2-(5-Methoxypyridin-2-yl)cyclopropyl)methoxy)-2-methylpyrimidin-5-yl)cyclohexanone

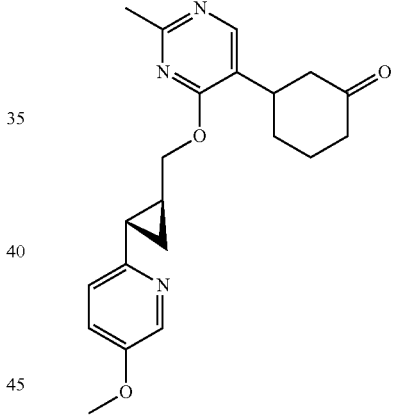

A 50 mL flask was charged with 3-(4-(((1S,2S)-2-(5-Methoxypyridin-2-yl)cyclopropyl)methoxy)-2-methylpyrimidin-5-yl)cyclohex-2-enone (80 mg, 0.22 mmol), NH$_4$Cl (234 mg, 4.4 mmol) in EtOH (5 mL) and H$_2$O (0.5 mL). The mixture was stirred at 70° C. for 1 h. Then Zn (143 mg, 2.2 mmol) was added. The reaction was stirred at 70° C. for 2 h. After cooled down to rt, the reaction was filtered and the filtrate was concentrated under reduced pressure. The residue was washed with H$_2$O, extracted with EtOAc, dried over Na$_2$SO$_4$ and concentrated to afford crude product, which was purified by pre-TLC (Petroleum ether/EtOAc=1/5) to give product as a yellow oil (40 mg, 50%): $^1$H NMR (400 MHz, CDCl$_3$) δ 8.15 (s, 2H), 7.08 (m, 2H), 4.40 (m, 2H), 3.82 (s, 3H), 3.10 (m, 1H), 2.64 (m, 1H), 2.55 (m, 4H), 2.43 (m, 1H), 2.29 (m, 1H), 2.08 (m, 2H), 1.95 (m, 2H), 1.83 (m, 1H), 1.72 (m, 1H), 1.30 (m, 1H), 1.05 (m, 1H); LC/MS m/z=368.1 [M+H]$^+$.

TABLE 15
| Example | Structure | IUPAC Name | LCMS m/z [M + H] |
|---|---|---|---|
| 207 | 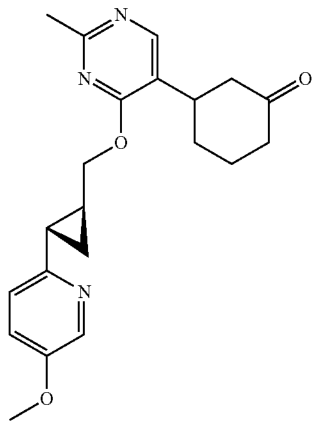 [SMILES: COc1ccc([C@H]2C[C@@H]2COc2nc(C)ncc2C2CCCC(=O)C2)nc1] | 3-(4-(((1S,2S)-2-(5-Methoxypyridin-2-yl)cyclopropyl)methoxy)-2-methylpyrimidin-5-yl)cyclohexanone | 368.1 |
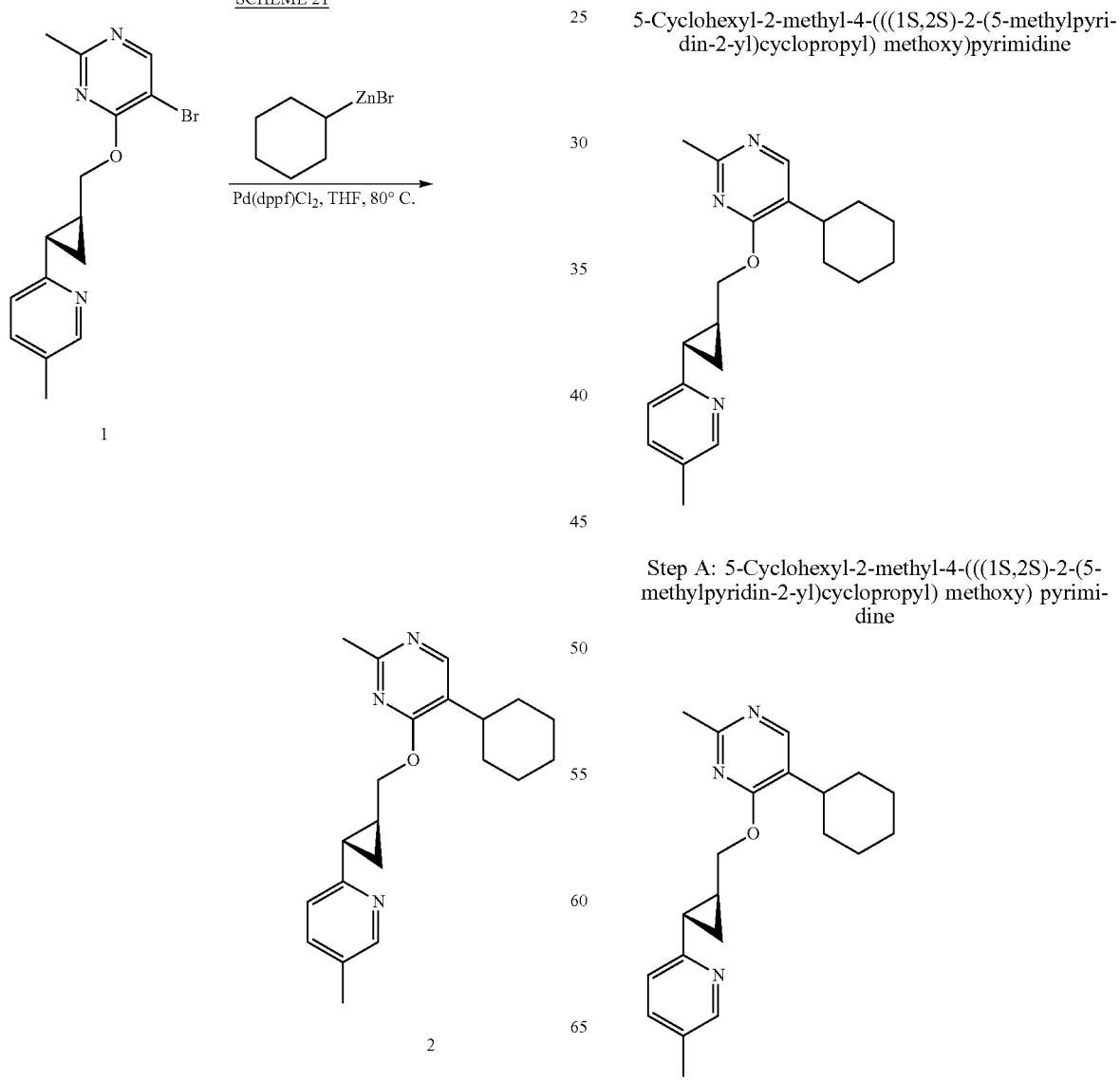
SCHEME 21
Example 208
5-Cyclohexyl-2-methyl-4-(((1S,2S)-2-(5-methylpyridin-2-yl)cyclopropyl) methoxy)pyrimidine
Step A: 5-Cyclohexyl-2-methyl-4-(((1S,2S)-2-(5-methylpyridin-2-yl)cyclopropyl) methoxy) pyrimidine A 10 mL reaction vial was charged with 5-bromo-2-methyl-4-(((1S,2S)-2-(5-methylpyridin-2-yl)cyclopropyl)methoxy)pyrimidine (100 mg, 0.3 mmol), cyclohexylzinc bromide (0.6 mL, 1 N, 0.6 mmol), Pd(dppf)Cl2 (24 mg, 0.03 mmol) in THF (2.0 mL). The vial was sealed and purged with nitrogen for several minutes. The reaction mixture was stirred at 80° for 16 h. The reaction mixture was diluted with EtOAc (20 mL), washed with sat. aq. NaHCO$_3$ (15 mL) and brine (15 mL), dried over Na$_2$SO$_4$, filtered, and concentrated in vacuo. The resulting residue was purified by Pre-TLC (PE/EA=0/1) afford the title compound as an oil. (16 mg, 23%). $^1$H NMR (400 MHz, CD3OD) δ 8.06 (s, 1H), 7.98 (s, 1H), 7.38 (d, 1H), 7.01 (d, 1H), 4.42 (dd, 1H), 4.34-4.06 (m, 1H), 2.65-2.45 (m, 1H), 2.38 (s, 3H), 2.16 (s, 3H), 2.08-1.91 (m, 1H), 1.71 (t, 5H), 1.58 (s, 1H), 1.41-1.18 (m, 3H), 1.13 (dd, 2H), 1.04-0.87 (m, 1H). HRMS m/z (M+H) 337.7 found, 337.2 required.

TABLE 16

| Example | Structure | IUPAC Name | LCMS m/z [M + H]$^+$ |
|---|---|---|---|
| 208 | 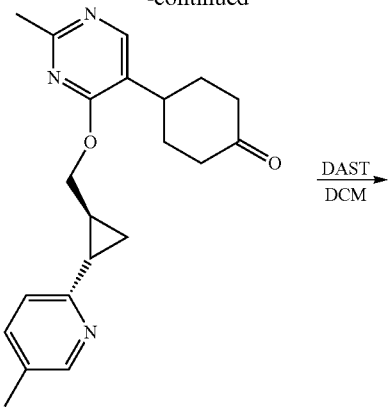 | 5-Cyclohexyl-2-methyl-4-(((1S,2S)-2-(5-methylpyridin-2-yl)cyclopropyl)methoxy)pyrimidine | 337.7 |

SCHEME 22

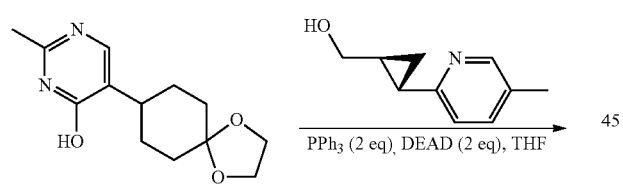

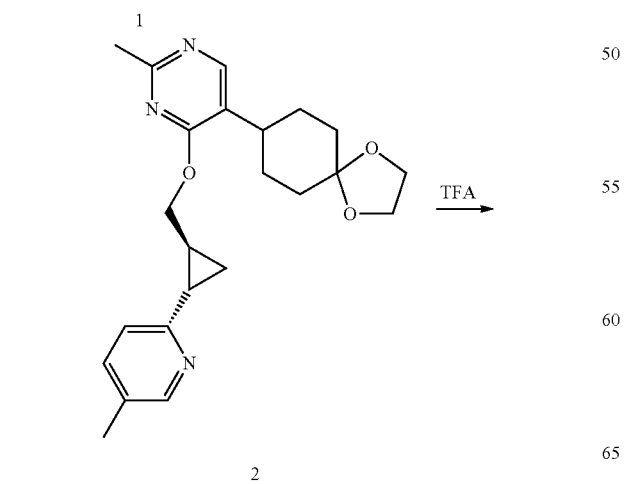

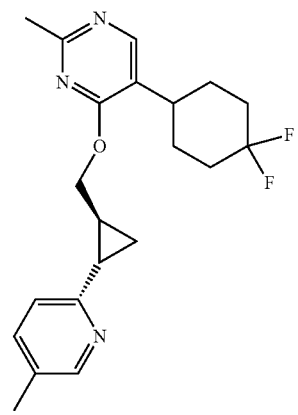

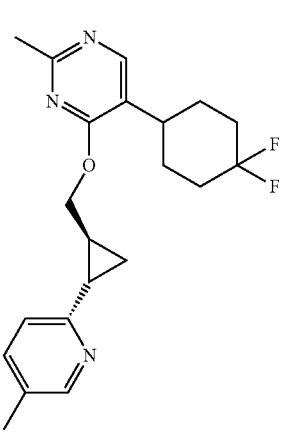

Example 209

5-(4,4-Difluorocyclohexyl)-2-methyl-4-(((1S,2S)-2-(5-methylpyridin-2-yl)cyclopropyl) methoxy)pyrimidine

Step A: 2-methyl-4-(((1S,2S)-2-(5-methylpyridin-2-yl)cyclopropyl)methoxy)-5-(1,4-dioxaspiro[4.5]decan-8-yl)pyrimidine

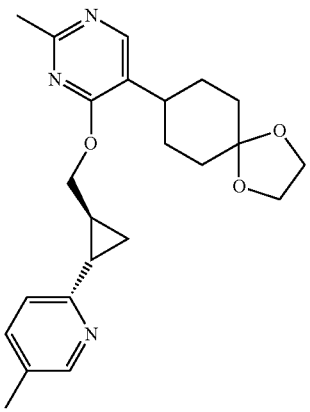

To a solution of 2-methyl-5-(1,4-dioxaspiro[4.5]decan-8-yl)pyrimidin-4-ol (100 mg, 0.4 mmol) in THF (5 mL) at 0° C. was added triphenylphosphine (126 mg, 0.48 mmol) and (((1S,2S)-2-(5-methylpyridin-2-yl)cyclopropyl)methanol (68 mg, 0.4 mmol), followed by dropwise addition of DIAD (0.10 mL, 0.48 mmol). The reaction mixture was warmed to ambient temperature. After 10 minutes, the reaction mixture was concentrated and the resulting residue was purified by column chromatography on silica gel chromatography eluted with $V_{PE}:V_{EA}=2:1$ to afford the title compound (85 mg, 39% yield) as a white solid. $^1$H NMR (400 MHz, CDCl$_3$) δ 8.17 (s, 1H), 7.42 (t, 1H), 6.90 (t, 2H), 4.41 (d, 2H), 3.97 (s, 4H), 2.75 (s, 1H), 2.55 (s, 3H), 2.48 (s, 3H), 2.17 (s, 1H), 2.09 (s, 1H), 1.77-1.63 (m, 4H), 1.58 (m, 1H), 1.45-1.26 (m, 2H), 1.24 (s, 2H), 1.08 (m, 1H). HRMS m/z (M+H) 395.7 found, 395.22 required.

Step B: 4-(2-Methyl-4-(((1S,2S)-2-(5-methylpyridin-2-yl)cyclopropyl)methoxy)pyrimidin-5-yl)cyclohexanone

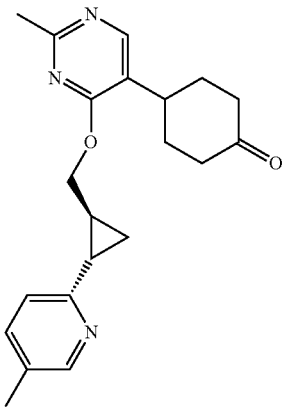

The solution of 2-methyl-4-(((1S,2S)-2-(5-methylpyridin-2-yl)cyclopropyl)methoxy)-5-(1,4-dioxaspiro[4.5]decan-8-yl)pyrimidine (100 mg, 0.25 mmol) in TFA (1 mL, 13 mmol) was stirred at rt for 5 hours. Then saturated sodium bicarbonate (5 mL) was added and the mixture was extracted with EtOAc (3×10 mL). The combined organics were dried over MgSO$_4$, filtered and concentrated in vacuo to afford the title compound (70 mg, 81% yield), which was sufficiently pure to use in the subsequent step without further purification. $^1$H NMR (400 MHz, CDCl$_3$) δ 8.27 (s, 1H), 8.16 (s, 1H), 7.37 (d, 1H), 7.03 (d, 1H), 4.50-4.24 (m, 2H), 3.16 (t, 1H), 2.57 (s, 3H), 2.47 (s, 4H), 2.29 (s, 3H), 2.18 (s, 2H), 2.08 (s, 1H), 1.95 (d, 3H), 1.43-1.26 (m, 1H), 1.09 (s, 1H). HRMS m/z (M+H) 351.7 found, 351.2 required.

Step C: 5-(4,4-Difluorocyclohexyl)-2-methyl-4-(((1S,2S)-2-(5-methylpyridin-2-yl)cyclopropyl)methoxy)pyrimidine

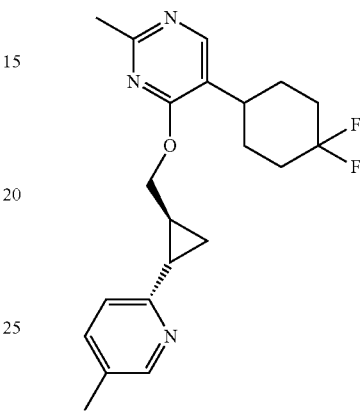

To a solution of 4-(2-methyl-4-(((1S,2S)-2-(5-methylpyridin-2-yl)cyclopropyl)methoxy) pyrimidin-5-yl)cyclohexanone (50 mg, 0.18 mmol) in DCM (2 mL) was added DAST (69 mg, 0.54 mmol). The mixture was stirred for 0.5 hour. The mixture was purified by reverse phase chromatography (Waters Sunfire Prep C18OBD, 5-60% acetonitrile in water with 0.1% NH$_3$OH modifier) to afford the title compound as a solid (28 mg, 65% yield). $^1$H NMR (400 MHz, CDCl$_3$) δ 8.22 (d, 1H), 8.14 (s, 1H), 7.37 (d, 1H), 7.04 (d, 1H), 4.41 (dt, 2H), 2.75 (s, 1H), 2.56 (s, 3H), 2.25 (d, 3H), 2.17 (s, 2H), 2.07 (dd, 1H), 1.82 (dd, 7H), 1.41-1.30 (m, 1H), 1.07 (dt, 1H). HRMS m/z (M+H) 373.7 found, 373.2 required.

TABLE 17

| Example | Structure | IUPAC Name | LCMS m/z [M + H]$^+$ |
|---|---|---|---|
| 209 | 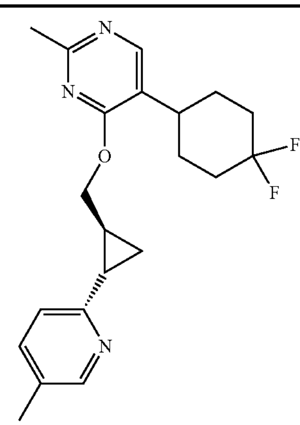 | 5-(4,4-Difluorocyclohexyl)-2-methyl-4-(((1S,2S)-2-(5-methylpyridin-2-yl)cyclopropyl)methoxy)pyrimidine | 373.7 |

SCHEME 23
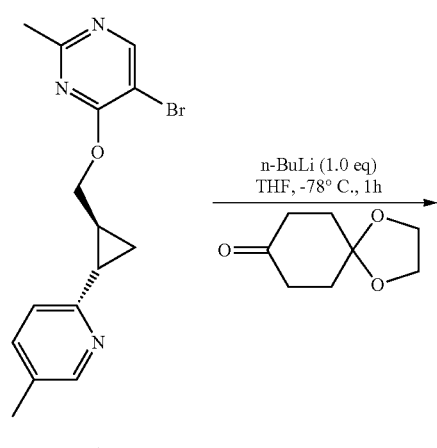
1
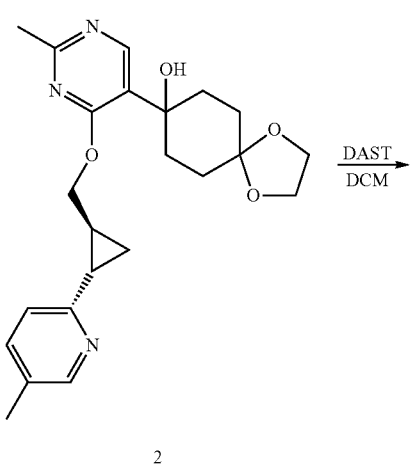
2
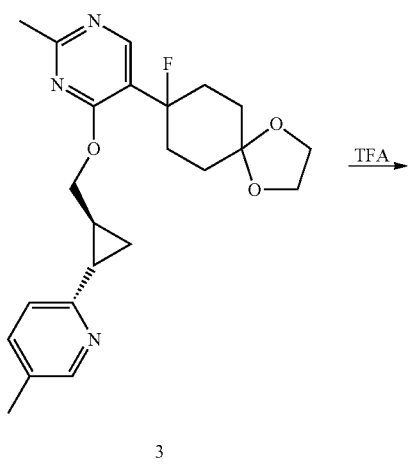
3
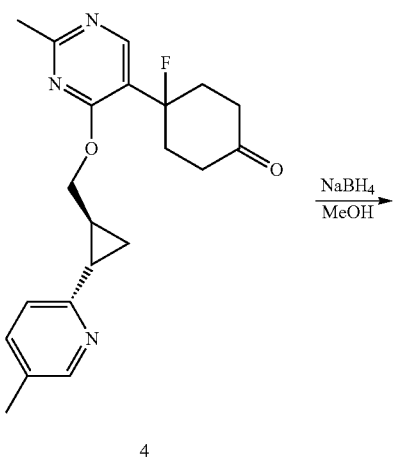
4
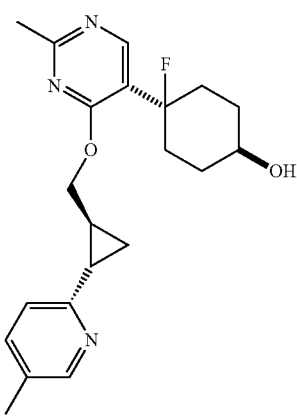
5
Example 210
Trans-4-fluoro-4-(2-methyl-4-(((1S,2S)-2-(5-methyl-pyridin-2-yl)cyclopropyl)methoxy) pyrimidin-5-yl) cyclohexanol

Step A: 4-Ethylene-ketal-1-(2-methyl-4-(((1S,2S)-2-(5-methylpyridin-2 yl)cyclopropyl)methyl)-pyrimidin-5-yl)cyclohexanol

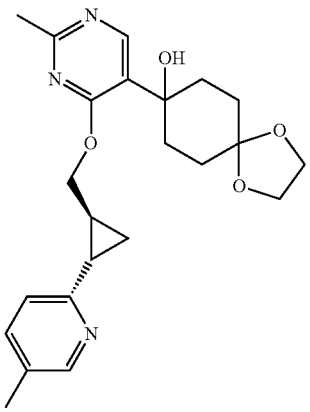

To a solution of 5-bromo-2-methyl-4-(((1S,2S)-2-(5-methylpyridin-2-yl)cyclopropyl)methyl)pyrimidine (100 mg, 0.3 mmol) and 1,4-cyclohexanedione monoethylene ketal (94 mg, 0.6 mmol) in THF (2 mL) was slowly added a solution on n-BuLi (0.1 mL, 3 M in THF) at −78° C. The resulting mixture was allowed to stir at the same temperature for 45 minutes. The reaction mixture was washed with sodium bicarbonate, extracted with EtOAc (2×500 mL), dried over MgSO$_4$, filtered and concentrated. The crude residue was purified by column chromatography to afford the title compound as a white solid. $^1$H NMR (400 MHz, CDCl$_3$) δ 8.31 (d, 2H), 7.39 (s, 1H), 7.06 (d, 1H), 4.49 (d, 2H), 3.95 (qd, 4H), 3.33 (s, 1H), 2.58 (s, 3H), 2.29 (s, 3H), 2.12-1.86 (m, 6H), 1.65 (s, 4H), 1.42-1.28 (m, 1H), 1.10 (s, 1H). HRMS m/z (M+H) 411.7 found, 411.5 required.

Step B: 5-(8-fluoro-1,4-dioxaspiro[4.5]decan-8-yl)-2-methyl-4-(((1S,2S)-2-(5-methylpyridin-2-yl)cyclopropyl)methoxy)pyrimidine

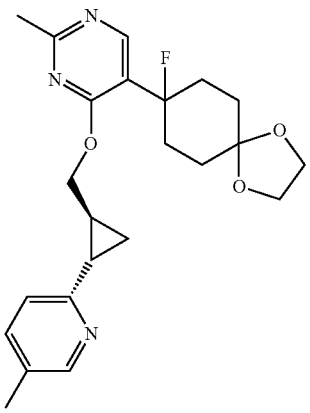

The title compound was prepared according to the procedure Example 237 step C. $^1$H NMR (400 MHz, CDCl$_3$) δ 8.47 (s, 1H), 8.27 (s, 1H), 7.32 (t, 1H), 7.05 (d, 1H), 4.48 (d, 2H), 4.02-3.65 (m, 4H), 2.73-2.43 (m, 4H), 2.27 (s, 3H), 2.17 (s, 3H), 1.87 (d, 3H), 1.70-1.60 (m, 3H), 1.41-1.29 (m, 1H), 1.12 (dt, 1H). HRMS m/z (M+H) 419.7 found, 419.2 required.

Step C: 4-Fluoro-4-(2-methyl-4-(((1S,2S)-2-(5-methylpyridin-2-)cyclopropyl)methoxy) pyrimidin-5-yl)cyclohexanone (3)

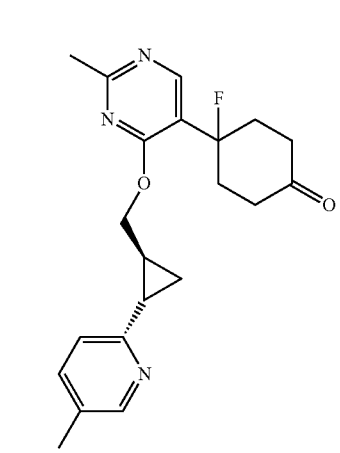

The title compound was prepared according to procedure Example 237 Step B.

Step D: (trans)-4-Fluoro-4-(2-methyl-4-(((1S,2S)-2-(5-methylpyridin-2-yl)cyclopropyl)methoxy)-pyrimidin-5-yl)cyclohexanol

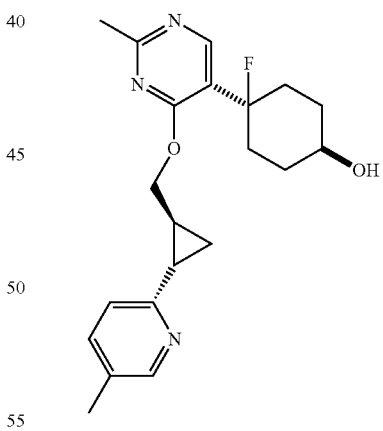

The title compound was prepared according to the procedure Example 208. $^1$H NMR (400 MHz, CDCl$_3$) δ 8.47 (s, 1H), 8.30 (s, 1H), 7.43 (d, 1H), 7.05 (t, 1H), 4.50-4.45 (m, 1H), 4.37-4.32 (m, 1H), 3.52-3.50 (m, 1H), 2.55 (s, 3H), 2.42-2.26 (m, 4H), 2.08-2.05 (m, 1H), 1.92-1.67 (m, 8H), 1.40-1.37 (m, 1H), 1.11 (t, 1H). HRMS m/z (M+H) 371.7 found, 371.2 required.

The following EXAMPLE 211 in Table 18 was prepared using the procedure of EXAMPLE 210, substituting the appropriate starting materials.

TABLE 18

| Example | Structure | IUPAC Name | LCMS m/z [M + H] |
|---|---|---|---|
| 210 | 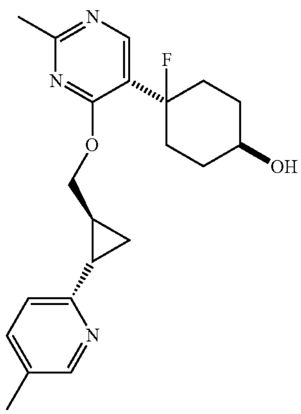 | (trans)-4-Fluoro-4-(2-methyl-4-(((1S,2S)-2-(5-methyl-pyridin-2-yl)cyclopropyl)methoxy)pyrimidin-5-yl)cyclohexanol | 371.7 |
| 211 | 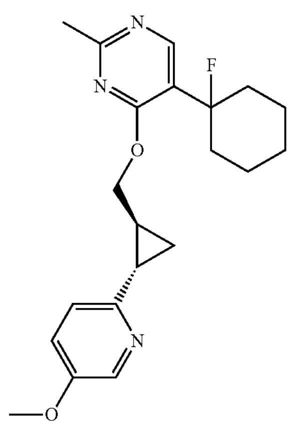 [SMILES: COc1ccc([C@H]2C[C@@H]2COc2nc(C)ncc2C2(F)CCCCC2)nc1] | 5-(1-fluoro-cyclohexyl)-4-(((1S,2S)-2-(5-methoxy-pyridin-2-yl)cyclopropyl)methoxy)-2-methyl-pyrimidine | 371.7 |

SCHEME 24

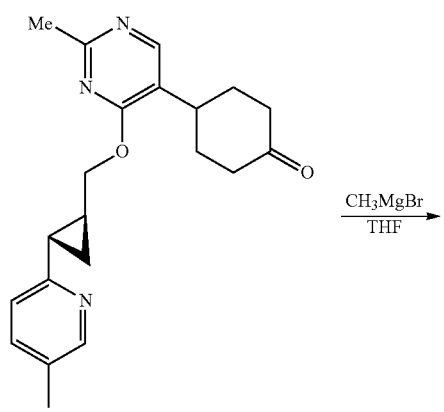

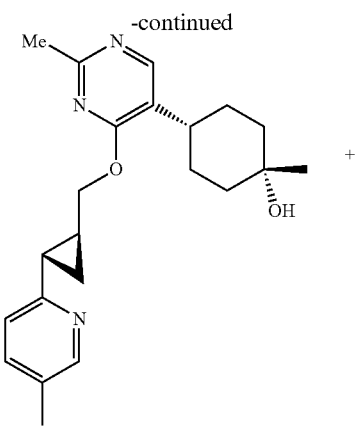

example 212

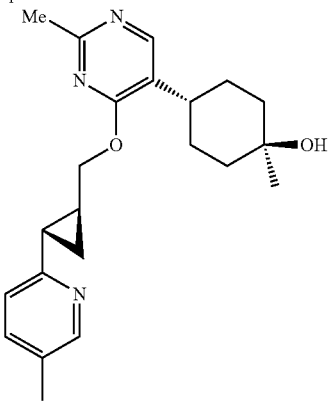

example 213

Example 212 and 213

Step A: (cis) 1-Methyl-4-(2-methyl-4-(((1S,2S)-2-(5-methylpyridin-2-yl)cyclopropyl)methoxy)pyrimidin-5-yl)cyclohexanol (example 240) and (trans)1-Methyl-4-(2-methyl-4-(((1S,2S)-2-(5-methylpyridin-2-1)cyclopropyl)methoxy)pyrimidin-5-yl)cyclohexanol (example 241)

To a solution of 4-(2-methyl-4-(((1S,2S)-2-(5-methylpyridin-2-yl)cyclopropyl) methoxy)pyrimidin-5-yl)cyclohexanone (100 mg, 0.29 mmol) in THF (5 mL) at −20° C. was added methylmagnesium bromide (0.54 mL, 1 N, 0.54 mmol). The reaction mixture was warmed to ambient temperature and stirred for 12 h. The reaction mixture was quenched by $NH_4Cl$ aq (2 mL), concentrated and the resulting residue was purified by column chromatography on silica gel chromatography eluted with PE/EA 2:1 to afford Example 240 (10 mg, 8% yield) and Example 213 (5 mg, 4% yield) as white solids.

Example 212

$^1$H NMR (400 MHz, $CDCl_3$) δ 8.27 (s, 1H), 8.13 (s, 1H), 7.35 (d, 1H), 7.03 (d, 1H), 4.39 (dd, 2H), 2.62 (t, 1H), 2.55 (s, 3H), 2.28 (s, 3H), 2.07-1.99 (m, 1H), 1.89 (t, 1H), 1.84-1.72 (m, 4H), 1.66 (t, 3H), 1.56 (d, 2H), 1.37-1.28 (m, 1H), 1.20 (s, 3H), 1.11-0.99 (m, 1H). HRMS m/z (M+H) 367.7 found, 367.2 required.

Example 213

¹H NMR (400 MHz, MeOD) δ 8.20 (d, 1H), 8.17 (s, 1H), 7.52 (d, 1H), 7.15 (s, 1H), 4.55 (dd, 2H), 2.70 (t, 1H), 2.54 (s, 3H), 2.31 (s, 3H), 2.15-2.00 (m, 2H), 1.89-1.63 (m, 6H), 1.53-1.46 (m, 2H), 1.31-1.26 (m, 1H), 1.23 (s, 3H), 1.18-1.14 (m, 1H). HRMS m/z (M+H) 367.7 found, 367.2 required.

The following EXAMPLE 214 and 215 in Table 19 were prepared using the procedure of EXAMPLE 212 and 213, substituting the appropriate starting materials.

TABLE 19

| Example | Structure | IUPAC Name | LCMS m/z [M + H]⁺ |
| --- | --- | --- | --- |
| 212 | 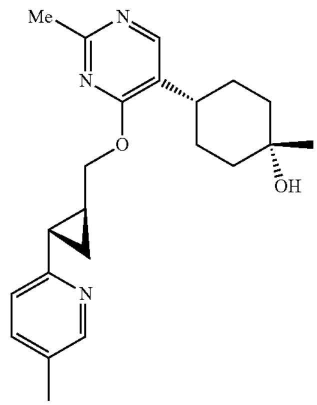 [SMILES: Cc1ccc([C@H]2C[C@@H]2COc2nc(C)ncc2[C@H]2CC[C@@](C)(O)CC2)nc1] | (cis)1-Methyl-4-(2-methyl-4-(((1S,2S)-2-(5-methylpyridin-2-yl)cyclopropyl)methoxy)pyrimidin-5-yl)cyclohexanol | 367.7 |
| 213 | 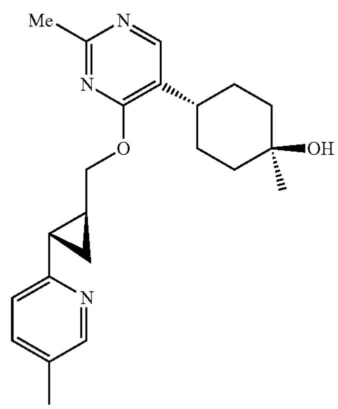 [SMILES: Cc1ccc([C@H]2C[C@@H]2COc2nc(C)ncc2[C@H]2CC[C@](C)(O)CC2)nc1] | (trans)1-Methyl-4-(2-methyl-4-(((1S,2S)-2-(5-methylpyridin-2-yl)cyclopropyl)methoxy)pyrimidin-5-yl)cyclohexanol | 367.7 |
| 214 | 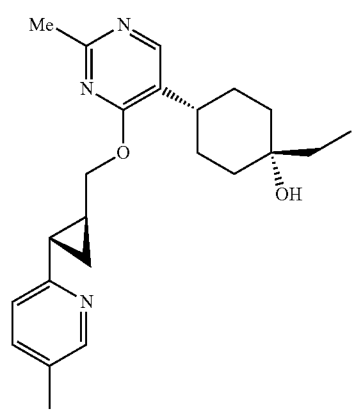 [SMILES: CC[C@]1(O)CC[C@@H](c2cnc(C)nc2OC[C@H]2C[C@@H]2c2ccc(C)cn2)CC1] | (cis)1-Ethyl-4-(2-methyl-4-(((1S,2S)-2-(5-methylpyridin-2-yl)cyclopropyl)methoxy)pyrimidin-5-yl)cyclohexanol | 381.7 |

TABLE 19-continued
| Example | Structure | IUPAC Name | LCMS m/z [M + H]+ |
|---|---|---|---|
| 215 | 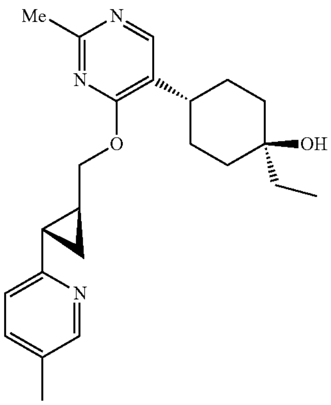 [SMILES: CC[C@]1(O)CC[C@H](c2cnc(C)nc2OC[C@H]2C[C@@H]2c2ccc(C)cn2)CC1] | (trans)1-Ethyl-4-(2-methyl-4-(((1S,2S)-2-(5-methylpyridin-2-1)cyclopropyl)methoxy)pyrimidin-5-yl)cyclohexanol | 381.7 |
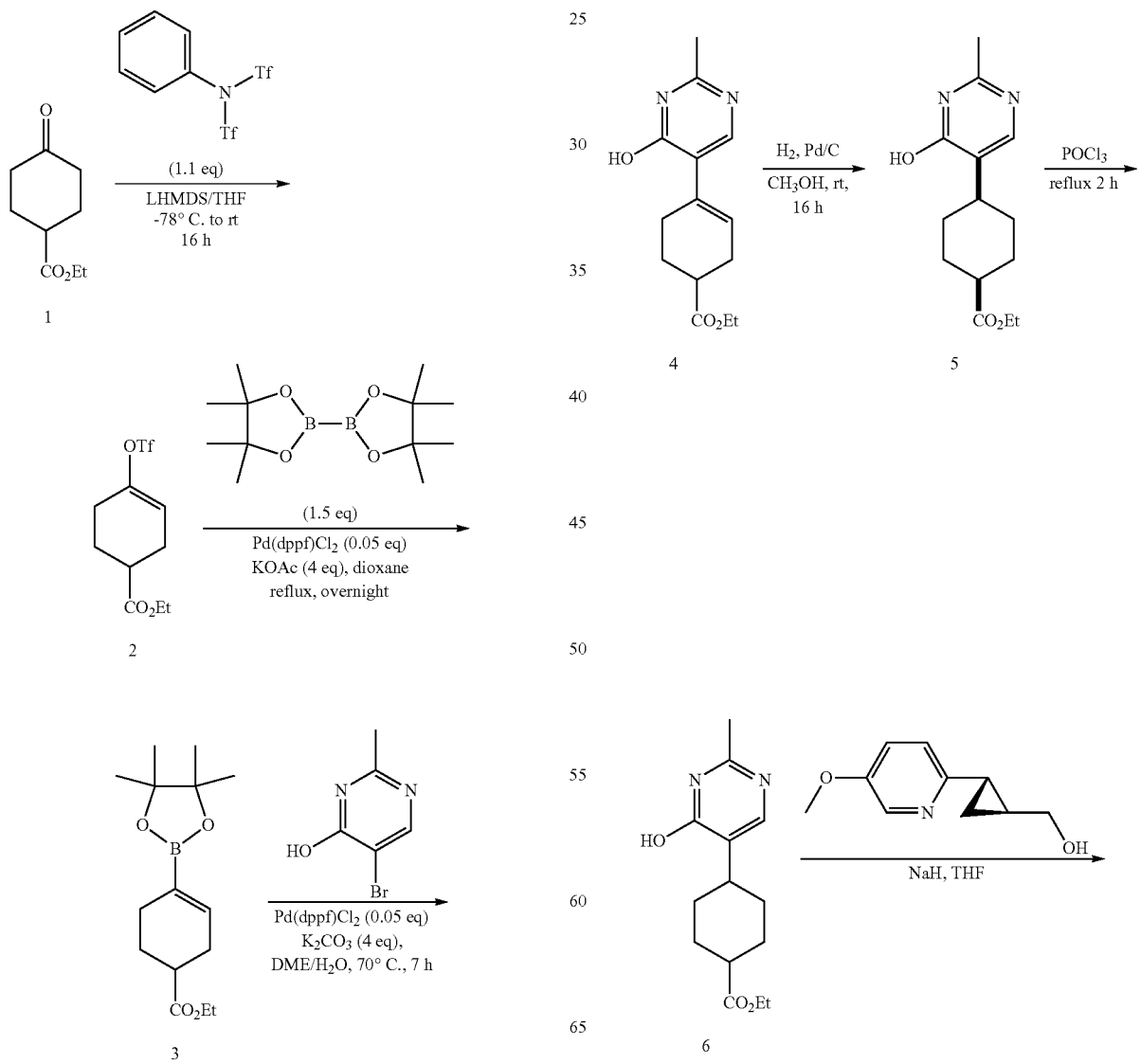

199
-continued

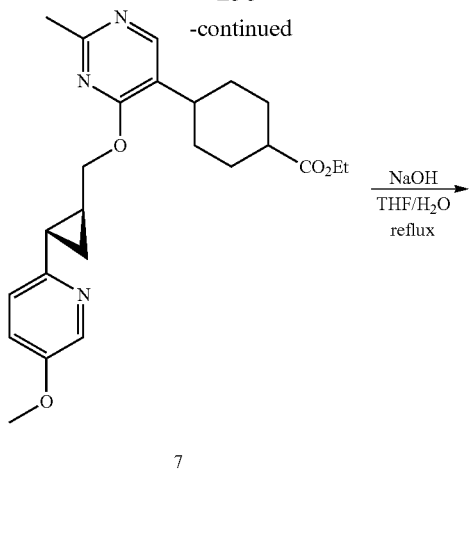

7

NaOH
THF/H₂O
reflux
→

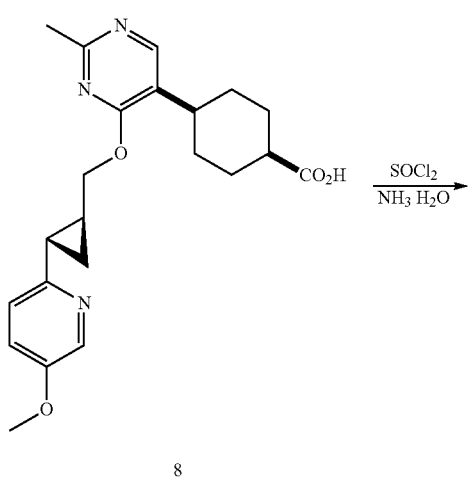

8

SOCl₂
NH₃ H₂O
→

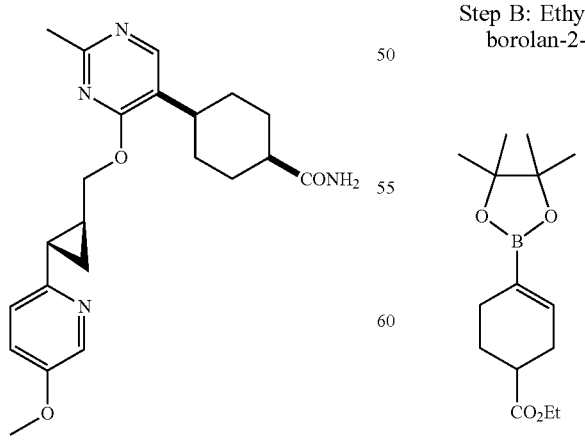

9

Example 216

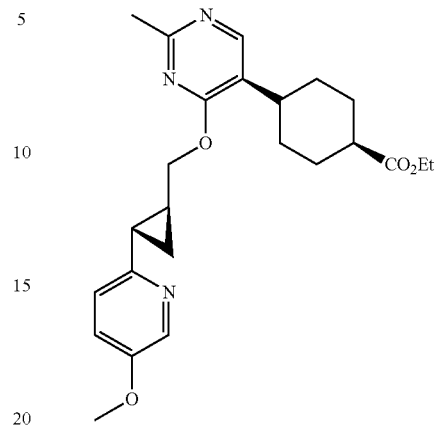

Step A: Ethyl-(trifluoromethylsulfonyloxy)cyclo-hex-3-enecarboxylate

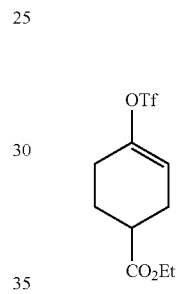

To a solution of 1 (500 mg, 3 mmol) in THF (10 mL) was added LHMDS (3.3 mL, 3.3 mmol, 1.0 M in THF) dropwise at −78° C. It was stirred for 0.5 h before trifluoro-N-phenyl-N-(trifluoromethylsulfonyl)methanesulfonamide (1.05 g, 3.3 mmol) was added. Then the resulting solution was allowed to warm to 0° C. and stirred for 1 h. The mixture was concentrated and purified by flash chromatography (10% EtOAc in petroleum) to provide the desired product (500 mg, 57%). LRMS m/z (M+H), 303.1 found, 303.0 required.

Step B: Ethyl 4-(4,4,5,5-tetramethyl-1,3,2-dioxa-borolan-2-yl)cyclohex-3-enecarboxylate (3)

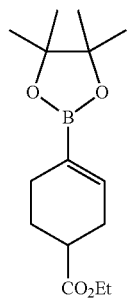

A mixture of 2 (303 mg, 1 mmol), bis(pinacolato)diboron (370 mg, 1.5 mmol), KOAc (400 mg, 4 mmol) and Pd(dppf)

Cl₂ (10 mg, 0.05 mmol) in dioxane (5 mL) under N₂ was heated to 110° C. for 16 h. After cooled to rt, the mixture was partitioned between EtOAc (10 mL) and NaHCO₃ (10 mL). The aqueous phase was extracted with EA (10 mL*2). The combined organic phases were washed with brine, dried over MgSO₄, filtered, concentrated and purified by flash chromatography (25% EtOAc in petroleum) to provide the desired product (250 mg, 89%). LRMS m/z (M+H), 281 found, 281 required.

Step C: Ethyl-4-(4-hydroxy-2-methylpyrimidin-5-yl)cyclohex-3-enecarboxy-late (4)

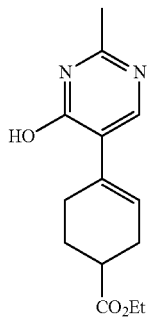 [SMILES: CCOC(=O)C1CC=C(c2cnc(C)nc2O)CC1]

A solution of 3 (140 mg, 0.5 mmol) and 5-bromo-2-methylpyrimidin-4-ol (94 mg, 0.5 mmol) in 1,2-dimethoxyethane (1.78 mL) and water (1 mL) was degassed for 10 minutes. Pd(dppf)Cl₂ (20 mg, 0.025 mmol) and potassium carbonate (276 mg, 2 mmol) were added and the reaction mixture was heated to 70° C. for 7 h. The reaction mixture was cooled and partitioned between EtOAc (10 mL) and NaHCO₃ (10 mL). The aqueous phase was extracted with EA (10 mL*2). The combined organic phases were washed with brine, dried over MgSO₄, filtered, concentrated and purified by flash chromatography (EtOAc) to provide the desired product (50 mg, 38%). LRMS m/z (M+H), 263.2 found, 263.1 required.

Step D: Ethyl 4-(4-hydroxy-2-methylpyrimidin-5-yl)cyclohexanecarboxylate (5)

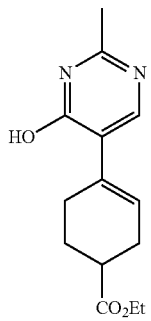 [SMILES: CCOC(=O)C1CC=C(c2cnc(C)nc2O)CC1]

A solution of 4 (1 g, 3.8 mmol) in CH₃OH (10 mL) was treated with Pd/C (100 mg) under H₂ and stirred overnight at room temperature. The reaction mixture was filtered and concentrated to afford target product (900 mg, 90%) as a yellow oil. LRMS m/z (M+H), 265 found, 265 required.

Step E: Ethyl 4-(4-chloro-2-methylpyrimidin-5-yl)cyclohexanecarboxylate (6)

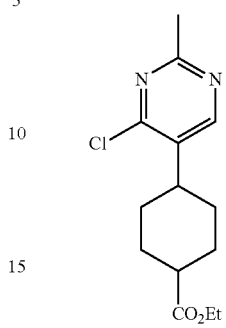

A solution of 5 (88 mg, 0.33 mmol) in POCl₃ (0.5 mL) was heated to reflux for 2 h, then the mixture was cooled to room temperature and concentrated. The residue was quenched by ice water (3 mL) and adjusted to PH 8 by saturated NaHCO₃ aq. The solution was extracted by DCM (10 mL×2). The combined organic layers were dried over MgSO₄ and concentrated to afford title compound (70 mg, 75%). LRMS m/z (M+H), 283 found, 283 required.

Step F: Ethyl4-(4-(((1S,2S)-2-(5-methoxypyridin-2-yl)cyclopropyl)methoxy)-2-methylpyrimidin-5-yl)cyclohexanecarboxylate (7)

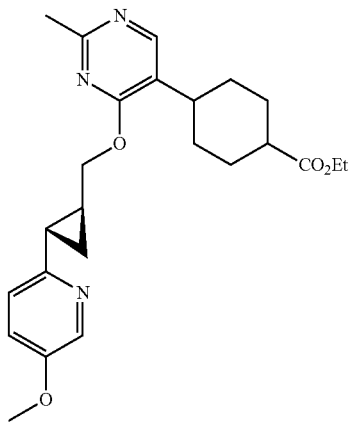 [SMILES: CCOC(=O)C1CCC(c2cnc(C)nc2OC[C@H]2C[C@@H]2c2ccc(OC)cn2)CC1]

To a solution of alcohol (1.1 g, 6.1 mmol) in THF (25 mL) was added sodium hydride (300 mg, 7.4 mmol). The reaction mixture stirred at ambient temperature for 30 minutes. 6 (1.72 g, 6.1 mmol) was added and the reaction mixture was stirred at ambient temperature for 12 h. NaHCO₃ (20 mL) was carefully added and the mixture was extracted with EtOAc (2×50 mL). The combined organic phases were dried over MgSO₄, filtered, concentrated and purified by Pre-HPLC to afford two isomers (total 500 mg, 19%) as white solids. trans: ¹H NMR (400 MHz, CDCl₃) δ 8.20-8.06 (m, 2H), 7.10 (m, 2H), 4.47-4.31 (m, 2H), 4.14 (q, 2H), 3.83 (s, 3H), 2.67 (t, 2H), 2.56 (s, 3H), 2.28 (dd, 2H), 2.06-1.93 (m, 1H), 1.82 (m, 3H), 1.62-1.42 (m, 4H), 1.35-1.21 (m, 4H), 1.04 (m, 1H); cis (Example 244): ¹H NMR (400 MHz, CDCl₃) δ 8.19-8.05 (m, 2H), 7.15-7.02 (m, 2H), 4.48-4.31 (m, 2H), 4.23-4.05 (m, 2H), 3.83 (s, 3H), 2.69 (s, 2H), 2.55

(s, 3H), 2.24 (d, 2H), 2.13-1.99 (m, 1H), 1.79 (d, 3H), 1.55 (d, 4H), 1.28 (dd, 4H), 1.08-1.00 (m, 1H).

Example 217

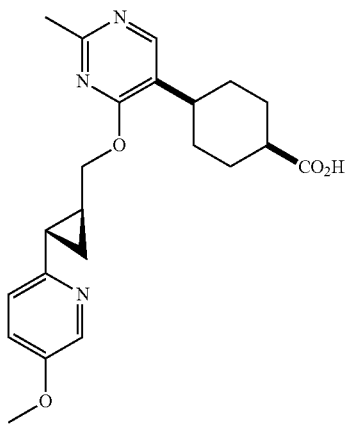

Step G: cis-4-(4-(((1S,2S)-2-(5-Methoxypyridin-2-yl)cyclopropyl)methoxy)-2-methylpyrimidin-5-yl)cyclohexanecarboxylic acid A mixture of cis-Ethyl4-(4-(((1S,2S)-2-(5-methoxypyridin-2-yl)cyclopropyl)methoxy)-2-methylpyrimidin-5-yl)cyclohexanecarboxylate (108 mg, 0.25 mmol) and NaOH (20 mg, 0.5 mmol) in THF/H$_2$O (0.5 mL/0.5 mL) was heated to reflux for 2 h. The reaction mixture was concentrated and neutralized by saturated NaHCO$_3$ aq. to pH 8, filtrated to afford title product (60 mg, 60%) as a grey solid. $^1$H NMR (400 MHz, CDCl$_3$) δ 8.20 (d, 2H), 7.22 (s, 1H), 7.02 (d, 1H), 4.57 (dd, 1H), 4.44 (dd, 1H), 3.85 (d, 3H), 2.75 (s, 1H), 2.59 (s, 4H), 2.41-2.25 (m, 3H), 2.04 (s, 3H), 1.83 (s, 1H), 1.59 (s, 2H), 1.23 (d, 1H), 1.12 (d, 2H).

Example 218

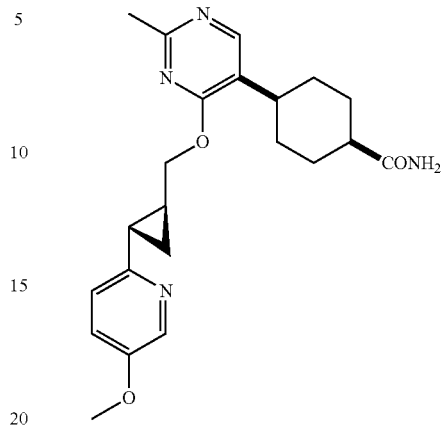

Step H: cis-4-(4-(((1S,2S)-2-(5-Methoxypyridin-2-yl)cyclopropyl)methoxy)-2-methylpyrimidin-5-yl)cyclohexanecarboxamide A solution of example 245 (40 mg, 0.1 mmol) in SOCl$_2$ (0.5 mL) was heated to reflux for 1 h. The mixture was concentrated and dissolved in THF (0.5 mL). Then the solution was added into NH$_3$H$_2$O (1 mL), the mixture was concentrated to afford title compound (10 mg, 25%). $^1$H-NMR (400 MHz, CDCl$_3$) δ 8.15 (s, 2H), 7.13-7.02 (m, 2H), 5.59 (s, 1H), 5.37 (s, 1H), 4.39 (d, 2H), 3.85 (d, 3H), 2.74 (d, 1H), 2.60 (s, 1H), 2.55 (s, 3H), 2.17-2.01 (m, 3H), 1.88-1.71 (m, 6H), 1.68 (d, 1H), 1.33-1.24 (m, 1H), 1.04 (dd, 1H).

The following EXAMPLE 219 in Table 20 was prepared using the procedure of EXAMPLE 216, substituting the appropriate starting materials.

TABLE 20

| Example | Structure | IUPAC Name | LCMS m/z [M + H]$^+$ |
|---------|-----------|------------|----------------------|
| 216 | 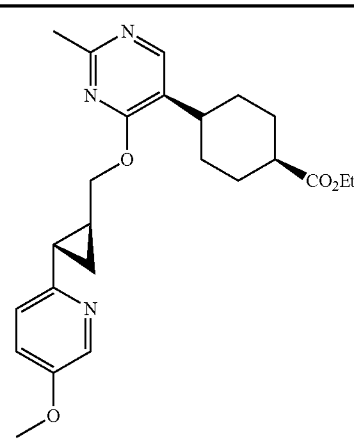 | cis-Ethyl4-(4-(((1S,2S)-2-(5-methoxypyridin-2-yl)cyclopropyl)methoxy)-2-methylpyrimidin-5-yl)cyclohexane-carboxylate | 425.7 |

TABLE 20-continued
| Example | Structure | IUPAC Name | LCMS m/z [M + H]+ |
|---|---|---|---|
| 217 | 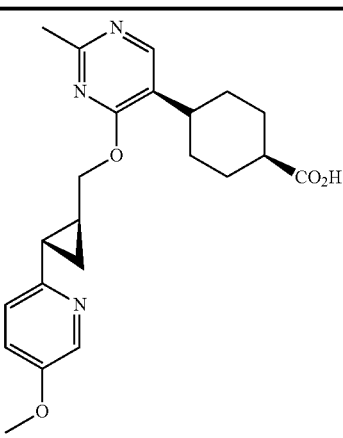 | cis-4-(4-(((1S,2S)-2-(5-Methoxypyridin-2-yl)cyclopropyl)methoxy)-2-methylpyrimidin-5-yl)cyclohexane-carboxylic acid | 398.1 |
| 218 | 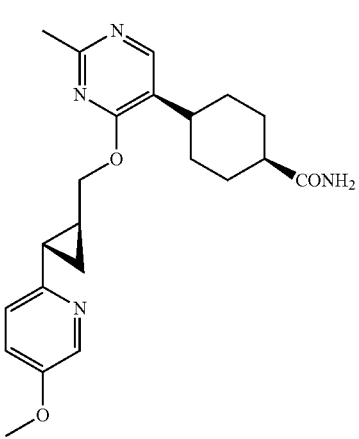 | cis-4-(4-(((1S,2S)-2-(5-Methoxypyridin-2-yl)cyclopropyl)methoxy)-2-methylpyrimidin-5-yl)cyclohexane-carboxamide | 397.1 |
| 219 | 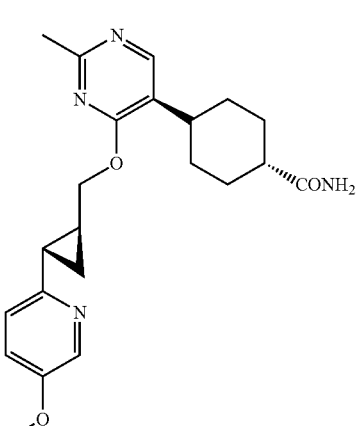 | trans-4-(4-(((1S,2S)-2-(5-Methoxypyridin-2-yl)cyclopropyl)methoxy)-2-methylpyrimidin-5-yl)cyclohexane-carboxamide | 397.1 |

SCHEME 26

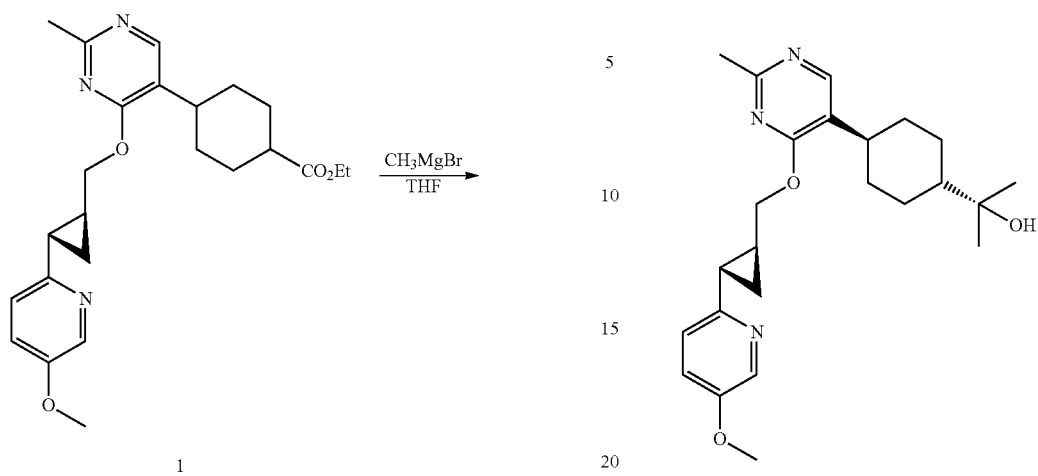

Example 220

Step A: (trans) 2-(4-(4-(((1S,2S)-2-(5-methoxypyridin-2-yl)cyclopropyl)methoxy)-2-methylpyrimidin-5-yl)cyclohexyl)propan-2-ol A solution of Ethyl-4-(4-(((1S,2S)-2-(5-methoxypyridin-2-yl)cyclopropyl)methoxy)-2-methylpyrimidin-5-yl)cyclohexanecarboxylate (102 mg, 0.25 mmol) in THF (2 mL) was treated with slowly with CH$_3$MgBr in THF (1 mL, 2.5 N). Then the mixture was stirred overnight and quenched with H$_2$O (1 ml). The mixture was concentrated and purified on reverse-phase column (CH$_3$OH:H$_2$O=0-100% in 10 mins) to get title compound as colorless oil (40 mg) yield: 40%. LC-MS (ESI) m/z=412.2 (M+H)$^+$. 412.2 required. $^1$H-NMR (500 MHz, CDCl$_3$) δ 8.37-7.98 (m, 2H), 7.09 (m, 2H), 7.01-6.99 (m, 1H), 4.51-4.21 (m, 2H), 3.82 (s, 3H), 2.70-2.47 (m, 4H), 2.16 (d, 1H), 2.09-1.74 (m, 6H), 1.55-1.40 (m, 3H), 1.23-1.16 (m, 8H), 1.09-0.97 (m, 1H).

The following EXAMPLE 221 in Table 21 was prepared using the procedure of EXAMPLE 220, substituting the appropriate starting materials.

TABLE 21

| Example | Structure | IUPAC Name | LCMS m/z [M + H]$^+$ |
|---|---|---|---|
| 220 | 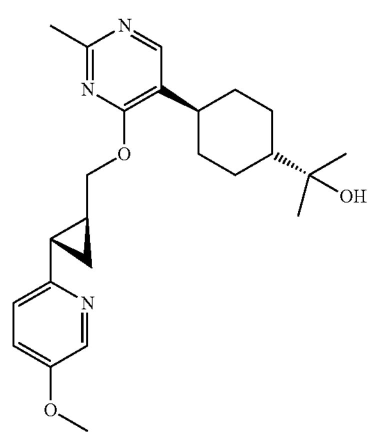 | (trans) 2-(4-4-(((1S,2S)-2-5-methoxypyridin-2-yl)cyclopropyl)methoxy)-2-methylpyrimidin-5-yl)cyclohexyl)propan-2-ol | 412.2 |

TABLE 21-continued

| Example | Structure | IUPAC Name | LCMS m/z [M + H]+ |
|---------|-----------|------------|-------------------|
| 221 | 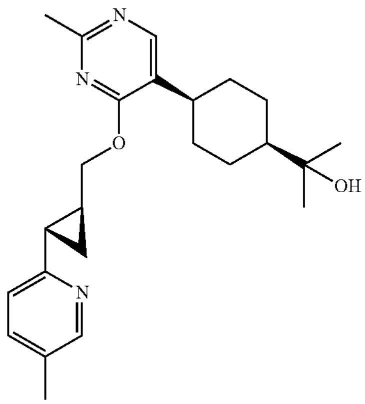 [SMILES: Cc1ccc([C@H]2C[C@@H]2COc2nc(C)ncc2[C@H]2CC[C@@H](C(C)(C)O)CC2)nc1] | (cis)2-(4-(2-methyl-4-(((1S,2S)-2-(5-methylpyridin-2-yl)cyclopropyl)methoxy)pyrimidin-5-yl)cyclohexyl)propan-2-ol | 396.1 |

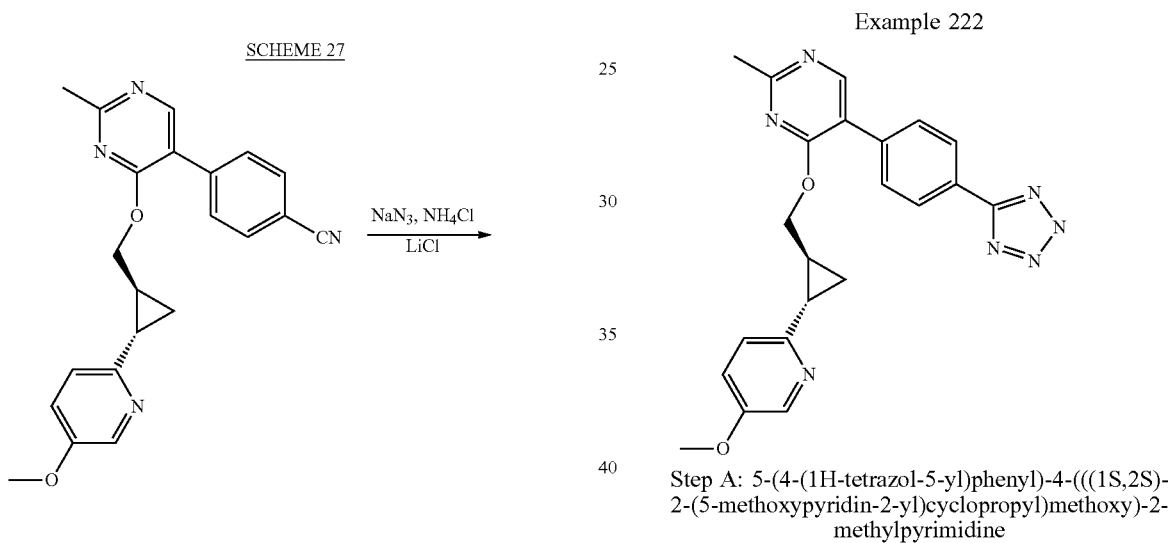

Example 222

Step A: 5-(4-(1H-tetrazol-5-yl)phenyl)-4-(((1S,2S)-2-(5-methoxypyridin-2-yl)cyclopropyl)methoxy)-2-methylpyrimidine A solution of 4-(4-(((1S,2S)-2-(5-methoxypyridin-2-yl)cyclopropyl)methoxy)-2-methylpyrimidin-5-yl)benzonitrile (500 mg, 1.34 mmol) in DMF (anhydrous) (5 mL) was placed in a flask that had been purged and maintained with an inert atmosphere of nitrogen Ammonium chloride (214 mg, 4.03 mmol) was added, followed by the addition of lithium chloride (11.3 mg, 0.27 mmol). To the mixture was added azidosodium (262 mg, 4.03 mmol). The resulting solution was stirred overnight, while maintaining the temperature at 100° C. The solids were filtered out and washed with EtOAc. The filtrate was combined and concentrated under vacuum. The residue was dissolved in 50 ml of 10% NaOH aqueous solution. The resulting solution was extracted with 100 mL of EtOAc and the aqueous layers were combined. The pH value of the combined solution was adjusted to 2 with concentrated HCl. It was extracted with ethyl acetate, the organic layer was dried over $Na_2SO_4$, concentrated and purified by prep-HPLC to afforded a white solid (448 mg). $^1$H NMR (400 MHz, $CD_3OD$) δ 8.37 (s, 1H), 7.98 (s, 1H), 7.97-7.92 (m, 2H), 7.69 (d, 2H), 7.19 (d, 1H), 7.07 (d, 1H), 4.51 (d, 1H), 4.37-4.26 (m, 1H), 3.72 (d, 3H), 2.53 (s, 3H), 2.12-2.00 (m, 1H), 1.69 (s, 1H), 1.20-1.09 (m, 1H), 1.01 (dd, 1H); LRMS m/z (M+H) 415.9 found; 416.4 required.

Example 221 and 224

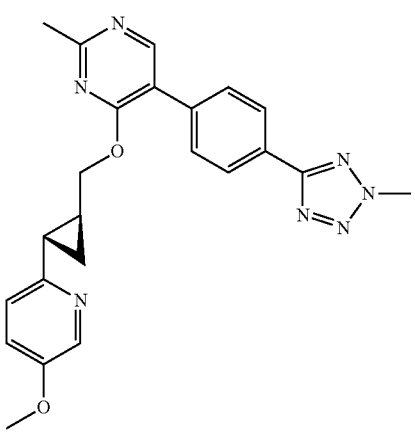

Example 223

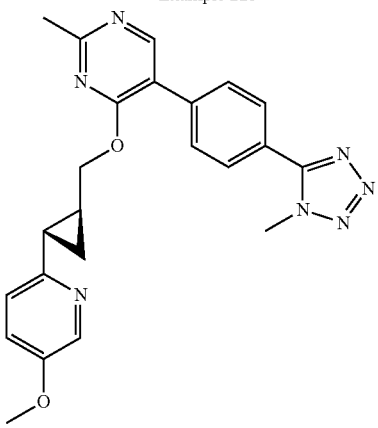

Example 224

Step A: 4-(((1S,2S)-2-(5-methoxypyridin-2-yl)cyclopropyl)methoxy)-2-methyl-5-(4-(2-methyl-2H-tetrazol-5-yl)phenyl)pyrimidine (Example 223) and 4-(((1S,2S)-2-(5-methoxypyridin-2-yl)cyclopropyl)methoxy)-2-methyl-5-(4-(1-methyl-1H-tetrazol-5-yl)phenyl)pyrimidine (Example 224)

To a solution of Example 250 (150 mg, 0.36 mmol) in DMF (2 mL) was added iodomethane (103 mg, 0.72 mmol) and $K_2CO_3$ (100 mg, 0.72 mmol). The resulting mixture was stirred at room temperature for 30 min. Then it was diluted with EtOAc, washed with saturated $NaHCO_3$ aq. and brine, dried over $MgSO_4$, filtered, concentrated in vacuo, and purified by prep-HPLC to afforded Example 251 and Example 252 as white solids. Example 223: $^1$H NMR (400 MHz, CD3OD) δ 8.49 (s, 1H), 8.05 (d, 1H), 7.87 (s, 4H), 7.29 (dd, 1H), 7.17 (d, 1H), 4.63 (dd, 1H), 4.43 (dd, 1H), 4.23 (s, 3H), 3.83 (s, 3H), 2.64 (s, 3H), 2.21-2.11 (m, 1H), 1.81 (d, 1H), 1.30-1.20 (m, 1H), 1.15-1.06 (m, 1H); LRMS m/z (M+H) 429.9 found, 430.4 required Example 224: $^1$H NMR (400 MHz, CD3OD) δ 8.44 (s, 1H), 8.10 (d, 2H), 8.04 (d, 1H), 7.73 (d, 2H), 7.27 (dd, 1H), 7.15 (d, 1H), 4.62 (dd, 1H), 4.43 (s, 3H), 4.38 (dd, 1H), 3.83 (s, 3H), 2.62 (s, 3H), 2.13 (dd, 1H), 1.79 (d, 1H), 1.29-1.20 (m, 1H), 1.10 (dt, 1H); LRMS m/z (M+H) 429.9 found, 430.4 required.

The following EXAMPLE 225-237 in Table 22 was prepared using the procedure of Example 222-224, substituting the appropriate starting materials.

TABLE 22

| Example | Structure | Name | MS m/z (M + H) |
|---|---|---|---|
| 222 | 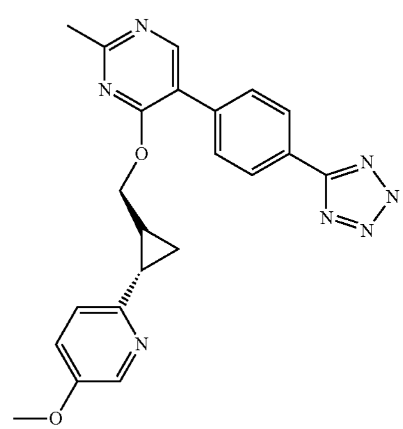 | 5-(4-(1H-tetrazol-5-yl)phenyl)-4-(((1S,2S)-2-(5-methoxypyridin-2-yl)cyclopropyl)methoxy)-2-methylpyrimidine | 416.1 |

TABLE 22-continued

| Example | Structure | Name | MS m/z (M + H) |
|---|---|---|---|
| 223 | 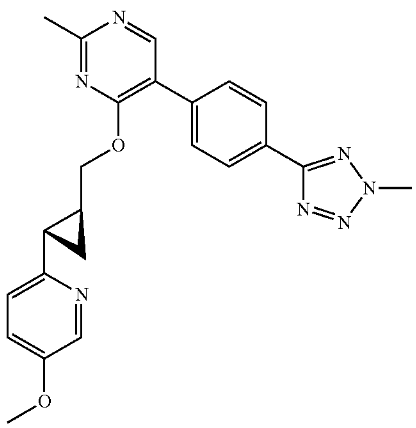 [SMILES: COc1ccc([C@H]2C[C@@H]2COc2nc(C)ncc2-c2ccc(-c3nnn(C)n3)cc2)nc1] | 4-(((1S,2S)-2-(5-methoxypyridin-2-yl)cyclopropyl)methoxy)-2-methyl-5-(4-(2-methyl-2H-tetrazol-5-yl)phenyl)pyrimidine | 429.9 |
| 224 | 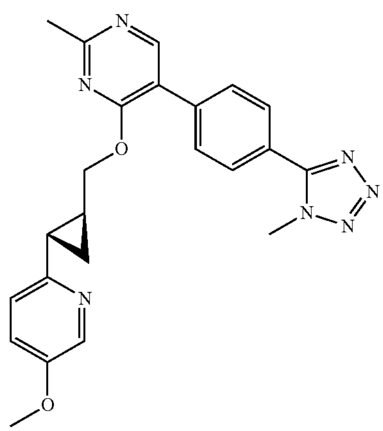 [SMILES: COc1ccc([C@H]2C[C@@H]2COc2nc(C)ncc2-c2ccc(-c3nnnn3C)cc2)nc1] | 4-(((1S,2S)-2-(5-methoxypyridin-2-yl)cyclopropyl)methoxy)-2-methyl-5-(4-(1-methyl-1H-tetrazol-5-yl)phenyl)pyrimidine | 429.9 |
| 225 | 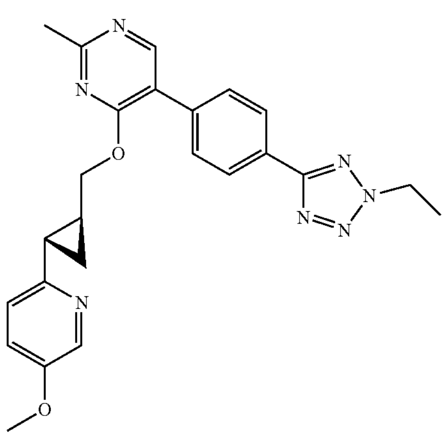 [SMILES: CCn1nnc(-c2ccc(-c3cnc(C)nc3OC[C@H]3C[C@@H]3c3ccc(OC)cn3)cc2)n1] | 5-(4-(2-ethyl-2H-tetrazol-5-yl)phenyl)-4-(((1S,2S)-2-(5-methoxypyridin-2-yl)cyclopropyl)methoxy)-2-methylpyrimidine | 444.1 |

TABLE 22-continued

| Example | Structure | Name | MS m/z (M + H) |
|---|---|---|---|
| 226 | 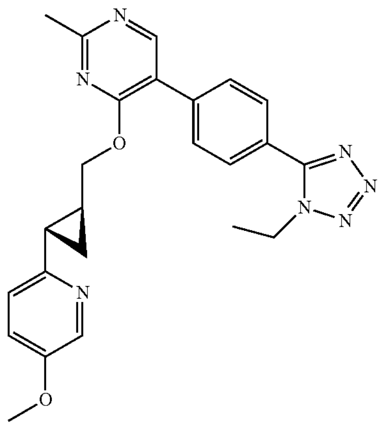 [SMILES: CCn1nnnc1-c1ccc(-c2cnc(C)nc2OC[C@H]2C[C@@H]2c2ccc(OC)cn2)cc1] | 5-(4-(1-ethyl-1H-tetrazol-5-yl)phenyl)-4-(((1S,2S)-2-(5-methoxypyridin-2-yl)cyclopropyl)methoxy)-2-methylpyrimidine | 444.1 |
| 227 | 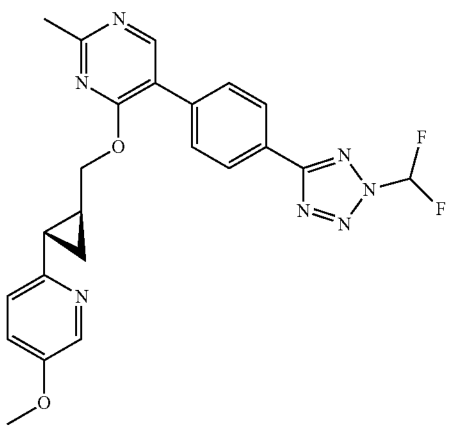 [SMILES: COc1ccc([C@H]2C[C@@H]2COc2nc(C)ncc2-c2ccc(-c3nnn(C(F)F)n3)cc2)nc1] | 5-(4-(2-(difluoromethyl)-2H-tetrazol-5-yl)phenyl)-4-(((1S,2S)-2-(5-methoxypyridin-2-yl)cyclopropyl)methoxy)-2-methylpyrimidine | 466.2 |
| 228 | 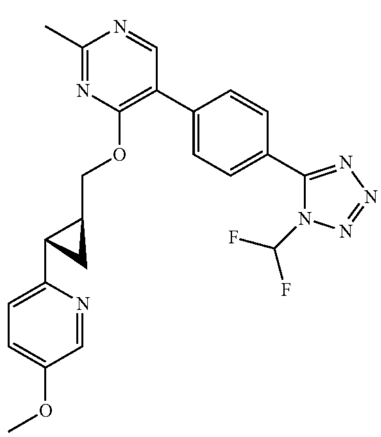 [SMILES: COc1ccc([C@H]2C[C@@H]2COc2nc(C)ncc2-c2ccc(-c3nnnn3C(F)F)cc2)nc1] | 5-(4-(1-(difluoromethyl)-1H-tetrazol-5-yl)phenyl)-4-(((1S,2S)-2-(5-methoxypyridin-2-yl)cyclopropyl)methoxy)-2-methylpyrimidine | 466.2 |

TABLE 22-continued

| Example | Structure | Name | MS m/z (M + H) |
|---|---|---|---|
| 229 | 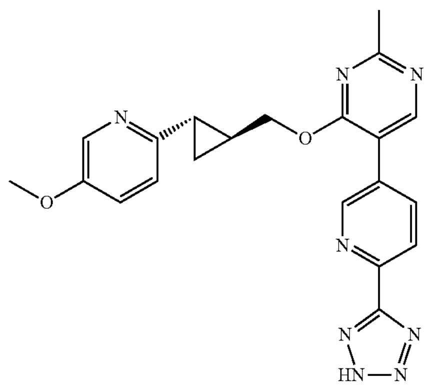 [SMILES: COc1ccc([C@H]2C[C@@H]2COc2nc(C)ncc2-c2ccc(-c3nn[nH]n3)nc2)nc1] | 5-(6-(2H-tetrazol-5-yl)pyridin-3-yl)-4-(((1S,2S)-2-(5-methoxypyridin-2-yl)cyclopropyl)methoxy)-2-methylpyrimidine | 417.3 |
| 230 | 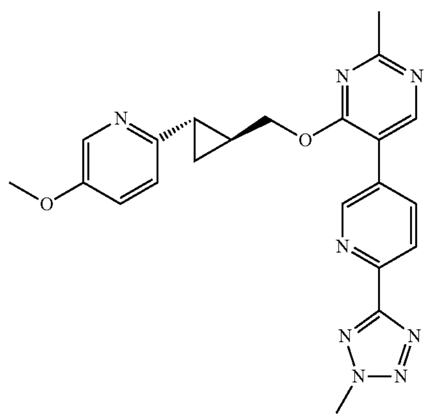 [SMILES: COc1ccc([C@H]2C[C@@H]2COc2nc(C)ncc2-c2ccc(-c3nnn(C)n3)nc2)nc1] | 4-(((1S,2S)-2-(5-methoxypyridin-2-yl)cyclopropyl)methoxy)-2-methyl-5-(6-(2-methyl-2H-tetrazol-5-yl)pyridin-3-yl)pyrimidine | 431.2 |
| 231 | 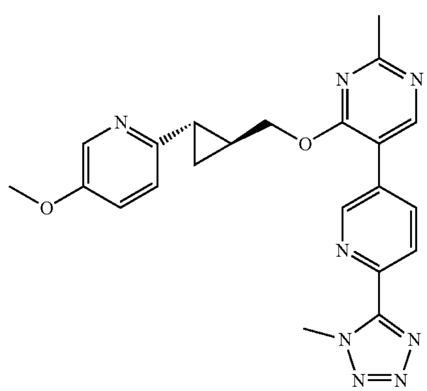 [SMILES: COc1ccc([C@H]2C[C@@H]2COc2nc(C)ncc2-c2ccc(-c3nnnn3C)nc2)nc1] | 4-(((1S,2S)-2-(5-methoxypyridin-2-yl)cyclopropyl)methoxy)-2-methyl-5-(6-(1-methyl-1H-tetrazol-5-yl)pyridin-3-yl)pyrimidine | 431.2 |
| 232 | 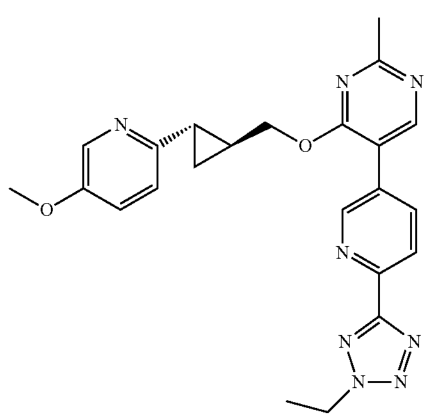 [SMILES: CCn1nnc(-c2ccc(-c3cnc(C)nc3OC[C@H]3C[C@@H]3c3ccc(OC)cn3)cn2)n1] | 5-(6-(2-ethyl-2H-tetrazol-5-yl)pyridin-3-yl)-4-(((1S,2S)-2-(5-methoxypyridin-2-yl)cyclopropyl)methoxy)-2-methylpyrimidine | 445.3 |

TABLE 22-continued

| Example | Structure | Name | MS m/z (M + H) |
|---|---|---|---|
| 233 | 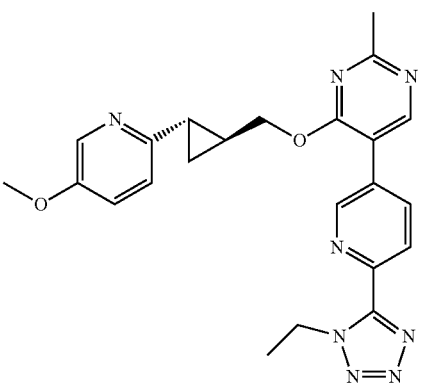 [SMILES: CCn1nnnc1-c1ccc(-c2cnc(C)nc2OC[C@H]2C[C@@H]2c2ccc(OC)cn2)cn1] | 5-(6-(1-ethyl-1H-tetrazol-5-yl)pyridin-3-yl)-4-(((1S,2S)-2-(5-methoxypyridin-2-yl)cyclopropyl)methoxy)-2-methylpyrimidine | 445.3 |
| 234 | 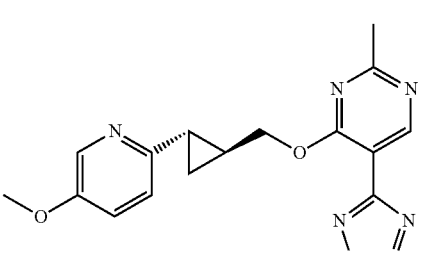 | 4-(((1S,2S)-2-(5-methoxypyridin-2-yl)cyclopropyl)methoxy)-2-methyl-5-(2H-tetrazol-5-yl)pyrimidine | 340.2 |
| 235 | 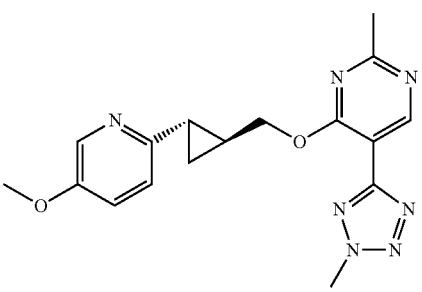 [SMILES: COc1ccc([C@H]2C[C@@H]2COc2nc(C)ncc2-c2nnn(C)n2)nc1] | 4-(((1S,2S)-2-(5-methoxypyridin-2-yl)cyclopropyl)methoxy)-2-methyl-5-(2-methyl-2H-tetrazol-5-yl)pyrimidine | 354.3 |
| 236 | 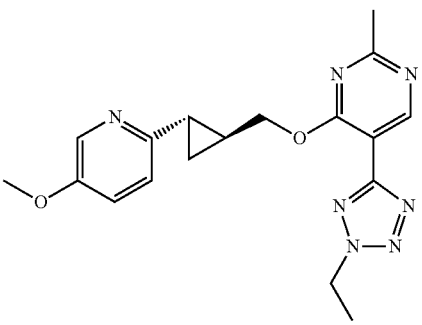 [SMILES: CCn1nnc(-c2cnc(C)nc2OC[C@H]2C[C@@H]2c2ccc(OC)cn2)n1] | 5-(2-ethyl-2H-tetrazol-5-yl)-4-(((1S,2S)-2-(5-methoxypyridin-2-yl)cyclopropyl)methoxy)-2-methylpyrimidine | 368.3 |

TABLE 22-continued
| Example | Structure | Name | MS m/z (M + H) |
|---|---|---|---|
| 237 | 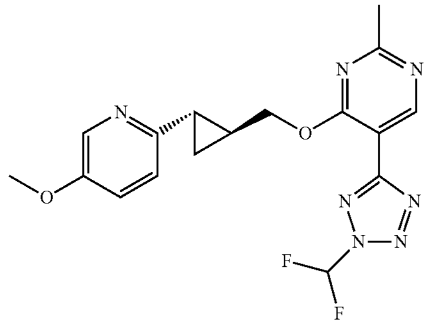 [SMILES: COc1ccc([C@H]2C[C@@H]2COc2nc(C)ncc2-c2nnn(C(F)F)n2)nc1] | 5-(2-(difluoromethyl)-2H-tetrazol-5-yl)-4-(((1S,2S)-2-(5-methoxypyridin-2-yl)cyclopropyl)methoxy)-2-methylpyrimidine | 390.3 |
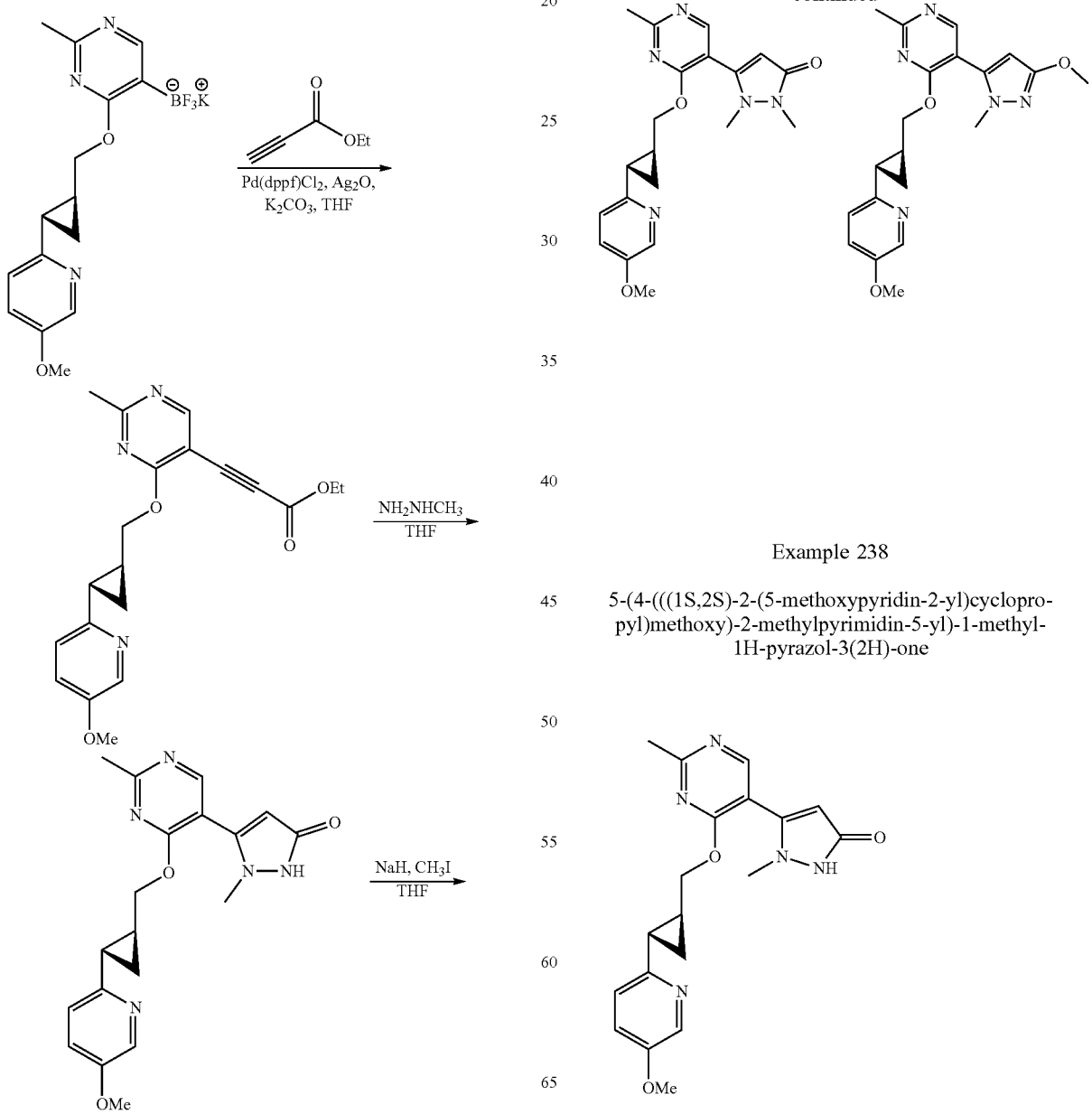
Example 238
5-(4-(((1S,2S)-2-(5-methoxypyridin-2-yl)cyclopropyl)methoxy)-2-methylpyrimidin-5-yl)-1-methyl-1H-pyrazol-3(2H)-one

Step A: Ethyl 3-(4-(((1S,2S)-2-(5-methoxypyridin-2-yl)cyclopropyl)methoxy)-2-methylpyrimidin-5-yl)propiolate

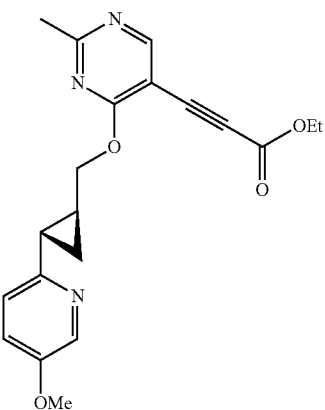 [SMILES: CCOC(=O)C#Cc1cnc(C)nc1OC[C@H]1C[C@@H]1c1ccc(OC)cn1]

A mixture of propiolic acid ethyl ester (130 mg, 1.32 mmol), potassium trifluoro(4-(((1S,2S)-2-(5-methoxypyridin-2-yl)Cyclopropyl)methoxy)-2-methylpyrimidin-5-yl)borate (250 mg, 0.66 mmol), Pd(dppf)Cl$_2$ (57 mg, 0.07 mmol), Ag$_2$O (382 mg, 1.65 mmol) and K$_2$CO$_3$ (445 mg, 0.33 mmol) in THF (5 mL) was purged with nitrogen for 1 min, the mixture was then refluxed overnight. After cooling to room temperature, the mixture was diluted with EtOAc (20 mL) and the resulting solution was washed with water (10 mL) and brine (10 mL). The organic layer was dried over Na$_2$SO$_4$, concentrated and purified by gradient elution on silica gel (0 to 30% EtOAc in petroleum) to afford title compound. LRMS (ES) calculated M+H for C$_{20}$H$_{21}$N$_3$O$_4$, 368.4. found: 368.2.

Step B: 5-(4-(((1S,2S)-2-(5-methoxypyridin-2-yl)cyclopropyl)methoxy)-2-methyl pyrimidin-5-yl)-1-methyl-1,2-dihydropyrazol-3-one

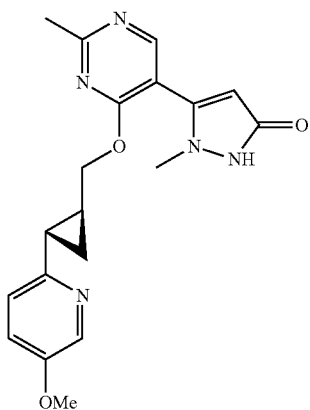 [SMILES: COc1ccc([C@H]2C[C@@H]2COc2nc(C)ncc2-c2cc(=O)[nH]n2C)nc1]

To a solution of ethyl 3-(4-(((1S,2S)-2-(5-methoxypyridin-2-yl)cyclopropyl)methoxy)-2-methylpyrimidin-5-yl)propiolate (60 mg, 0.163 mmol) in THF (2 mL) was added methylhydrazine (187 mg, 1.63 mmol). The mixture was heated to 70° C. for 1.5 h, and then concentrated under reduced pressure to afford a crude product, which was purified by Prep-HPLC to afford the title compound (28 mg, 35%) as a yellow oil. $^1$H NMR (400 MHz, MeOD) δ 8.20 (s, 1H), 8.04 (d, 1H), 7.20 (dd, 1H), 7.07 (d, 1H), 5.33 (s, 1H), 4.48 (m, 1H), 4.34 (m, 1H), 3.74 (s, 3H), 3.30 (s, 3H), 3.23 (s, 1H), 2.54 (s, 3H), 2.02-2.06 (m, 1H), 1.72-7.76 (m, 1H), 1.10-1.15 (m, 1H), 0.96-1.01 (m, 1H). LRMS (ES) calculated M+H for C$_{19}$H$_{21}$N$_5$O$_3$, 368.4. found: 368.1

Example 239 and 240

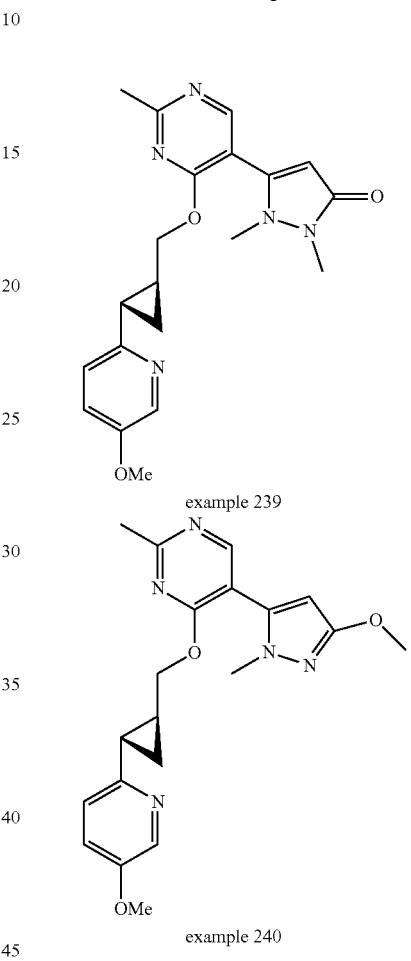

example 239 example 240

Step A: 5-(4-(((1S,2S)-2-(5-methoxypyridin-2-yl)cyclopropyl)methoxy)-2-methyl pyrimidin-5-yl)-1,2-dimethyl-1,2-dihydropyrazol-3-one (Example 239) and 5-(3-methoxy-1-methyl-2,3-dihydro-1H-pyrazol-5-yl)-4-(((1S,2S)-2-(5-methoxypyridin-2-yl)cyclopropyl)methoxy)-2-methylpyrimidine (Example 240)

To a solution of 5-(4-(((1S,2S)-2-(5-methoxypyridin-2-yl)cyclopropyl)methoxy)-2-methylpyrimidin-5-yl)-1-methyl-1,2-dihydropyrazol-3-one (110 mg, 0.30 mmol) in THF (5 mL) was added sodium hydride (20 mg, 0.45 mmol) at 0° C. The mixture was stirred at room temperature for 10 min, iodomethane (63 mg, 0.45 mmol) was added and continue stirring for 10 h. The mixture was quenched with water (0.5 mL), and the mixture was purified by Prep-HPLC to afford the title compound Example 239 (10 mg, 8.7%) and Example 240 (28 mg, 24.36%). Example 239: $^1$H NMR (400 MHz, MeOD) δ 8.41 (s, 1H), 8.04 (d, 1H), 7.28 (dd, 1H), 7.16 (d, 1H), 5.54 (s, 1H), 4.62 (m, 1H), 4.42 (m, 1H), 3.82

(s, 3H), 3.46 (s, 3H), 3.34 (s, 3H), 2.64 (s, 3H), 2.02-2.06 (m, 1H), 1.72-7.76 (m, 1H), 1.10-1.15 (m, 1H), 0.96-1.01 (m, 1H). LRMS (ES) calculated M+H for $C_{20}H_{23}N_5O_3$, 382.4. found: 382.2. Example 240: $^1$H NMR (400 MHz, MeOD) δ 8.40 (s, 1H), 8.04 (d, 1H), 7.27 (dd, 1H), 7.14 (d, 1H), 5.79 (s, 1H), 4.56-4.61 (m, 1H), 4.39-4.44 (m, 1H), 3.82 (s, 6H), 3.53 (s, 3H), 2.63 (s, 3H), 2.01-2.16 (m, 1H), 1.80-1.84 (m, 1H), 1.10-1.24 (m, 1H), 1.06-1.09 (m, 1H). LRMS (ES) calculated M+H for $C_{20}H_{23}N_5O_3$, 382.4. found: 382.2.

The following EXAMPLE 241 in Table 23 was prepared using the procedure of EXAMPLE 238, substituting the appropriate starting materials.

TABLE 23

| Example | Structure | Name | MS m/z (M + H) |
|---|---|---|---|
| 238 | 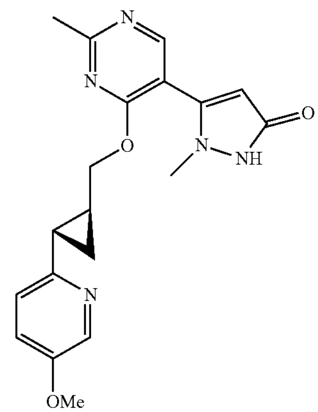 [SMILES: COc1ccc([C@H]2C[C@@H]2COc2nc(C)ncc2-c2cc(=O)[nH]n2C)nc1] | 5-(4-(((1S,2S)-2-(5-methoxypyridin-2-yl)cyclopropyl)methoxy)-2-methylpyrimidin-5-yl)-1-methyl-1,2-dihydropyrazol-3-one | 368.1 |
| 239 | 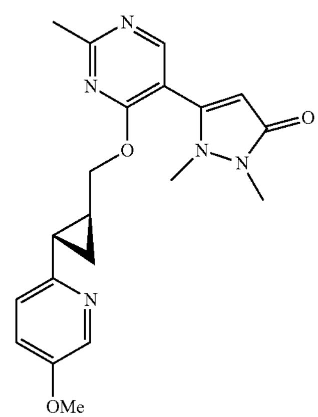 [SMILES: COc1ccc([C@H]2C[C@@H]2COc2nc(C)ncc2-c2cc(=O)n(C)n2C)nc1] | 5-(4-(((1S,2S)-2-(5-methoxypyridin-2-yl)cyclopropyl)methoxy)-2-methylpyrimidin-5-yl)-1,2-dimethyl-1,2-dihydropyrazol-3-one | 382.2 |
| 240 | 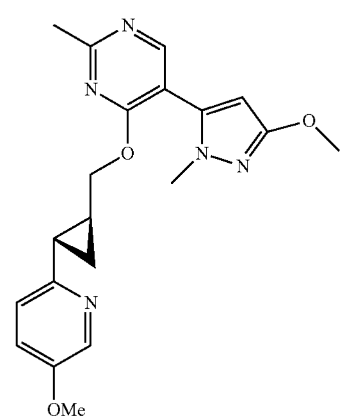 [SMILES: COc1ccc([C@H]2C[C@@H]2COc2nc(C)ncc2-c2cc(OC)nn2C)nc1] | 5-(3-methoxy-1-methyl-1H-pyrazol-5-yl)-4-(((1S,2S)-2-(5-methoxypyridin-2-yl)cyclopropyl)methoxy)-2-methylpyrimidine | 382.2 |

TABLE 23-continued
| Example | Structure | Name | MS m/z (M + H) |
|---|---|---|---|
| 241 | 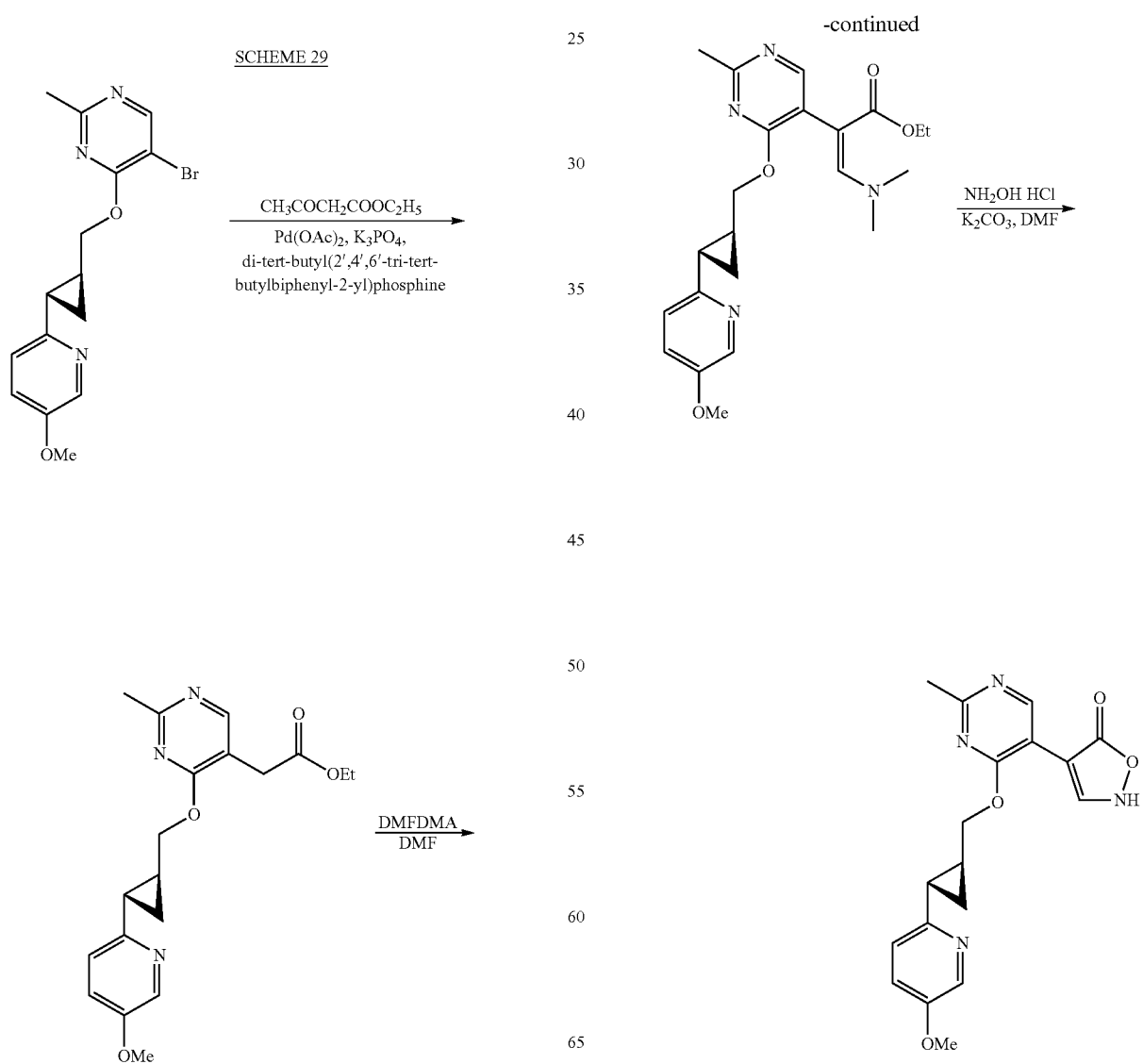 | 5-(4-((((1S,2S)-2-(5-methoxypyridin-2-yl)cyclopropyl)methoxy)-2-methylpyrimidin-5-yl)-1,2-dihydropyrazol-3-one | 354.1 |
SCHEME 29

Example 242

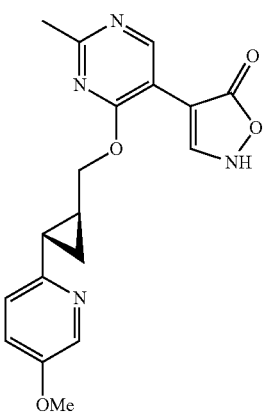 [SMILES: COc1ccc([C@H]2C[C@@H]2COc2nc(C)ncc2-c2c[nH]oc2=O)nc1]

Step A: Ethyl 2-(4-(((1S,2S)-2-(5-methoxypyridin-2-yl)cyclopropyl)methoxy)-2-methyl pyrimidin-5-yl)acetate A mixture of 5-bromo-4-(((1S,2S)-2-(5-methoxypyridin-2-yl)cyclopropyl)methoxy)-2-methylpyrimidine (400 mg, 1.14 mmol), Pd(OAc)$_2$ (10 mg, 0.04 mmol), di-tert-butyl(2', 4',6'-tri-tert-butylbiphenyl-2-yl)phosphine (36 mg, 0.08 mmol), K$_3$PO$_4$ (1.2 g, 5.7 mmol) and ethyl acetoacetate (445 mg, 3.42 mmol) in toluene (2 mL) was heated to 90° C. overnight. After it was cooled to room temperature, it was concentrated and purified by gradient elution on silica gel (0 to 50% EtOAc in petroleum) to afford the title compound (200 mg, 49.26%) as a brown oil. $^1$H NMR (400 MHz, CDCl3) δ 8.14-8.18 (br, 2H), 7.04-7.10 (m, 2H), 4.37-4.32 (m, 2H), 4.067-4.12 (m, 2H), 3.81 (s, 3H), 3.49 (s, 2H), 2.57 (s, 3H), 2.01-2.06 (m, 1H), 1.78-1.84 (br, 1H), 1.22-1.26 (m, 1H), 1.18 (t, 3H), 0.99-1.03 (m, 1H). LRMS (ES) calculated M+H for C$_{19}$H$_{23}$N$_3$O$_4$, 358.4. found: 358.1.

Step B: (Z)-ethyl 3-(dimethylamino)-2-(4-(((1S,2S)-2-(5-methoxypyridin-2-yl)cyclopropyl)methoxy)-2-methylpyrimidin-5-yl)acrylate A mixture of ethyl 2-(4-(((1S,2S)-2-(5-methoxypyridin-2-yl)cyclopropyl)methoxy)-2-methylpyrimidin-5-yl) acetate (110 mg, 0.308 mmol) and DMFDMA (367 mg, 3.08 mmol) in DMF (1 mL) was heated to 90° C. overnight, and the mixture was concentrated to give the crude product. LRMS (ES) calculated M+H for C$_{22}$H$_{28}$N$_4$O$_4$, 413.5. found: 413.1.

Step C: 4-(4-(((1S,2S)-2-(5-methoxypyridin-2-yl)cyclopropyl)methoxy)-2-methyl pyrimidin-5-yl)isoxazol-5(2H)-one To a solution of (Z)-ethyl 3-(dimethylamino)-2-(4-(((1S, 2S)-2-(5-methoxypyridin-2-yl)cyclopropyl)m ethoxy)-2-methylpyrimidin-5-yl)acrylate (50 mg, 0.12 mmol) and K$_2$CO$_3$ (66 mg, 0.48 mmol) in DMF (1 mL) was added hydroxylamine hydrochloride (33 mg, 0.48 mmol), the mixture was stirred at 80° C. for 2 h. The reaction mixture was purified by reserved phase (H$_2$O: MeOH=90%-10%) to afford the title compound (30 mg, 71%) as a white solid. $^1$H NMR (400 MHz, MeOD) δ 9.16 (s, 1H), 8.54 (s, 1H), 8.12 (d, 1H), 7.38 (dd, 1H), 7.28 (d, 1H), 4.78-4.88 (m, 1H), 4.52-4.57 (m, 1H), 3.87 (s, 3H), 2.68 (s, 3H), 2.26-2.30 (m, 1H), 1.95-1.99 (br, 1H), 1.36-1.40 (m, 1H), 1.20-1.24 (m, 1H). LRMS (ES) calculated M+H for C$_{18}$H$_{18}$N$_4$O$_4$, 355.4 found: 355.1.

The following EXAMPLE 243 and 244 in Table 24 were prepared using the procedure of EXAMPLE 270, substituting the appropriate starting materials.

TABLE 24

| Example | Structure | Name | MS m/z (M + H) |
|---------|-----------|------|----------------|
| 242 | 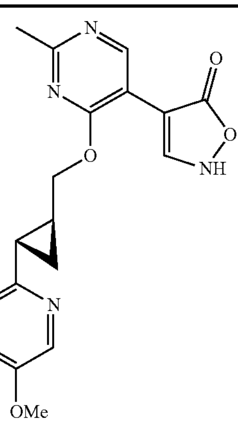 | 4-(4-(((1S,2S)-2-(5-methoxypyridin-2-yl)cyclopropyl)methoxy)-2-methylpyrimidin-5-yl)isoxazol-5(2H)-one | 355.1 |

TABLE 24-continued
| Example | Structure | Name | MS m/z (M + H) |
|---|---|---|---|
| 243 | 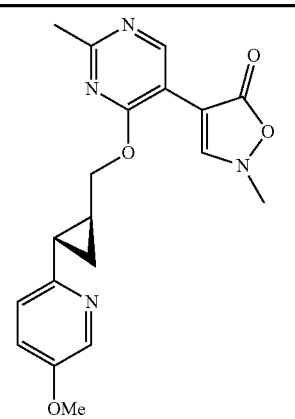 | 4-(4-(((1S,2S)-2-(5-methoxypyridin-2-yl)cyclopropyl)methoxy)-2-methylpyrimidin-5-yl)-2-methylisoxazol-5(2H)-one | 369.1 |
| 244 | 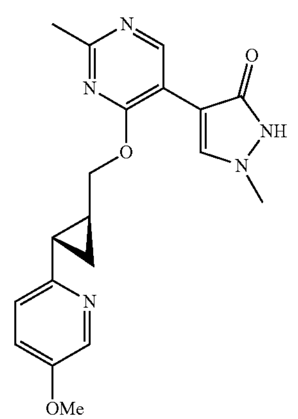 [SMILES: COc1ccc([C@H]2C[C@@H]2COc2nc(C)ncc2-c2cn(C)[nH]c2=O)nc1] | 4-(4-(((1S,2S)-2-(5-methoxypyridin-2-yl)cyclopropyl)methoxy)-2-methylpyrimidin-5-yl)-1-methyl-1,2-dihydropyrazol-3-one | 368.1 |
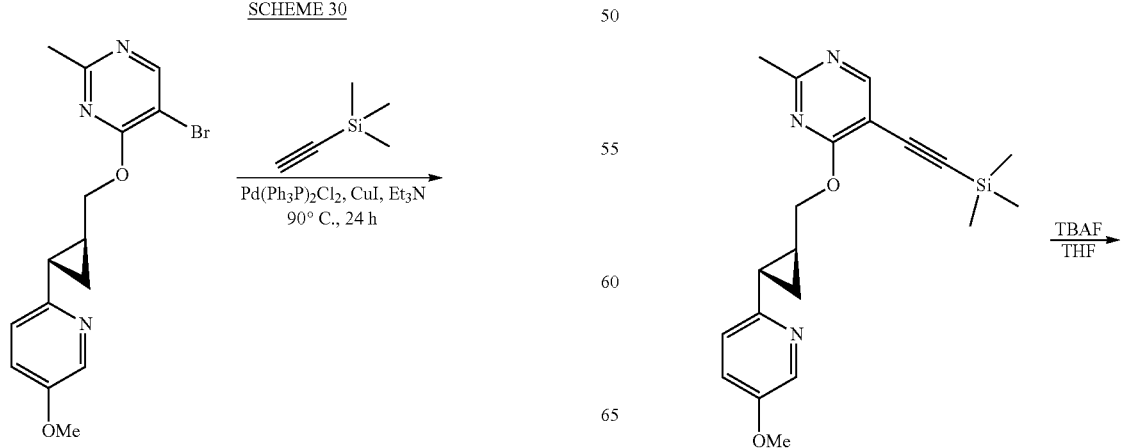

233

-continued

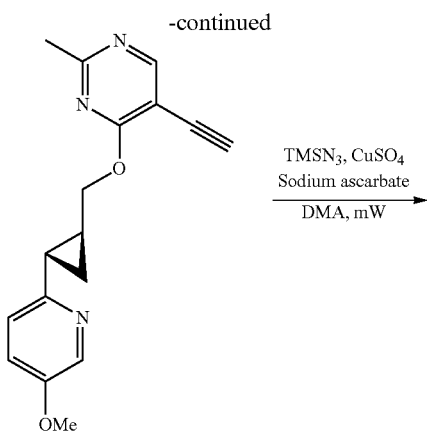

TMSN₃, CuSO₄
Sodium ascarbate
———————————→
DMA, mW

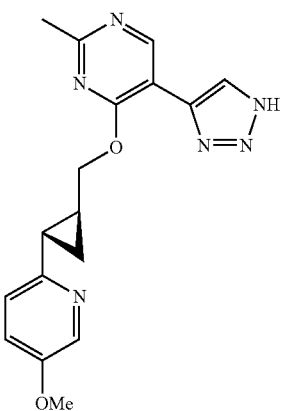

Example 245

4-(((1S,2S)-2-(5-methoxypyridin-2-yl)cyclopropyl)methoxy)-2-methyl-5-(1H-1,2,3-triazol-4-yl)pyrimidine

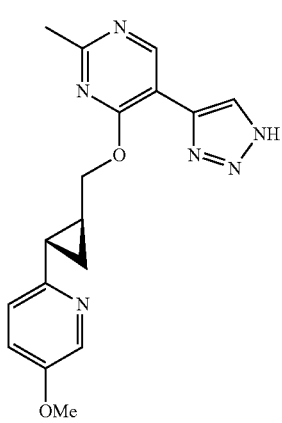 [SMILES: COc1ccc([C@H]2C[C@@H]2COc2nc(C)ncc2-c2c[nH]nn2)nc1]

234

Step A: 4-(((1S,2S)-2-(5-methoxypyridin-2-yl)cyclopropyl)methoxy)-2-methyl-5-((trimethylsilyl)ethynyl)pyrimidine A mixture of 5-bromo-4-((((1S,2S)-2-(5-methoxypyridin-2-yl)cyclopropyl)methoxy)-2-methylpyrimidine (100 mg, 0.29 mmol), ethynyltrimethylsilane1 (112 mg, 1.15 mmol), CuI (2.7 mg, 0.14 mmol), (PPh₃)₂PdCl₂ (10 mg, 0.14 mmol) in Et₃N (1 mL) was purged with nitrogen for 1 min, the mixture was stirred at 95° C. overnight. After cooling to room temperature, the reaction mixture was diluted with water (10 mL), extracted with EtOAc (15×3 mL), concentrated to afford crude product (85 mg, 81%). The crude product was used in the subsequent step without further purification. LRMS (ES) calculated M+H for $C_{20}H_{25}N_3O_2Si$: 368.5.3. Found: 368.1.

Step B: 5-ethynyl-4-(((1S,2S)-2-(5-methoxypyridin-2-yl)cyclopropyl)methoxy)-2-methylpyrimidine To a solution of 4-(((1S,2S)-2-(5-methoxypyridin-2-yl)cyclopropyl)methoxy)-2-methyl-5-((trimethylsilyl)ethynyl)pyrimidine (1.5 g, 4.08 mmol) was added 1M TBAF (20 mL), The mixture was stirred at room temperature for 4 h, then the reaction mixture was concentrated and purified by gradient elution on silica gel (0 to 20% EtOAc in petroleum) to afford title compound (1.08 g, 90%). ¹H NMR (400 MHz, CDCl₃) δ 8.46 (s, 1H), 8.19 (d, 1H), 7.16-6.97 (m, 2H), 4.64-4.35 (m, 2H), 4.01-3.68 (m, 3H), 3.47-3.15 (m, 1H), 2.88-2.41 (m, 3H), 2.19-2.07 (m, 1H), 1.95-1.72 (m, 1H), 1.37-1.22 (m, 1H), 1.08 (dt, 1H). LRMS (ES) calculated M+H for $C_{12}H_{12}N_3O_2$: 296.3. Found: 296.1.

Step C: 4-(((1S,2S)-2-(5-methoxypyridin-2-yl)cyclopropyl)methoxy)-2-methyl-5-(1H-1,2,3-triazol-4-yl)pyrimidine A mixture of 5-ethynyl-4-(((1S,2S)-2-(5-methoxypyridin-2-yl)cyclopropyl)methoxy)-2-methylpyrimidine (100 mg, 0.34 mmol), TMSN₃ (78 mg, 0.68 mmol), CuSO₄ (6 mg, 0.03 mmol) and sodium ascorbate (13 mg, 0.07 mmol) in DMA (2 mL) was purged with nitrogen for 1 min, which was heated to 100° C. in microwave reactor for 4 h, then the mixture was diluted with water (10 mL), extracted with EtOAc (15×3 mL), dried over Na₂SO₄, concentrated and purified by gradient elution on silica gel (PE:EA=2:1-DCM:MeOH=30:1) to afford the title compound (40 mg, 36%). ¹H NMR (400 MHz, CDCl₃) δ 9.06 (s, 1H), 8.33 (s, 1H), 8.21 (s, 1H), 7.19-6.98 (m, 2H), 4.65 (s, 1H), 4.41 (s, 1H), 3.85 (s, 3H), 2.66 (s, 3H), 2.18 (s, 1H), 1.88 (s, 1H), 1.41 (s, 1H), 1.12 (s, 1H). LRMS (ES) calculated M+H for $C_{12}H_{18}N_6O_2$: 339.4. Found: 339.0.

SCHEME 31

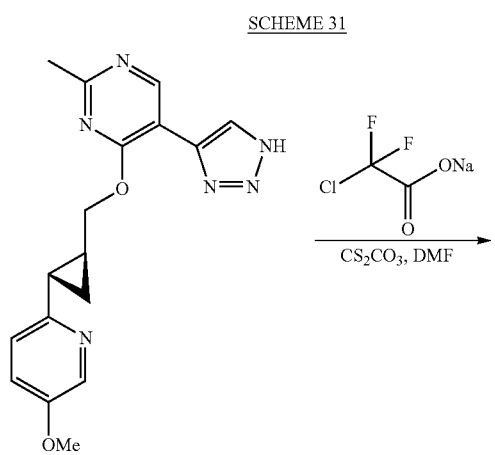

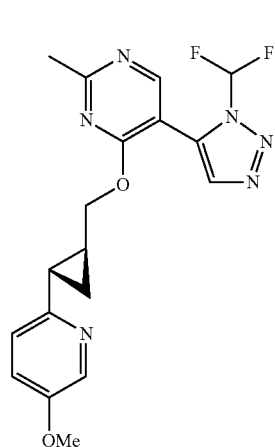

Example 246

5-(1-(difluoromethyl)-1H-1,2,3-triazol-5-yl)-4-(((1S,2S)-2-(5-methoxypyridin-2-yl)cyclopropyl)methoxy)-2-methylpyrimidine

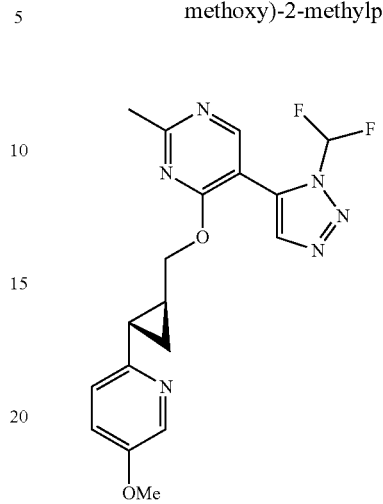

A mixture of 4-(((1S,2S)-2-(5-methoxypyridin-2-yl)cyclopropyl)methoxy)-2-methyl-5-(1H-1,2,3-triazol-4-yl)pyrimidine (80 mg, 0.237 mmol), sodium 2-chloro-2,2-difluoroacetate (91 mg, 0.60 mmol) and Cs$_2$CO$_3$ (117 mg, 0.36 mmol) in DMF (1.5 mL) was purged with nitrogen for 1 min, which was heated to 70° C. for 1 h, the mixture was purified was diluted with EtOAc (20 mL), the resulting solution was washed with water (10 mL) and brine (10 mL), organic layer was dried over Na$_2$SO$_4$, concentrated and purified by Prep-HPLC to afford the title compound (25 mg, 27%). H NMR (400 MHz, MeOD) δ 9.17 (s, 1H), 8.59 (s, 1H), 8.07 (d, 1H), 7.98 (s, 1H), 7.29 (dd, 1H), 7.20 (d, 1H), 4.74 (dd, 1H), 4.44 (dd, 1H), 3.83 (s, 3H), 2.63 (s, 3H), 2.43-2.11 (m, 1H), 2.00-1.70 (m, 1H), 1.45-1.24 (m, 1H), 1.16 (dt, 1H). LRMS (ES) calculated M+H for LRMS (ES) calculated M+H for C$_{18}$H$_{18}$F$_2$N$_6$O$_2$: 389.7. found: 389.2.

The following EXAMPLE 247 in Table 25 was prepared using the procedure of EXAMPLE 245, substituting the appropriate starting materials.

TABLE 25

| Example | Structure | Name | MS m/z (M + H) |
|---------|-----------|------|----------------|
| 245 | 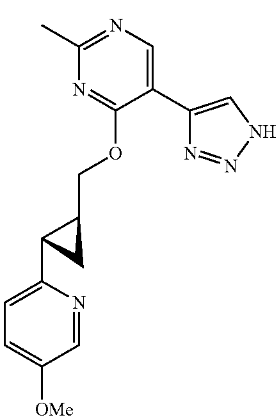 [SMILES: COc1ccc([C@H]2C[C@@H]2COc2nc(C)ncc2-c2c[nH]nn2)nc1] | 4-(((1S,2S)-2-(5-methoxypyridin-2-yl)cyclopropyl)methoxy)-2-methyl-5-(1H-1,2,3-triazol-4-yl)pyrimidine | 339.0 |

TABLE 25-continued
| Example | Structure | Name | MS m/z (M + H) |
|---|---|---|---|
| 246 | 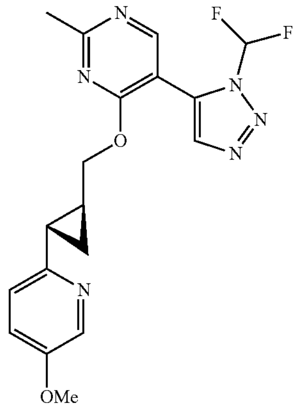 [SMILES: COc1ccc([C@H]2C[C@@H]2COc2nc(C)ncc2-c2cnnn2C(F)F)nc1] | 5-(3-(difluoromethyl)-3H-1,2,3-triazol-4-yl)-4-(((1S,2S)-2-(5-methoxypyridin-2-yl)cyclopropyl)methoxy)-2-methylpyrimidine | 389.1 |
| 247 | 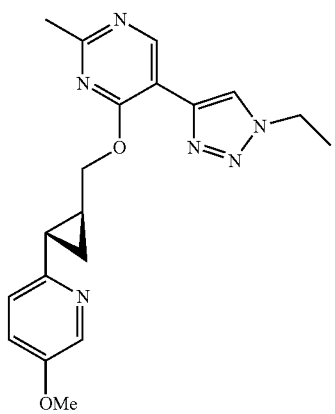 [SMILES: CCn1cc(-c2cnc(C)nc2OC[C@H]2C[C@@H]2c2ccc(OC)cn2)nn1] | 5-(1-ethyl-1H-1,2,3-triazol-4-yl)-4-(((1S,2S)-2-(5-methoxypyridin-2-yl)cyclopropyl)methoxy)-2-methylpyrimidine | 367.2 |
SCHEME 32
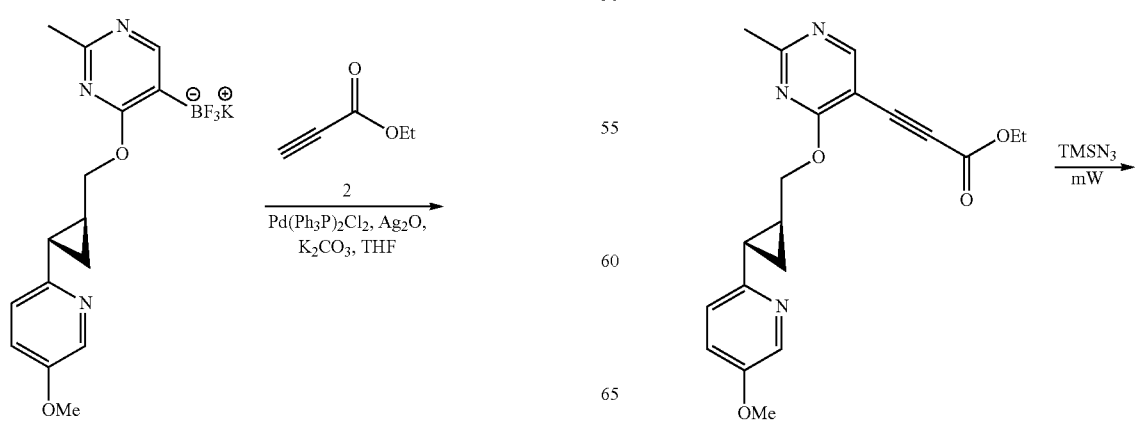
-continued -continued

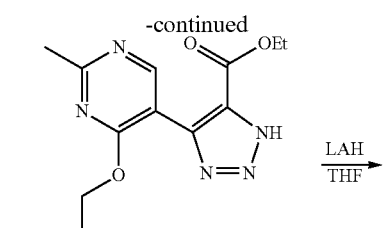

LAH / THF →

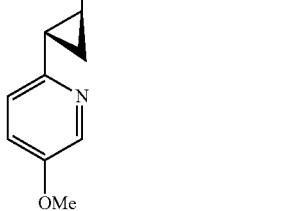

Example 248 ethyl 4-(4-(((1S,2S)-2-(5-methoxypyridin-2-yl)cyclopropyl)methoxy)-2-methylpyrimidin-5-yl)-1H-1,2,3-triazole-5-carboxylate

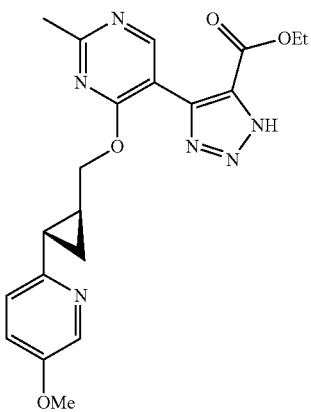 [SMILES: CCOC(=O)c1[nH]nnc1-c1cnc(C)nc1OC[C@H]1C[C@@H]1c1ccc(OC)cn1]

Step A: Ethyl3-(4-(((1S,2S)-2-(5-methoxypyridin-2-yl)cyclopropyl)methoxy)-2-methyl pyrimidin-5-yl)propiolate A mixture of propiolic acid ethyl ester (130 mg, 1.32 mmol), potassium trifluoro(4-(((1S,2S)-2-(5-methoxypyridin-2-yl)Cyclopropyl)methoxy)-2-methylpyrimidin-5-yl)borate (250 mg, 0.66 mmol), Pd(Ph₃P)₂Cl₂ (57 mg, 0.07 mmol), Ag₂O (382 mg, 1.65 mmol) and K₂CO₃ (445 mg, 0.33 mmol) in THF (5 mL) was purged with nitrogen for 1 min, then the mixture was refluxed overnight. After it was cooled to room temperature, the mixture was diluted with EtOAc (20 mL), washed with water (10 mL) and brine (10 mL). The organic layer was dried over Na₂SO₄, concentrated and purified by gradient elution on silica gel (0 to 30% EtOAc in petroleum) to afford title compound. LRMS (ES) calculated M+H for $C_{20}H_{21}N_3O_4$, 368.4. found: 368.2.

Step B: Ethyl 5-(4-(((1S,2S)-2-(5-methoxypyridin-2-yl)cyclopropyl)methoxy)-2-methylpyrimidin-5-yl)-3H-1,2,3-triazole-4-carboxylate A mixture of Ethyl 3-(4-(((1S,2S)-2-(5-methoxypyridin-2-yl)cyclopropyl)methoxy)-2-methylpyrimidin-5-yl)propiolate (120 mg, 0.33 mmol) in TMSN₃ (2 mL) was heated to 135° C. in a microwave reactor for 10 h, then the mixture was concentrated in vacuum. The residue was purified by reverse chromatograph to afford the title compound (50 mg, 37%). ¹H NMR (400 MHz, CDCl₃) δ 8.78 (s, 1H), 8.31 (d, 1H), 7.26 (s, 1H), 7.16 (dd, 1H), 7.03 (d, 1H), 5.04 (dd, 1H), 4.39 (q, 2H), 3.98 (t, 1H), 3.83 (s, 3H), 2.64 (s, 3H), 2.15 (dd, 1H), 1.55-1.44 (m, 1H), 1.33 (m, 4H), 1.12-1.02 (m, 1H). LRMS (ES) calculated M+H for $C_{20}H_{22}N_6O_4$, 411.4. found: 411.2.

Example 249

(4-(4-(((1S,2S)-2-(5-methoxypyridin-2-yl)cyclopropyl)methoxy)-2-methylpyrimidin-5-yl)-1H-1,2,3-triazol-5-yl)methanol

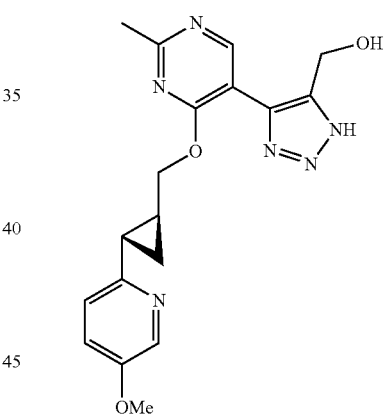

Step C: (5-(4-(((1S,2S)-2-(5-methoxypyridin-2-yl)cyclopropyl)methoxy)-2-methyl pyrimidin-5-yl)-3H-1,2,3-triazol-4-yl)methanol To a solution of Ethyl5-(4-(((1S,2S)-2-(5-methoxypyridin-2-yl)cyclopropyl)methoxy)-2-methylpyrimidin-5-yl)-3H-1,2,3-triazole-4-carboxylate (30 mg, 0.07 mmol) in THF (1 mL) was added LAH (13 mg, 0.35 mmol) at 0° C. After addition, the mixture was stirred at room temperature overnight. After the mixture was quenched with water (0.1 mL), 10% of NaOH (0.1 mL) and water (0.3 mL), the resulting solution was extracted with DCM (5 mL×3) and organic layer was concentrated and purified by prep-HPLC to afford the title compound (5 mg, 20%). ¹H NMR (400 MHz, MeOD) δ 8.69 (s, 1H), 8.31 (d, 1H), 7.97 (d, 1H), 7.58 (d, 1H), 4.76 (br, 3H), 4.52-4.57 (m, 1H), 4.39 (s, 3H), 2.71 (s, 3H), 2.40 (br, 1H), 2.08 (br, 1H), 1.47 (br, 2H), LRMS (ES) calculated M+H for $C_{18}H_{20}N_6O_3$, 369.4. found: 369.1.

TABLE 26
| Example | Structure | Name | MS m/z (M + H) |
|---|---|---|---|
| 248 | 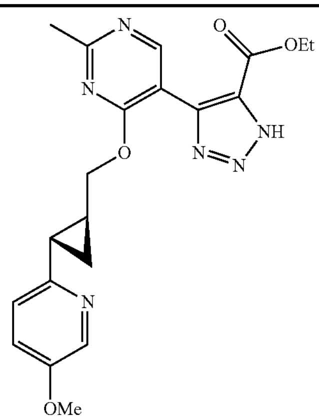 | ethyl 5-(4-(((1S,2S)-2-(5-methoxypyridin-2-yl)cyclopropyl)methoxy)-2-methylpyrimidin-5-yl)-3H-1,2,3-triazole-4-carboxylate | 411.2 |
| 249 | 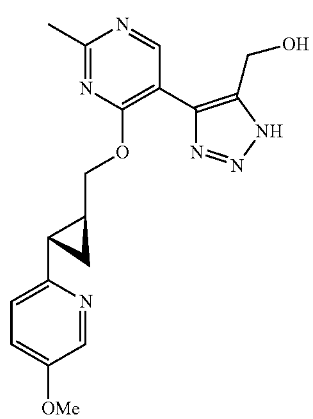 [SMILES: COc1ccc([C@H]2C[C@@H]2COc2nc(C)ncc2-c2nn[nH]c2CO)nc1] | (5-(4-(((1S,2S)-2-(5-methoxypyridin-2-yl)cyclopropyl)methoxy)-2-methylpyrimidin-5-yl)-3H-1,2,3-triazol-4-yl)methanol | 369.1 |
SCHEME 33
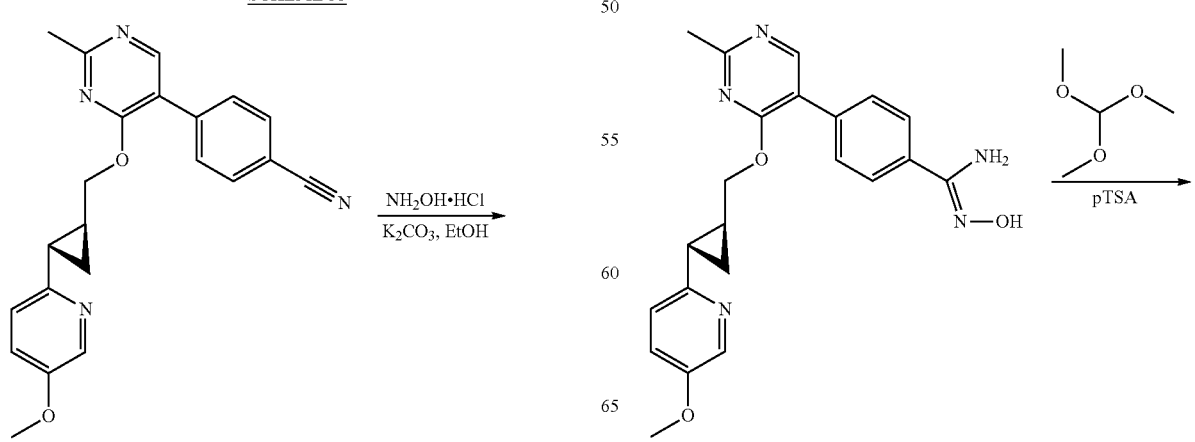

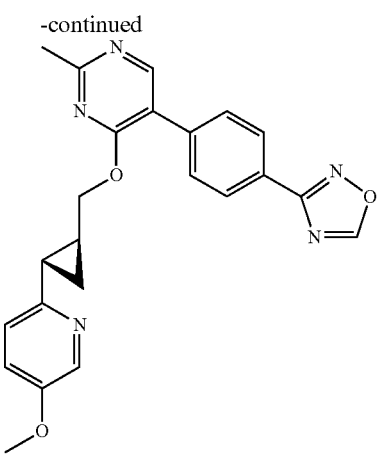

Example 250

3-(4-(4-(((1S,2S)-2-(5-methoxypyridin-2-yl)cyclopropyl)methoxy)-2-methylpyrimidin-5-yl)phenyl)-1,2,4-oxadiazole

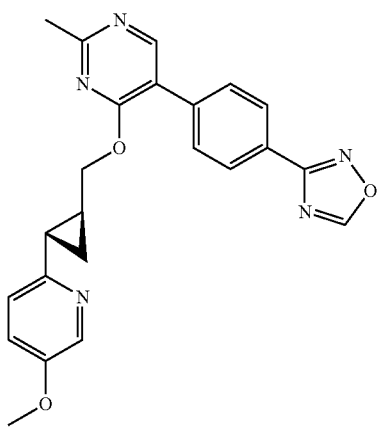 [SMILES: COc1ccc([C@H]2C[C@@H]2COc2nc(C)ncc2-c2ccc(-c3ncon3)cc2)nc1]

Step A: (Z)—N'-hydroxy-4-(4-(((1S,2S)-2-(5-methoxypyridin-2-yl)cyclopropyl)methoxy)-2-methylpyrimidin-5-yl)benzimidamide A mixture of 4-(4-(((1S,2S)-2-(5-methoxypyridin-2-yl)cyclopropyl)methoxy)-2-methylpyrimidin-5-yl)benzonitrile (500 mg, 1.69 mmol), hydroxyamine hydrochloride (590 mg, 4.2 mmol), potassium carbonate (1160 mg, 4.2 mmol) in 25 ml of ethanol were stirred at 85° C. overnight. After cooled, the mixture was filtered, concentrated to give the product (550 mg, 80%) as a white solid. LRMS m/z (M+H) 406.1 found, 406.18 required.

Step B: 3-(4-(4-(((1S,2S)-2-(5-methoxypyridin-2-yl)cyclopropyl)methoxy)-2-methyl pyrimidin-5-yl)phenyl)-1,2,4-oxadiazole N'-hydroxy-4-(4-(((1S,2S)-2-(5-methoxypyridin-2-yl)cyclopropyl)methoxy)-2-methyl pyrimidin-5-yl)benzimidamide (100 mg, 0.25 mmol) was dissolved in 10 mL of trimethyl orthoformate and p-toluenesulfonic acid monohydrate (10 mg) was added, then the mixture was heated under reflux for 1 h. After cooled, the mixture was concentrated and 50 mL of EA was added. The organic layer was washed with saturated NaHCO₃ (10 ml*2), then washed with brine (10 ml), dried over MgSO₄, filtered and concentrated in vacuo. The resulting residue was purified by Pre-TLC (Hex/EA=3:1) to afford the title compound as a white solid (35 mg, 34%). ¹H NMR (400 MHz, CD₃OD) δ 9.30 (s, 1H), 8.47 (s, 1H), 8.12 (d, 2H), 8.06 (d, 1H), 7.77 (d, 2H), 7.29 (dd, 1H), 7.16 (d, 1H), 4.65 (dd, 1H), 4.39 (dd, 1H), 3.84 (s, 3H), 2.64 (s, 3H), 2.25-2.06 (m, 1H), 1.80 (d, 1H), 1.27 (dt, 1H), 1.17-1.04 (m, 1H); LRMS m/z (M+H) 416.0 found, 416.16 required.

SCHEME 34

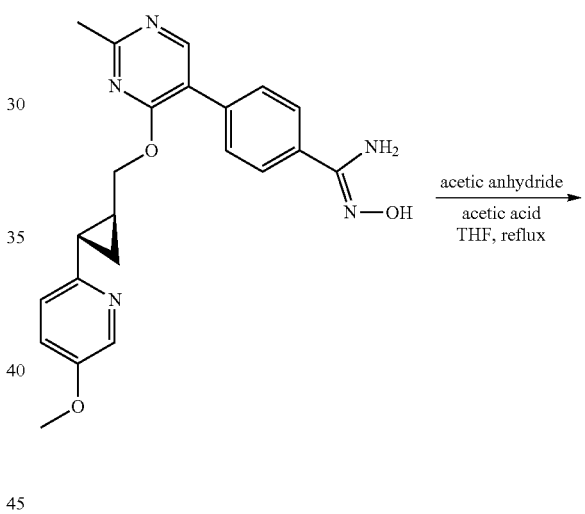

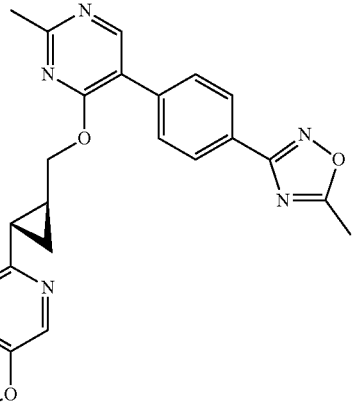

Example 251

3-(4-(4-(((1S,2S)-2-(5-methoxypyridin-2-yl)cyclopropyl)methoxy)-2-methylpyrimidin-5-yl)phenyl)-5-methyl-1,2,4-oxadiazole

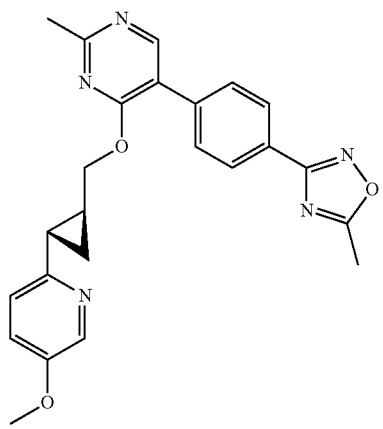 [SMILES: COc1ccc([C@H]2C[C@@H]2COc2nc(C)ncc2-c2ccc(-c3noc(C)n3)cc2)nc1]

Step A: 3-(4-(4-(((1S,2S)-2-(5-methoxypyridin-2-yl)cyclopropyl)methoxy)-2-methyl pyrimidin-5-yl)phenyl)-5-methyl-1,2,4-oxadiazole A solution of N'-hydroxy-4-(4-(((1S,2S)-2-(5-methoxypyridin-2-yl)cyclopropyl) methoxy)-2-methylpyrimidin-5-yl)benzimidamide (50 mg, 0.17 mmol), acetic anhydride (25 mg, 0.26 mmol) and a catalystic amount of acetic acid in THF (3 mL) was refluxed overnight. The mixture was poured into water and extracted with EA (20 mL*3), the organic phase was washed with brine, dried over MgSO$_4$, filtered and concentrated in vacuo. The resulting residue was purified by Pre-TLC (Hex/EA=1:1) to afford the title compound as a white solid (35 mg, 48%). $^1$H NMR (400 MHz, CD$_3$OD) δ 8.44 (s, 1H), 8.04 (d, 3H), 7.73 (d, 2H), 7.27 (dd, 1H), 7.15 (d, 1H), 4.61 (dt, 1H), 4.38 (dd, 1H), 3.84 (s, 3H), 2.67 (s, 3H), 2.63 (s, 3H), 2.21-2.06 (m, 1H), 1.88-1.65 (m, 1H), 1.31-1.21 (m, 1H), 1.13-1.00 (m, 1H); LRMS m/z (M+H) 430.1 found, 430.18 required.

SCHEME 35

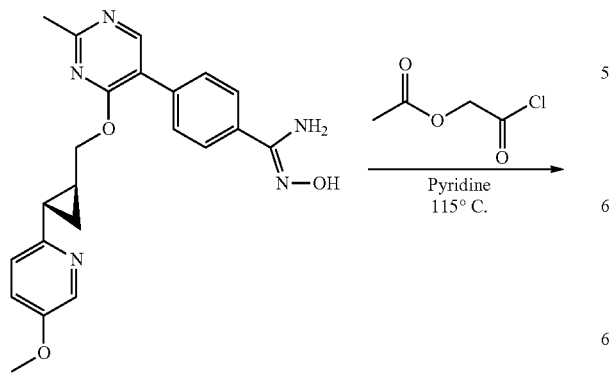

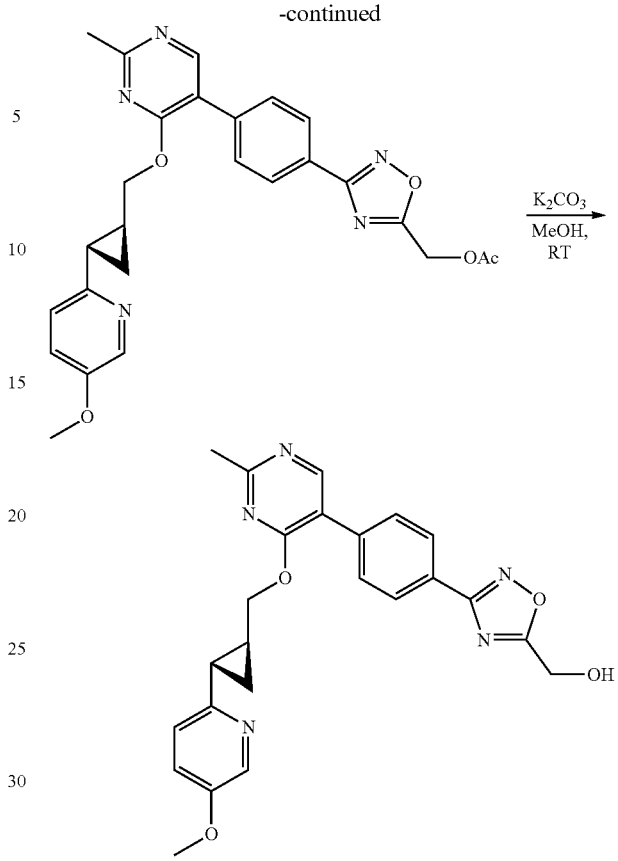

Example 252

(3-(4-(4-(((1S,2S)-2-(5-methoxypyridin-2-yl)cyclopropyl)methoxy)-2-methylpyrimidin-5-yl)phenyl)-1,2,4-oxadiazol-5-yl)methanol

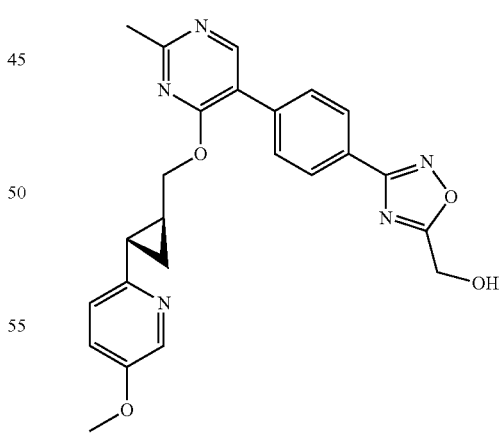

Step A: (3-(4-(4-(((1S,2S)-2-(5-methoxypyridin-2-yl)cyclopropyl)methoxy)-2-methyl pyrimidin-5-yl)phenyl)-1,2,4-oxadiazol-5-yl)methyl acetate To a solution of N'-hydroxy-4-(4-(((1S,2S)-2-(5-methoxypyridin-2-yl)cyclopropyl)methoxy)-2-methylpyrimidin-5-yl)benzimidamide (100 mg, 0.25 mmol) in pyridine was added 2-chloro-2-oxoethyl acetate (75 mg, 0.50 mmol). The mixture was stirred at 115° C. for 6 h. Then the mixture was washed with water (20 mL) and extracted with EtOAc (50 mL). Concentrated to afforded crude title product (110 mg, 92%), which was used directly for the next step.

Step B: (3-(4-(4-(((1S,2S)-2-(5-methoxypyridin-2-yl)cyclopropyl)methoxy)-2-methylpyrimidin-5-yl)phenyl)-1,2,4-oxadiazol-5-yl)methanol To a 50 mL flask was charged with (3-(4-(4-(((1S,2S)-2-(5-methoxypyridin-2-yl)cyclopropyl)methoxy)-2-methylpyrimidin-5-yl)phenyl)-1,2,4-oxadiazol-5-yl)methyl acetate (80 mg, 0.16 mmol), K$_2$CO$_3$ (67 mg, 0.48 mmol) and MeOH (3 mL). The mixture was stirred at RT for 1 h. Then the mixture was filtered and the filtrate was concentrated. The residue was purified by prep-HPLC to afford an oil (30 mg, 43%). $^1$H NMR (400 MHz, CD$_3$OD) δ 8.75 (s, 1H), 8.34 (s, 1H), 8.15 (d, 2H), 8.00 (d, 1H), 7.81 (d, 2H), 7.58 (d, 1H), 4.91 (s, 2H), 4.84 (dd, 1H), 4.62 (dd, 1H), 4.01 (s, 3H), 2.81 (s, 3H), 2.51 (m, 1H), 2.09 (m, 1H), 1.52 (m, 2H); LRMS m/z (M+H) 446.0 found, 446.1 required.

SCHEME 36

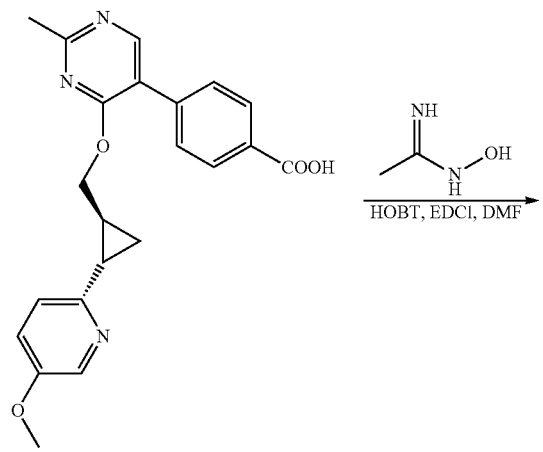

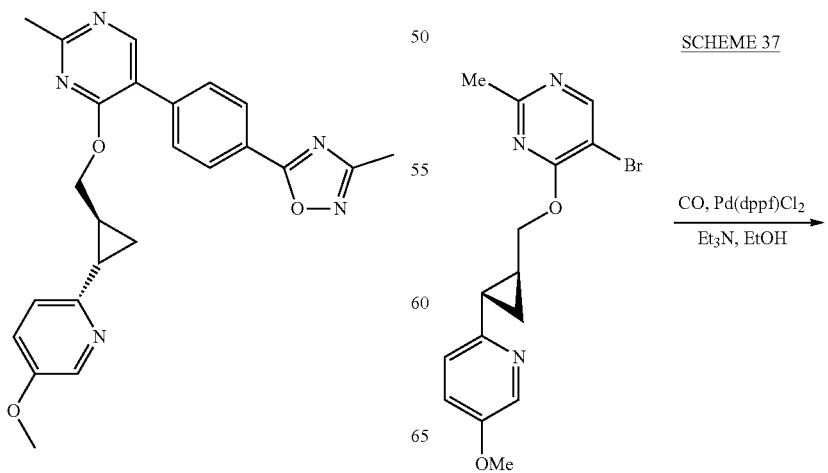

Example 253

5-(4-(4-(((1S,2S)-2-(5-methoxypyridin-2-yl)cyclopropyl)methoxy)-2-methylpyrimidin-5-yl)phenyl)-3-methyl-1,2,4-oxadiazole

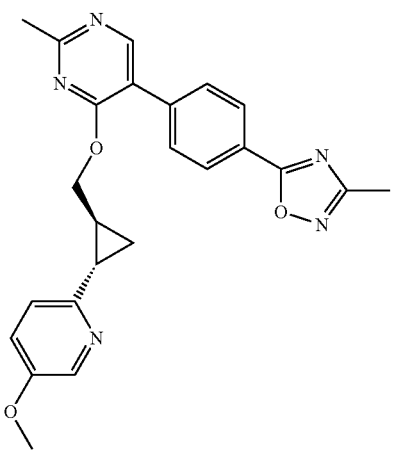 [SMILES: COc1ccc([C@H]2C[C@@H]2COc2nc(C)ncc2-c2ccc(-c3nc(C)no3)cc2)nc1]

Step A: 5-(4-(4-(((1S,2S)-2-(5-methoxypyridin-2-yl)cyclopropyl)methoxy)-2-methylpyrimidin-5-yl)phenyl)-3-methyl-1,2,4-oxadiazole The solution of 4-(4-(4-(((1S,2S)-2-(5-methoxypyridin-2-yl)cyclopropyl)methoxy)-2-methylpyrimidin-5-yl)benzoic acid (100 mg, 0.256 mmol), HOBT (103.6 mg, 0.77 mmol), EDCI (147 mg, 0.77 mmol) and N-hydroxyacetimidamide (56.8 mg, 0.77 mmol) in DMF (1 mL) was stirred at 120° C. for 24 h. Water was then added to the mixture, and the mixture was extracted with EtOAc. The organic layer was washed with sat. NaHCO$_3$ aq. and brine, dried over MgSO$_4$, filtered, concentrated in vacuo and purified by Pre-TLC (PE:EA=1:1) to afford a white solid. $^1$H NMR (400 MHz, CD3OD) δ 8.51 (s, 1H), 8.16 (d, 1H), 8.06 (d, 2H), 7.80 (dd, 1H), 7.74 (d, 2H), 7.42 (d, 1H), 4.63 (dd, 1H), 4.43 (dd, 1H), 3.88 (d, 3H), 2.59 (s, 3H), 2.36 (s, 3H), 2.29-2.21 (m, 1H), 1.94 (s, 1H), 1.26 (s, 1H), 0.87-0.78 (m, 1H); LRMS m/z (M+H) 354.1 found, 354.4 required.

SCHEME 37

-continued

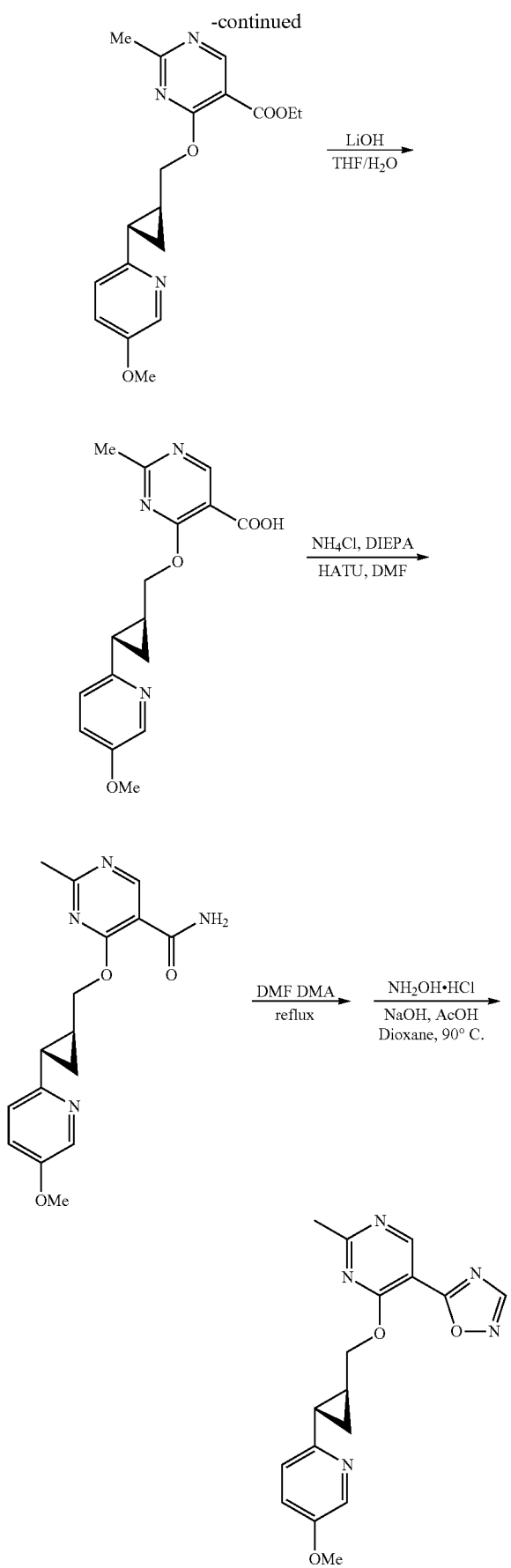

Example 254

5-(4-(((1S,2S)-2-(5-methoxypyridin-2-yl)cyclopropyl)methoxy)-2-methylpyrimidin-5-yl)-1,2,4-oxadiazole

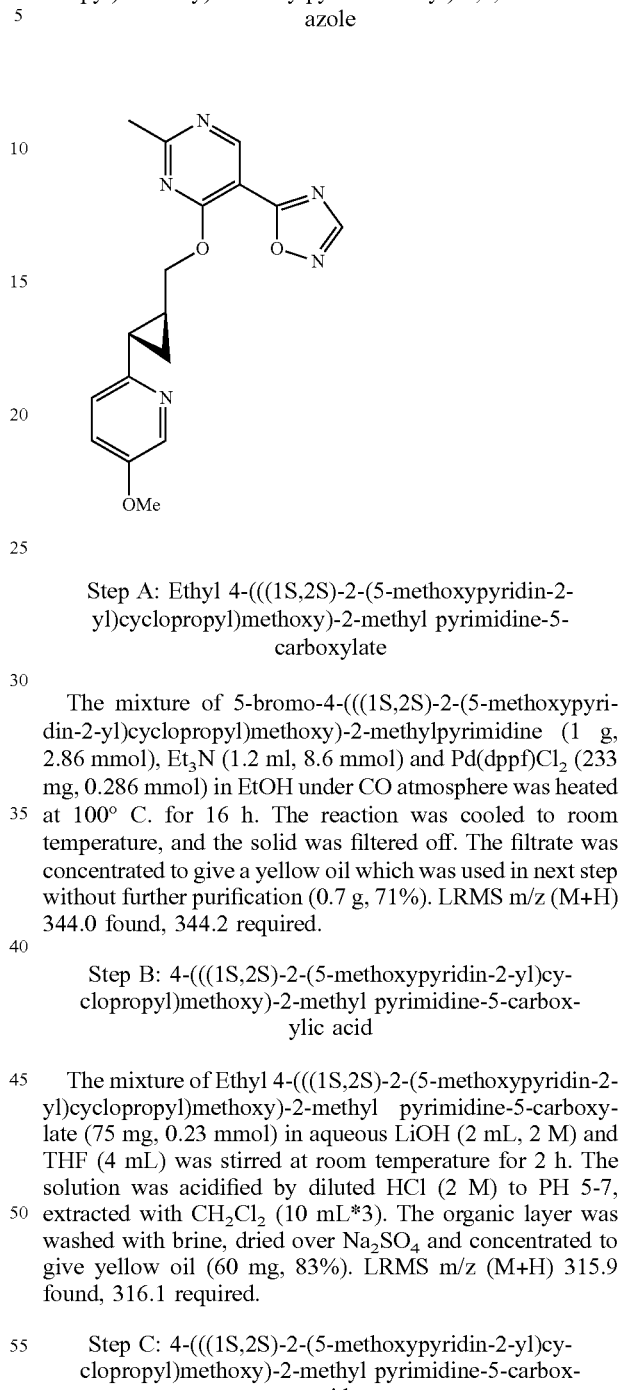

Step A: Ethyl 4-(((1S,2S)-2-(5-methoxypyridin-2-yl)cyclopropyl)methoxy)-2-methyl pyrimidine-5-carboxylate The mixture of 5-bromo-4-(((1S,2S)-2-(5-methoxypyridin-2-yl)cyclopropyl)methoxy)-2-methylpyrimidine (1 g, 2.86 mmol), Et$_3$N (1.2 ml, 8.6 mmol) and Pd(dppf)Cl$_2$ (233 mg, 0.286 mmol) in EtOH under CO atmosphere was heated at 100° C. for 16 h. The reaction was cooled to room temperature, and the solid was filtered off. The filtrate was concentrated to give a yellow oil which was used in next step without further purification (0.7 g, 71%). LRMS m/z (M+H) 344.0 found, 344.2 required.

Step B: 4-(((1S,2S)-2-(5-methoxypyridin-2-yl)cyclopropyl)methoxy)-2-methyl pyrimidine-5-carboxylic acid The mixture of Ethyl 4-(((1S,2S)-2-(5-methoxypyridin-2-yl)cyclopropyl)methoxy)-2-methyl pyrimidine-5-carboxylate (75 mg, 0.23 mmol) in aqueous LiOH (2 mL, 2 M) and THF (4 mL) was stirred at room temperature for 2 h. The solution was acidified by diluted HCl (2 M) to PH 5-7, extracted with CH$_2$Cl$_2$ (10 mL*3). The organic layer was washed with brine, dried over Na$_2$SO$_4$ and concentrated to give yellow oil (60 mg, 83%). LRMS m/z (M+H) 315.9 found, 316.1 required.

Step C: 4-(((1S,2S)-2-(5-methoxypyridin-2-yl)cyclopropyl)methoxy)-2-methyl pyrimidine-5-carboxamide A solution of 4-(((1S,2S)-2-(5-methoxypyridin-2-yl)cyclopropyl)methoxy)-2-methyl pyrimidine-5-carboxylic acid (500 mg, 1.59 mmol), HATU (665 mg, 1.75 mmol), and NH$_4$Cl (840 mg, 15.9 mmol) in DIEPA (3 mL) and DMF (5 mL) was stirred at room temperature for 16 h. The reaction mixture was diluted with EtOAc, washed with sat. aq. NaHCO$_3$ and brine, dried over MgSO$_4$, filtered, concentrated in vacuo. and purified by Pre-HPLC to afford a yellow solid. LRMS m/z (M+H) 315.0 found, 315.1 required.

Step D: 5-(4-(((1S,2S)-2-(5-methoxypyridin-2-yl)cyclopropyl)methoxy)-2-methylpyrimidin-5-yl)-1,2,4-oxadiazole A solution of 4-(((1S,2S)-2-(5-methoxypyridin-2-yl)cyclopropyl)methoxy)-2-methyl pyrimidine-5-carboxamide (100 mg, 0.32 mmol) in DMFDMA (2 mL) was heated at 80° C. for 2 h, then the solvent was removed under vacuum and the residue was added hydroxylamine hydrochloride (44 mg, 0.64 mmol), dioxane (1 mL), 5 N NaOH aq. (0.2 mL) and AcOH (2 mL). The mixture was stirred for 10 min at rt then heated at 80° C. for 10 min. After cooled, the reaction mixture was diluted with EtOAc, washed with sat. aq. NaHCO$_3$ and brine, dried over MgSO$_4$, filtered, and concentrated in vacuo. The resulting residue was purified by Pre-HPLC to afford the title compound as a white solid. $^1$H NMR (500 MHz, CD3OD) δ 9.00 (s, 1H), 8.68 (s, 1H), 7.94 (d, 1H), 7.18 (dd, 1H), 7.11 (d, 1H), 4.59 (dd, 1H), 4.51 (dd, 1H), 3.73 (s, 3H), 2.58 (s, 3H), 2.18-2.09 (m, 1H), 1.83-1.73 (m, 1H), 1.16 (dt, 1H), 1.11-1.01 (m, 1H); LRMS m/z (M+H) 340.1 found, 340.3 required.

SCHEME 38

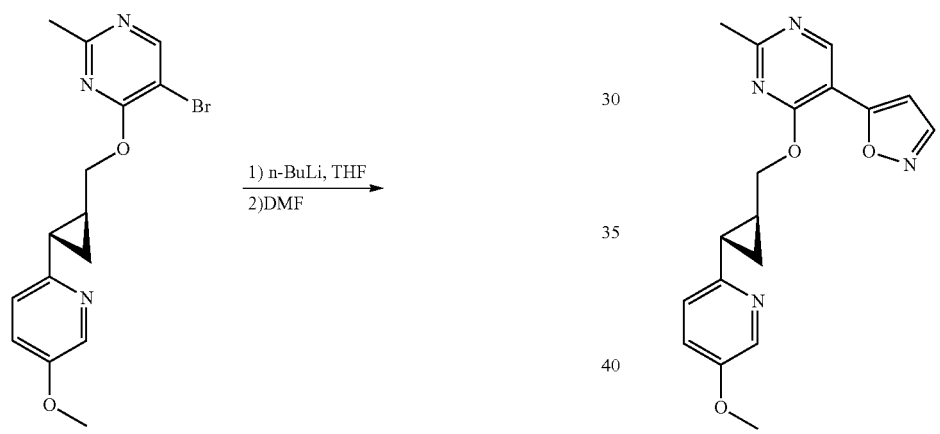

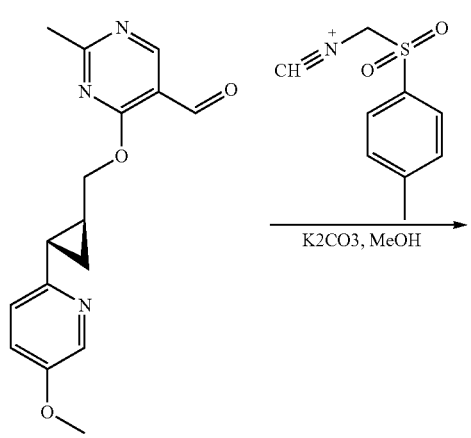

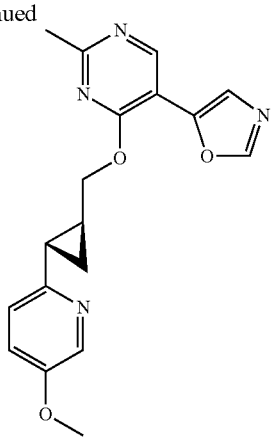

Example 255

5-(4-(((1S,2S)-2-(5-methoxypyridin-2-yl)cyclopropyl)methoxy)-2-methylpyrimidin-5-yl)oxazole

Step A: 4-(((1S,2S)-2-(5-methoxypyridin-2-yl)cyclopropyl)methoxy)-2-methyl pyrimidine-5-carbaldehyde n-BuLi (2.5M, 0.7 mL, 1.75 mmol) was added to a solution of 5-bromo-4-(((1S,2S)-2-(5-methoxypyridin-2-yl)cyclopropyl)methoxy)-2-methylpyrimidine (500 mg, 1.42 mmol) in THF (5 mL) at −78° C. After the mixture was kept for 30 min, DMF (3 mL) was added. The resulting solution was stirred at −78° C. for 20 min. Sat. NH$_4$Cl was added. The reaction mixture was diluted with EtOAc, washed with sat. aq. NaHCO$_3$ and brine, and dried over MgSO$_4$. The solvent was evaporated and the residue was purified by prep-HPLC to afford the title compound.

Step B: 5-(4-(((1S,2S)-2-(5-methoxypyridin-2-yl)cyclopropyl)methoxy)-2-methyl pyrimidin-5-yl)oxazole A mixture of N-methylidyne-1-Tosylmethanaminium (313 mg, 1.6 mmol), 4-(((1S,2S)-2-(5-methoxypyridin-2-yl)cyclopropyl)methoxy)-2-methyl pyrimidine-5-carbaldehyde (400 mg, 1.34 mmol) and K$_2$CO$_3$ (462 mg, 3.34 mmol) in MeOH (4 mL) was heated under reflux for 30 min. After concentrating under reduced pressure, the residue was stirred with water. The reaction mixture was diluted with EtOAc, washed with sat. aq. NaHCO$_3$ and brine, dried over MgSO$_4$, filtered, concentrated in vacuo, and purified by prep-HPLC to afford the compound.

The following EXAMPLE 256 in Table 27 was prepared using the procedure of EXAMPLE 252, substituting the appropriate starting materials.

The following EXAMPLE 257 in Table 27 was prepared using the procedure of EXAMPLE 255, substituting the appropriate starting materials.

TABLE 27

| Example | Structure | Name | MS m/z (M + H) |
|---|---|---|---|
| 250 | 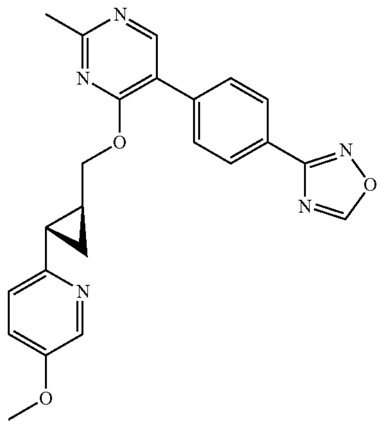 [SMILES: COc1ccc([C@H]2C[C@@H]2COc2nc(C)ncc2-c2ccc(-c3ncon3)cc2)nc1] | 3-(4-(4-(((1S,2S)-2-(5-methoxypyridin-2-yl)cyclopropyl)methoxy)-2-methylpyrimidin-5-yl)phenyl)-1,2,4-oxadiazole | 416.0 |
| 251 | 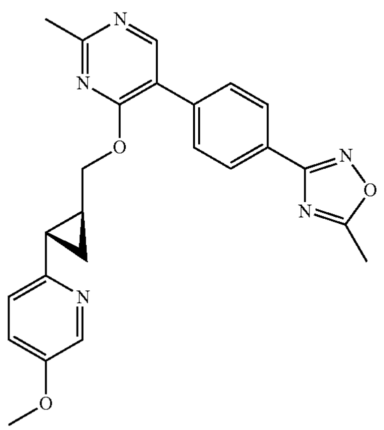 [SMILES: COc1ccc([C@H]2C[C@@H]2COc2nc(C)ncc2-c2ccc(-c3noc(C)n3)cc2)nc1] | 3-(4-(4-(((1S,2S)-2-(5-methoxypyridin-2-yl)cyclopropyl)methoxy)-2-methylpyrimidin-5-yl)phenyl)-5-methyl-1,2,4-oxadiazole | 430.1 |
| 252 | 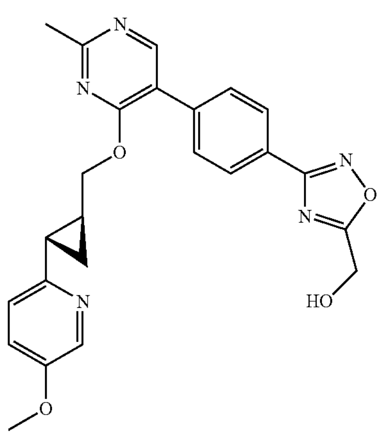 [SMILES: COc1ccc([C@H]2C[C@@H]2COc2nc(C)ncc2-c2ccc(-c3noc(CO)n3)cc2)nc1] | (3-(4-(4-(((1S,2S)-2-(5-methoxypyridin-2-yl)cyclopropyl)methoxy)-2-methylpyrimidin-5-yl)phenyl)-1,2,4-oxadiazol-5-yl)methatiol | 446.0 |

TABLE 27-continued

| Example | Structure | Name | MS m/z (M + H) |
|---|---|---|---|
| 253 | 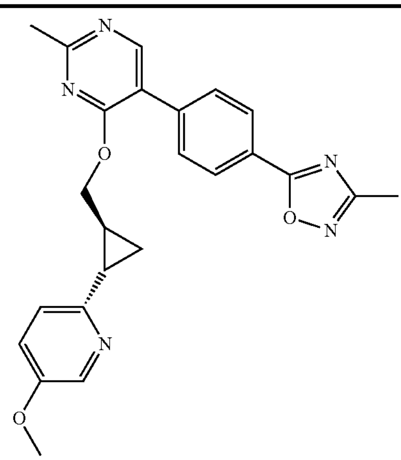 | 5-(4-(4-(((1S,2S)-2-(5-methoxypyridin-2-yl)cyclopropyl)methoxy)-2-methylpyrimidin-5-yl)phenyl)-3-methyl-1,2,4-oxadiazole | 353.1 |
| 254 | 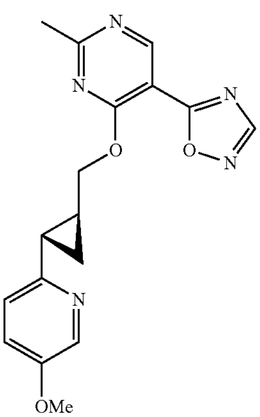 [SMILES: COc1ccc([C@H]2C[C@@H]2COc2nc(C)ncc2-c2ncno2)nc1] | 5-(4-(((1S,2S)-2-(5-methoxypyridin-2-yl)cyclopropyl)methoxy)-2-methylpyrimidin-5-yl)-1,2,4-oxadiazole | 340.1 |
| 255 | 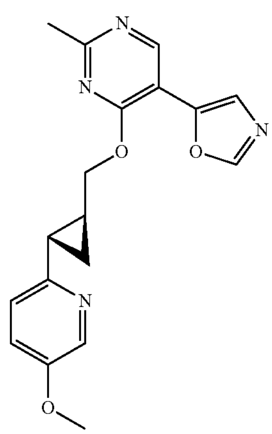 [SMILES: COc1ccc([C@H]2C[C@@H]2COc2nc(C)ncc2-c2cnco2)nc1] | 5-(4-(((1S,2S)-2-(5-methoxypyridin-2-yl)cyclopropyl)methoxy)-2-methylpyrimidin-5-yl)oxazole | 339.1 |
| 256 | 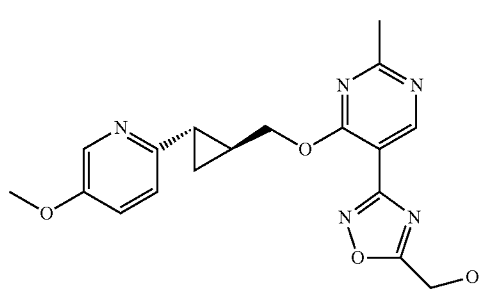 [SMILES: COc1ccc([C@H]2C[C@@H]2COc2nc(C)ncc2-c2noc(CO)n2)nc1] | (3-(4-(((1S,2S)-2-(5-methoxypyridin-2-yl)cyclopropyl)methoxy)-2-methylpyrimidin-5-yl)-1,2,4-oxadiazol-5-yl)methanol | 370.1 |

TABLE 27-continued

| Example | Structure | Name | MS m/z (M + H) |
|---|---|---|---|
| 257 | 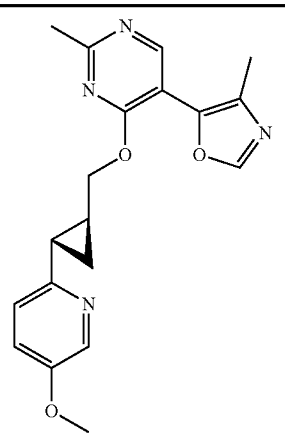 | 5-(4-(((1S,2S)-2-(5-methoxypyridin-2-yl)cyclopropyl)methoxy)-2-methylpyrimidin-5-yl)-4-methyloxazole | 353.1 |

The compounds of the following examples had activity in inhibiting the human PDE10 enzyme in the aforementioned assays with an Ki of about 0.001 nM to about 100 nM as indicated in Table 28 below.

The following table 28 shows representative data for the compounds of the Examples as PDE10 inhibitors as determined by the foregoing assays wherein the PDE10 Ki is a measure of the ability of the test compound to inhibit the action of the PDE10 enzyme. Representative compounds of the invention had the Ki values specified in parentheses immediately following the compound number in the above-described assay.

TABLE 28

| Compound/example | PDE10A Ki (nM) |
|---|---|
| 1 | 0.83 |
| 2 | 2.44 |
| 3 | 0.30 |
| 4 | 2.14 |
| 5 | 3.15 |
| 6 | 1.42 |
| 7 | 0.46 |
| 8 | 3.24 |
| 9 | 1.13 |
| 10 | 5.71 |
| 11 | 4.43 |
| 12 | 1.11 |
| 13 | 0.70 |
| 14 | 3.10 |
| 15 | 1.11 |
| 16 | 0.74 |
| 17 | 0.59 |
| 18 | 2.56 |
| 19 | 0.55 |
| 20 | 1.30 |
| 21 | 0.33 |
| 22 | 0.01 |
| 23 | 1.21 |
| 24 | 0.35 |
| 25 | 7.23 |
| 26 | 0.02 |
| 27 | 0.93 |
| 28 | 0.10 |
| 29 | 1.66 |
| 30 | 0.37 |
| 31 | 7.95 |
| 32 | 0.06 |
| 33 | 1.25 |
| 34 | 0.01 |

TABLE 28-continued

| Compound/example | PDE10A Ki (nM) |
|---|---|
| 35 | 1.05 |
| 36 | 0.09 |
| 37 | 7.24 |
| 38 | 0.03 |
| 39 | 0.87 |
| 40 | 0.04 |
| 41 | 5.08 |
| 42 | 0.02 |
| 43 | 0.08 |
| 44 | 2.20 |
| 45 | 0.02 |
| 46 | 0.06 |
| 47 | 2.20 |
| 48 | 3.25 |
| 49 | 22.35 |
| 50 | 4.28 |
| 51 | 1.96 |
| 52 | 2.36 |
| 53 | 25.48 |
| 54 | 10.38 |
| 55 | 0.87 |
| 56 | 6.12 |
| 57 | 0.57 |
| 58 | 3.02 |
| 59 | 4.34 |
| 60 | 13.86 |
| 61 | 1.51 |
| 62 | 2.02 |
| 63 | 2.95 |
| 64 | 1.75 |
| 65 | 2.62 |
| 66 | 3.14 |
| 67 | 0.10 |
| 68 | 0.43 |
| 69 | 0.94 |
| 70 | 1.64 |
| 71 | 4.78 |
| 72 | 0.50 |
| 73 | 1.13 |
| 74 | 0.18 |
| 75 | 0.14 |
| 76 | 0.48 |
| 77 | 6.28 |
| 78 | 8.35 |
| 79 | 5.60 |
| 80 | 5.48 |
| 81 | 4.97 |
| 82 | 0.20 |
| 83 | 0.15 |
| 84 | 0.51 |

TABLE 28-continued

| Compound/example | PDE10A Ki (nM) |
|---|---|
| 85 | 0.86 |
| 86 | 11.64 |
| 87 | 0.44 |
| 88 | 0.99 |
| 89 | 0.06 |
| 90 | 2.13 |
| 91 | 0.16 |
| 92 | 0.12 |
| 93 | 0.15 |
| 94 | 1.17 |
| 95 | 0.93 |
| 96 | 1.26 |
| 97 | 9.74 |
| 98 | 11.98 |
| 99 | 2.68 |
| 100 | 4.01 |
| 101 | 11.92 |
| 102 | 10.27 |
| 103 | 2.35 |
| 104 | 0.67 |
| 105 | 1.41 |
| 106 | 0.64 |
| 107 | 1.06 |
| 108 | 3.75 |
| 1-9 | 0.94 |
| 110 | 41.57 |
| 111 | 0.79 |
| 112 | 19.20 |
| 113 | 0.89 |
| 114 | 0.93 |
| 115 | 0.76 |
| 116 | 9.01 |
| 117 | 23.46 |
| 118 | 0.10 |
| 119 | 2.15 |
| 120 | 1.04 |
| 121 | 5.05 |
| 122 | 2.85 |
| 123 | 1.09 |
| 124 | 8.57 |
| 125 | 0.40 |
| 126 | 0.00 |
| 127 | 0.51 |
| 128 | 0.12 |
| 129 | 0.02 |
| 130 | 0.39 |
| 131 | 0.04 |
| 132 | 0.81 |
| 133 | 0.06 |
| 134 | 4.03 |
| 135 | 37.33 |
| 136 | 0.04 |
| 137 | 0.63 |
| 138 | 0.23 |
| 139 | 0.37 |
| 140 | 1.63 |
| 141 | 0.24 |
| 142 | 0.37 |
| 143 | 0.16 |
| 144 | 0.73 |
| 145 | 0.54 |
| 146 | 0.25 |
| 147 | 0.40 |
| 148 | 0.98 |
| 149 | 0.14 |
| 150 | 0.47 |
| 151 | 0.02 |
| 152 | 1.78 |
| 153 | 0.01 |
| 154 | 0.01 |
| 155 | 0.01 |
| 156 | 0.12 |
| 157 | 0.02 |
| 158 | 0.56 |
| 159 | 1.47 |
| 160 | 2.92 |
| 161 | 2.28 |
| 162 | 0.13 |
| 163 | 0.24 |
| 164 | 0.04 |
| 165 | 0.05 |
| 166 | 8.11 |
| 167 | 5.44 |
| 168 | 1.56 |
| 169 | 1.41 |
| 170 | 1.48 |
| 171 | 1.19 |
| 172 | 0.29 |
| 173 | 0.51 |
| 174 | 8.42 |
| 175 | 0.20 |
| 176 | 14.85 |
| 177 | 0.38 |
| 178 | 35.60 |
| 179 | 0.57 |
| 180 | 5.95 |
| 181 | 0.05 |
| 182 | 17.79 |
| 183 | 13.53 |
| 184 | 2.81 |
| 185 | 3.73 |
| 186 | 6.67 |
| 187 | 18.55 |
| 188 | 2.84 |
| 189 | 3.75 |
| 190 | 0.06 |
| 191 | 0.06 |
| 192 | 0.01 |
| 193 | 0.07 |
| 194 | 2.98 |
| 195 | 3.48 |
| 196 | 0.50 |
| 197 | 1.73 |
| 198 | 27.57 |
| 199 | 4.79 |
| 200 | 1.61 |
| 201 | 17.11 |
| 202 | 2.96 |
| 203 | 30.77 |
| 204 | 0.73 |
| 205 | 7.08 |
| 206 | 6.28 |
| 207 | 0.48 |
| 208 | 2.28 |
| 209 | 12.11 |
| 210 | 7.85 |
| 211 | 19.41 |
| 212 | 12.45 |
| 213 | 6.86 |
| 214 | 19.40 |
| 215 | 15.35 |
| 216 | 7.90 |
| 217 | 5.29 |
| 218 | 0.50 |
| 219 | 0.65 |
| 220 | 0.64 |
| 221 | 12.62 |
| 222 | 0.10 |
| 223 | 2.02 |
| 224 | 1.08 |
| 225 | 1.42 |
| 226 | 0.77 |
| 227 | 3.30 |
| 228 | 2.06 |
| 229 | 0.13 |
| 230 | 1.64 |
| 231 | 1.78 |
| 232 | 0.77 |
| 233 | 1.16 |
| 234 | 9.43 |
| 235 | 21.47 |
| 236 | 19.41 |
| 237 | 32.85 |
| 238 | 22.9 |
| 239 | 7.7 |
| 240 | 29.9 |

TABLE 28-continued

| Compound/example | PDE10A Ki (nM) |
|---|---|
| 241 | 0.9 |
| 242 | 2.36 |
| 243 | 6.59 |
| 244 | 0.71 |
| 245 | 1.36 |
| 246 | 6.60 |
| 247 | 2.43 |
| 248 | 14.02 |
| 249 | 15.74 |
| 250 | 1.16 |
| 251 | 1.97 |
| 252 | 2.03 |
| 253 | 3.02 |
| 254 | 22.91 |
| 255 | 7.70 |
| 256 | 29.87 |
| 257 | 0.91 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

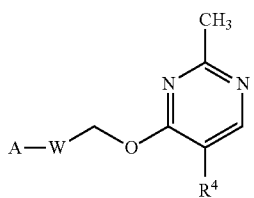

I wherein:
A is selected from the group consisting of:
  (1) pyridyl,
  (2) quinolinyl,
  (3) cyclopentapyridinyl and
  (4) tetrahydroquinolinyl,
  said pyridyl, quinolinyl, and cyclopentapyridinyl optionally substituted with 1 to 3 groups of $R^a$
W is cycylopropyl or —CH(CH$_3$)—CH$_2$—
$R^4$ is selected from the group consisting of:
  (1) oxadiazolyl,
  (2) pyrazolopyridinyl,
  (3) dioxaspirodecanyl,
  (4) pyrazinyl,
  (5)
  (6) imidazopyridinyl,
  (7) pyridyl,
  (8) pyrimidinyl,
  (9) indolyl,
  (10) pyranone,
  (11) pyranyl,
  (12) pyridazinyl,
  (13) isothiazolyl,
  (14) dihydropyrazolone,
  (15) pyrazolyl,
  (16) thiazolyl,
  (17) phenyl,
  (18) cyclohexyl, said group (1) through (18) optionally substituted with 1 to 3 groups of $R^a$, $R^a$ selected from the group consisting of:
  (1) (O)$_m$C$_{1-4}$, haloalkyl, said alkyl optionally substituted with 1 to 3 groups of $R^b$,
  (2) halogen,
  (3) OR,
  (4) C$_{1-6}$alkyl, where the alkyl is unsubstituted or substituted with one or more substituents selected from $R^b$,
  (5) C$_{3-6}$cycloalkyl, where the cycloalkyl is unsubstituted or substituted with one or more substituents selected from $R^b$,
  (6) —O(CH$_2$)$_n$cycloalkyl, where the cycloalkyl is unsubstituted or substituted with one or more substituents selected from $R^b$,
  (7) C$_{5-10}$heterocyclyl, where the heterocyclyl is unsubstituted or substituted with one or more substituents selected from $R^b$,
  (8) —(C=O)$_m$—N(R)$_2$,
  (9) —CO$_2$R,
  (10) —CN,
  (11) —O—,
  (12) —O(CHR)CH$_2$OR, and
  (13) S(O)pR;
$R^b$ is selected from the group consisting of:
  (1) (CH$_2$)nOR,
  (2) CF$_3$,
  (3) CF$_2$
  (4) C$_{1-6}$alkyl,
  (5) cyano,
  (6) N(R)$_2$,
  (7) halogen;
R is selected from the group consisting of:
  (1) hydrogen,
  (2) C$_{1-6}$alkyl, said alkyl optionally substituted with 1 to 3 groups of $R^b$, and
  (3) (O)$_m$C$_{1-4}$, haloalkyl,
  m is 0 or 1,
  n is 0, 1, 2, 3, or 4,
  p is 1 or 2,
or a pharmaceutically acceptable salt thereof, with the proviso that
1) when A is methoxypyridyl and $R^4$ is pyrazole then the pyrazole cannot be substituted with amino, ethanol, methanol, propanol, methoxyethyl, methylbutyl, methylpropranol, pyridyl, CH$_2$pyridyl, methylmethanol, or with only methyl groups;
2) when A is methylpyridyl or pyridyl and $R^4$ is pyrazole then the pyrazole can't only be substituted with methyl;
3) when A is methoxypyridyl or methyl pyridyl and $R^4$ is pyridyl, then the pyridyl must be substituted and when substituted with a methyl, methoxy, or propanol must contain at least one other substituent;
4) A is not methoxypyridyl when $R^4$ is imidazopyridine;
5) when A is methoxypyridyl then $R^4$ is not methyltriazole;
6) when A is cyclopentapyridine and $R^4$ is pyrazole then the pyrazole cannot be substituted with three methyl groups;
7) when A is methylpyridyl or methoxypyridyl and $R^4$ is a substituted cyclohexyl or cyclohexenol then the substituent can't only be a hydroxyl group.

2. The compound according to claim 1 wherein A is optionally substituted pyridyl.

3. The compound according to claim 1 wherein W is cyclopropyl.

4. The compound according to claim 1 represented by formula Ia:

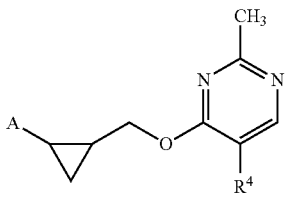

or a pharmaceutically acceptable salt thereof, wherein A is optionally substituted pyridyl or quinolinyl and $R^4$ is an optionally substituted group selected from oxadiazolyl, dioxaspirodecanyl, imidazopyridinyl, pyridyl, phenyl, cyclohexyl, and pyrazolyl.

5. The compound according to claim 1 represented by formula Ia':

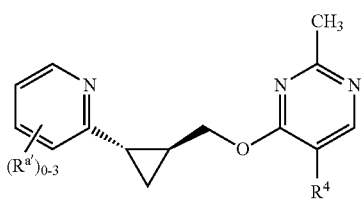

or a pharmaceutically acceptable salt thereof, wherein $R^{a'}$ is $R^a$.

6. The compound according to claim 5 wherein $R^{a'}$ is $C_{1-6}$ alkyl or OR, and $R^4$ is an optionally substituted group selected from oxadiazolyl, dioxaspirodecanyl, imidazopyridinyl, pyridyl, phenyl, cyclohexyl, and pyrazolyl.

7. The compound according to claim 6 wherein $R^4$ is selected from of dioxaspirodecanyl, pyridyl, phenyl, cyclohexyl, and pyrazolyl, said groups optionally substituted with 1 to 3 groups selected from the group consisting of OH, $CH_2OH$, $OCH(CH_3)_2$, $OCF_3$, halogen, $CF_3$, $OCH_3$, COOR, CN, $NH_2$, methoxyethoxy, $CHCH_3OH$, $OCH_2CH_3$, $C(CH_3)$ OH, $S(O)CH_3$, $CH(CF_2)OH$, $OCH(CH_2)_2OH$, $OCH_2$cyclopropyl, $CH(CF_3)OH$, $CONHCH_3$, $CONHCH_2CF_3$, $CONH_2$, and optionally substituted $C_{1-6}$ alkyl, cyclopropyl, oxetanyl, tetrazolyl, and oxadiazolyl.

8. A compound which is selected from the group consisting of:

2-Methyl-4-(((1S,2S)-2-(5-methylpyridin-2-yl)cyclopropyl)methoxy)-5-(3-(trifluoromethyl)phenyl)pyrimidine, 5-(2,4-dimethylphenyl)-2-methyl-4-(((1S,2S)-2-(5-methylpyridin-2-yl)cyclopropyl)methoxy)pyrimidine, 5-(3-isopropoxyphenyl)-2-methyl-4-(((1S,2S)-2-(5-methylpyridin-2-yl)cyclopropyl)methoxy)pyrimidine, 5-(3-isopropylphenyl)-2-methyl-4-(((1S,2S)-2-(5-methylpyridin-2-yl)cyclopropyl)methoxy)pyrimidine, 2-methyl-4-(((1S,2S)-2-(5-methylpyridin-2-yl)cyclopropyl)methoxy)-5-(2-(trifluoromethoxy)phenyl)pyrimidine, 5-(2,6-difluorophenyl)-2-methyl-4-(((1S,2S)-2-(5-methylpyridin-2-yl)cyclopropyl)methoxy)pyrimidine, 5-(3,5-difluorophenyl)-2-methyl-4-(((1S,2S)-2-(5-methylpyridin-2-yl)cyclopropyl)methoxy)pyrimidine, 5-(2-ethylphenyl)-2-methyl-4-(((1S,2S)-2-(5-methylpyridin-2-yl)cyclopropyl)methoxy)pyrimidine, 5-(4-fluoro-3-methylphenyl)-2-methyl-4-(((1S,2S)-2-(5-methylpyridin-2-yl)cyclopropyl)methoxy)pyrimidine, 2-methyl-4-(((1S,2S)-2-(5-methylpyridin-2-yl)cyclopropyl)methoxy)-5-(4-(trifluoromethyl)phenyl)pyrimidine, 5-(2,6-dimethylphenyl)-2-methyl-4-(((1S,2S)-2-(5-methylpyridin-2-yl)cyclopropyl)methoxy)pyrimidine, 2-methyl-4-(((1S,2S)-2-(5-methylpyridin-2-yl)cyclopropyl)methoxy)-5-(3-(trifluoromethoxy)phenyl)pyrimidine, 5-(2,5-dimethylphenyl)-2-methyl-4-(((1S,2S)-2-(5-methylpyridin-2-yl)cyclopropyl)methoxy)pyrimidine, 2-methyl-4-(((1S,2S)-2-(5-methylpyridin-2-yl)cyclopropyl)methoxy)-5-(2-(trifluoromethyl)phenyl)pyrimidine, 5-(3,4-difluorophenyl)-2-methyl-4-(((1S,2S)-2-(5-methylpyridin-2-yl)cyclopropyl)methoxy)pyrimidine, 5-(2-methoxypyridin-3-yl)-2-methyl-4-(((1S,2S)-2-(5-methylpyridin-2-yl)cyclopropyl)methoxy)pyrimidine, 2-methyl-4-(((1S,2S)-2-(5-methylpyridin-2-yl)cyclopropyl)methoxy)-5-(3-(trifluoromethyl)pyridin-4-yl)pyrimidine, 2-methyl-4-(((1S,2S)-2-(5-methylpyridin-2-yl)cyclopropyl)methoxy)-5,5'-bipyrimidine, 5-(2-fluoropyridin-4-yl)-2-methyl-4-(((1S,2S)-2-(5-methylpyridin-2-yl)cyclopropyl)methoxy)-pyrimidine, 5-(6-chloropyridin-3-yl)-4-(((1S,2S)-2-(5-methoxypyridin-2-yl)cyclopropyl)methoxy)-2-methylpyrimidine, 5-(2-fluoropyridin-4-yl)-4-(((1S,2S)-2-(5-methoxypyridin-2-yl)cyclopropyl)methoxy)-2-methylpyrimidine, 4-(2-methyl-4-(((1S,2S)-2-(quinolin-2-yl)cyclopropyl)methoxy)pyrimidin-5-yl)benzoic acid (enantiomer A) and (enantiomer B), 2-((1S,2S)-2-((2-methyl-5-p-tolylpyrimidin-4-yloxy)methyl)cyclopropyl)quinoline (enantiomer A) and (enantiomer B), 2-((1S,2S)-2-((2-methyl-5-(pyridin-4-yl)pyrimidin-4-yloxy)methyl)cyclopropyl)quinoline (enantiomer A) and (enantiomer B), 2-((1S,2S)-2-((5-(4-methoxyphenyl)-2-methylpyrimidin-4-yloxy)methyl)cyclopropyl)quinoline (enantiomer A) and (enantiomer B), 2-((1S,2S)-2-((5-(4-ethylphenyl)-2-methylpyrimidin-4-yloxy)methyl)cyclopropyl)quinoline (enantiomer A) and and (enantiomer B), 4-(2-methyl-4-(((1S,2S)-2-(quinolin-2-yl)cyclopropyl)methoxy)pyrimidin-5-yl)benzonitrile (enantiomer A) and (enantiomer B), 1-(4-(2-methyl-4-(((1S,2S)-2-(quinolin-2-yl)cyclopropyl)methoxy)pyrimidin-5-yl)phenyl)ethanol (enantiomer A) and (enantiomer B), 2-((1S,2S)-2-((2-methyl-5-m-tolylpyrimidin-4-yloxy)methyl)cyclopropyl)quinoline (enantiomer A) and (enantiomer B), (4-(2-methyl-4-(((1S,2S)-2-(quinolin-2-yl)cyclopropyl)methoxy)pyrimidin-5-yl)phenyl)methanol (enantiomer A) and (enantiomer B), 5-(3-ethoxyphenyl)-2-methyl-6-(((1S,2S)-2-(quinolin-2-yl)cyclopropyl)methoxy)pyrimidin-1-ium 2,2,2-trifluoroacetate (enantiomer A) and (enantiomer B), 2-((1S,2S)-2-((2-methyl-5-(6-methylpyridin-3-yl)pyrimidin-4-yloxy)methyl)cyclopropyl)-quinoline, 2-((1S,2S)-2-((2-methyl-5,5'-bipyrimidin-4-yloxy)methyl)cyclopropyl)quinoline (enantiomer A) and (enantiomer B), 2-(4-Methyl-5-(2-methyl-4-(((1S,2S)-2-(5-methylpyridin-2-yl)cyclopropyl)methoxy) pyrimidin-5-yl)pyridin-2-yl)propan-2-ol,
2-(5-(2-methyl-4-(((1S,2S)-2-(5-methylpyridin-2-yl)cyclopropyl)methoxy)pyrimidin-5-yl)pyridin-2-yl)propan-2-ol (enantiomer A) and (enantiomer B),
methyl 5-(2-methyl-4-(((1S,2S)-2-(5-methylpyridin-2-yl)cyclopropyl)methoxy)pyrimidin-5-yl)picolinate,
5-(2-methyl-4-(((1S,2S)-2-(5-methylpyridin-2-yl)cyclopropyl)methoxy)pyrimidin-5-yl)-1H-indole,
3-(2-methyl-4-(((1S,2S)-2-(5-methylpyridin-2-yl)cyclopropyl)methoxy)pyrimidin-5-yl)-2H-pyran-2-one,
5-(2-methyl-4-(((1S,2S)-2-(5-methylpyridin-2-yl)cyclopropyl)methoxy)pyrimidin-5-yl)-2H-pyran-2-one,
5-(3,6-dihydro-2H-pyran-4-yl)-2-methyl-4-(((1S,2S)-2-(5-methylpyridin-2-yl)cyclopropyl)-methoxy)pyrimidine,
4-chloro-3-methoxy-5-(2-methyl-4-(((1S,2S)-2-(5-methylpyridin-2-yl)cyclopropyl)methoxy)-pyrimidin-5-yl)pyridazine,
2-(2-methyl-4-(((1S,2S)-2-(5-methylpyridin-2-yl)cyclopropyl)methoxy)pyrimidin-5-yl)pyridin-4-ol,
2-methyl-4-(((1S,2S)-2-(5-methylpyridin-2-yl)cyclopropyl)methoxy)-5-vinylpyrimidine,
5-(4,6-dimethylpyridin-3-yl)-2-methyl-4-(((1S,2S)-2-(5-methylpyridin-2-yl)cyclopropyl)-methoxy)pyrimidine,
3-methoxy-5-(2-methyl-4-(((1S,2S)-2-(5-methylpyridin-2-yl)cyclopropyl)methoxy)pyrimidin-5-yl)pyridazine,
5-(6-(2-methoxyethoxy)pyridin-3-yl)-2-methyl-4-(((1S,2S)-2-(5-methylpyridin-2-yl)cyclopropyl)methoxy)pyrimidine,
3-methyl-5-(2-methyl-4-(((1S,2S)-2-(5-methylpyridin-2-yl)cyclopropyl)methoxy)pyrimidin-5-yl)pyridazine,
3-bromo-5-(2-methyl-4-(((1S,2S)-2-(5-methylpyridin-2-yl)cyclopropyl)methoxy)pyrimidin-5-yl)pyridazine,
4-(2-methyl-4-(((1S,2S)-2-(5-methylpyridin-2-yl)cyclopropyl)methoxy)pyrimidin-5-yl)furan-2(5H)-one,
5-(6-isopropoxy-2-methylpyridin-3-yl)-2-methyl-4-(((1S,2S)-2-(5-methylpyridin-2-yl)cyclopropyl)methoxy)pyrimidine,
4-(2-methyl-4-(((1S,2S)-2-(5-methylpyridin-2-yl)cyclopropyl)methoxy)pyrimidin-5-yl)isothiazole,
4-(((1S,2S)-2-(5-methoxypyridin-2-yl)cyclopropyl)methoxy)-2-methyl-5-(6-(methylsulfonyl)pyridin-3-yl)pyrimidine,
4-(((1S,2S)-2-(5-methoxypyridin-2-yl)cyclopropyl)methoxy)-2-methyl-5-(6-(methylsulfinyl)pyridin-3-yl)pyrimidine (R or S),
2-(5-(4-(((1S,2S)-2-(5-methoxypyridin-2-yl)cyclopropyl)methoxy)-2-methylpyrimidin-5-yl)pyrazin-2-yl)propan-2-ol,
2,2-difluoro-1-(5-(4-(((1S,2S)-2-(5-methoxypyridin-2-yl)cyclopropyl)methoxy)-2-methylpyrimidin-5-yl)pyridin-2-yl)ethanol (R or S),
5-(4-(((1S,2S)-2-(5-methoxypyridin-2-yl)cyclopropyl)methoxy)-2-methylpyrimidin-5-yl)pyridin-2-ol,
4'-(((1S,2S)-2-(5-methoxypyridin-2-yl)cyclopropyl)methoxy)-2'-methyl-5,5'-bipyrimidin-2-ol,
2-(5-(4-(((1S,2S)-2-(5-methoxypyridin-2-yl)cyclopropyl)methoxy)-2-methylpyrimidin-5-yl)pyridin-2-yloxy)propane-1,3-diol,
5-(6-(cyclopropylmethoxy)pyridin-3-yl)-4-(((1S,2S)-2-(5-methoxypyridin-2-yl)cyclopropyl)methoxy)-2-methylpyrimidine,
4-(4-(((1S,2S)-2-(5-methoxypyridin-2-yl)cyclopropyl)methoxy)-2-methylpyrimidin-5-yl)isothiazole,
5-(2-isopropoxypyridin-4-yl)-4-(((1S,2S)-2-(5-methoxypyridin-2-yl)cyclopropyl)methoxy)-2-methylpyrimidine,
5-(2-ethoxypyridin-4-yl)-4-(((1S,2S)-2-(5-methoxypyridin-2-yl)cyclopropyl)methoxy)-2-methylpyrimidine,
3-(4-(((1S,2S)-2-(5-methoxypyridin-2-yl)cyclopropyl)methoxy)-2-methylpyrimidin-5-yl)cyclopent-2-enone,
3-(4-(((1S,2S)-2-(5-methoxypyridin-2-yl)cyclopropyl)methoxy)-2-methylpyrimidin-5-yl)cyclopent-2-enone (R,R),
3-(4-(((1S,2S)-2-(5-methoxypyridin-2-yl)cyclopropyl)methoxy)-2-methylpyrimidin-5-yl)cyclopentanone,
(1R,3S)-3-(4-(((1S,2S)-2-(5-methoxypyridin-2-yl)cyclopropyl)methoxy)-2-methylpyrimidin-5-yl)cyclopentanol,
(1R,3R)-3-(4-(((1S,2S)-2-(5-methoxypyridin-2-yl)cyclopropyl)methoxy)-2-methylpyrimidin-5-yl)cyclopentanol,
5-(4-bromophenyl)-4-(((1S,2S)-2-(5-methoxypyridin-2-yl)cyclopropyl)methoxy)-2-methylpyrimidine,
4-(((1S,2S)-2-(5-methoxypyridin-2-yl)cyclopropyl)methoxy)-2-methyl-5-(1-methyl-3-(trifluoromethyl)-1H-pyrazol-4-yl)pyrimidine,
2,2,2-trifluoro-1-(5-(4-(((1S,2S)-2-(5-methoxypyridin-2-yl)cyclopropyl)methoxy)-2-methylpyrimidin-5-yl)pyridin-2-yl)ethanol (R or S),
2,2,2-trifluoro-1-(5-(4-(((1S,2S)-2-(5-methoxypyridin-2-yl)cyclopropyl)methoxy)-2-methylpyrimidin-5-yl)pyridin-2-yl)ethanol (S or R),
5-(6-ethylpyridin-3-yl)-4-(((1S,2S)-2-(5-methoxypyridin-2-yl)cyclopropyl)methoxy)-2-methylpyrimidine,
5-(5-bromopyridin-2-yl)-4-(((1S,2S)-2-(5-methoxypyridin-2-yl)cyclopropyl)methoxy)-2-methylpyrimidine,
5-(2-chloro-5-(trifluoromethyl)pyridin-3-yl)-4-(((1S,2S)-2-(5-methoxypyridin-2-yl)cyclopropyl)methoxy)-2-methylpyrimidine,
5-(2-chloro-5-(trifluoromethyl)pyridin-4-yl)-4-(((1S,2S)-2-(5-methoxypyridin-2-yl)cyclopropyl)methoxy)-2-methylpyrimidine,
1-(5-(4-(((1S,2S)-2-(5-methoxypyridin-2-yl)cyclopropyl)methoxy)-2-methylpyrimidin-5-yl)pyridin-2-yl)cyclopentanol,
5-(4-(((1S,2S)-2-(5-methoxypyridin-2-yl)cyclopropyl)methoxy)-2-methylpyrimidin-5-yl)-1H-indole,
3-(5-(4-(((1S,2S)-2-(5-methoxypyridin-2-yl)cyclopropyl)methoxy)-2-methylpyrimidin-5-yl)pyridin-2-yl)oxetan-3-ol,
1-(5-(4-(((1S,2S)-2-(5-methoxypyridin-2-yl)cyclopropyl)methoxy)-2-methylpyrimidin-5-yl)pyridin-2-yl)cyclobutanol,
5-(4-(4-(((1S,2S)-2-(5-methoxypyridin-2-yl)cyclopropyl)methoxy)-2-methylpyrimidin-5-yl)phenyl)-1,2,4-oxadiazole,
3-(chloromethyl)-5-(4-(4-((1S,2S)-2-(5-methoxypyridin-2-yl)cyclopropyl)methoxy)-2-methylpyrimidin-5-yl)phenyl)-1,2,4-oxadiazole,
(5-(4-(4-(((1S,2S)-2-(5-methoxypyridin-2-yl)cyclopropyl)methoxy)-2-methylpyrimidin-5-yl)phenyl)-1,2,4-oxadiazol-3-yl)methanol,
5-(4-(((1S,2S)-2-(5-methoxypyridin-2-yl)cyclopropyl)methoxy)-2-methylpyrimidin-5-yl)pyrazine-2-carboxylic acid,
methyl 5-(4-(((1S,2S)-2-(5-methoxypyridin-2-yl)cyclopropyl)methoxy)-2-methylpyrimidin-5-yl)pyrazine-2-carboxylate, (5-(4-(((1S,2S)-2-(5-methoxypyridin-2-yl)cyclopropyl)methoxy)-2-methylpyrimidin-5-yl)pyrazin-2-yl)methanol,
6-(4-(((1S,2S)-2-(5-methoxypyridin-2-yl)cyclopropyl)methoxy)-2-methylpyrimidin-5-yl)pyridazine-3-carboxylic acid,
2-(6-(4-(((1S,2S)-2-(5-methoxypyridin-2-yl)cyclopropyl)methoxy)-2-methylpyrimidin-5-yl)pyridazin-3-yl)propan-2-ol,
(6-(4-(((1S,2S)-2-(5-methoxypyridin-2-yl)cyclopropyl)methoxy)-2-methylpyrimidin-5-yl)pyridazin-3-yl)methanol,
3-(4-(((1S,2S)-2-(5-methoxypyridin-2-yl)cyclopropyl)methoxy)-2-methylpyrimidin-5-yl)-6-methylpyridazine,
5-(4-(((1S,2S)-2-(5-methoxypyridin-2-yl)cyclopropyl)methoxy)-2-methylpyrimidin-5-yl)-N-methylpicolinamide,
5-(4-(((1S,2S)-2-(5-methoxypyridin-2-yl)cyclopropyl)methoxy)-2-methylpyrimidin-5-yl)-N-(2,2,2-trifluoroethyl)picolinamide,
5-(4-(((1S,2S)-2-(5-methoxypyridin-2-yl)cyclopropyl)methoxy)-2-methylpyrimidin-5-yl)picolinamide,
N-(2-hydroxyethyl)-5-(4-(((1S,2S)-2-(5-methoxypyridin-2-yl)cyclopropyl)methoxy)-2-methylpyrimidin-5-yl)picolinamide,
N-(2-hydroxyethyl)-4-(4-(((1S,2S)-2-(5-methoxypyridin-2-yl)cyclopropyl)methoxy)-2-methylpyrimidin-5-yl)benzamide,
2-amino-4-(4-(((1S,2S)-2-(5-methoxypyridin-2-yl)cyclopropyl)methoxy)-2-methylpyrimidin-5-yl)nicotinonitrile,
5-(4-(((1S,2S)-2-(5-methoxypyridin-2-yl)cyclopropyl)methoxy)-2-methylpyrimidin-5-yl)-1-methyl-1H-pyrrole-2-carbonitrile,
ethyl 6-hydroxy-4-(4-(((1 S,2 S)-2-(5-methoxypyridin-2-yl)cyclopropyl)methoxy)-2-methylpyrimidin-5-yl)nicotinate,
5-(2-chloro-5-methoxypyridin-4-yl)-4-(((1S,2S)-2-(5-methoxypyridin-2-yl)cyclopropyl)methoxy)-2-methylpyrimidine,
5-(2-chloro-5-((2-(trimethyl silyl)ethoxy)methoxy)pyridin-4-yl)-4-(((1S,2S)-2-(5-methoxypyridin-2-yl)cyclopropyl)methoxy)-2-methylpyrimidine,
4-(4-(((1S,2S)-2-(5-methoxypyridin-2-yl)cyclopropyl)methoxy)-2-methylpyrimidin-5-yl)-1-methyl-1H-pyrrole-2-carbonitrile,
2,2,2-trifluoro-1-(4-(4-(((1S,2S)-2-(5-methoxypyridin-2-yl)cyclopropyl)methoxy)-2-methylpyrimidin-5-yl)-1-methyl-1H-pyrazol-3-yl)ethanol,
5-(3,6-dihydro-2H-pyran-4-yl)-4-(((1S,2S)-2-(5-methoxypyridin-2-yl)cyclopropyl)methoxy)-2-methylpyrimidine,
(1-methyl-4-(2-methyl-4-(((1S,2S)-2-(pyridin-2-yl)cyclopropyl)methoxy)pyrimidin-5-yl)-1H-pyrazol-3-yl)methanol(1S,2S),
2-methyl-4-(((1S,2S)-2-(pyridin-2-yl)cyclopropyl)methoxy)-5-(6-(trifluoromethyl)pyridin-3-yl)pyrimidine,
2-(4-methyl-5-(2-methyl-4-(((1S,2S)-2-(pyridin-2-yl)cyclopropyl)methoxy)pyrimidin-5-yl)pyridin-2-yl)propan-2-ol,
2-(6-methyl-5-(2-methyl-4-(((1S,2S)-2-(pyridin-2-yl)cyclopropyl)methoxy)pyrimidin-5-yl)pyridin-2-yl)propan-2-ol,
1-(5-(2-methyl-4-(((1S,2S)-2-(pyridin-2-yl)cyclopropyl)methoxy)pyrimidin-5-yl)pyridin-2-yl)cyclopentanol,
1-(4-(2-methyl-4-(((1S,2S)-2-(pyridin-2-yl)cyclopropyl)methoxy)pyrimidin-5-yl)phenyl)ethanol,
2-(5-(2-methyl-4-(((1S,2S)-2-(pyridin-2-yl)cyclopropyl)methoxy)pyrimidin-5-yl)pyridin-2-yl)propan-2-ol,
2-(5-(4-(((1R,2R)-2-(5-bromopyridin-2-yl)cyclopropyl)methoxy)-2-methylpyrimidin-5-yl)pyridin-2-yl)propan-2-ol,
5-(3-(difluoromethyl)-1-methyl-1H-pyrazol-4-yl)-2-methyl-4-(((1S,2S)-2-(5-methylpyridin-2-yl)cyclopropyl)methoxy)pyrimidine,
2-(4-methyl-5-(2-methyl-4-(((1S,2S)-2-(quinolin-2-yl)cyclopropyl)methoxy)pyrimidin-5-yl)pyridin-2-yl)propan-2-ol,
2-((1S,2S)-2-((5-(3-fluoropyridin-2-yl)-2-methylpyrimidin-4-yloxy)methyl)cyclopropyl)-quinoline,
2-((1S,2S)-2-((2-methyl-5-(4-methylpyridin-2-yl)pyrimidin-4-yloxy)methyl)cyclopropyl)-quinoline,
2-((1S,2S)-2-((2-methyl-5-(3-methylimidazo[1,2-a]pyridin-6-yl)pyrimidin-4-yloxy)methyl-cyclopropyl)quinoline,
3-methyl-6-(2-methyl-4-(((1S,2S)-2-(5-methylpyridin-2-yl)cyclopropyl)methoxy)pyrimidin-5-yl)imidazo[1,2-a]pyridine,
2-((1S,2S)-2-((5-(5-methoxyimidazo[1,2-a]pyridin-7-yl)-2-methylpyrimidin-4-yloxy)methyl)cyclopropyl)quinoline,
5-methoxy-7-(2-methyl-4-(((1S,2S)-2-(5-methylpyridin-2-yl)cyclopropyl)methoxy)pyrimidin-5-yl)imidazo[1,2-a]pyridine,
2-((1S,2S)-2-((5-(imidazo[1,2-a]pyridin-3-yl)-2-methylpyrimidin-4-yloxy)methyl)cyclopropyl)-quinoline,
2-((1S,2S)-2-((5-(imidazo[1,2-a]pyridin-8-yl)-2-methylpyrimidin-4-yloxy)methyl)cyclopropyl)-quinoline,
8-(2-methyl-4-(((1S,2S)-2-(5-methylpyridin-2-yl)cyclopropyl)methoxy)pyrimidin-5-yl)imidazo[1,2-a]pyridine,
2-((1S,2S)-2-((5-(imidazo[1,2-a]pyridin-6-yl)-2-methylpyrimidin-4-yloxy)methyl)cyclopropyl)-quinoline,
6-(2-methyl-4-(((1S,2S)-2-(5-methylpyridin-2-yl)cyclopropyl)methoxy)pyrimidin-5-yl)imidazo[1,2-a]pyridine,
2-(6-Methyl-5-(2-methyl-4-(((1S,2S)-2-(5-methylpyridin-2-yl)cyclopropyl)methoxy)pyrimidin-5-yl)pyridin-2-yl)propan-2-ol,
2-methyl-1-(5-(2-methyl-4-(((1S,2S)-2-(5-methylpyridin-2-yl)cyclopropyl)methoxy)pyrimidin-5-yl)pyridin-2-yl)propan-1-ol,
1-(5-(2-methyl-4-(((1S,2S)-2-(5-methylpyridin-2-yl)cyclopropyl)methoxy)pyrimidin-5-yl)pyridin-2-yl)ethanol,
5-(2-methyl-4-(((1S,2S)-2-(5-methylpyridin-2-yl)cyclopropyl)methoxy)pyrimidin-5-yl)-1H-pyrazolo[3,4-b]pyridine,
1-(5-(2-methyl-4-(((1S,2S)-2-(5-methylpyridin-2-yl)cyclopropyl)methoxy)pyrimidin-5-yl)pyridin-2-yl)propan-1-ol,
2,2,2-trifluoro-1-(5-(2-methyl-4-(((1S,2S)-2-(5-methylpyridin-2-yl)cyclopropyl)methoxy)-pyrimidin-5-yl)pyridin-2-yl)ethanol,
2-methyl-4-(((1S,2S)-2-(5-methylpyridin-2-yl)cyclopropyl)methoxy)-5-(3-methylpyridin-4-yl)pyrimidine,
1-(5-(2-methyl-4-(((1S,2S)-2-(5-methylpyridin-2-yl)cyclopropyl)methoxy)pyrimidin-5-yl)pyridin-2-yl)ethanol,
5-(3-methoxypyridin-4-yl)-2-methyl-4-(((1S,2S)-2-(5-methylpyridin-2-yl)cyclopropyl)-methoxy)pyrimidine, 2-((1S,2S)-2-((2-methyl-5-(1H-pyrazolo[3,4-b]pyridin-5-yl)pyrimidin-4-yloxy)methyl)-cyclopropyl)quinoline (enantiomer A) and (enantiomer B), 2-((1S,2S)-2-((2-methyl-5-(2-methylpyridin-4-yl)pyrimidin-4-yloxy)methyl)cyclopropyl)-quinoline, (5-(2-methyl-4-(((1S,2S)-2-(quinolin-2-yl)cyclopropyl)methoxy)pyrimidin-5-yl)pyridin-2-yl)methanol, 2-((1S,2S)-2-((2-methyl-5-(pyridin-3-yl)pyrimidin-4-yloxy)methyl)cyclopropyl)quinoline, 2-((1S,2S)-2-((2-methyl-5-(6-(trifluoromethyl)pyridin-3-yl)pyrimidin-4-yloxy)methyl)-cyclopropyl)quinoline, 2-(5-(2-methyl-4-(((1S,2S)-2-(quinolin-2-yl)cyclopropyl)methoxy)pyrimidin-5-yl)pyridin-2-yl)propan-2-ol, 1-(1-methyl-4-(2-methyl-4-(((1S,2S)-2-(6-methylpyridin-2-yl)cyclopropyl)methoxy)pyrimidin-5-yl)-1H-pyrazol-3-yl)ethanol, 1-(1-methyl-4-(2-methyl-4-(((1S,2S)-2-(4-methylpyridin-2-yl)cyclopropyl)methoxy)pyrimidin-5-yl)-1H-pyrazol-3-yl)ethanol, 1-(1-methyl-4-(2-methyl-4-(((1S,2S)-2-(6-methylpyridin-2-yl)cyclopropyl)methoxy)pyrimidin-5-yl)-1H-pyrazol-3-yl)ethanol, 1-(4-(4-(((1S,2S)-2-(5-ethylpyridin-2-yl)cyclopropyl)methoxy)-2-methylpyrimidin-5-yl)-1-methyl-1H-pyrazol-3-yl)ethanol, 1-(4-(4-(((1R,2R)-2-(6,7-dihydro-5H-cyclopenta[b]pyridin-2-yl)cyclopropyl)methoxy)-2-methylpyrimidin-5-yl)-1-methyl-1H-pyrazol-3-yl)ethanol(enantiomer A, R or S), 1-(4-(4-(((1R,2R)-2-(6,7-dihydro-5H-cyclopenta[b]pyridin-2-yl)cyclopropyl)methoxy)-2-methylpyrimidin-5-yl)-1-methyl-1H-pyrazol-3-yl)ethanol(enantiomer A, S or R), 1-(4-(4-(((1R,2R)-2-(6,7-dihydro-5H-cyclopenta[b]pyridin-2-yl)cyclopropyl)methoxy)-2-methylpyrimidin-5-yl)-1-methyl-1H-pyrazol-3-yl)ethanol(enantiomer B, R or S), 1-(4-(4-(((1R,2R)-2-(6,7-dihydro-5H-cyclopenta[b]pyridin-2-yl)cyclopropyl)methoxy)-2-methylpyrimidin-5-yl)-1-methyl-1H-pyrazol-3-yl)ethanol(enantiomer B, S or R), 1-(1-methyl-4-(2-methyl-4-(((1S,2S)-2-(pyridin-2-yl)cyclopropyl)methoxy)pyrimidin-5-yl)-1H-pyrazol-3-yl)ethanol(R or S), 1-(1-methyl-4-(2-methyl-4-(((1S,2S)-2-(pyridin-2-yl)cyclopropyl)methoxy)pyrimidin-5-yl)-1H-pyrazol-3-yl)ethanol(S or R), 2,2-difluoro-1-(1-methyl-4-(2-methyl-4-(((1S,2S)-2-(5-methylpyridin-2-yl)cyclopropyl)-methoxy)pyrimidin-5-yl)-1H-pyrazol-3-yl)ethanol, 4-(4-(((1S,2S)-2-(5-methoxypyridin-2-yl)cyclopropyl)methoxy)-2-methylpyrimidin-5-yl)benzonitrile, 4-(4-(((1S,2S)-2-(5-methoxypyridin-2-yl)cyclopropyl)methoxy)-2-methylpyrimidin-5-yl)benzoic acid, 2-(5-(2-methyl-4-(((1S,2S)-2-(3-methylpyridin-2-yl)cyclopropyl)methoxy)pyrimidin-5-yl)pyridin-2-yl)propan-2-ol (enantiomer A) and (enantiomer B), 2-(5-(2-methyl-4-(((1S,2S)-2-(6-methylpyridin-2-yl)cyclopropyl)methoxy)pyrimidin-5-yl)pyridin-2-yl)propan-2-ol (enantiomer A), 2-(5-(2-methyl-4-(((1S,2S)-2-(6-methylpyridin-2-yl)cyclopropyl)methoxy)pyrimidin-5-yl)pyridin-2-yl)propan-2-ol (1R,2R,mixture), 2-(5-(2-methyl-4-(((1S,2S)-2-(4-methylpyridin-2-yl)cyclopropyl)methoxy)pyrimidin-5-yl)pyridin-2-yl)propan-2-ol (enantiomer A) and (enantiomer B), 2-(5-(4-(((1S,2S)-2-(5-fluoropyridin-2-yl)cyclopropyl)methoxy)-2-methylpyrimidin-5-yl)pyridin-2-yl)propan-2-ol, 2-(5-(4-(((1S,2S)-2-(5-ethylpyridin-2-yl)cyclopropyl)methoxy)-2-methylpyrimidin-5-yl)pyridin-2-yl)propan-2-ol (enantiomer A) and (enantiomer B), 6-((1S,2S)-2-((5-(6-(2-hydroxypropan-2-yl)pyridin-3-yl)-2-methylpyrimidin-4-yloxy)methyl)cyclopropyl)nicotinonitrile, 2-(5-(2-methyl-4-(((1S,2S)-2-(5-(trifluoromethyl)pyridin-2-yl)cyclopropyl)methoxy)pyrimidin-5-yl)pyridin-2-yl)propan-2-ol, 2-methyl-4-(((1S,2S)-2-(5-methylpyridin-2-yl)cyclopropyl)methoxy)-5-(1,4-dioxaspiro-[4.5]decan-8-yl)pyrimidine, 4-(2-methyl-4-(((1S,2S)-2-(5-methylpyridin-2-yl)cyclopropyl)methoxy)pyrimidin-5-yl)cyclohexanone, 2-methyl-4-(((1S,2S)-2-(6-methylpyridin-2-yl)cyclopropyl)methoxy)-5-(1,4-dioxaspiro[4.5]decan-8-yl)pyrimidine, 4-(2-methyl-4-(((1S,2S)-2-(6-methylpyridin-2-yl)cyclopropyl)methoxy)pyrimidin-5-yl)cyclohexanone, 4-(((1S,2S)-2-(5-methoxypyridin-2-yl)cyclopropyl)methoxy)-2-methyl-5-(1,4-dioxaspiro[4.5]decan-8-yl)pyrimidine, 4-(4-(((1S,2S)-2-(5-methoxypyridin-2-yl)cyclopropyl)methoxy)-2-methylpyrimidin-5-yl)cyclohexanone, 2-((1S,2S)-2-((2-methyl-5-(1,4-dioxaspiro[4.5]decan-8-yl)pyrimidin-4-yloxy)methyl)-cyclopropyl)quinoline, 4-(2-methyl-4-(((1S,2S)-2-(quinolin-2-yl)cyclopropyl)methoxy)pyrimidin-5-yl)cyclohexanone, Trans-4-(2-methyl-4-(((1S,2R)-2-(quinolin-2-yl)cyclopropyl)methoxy)pyrimidin-5-yl)cyclohexanol, (1R,4s)-4-(2-methyl-4-(((1S,2R)-2-(quinolin-2-yl)cyclopropyl)methoxy)pyrimidin-5-yl)cyclohexanol, 4-(((1S,2R)-2-(5-ethylpyridin-2-yl)cyclopropyl)methoxy)-2-methyl-5-(1,4-dioxaspiro[4.5]decan-8-yl)pyrimidine, 4-(4-(((1S,2R)-2-(5-ethylpyridin-2-yl)cyclopropyl)methoxy)-2-methylpyrimidin-5-yl)cyclohexanone, Trans-4-(4-(((1S,2R)-2-(5-ethylpyridin-2-yl)cyclopropyl)methoxy)-2-methylpyrimidin-5-yl)cyclohexanol, (1R,4s)-4-(4-(((1S,2R)-2-(5-ethylpyridin-2-yl)cyclopropyl)methoxy)-2-methylpyrimidin-5-yl)cyclohexanol, 2-methyl-4-(((1S,2R)-2-(pyridin-2-yl)cyclopropyl)methoxy)-5-(1,4-dioxaspiro[4.5]decan-8-yl)pyrimidine, Trans-4-(2-methyl-4-(((1S,2S)-2-(pyridin-2-yl)cyclopropyl)methoxy)pyrimidin-5-yl)cyclohexanol, 4-(((1S,2S)-2-(6-methoxypyridin-2-yl)cyclopropyl)methoxy)-2-methyl-5-(1,4-dioxaspiro[4.5]decan-8-yl)pyrimidine, 2-methyl-4-(((1S,2S)-2-(4-methylpyridin-2-yl)cyclopropyl)methoxy)-5-(1,4-dioxaspiro[4.5]decan-8-yl)pyrimidine, 4-(4-(((1S,2S)-2-(6-methoxypyridin-2-yl)cyclopropyl)methoxy)-2-methylpyrimidin-5-yl)cyclohexanone, 4-(2-methyl-4-(((1S,2S)-2-(4-methylpyridin-2-yl)cyclopropyl)methoxy)pyrimidin-5-yl)cyclohexanone, 2-((2S)-2-methyl-3-(2-methyl-5-(1,4-dioxaspiro[4.5]decan-8-yl)pyrimidin-4-yloxy)propyl)quinoline, (7R,8S)-8-(2-methyl-4-(((1S,2S)-2-(quinolin-2-yl)cyclopropyl)methoxy)pyrimidin-5-yl)-1,4-dioxaspiro[4.5]decan-7-ol, 8-(2-methyl-4-(((1S,2S)-2-(quinolin-2-yl)cyclopropyl)methoxy)pyrimidin-5-yl)-1,4-dioxaspiro[4.5]decan-8-ol, 3-(4-(((1S,2S)-2-(5-Methoxypyridin-2-yl)cyclopropyl)methoxy)-2-methylpyrimidin-5-yl)cyclohexanone, 5-Cyclohexyl-2-methyl-4-(((1S,2S)-2-(5-methylpyridin-2-yl)cyclopropyl) methoxy) pyrimidine, 5-(4,4-Difluorocyclohexyl)-2-methyl-4-(((1S,2S)-2-(5-methylpyridin-2-yl)cyclopropyl)-methoxy)pyrimidine, (trans)-4-Fluoro-4-(2-methyl-4-(((1S,2S)-2-(5-methyl-pyridin-2-yl)cyclopropyl)methoxy)-pyrimidin-5-yl)cyclohexanol, 5-(1-fluorocyclohexyl)-4-((1S,2S)-2-(5-methoxypyridin-2-yl)cyclopropyl)methoxy)-2-methylpyrimidine, (cis)1-Methyl-4-(2-methyl-4-(((1S,2S)-2-(5-methylpyridin-2-yl)cyclopropyl)methoxy) pyrimidin-5-yl)cyclohexanol, (trans)1-Methyl-4-(2-methyl-4-(((1S,2S)-2-(5-methyl-pyridin-2-yl)cyclopropyl)methoxy) pyrimidin-5-yl)cyclohexanol, (cis)1-Ethyl-4-(2-methyl-4-(((1S,2S)-2-(5-methylpyridin-2-yl)cyclopropyl)methoxy) pyrimidin-5-yl)cyclohexanol, (trans)1-Ethyl-4-(2-methyl-4-(((1S,2S)-2-(5-methylpyridin-2-1)cyclopropyl)methoxy) pyrimidin-5-yl)cyclohexanol, cis-Ethyl4-(4-(((1S,2S)-2-(5-methoxypyridin-2-yl)cyclopropyl)methoxy)-2-methylpyrimidin-5-yl)cyclohexanecarboxylate, cis-4-(4-(((1S,2S)-2-(5-Methoxypyridin-2-yl)cyclopropyl)methoxy)-2-methylpyrimidin-5-yl)cyclohexanecarboxylic acid, cis-4-(4-(((1S,2S)-2-(5-Methoxypyridin-2-yl)cyclopropyl)methoxy)-2-methylpyrimidin-5-yl)cyclohexanecarboxamide, trans-4-(4-(((1S,2S)-2-(5-Methoxypyridin-2-yl)cyclopropyl)methoxy)-2-methylpyrimidin-5-yl)cyclohexanecarboxamide, (trans)2-(4-(4-(((1S,2S)-2-(5-methoxypyridin-2-yl)cyclopropyl)methoxy)-2-methylpyrimidin-5-yl)cyclohexyl)propan-2-ol, (cis)2-(4-(2-methyl-4-(((1S,2S)-2-(5-methylpyridin-2-yl)cyclopropyl)methoxy)pyrimidin-5-yl)cyclohexyl)propan-2-ol, 5-(4-(1H-tetrazol-5-yl)phenyl)-4-(((1S,2S)-2-(5-methoxypyridin-2-yl)cyclopropyl)methoxy)-2-methylpyrimidine, 4-(((1S,2S)-2-(5-methoxypyridin-2-yl)cyclopropyl)methoxy)-2-methyl-5-(4-(2-methyl-2H-tetrazol-5-yl)phenyl)pyrimidine, 4-(((1S,2S)-2-(5-methoxypyridin-2-yl)cyclopropyl)methoxy)-2-methyl-5-(4-(1-methyl-1H-tetrazol-5-yl)phenyl)pyrimidine, 5-(4-(2-ethyl-2H-tetrazol-5-yl)phenyl)-4-(((1S,2S)-2-(5-methoxypyridin-2-yl)cyclopropyl)methoxy)-2-methylpyrimidine, 5-(4-(1-ethyl-1H-tetrazol-5-yl)phenyl)-4-(((1S,2S)-2-(5-methoxypyridin-2-yl)cyclopropyl)methoxy)-2-methylpyrimidine, 5-(4-(2-(difluoromethyl)-2H-tetrazol-5-yl)phenyl)-4-(((1S,2S)-2-(5-methoxypyridin-2-yl)cyclopropyl)methoxy)-2-methylpyrimidine, 5-(4-(1-(difluoromethyl)-1H-tetrazol-5-yl)phenyl)-4-(((1S,2S)-2-(5-methoxypyridin-2-yl)cyclopropyl)methoxy)-2-methylpyrimidine, 5-(6-(2H-tetrazol-5-yl)pyridin-3-yl)-44(1S,2S)-2-(5-methoxypyridin-2-yl)cyclopropyl)-methoxy)-2-methylpyrimidine, 4-(((1S,2S)-2-(5-methoxypyridin-2-yl)cyclopropyl)methoxy)-2-methyl-5-(6-(2-methyl-2H-tetrazol-5-yl)pyridin-3-yl)pyrimidine, 4-(((1S,2S)-2-(5-methoxypyridin-2-yl)cyclopropyl)methoxy)-2-methyl-5-(6-(1-methyl-1H-tetrazol-5-yl)pyridin-3-yl)pyrimidine, 5-(6-(2-ethyl-2H-tetrazol-5-yl)pyridin-3-yl)-4-(((1S,2S)-2-(5-methoxypyridin-2-yl)cyclopropyl)methoxy)-2-methylpyrimidine, 5-(6-(1-ethyl-1H-tetrazol-5-yl)pyridin-3-yl)-4-(((1S,2S)-2-(5-methoxypyridin-2-yl)cyclopropyl)methoxy)-2-methylpyrimidine, 4-(((1S,2S)-2-(5-methoxypyridin-2-yl)cyclopropyl)methoxy)-2-methyl-5-(2H-tetrazol-5-yl)pyrimidine, 4-(((1S,2S)-2-(5-methoxypyridin-2-yl)cyclopropyl)methoxy)-2-methyl-5-(2-methyl-2H-tetrazol-5-yl)pyrimidine, 5-(2-ethyl-2H-tetrazol-5-yl)-4-(((1S,2S)-2-(5-methoxypyridin-2-yl)cyclopropyl)methoxy)-2-methylpyrimidine, 5-(2-(difluoromethyl)-2H-tetrazol-5-yl)-4-(((1S,2S)-2-(5-methoxypyridin-2-yl)cyclopropyl)methoxy)-2-methylpyrimidine, 5-(4-(((1S,2S)-2-(5-methoxypyridin-2-yl)cyclopropyl)methoxy)-2-methylpyrimidin-5-yl)-1-methyl-1,2-dihydropyrazol-3-one, 5-(4-(((1S,2S)-2-(5-methoxypyridin-2-yl)cyclopropyl)methoxy)-2-methylpyrimidin-5-yl)-1,2-dimethyl-1,2-dihydropyrazol-3-one, 5-(3-methoxy-1-methyl-1H-pyrazol-5-yl)-4-(((1S,2S)-2-(5-methoxypyridin-2-yl)cyclopropyl)methoxy)-2-methylpyrimidine, 5-(4-(((1S,2S)-2-(5-methoxypyridin-2-yl)cyclopropyl)methoxy)-2-methylpyrimidin-5-yl)-1,2-dihydropyrazol-3-one, 4-(4-(((1S,2S)-2-(5-methoxypyridin-2-yl)cyclopropyl)methoxy)-2-methylpyrimidin-5-yl)isoxazol-5(2H)-one, 4-(4-(((1S,2S)-2-(5-methoxypyridin-2-yl)cyclopropyl)methoxy)-2-methylpyrimidin-5-yl)-2-methylisoxazol-5 (2H)-one, 4-(4-(((1S,2S)-2-(5-methoxypyridin-2-yl)cyclopropyl)methoxy)-2-methylpyrimidin-5-yl)-1-methyl-1,2-dihydropyrazol-3-one, 4-(((1S,2S)-2-(5-methoxypyridin-2-yl)cyclopropyl)methoxy)-2-methyl-5-(1H-1,2,3-triazol-4-yl)pyrimidine, 5-(3-(difluoromethyl)-3H-1,2,3-triazol-4-yl)-4-(((1S,2S)-2-(5-methoxypyridin-2-yl)cyclopropyl)methoxy)-2-methylpyrimidine, 5-(1-ethyl-1H-1,2,3-triazol-4-yl)-4-(((1S,2S)-2-(5-methoxypyridin-2-yl)cyclopropyl)methoxy)-2-methylpyrimidine, ethyl 5-(4-(((1S,2S)-2-(5-methoxypyridin-2-yl)cyclopropyl)methoxy)-2-methylpyrimidin-5-yl)-3H-1,2,3-triazole-4-carboxylate, (5-(4-(((1S,2S)-2-(5-methoxypyridin-2-yl)cyclopropyl)methoxy)-2-methylpyrimidin-5-yl)-3H-1,2,3-triazol-4-yl)methanol, 3-(4-(4-(((1S,2S)-2-(5-methoxypyridin-2-yl)cyclopropyl)methoxy)-2-methylpyrimidin-5-yl)phenyl)-1,2,4-oxadiazole, 3-(4-(4-(((1S,2S)-2-(5-methoxypyridin-2-yl)cyclopropyl)methoxy)-2-methylpyrimidin-5-yl)phenyl)-5-methyl-1,2,4-oxadiazole, (3-(4-(4-(((1S,2S)-2-(5-methoxypyridin-2-yl)cyclopropyl)methoxy)-2-methylpyrimidin-5-yl)phenyl)-1,2,4-oxadiazol-5-yl)methanol, 5-(4-(4-(((1S,2S)-2-(5-methoxypyridin-2-yl)cyclopropyl)methoxy)-2-methylpyrimidin-5-yl)phenyl)-3-methyl-1,2,4-oxadiazole, 5-(4-(((1S,2S)-2-(5-methoxypyridin-2-yl)cyclopropyl)methoxy)-2-methylpyrimidin-5-yl)-1,2,4-oxadiazole, 5-(4-(((1S,2S)-2-(5-methoxypyridin-2-yl)cyclopropyl)methoxy)-2-methylpyrimidin-5-yl)oxazole, (3-(4-(((1S,2S)-2-(5-methoxypyridin-2-yl)cyclopropyl)methoxy)-2-methylpyrimidin-5-yl)-1,2,4-oxadiazol-5-yl)methanol, 5-(4-(((1S,2S)-2-(5-methoxypyridin-2-yl)cyclopropyl)methoxy)-2-methylpyrimidin-5-yl)-4-methyloxazole, or a pharmaceutically acceptable salt thereof.

9. A pharmaceutical composition which comprises a pharmaceutically acceptable carrier and a compound of claim 1 or a pharmaceutically acceptable salt thereof.

10. A method for treating schizophrenia in a mammalian patient in need thereof which comprises administering to the patient a therapeutically effective amount of a compound of claim 1 or a pharmaceutically acceptable salt thereof.

* * * * *